United States Patent
Pyle et al.

(10) Patent No.: US 12,365,875 B2
(45) Date of Patent: Jul. 22, 2025

(54) METHODS FOR GENERATING SKELETAL MUSCLE PROGENITOR CELLS

(71) Applicant: The Regents of the University of California, Oakland, CA (US)

(72) Inventors: April D. Pyle, Los Angeles, CA (US); Michael R. Hicks, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 646 days.

(21) Appl. No.: 16/474,895

(22) PCT Filed: Dec. 15, 2017

(86) PCT No.: PCT/US2017/066794
§ 371 (c)(1),
(2) Date: Jun. 28, 2019

(87) PCT Pub. No.: WO2018/128779
PCT Pub. Date: Jul. 12, 2018

(65) Prior Publication Data
US 2021/0139854 A1 May 13, 2021

Related U.S. Application Data

(60) Provisional application No. 62/443,499, filed on Jan. 6, 2017.

(51) Int. Cl.
*C12N 5/077* (2010.01)
(52) U.S. Cl.
CPC ...... *C12N 5/0658* (2013.01); *C12N 2501/105* (2013.01); *C12N 2501/33* (2013.01)
(58) Field of Classification Search
CPC .......... C12N 5/0658; C12N 2501/105
See application file for complete search history.

(56) References Cited

U.S. PATENT DOCUMENTS

| | | | |
|---|---|---|---|
| 2004/0265996 A1 | 12/2004 | Schwarz et al. | |
| 2015/0147807 A1* | 5/2015 | Zon | C12N 5/0658 435/377 |

FOREIGN PATENT DOCUMENTS

| | | |
|---|---|---|
| WO | 2005049810 A1 | 6/2005 |
| WO | 2013030243 A1 | 3/2013 |
| WO | 2016108288 A1 | 7/2016 |
| WO | 2016137400 A1 | 9/2016 |
| WO | 2016168890 A1 | 10/2016 |
| WO | 2017188458 A1 | 11/2017 |
| WO | 2017196175 A1 | 11/2017 |

OTHER PUBLICATIONS

Gomez-Lopez et al., "Sox2 and Pax6 Maintain the Proliferative and Developmental Potential of Gliogenic Neural Stem Cells In Vitro", Glia, 2011, vol. 59, pp. 1588-1599. (Year: 2011).*
Birbrair et al., "Skeletal muscle neural progenitor cells exhibit properties of NG2-glia", Exp Cell Res. Jan. 1, 2013; 319(1): 45-63, pp. 1-32. (Year: 2013).*
Partial European Search report received in EP17890677, mailed Jul. 7, 2020.
Supplementary European Search report received in EP17890677, mailed Nov. 4, 2020.
Written Opinion received in EP17890677, mailed Nov. 4, 2020.
Chal et al., "Differentiation of pluripotent stem cells to muscle fiber to model Duchenne muscular dystrophy", Aug. 3, 2015, pp. 962-969, vol. 33, No. 9, Publisher: Nat Biotechnol.
Darabi & Perlingeiro, "Derivation of Skeletal Myogenic Precursors from Human Pluripotent Stem Cells Using Conditional Expression of PAX7", 2016, pp. 423-439, vol. 1357, Publisher: Methods Mol Biol.
Delaney et al., "The role of TGF-1 during skeletal muscle regeneration", Dec. 29, 2016, pp. 706-715, vol. 41, No. 7, Publisher: Cell Biol Int.
Filvaroff et al., "Inhibition of myogenic differentiation in myoblasts expressing a truncated type II TGF-beta receptor", May 1994, pp. 1085-1095, vol. 120, No. 5, Publisher: Development.
Hicks et al., "ERBB3 and NGFR mark a distinct skeletal muscle progenitor cell in human development and hPSCs", Dec. 18, 2017, pp. 46-57, vol. 20, No. 1, Publisher: Nat Cell Biol.
Ho & Blau, "Muscling toward therapy with ERBB3 and NGFR", Jan. 2018, pp. 6-7, vol. 20, No. 1, Publisher: Nat Cell Biol.
Hosoyama et al., "Derivation of myogenic progenitors directly from human pluripotent stem cells using a sphere-based culture", Mar. 21, 2014, pp. 564-574, vol. 3, No. 5, Publisher: Stem Cells Transl Med.
Kim et al., "Generation of craniofacial myogenic progenitor cells from human induced pluripotent stem cells for skeletal muscle tissue regeneration", Apr. 2, 2020, pp. 119995, vol. 248, Publisher: Biomaterials.
Krueger & Hoffmann, "Identification of retinoic acid in a high content screen for agents that overcome the anti-myogenic effect of TGF-beta-1", Nov. 30, 2010, p. e15511, vol. 5, No. 11, Publisher: PLoS One.
Sakai-Takemura, et al., "Premyogenic progenitors derived from human pluripotent stem cells expand in floating culture and differentiate into transplantable myogenic progenitor", Apr. 26, 2018, p. 6555, vol. 8, Publisher: Sci Rep.
Xi et al., "A Human Skeletal Muscle Atlas Identifies the Trajectories of Stem and Progenitor Cells across Development and from Human Pluripotent Stem Cells", Jul. 2, 2020, pp. 158-176e10, vol. 27, No. 1, Publisher: Cell Stem Cell.

(Continued)

*Primary Examiner* — Laura Schuberg
(74) *Attorney, Agent, or Firm* — Suzannah K. Sundby, Esq.; Canady + Lortz LLP

(57) ABSTRACT

The present disclosure provides methods of generating skeletal muscle progenitor cells (SMPCs). The present disclosure provides methods of generating immature SMPCs and multinucleated muscle cells, and matured SMPCs and multinucleated muscle cells. The present disclosure provides engraftment methods and treatment methods, involving generating SMPCs and introducing the SMPCs into an individual.

17 Claims, 77 Drawing Sheets
Specification includes a Sequence Listing.

(56) References Cited

OTHER PUBLICATIONS

International Search Report received in PCT/US2017/066794 mailed Apr. 20, 2018.
Written Opinion received in PCT/US2017/066794 mailed Apr. 20, 2018.
Atkinson et al., "Potential for pharmacological manipulation of human embryonic stem cells", May 2013, pp. 269-289, vol. 169, No. 2, Publisher: British Journal of Pharmacology.
Martins-Taylor, et al., "Role of DNMT3B in the regulation of early neural and neural crest specifiers", Jan. 1, 2012, pp. 71-82, vol. 7, No. 1, Publisher: Epigenetics.
Shelton, et al., "Robust generation and expansion of skeletal muscle progenitors and myocytes from human pluripotent stem cells", May 15, 2016, pp. 73-84, vol. 101, Publisher: Methods.
Swartz et al., "A Novel Protocol for Directed Differentiation of C9orf72Associated Human Induced Pluripotent Stem Cells Into Contractile Skeletal Myotubes", Jul. 1, 2016, pp. 1461-1472, vol. 5, No. 11.
Uezumi, et al., "Cell-Surface Protein Profiling Identifies Distinctive Markers of Progenitor Cells in Human Skeletal Muscle", Aug. 9, 2016, pp. 263-278, vol. 7, No. 2, Publisher: Stem Cell Reports.
Xi et al., "In Vivo Human Somitogenesis Guides Somite Development from hPSCs", Feb. 7, 2017, pp. 1573-1585, vol. 18, No. 6, Publisher: Cell Reports.
Yin, et al., "Opposing Roles for the lncRNA Haunt and Its Genomic Locus in Regulating HOXA Gene Activation during Embryonic Stem Cell Differentiation", May 7, 2015, pp. 504-516, vol. 16, No. 5, Publisher: Cell Stem Cell.

* cited by examiner

FIG. 1A
Directed Differentiation Method 1
With a WNT activator only
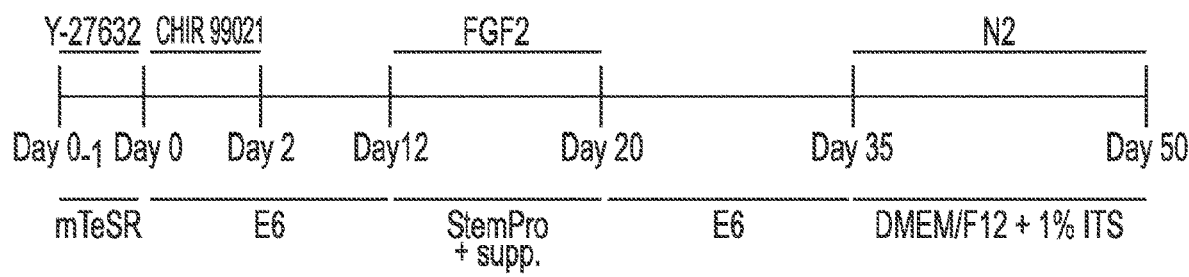
PAX7
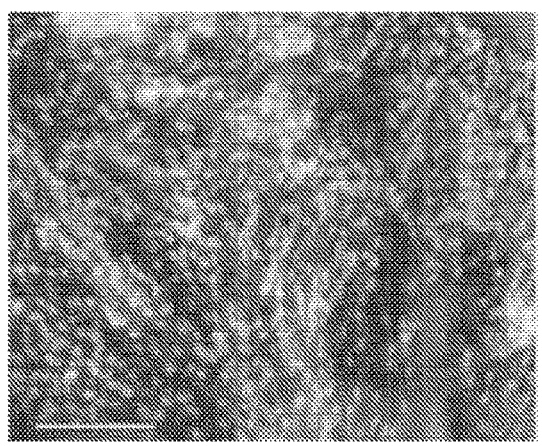
MYOD
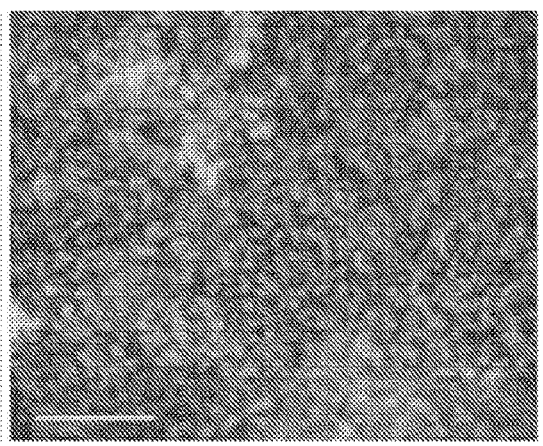
MYHC
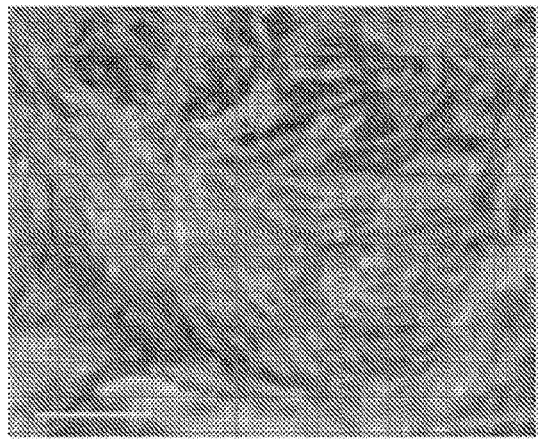
MYOG
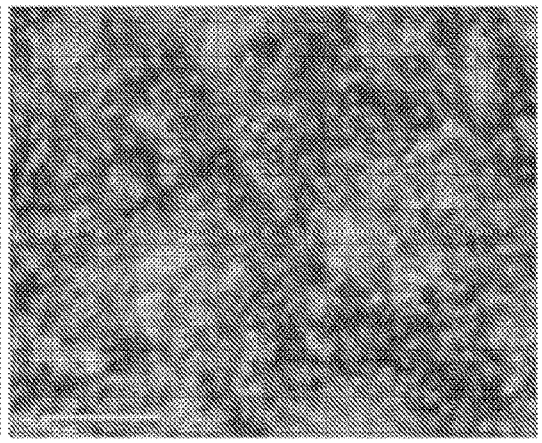

FIG. 1B
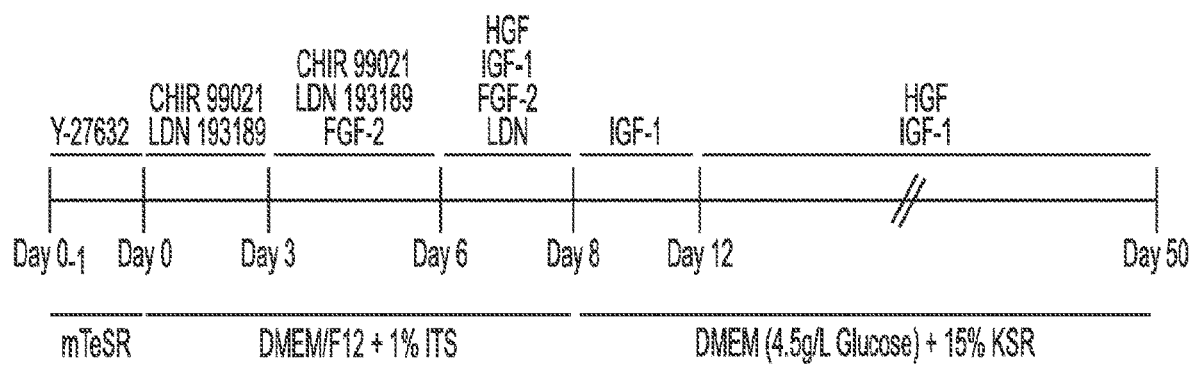
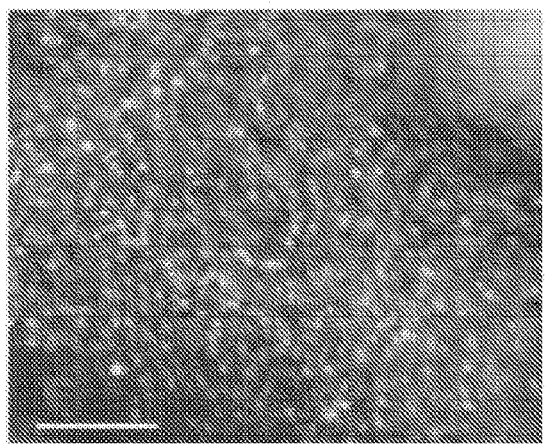
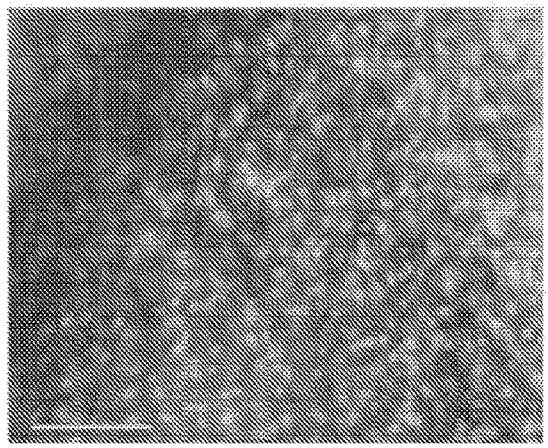
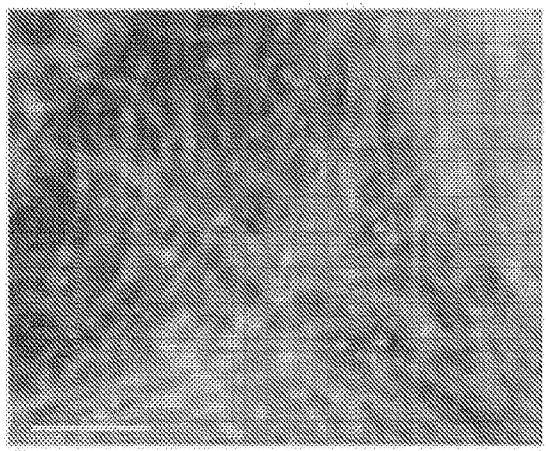
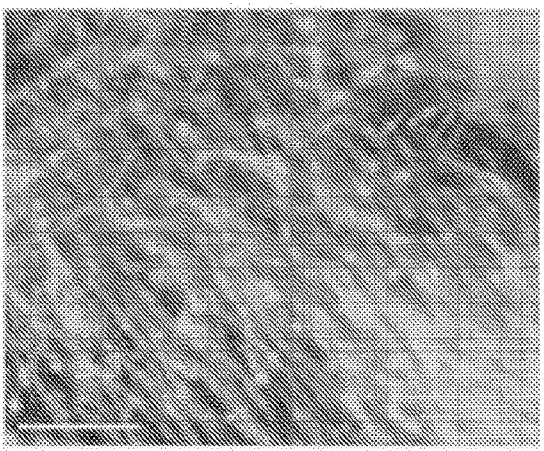

FIG. 3 (Cont.)
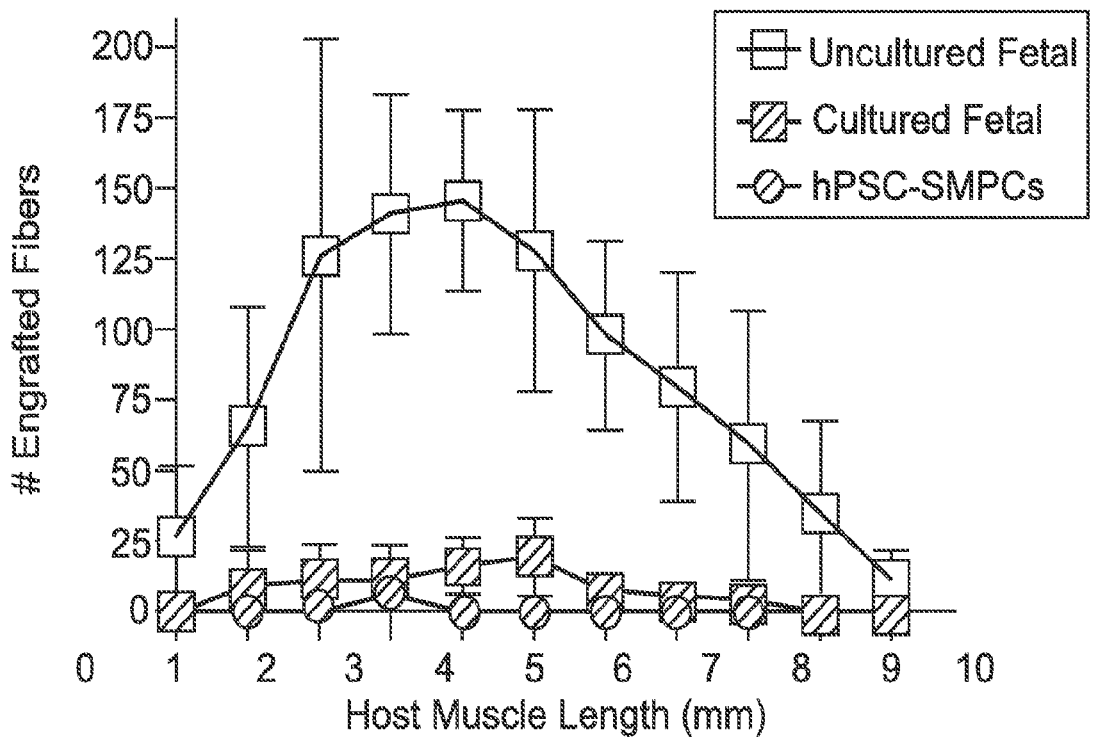
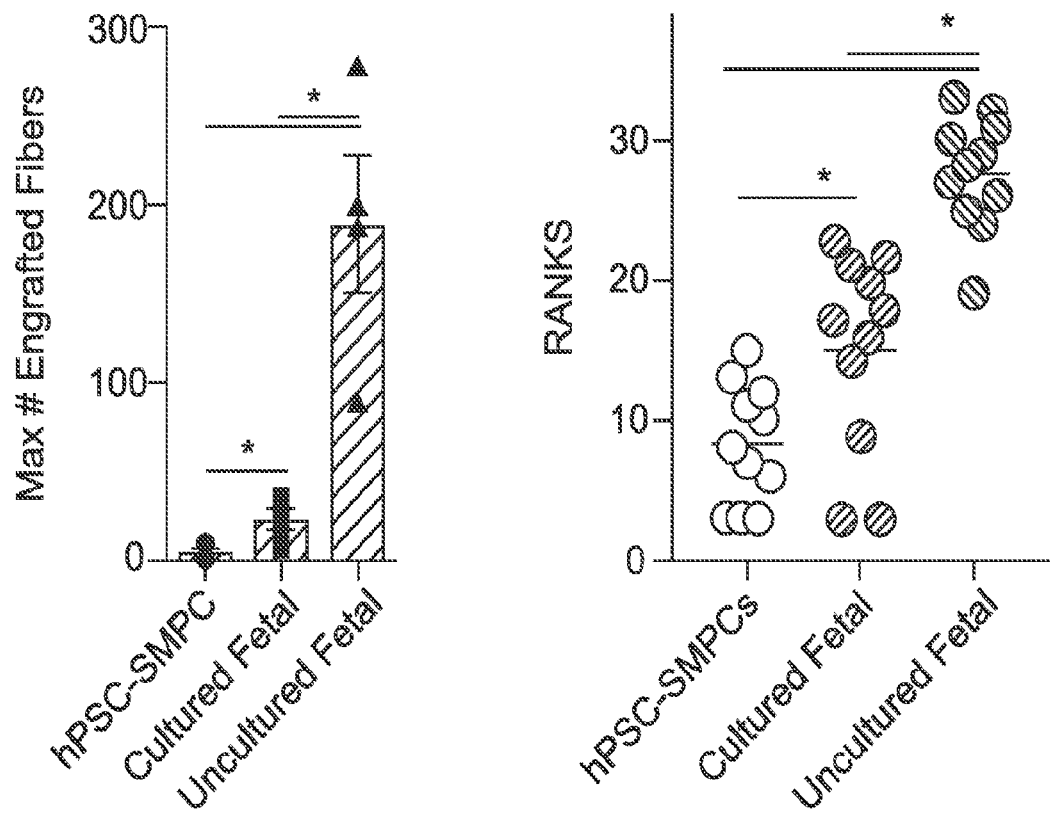

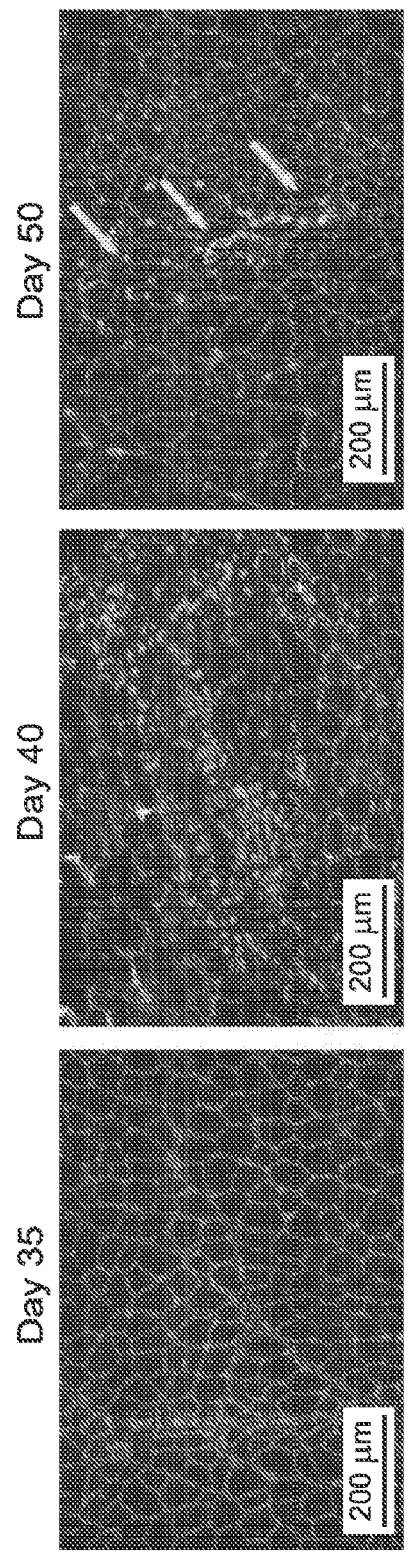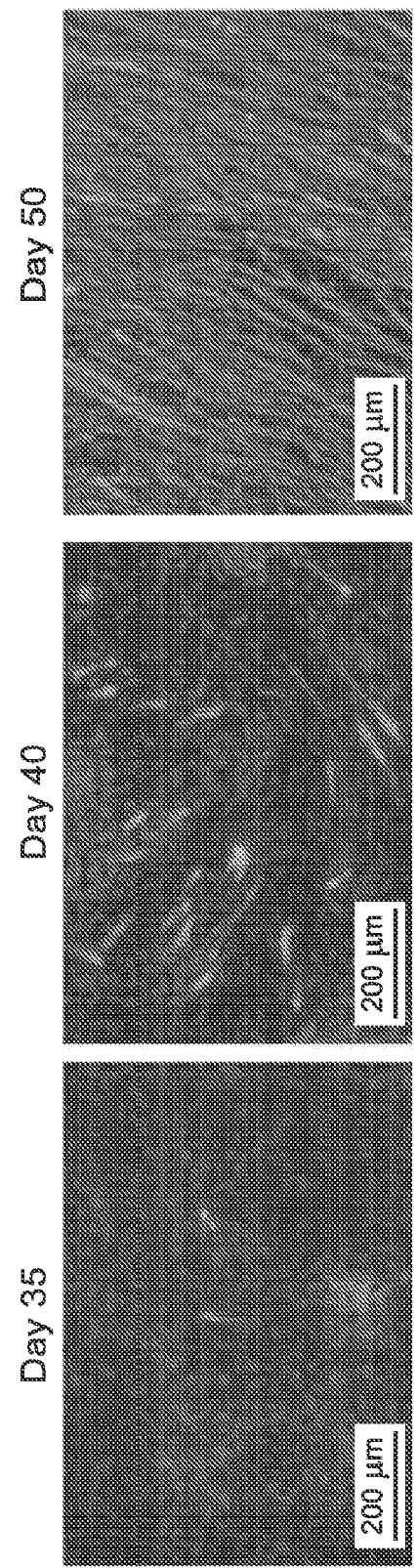

Cell lineage heterogeneity in directed differentiation cultures.

| Cell Lineage | Receptor | % day 50 hPSCs |
|---|---|---|
| Neural crest | HNK1 | 18.8% |
| Neuronal | A2B5 | 7.95% |
| Mesoderm | PDGFRα | 6.79% |
| Mesoderm | CD73 | 4.52% |
| Vascular | VEGFR2 | 0.75% |
| Neuronal/Skeletal muscle | NCAM | 45.5% |

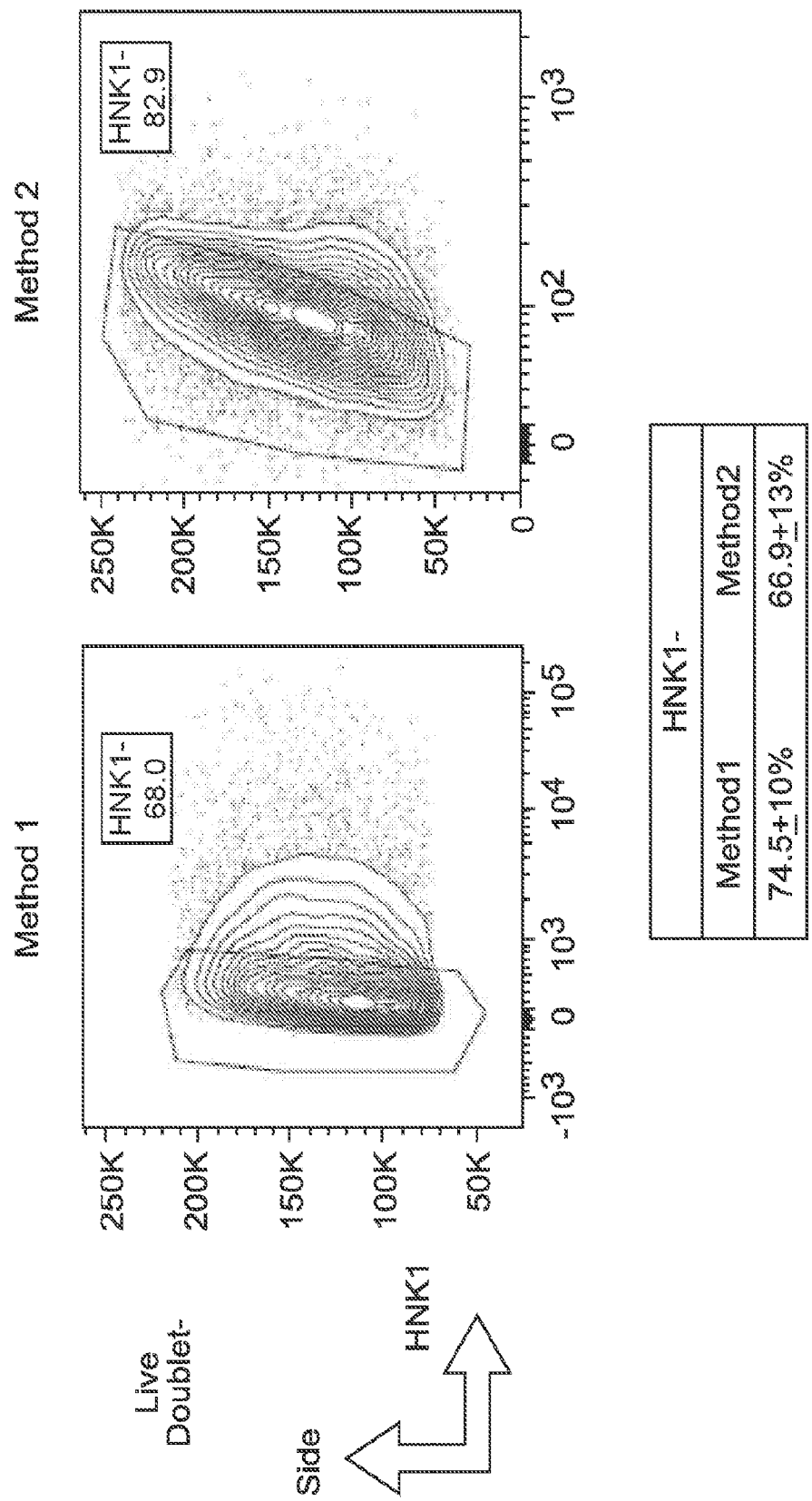

FIG. 5A (Cont.)
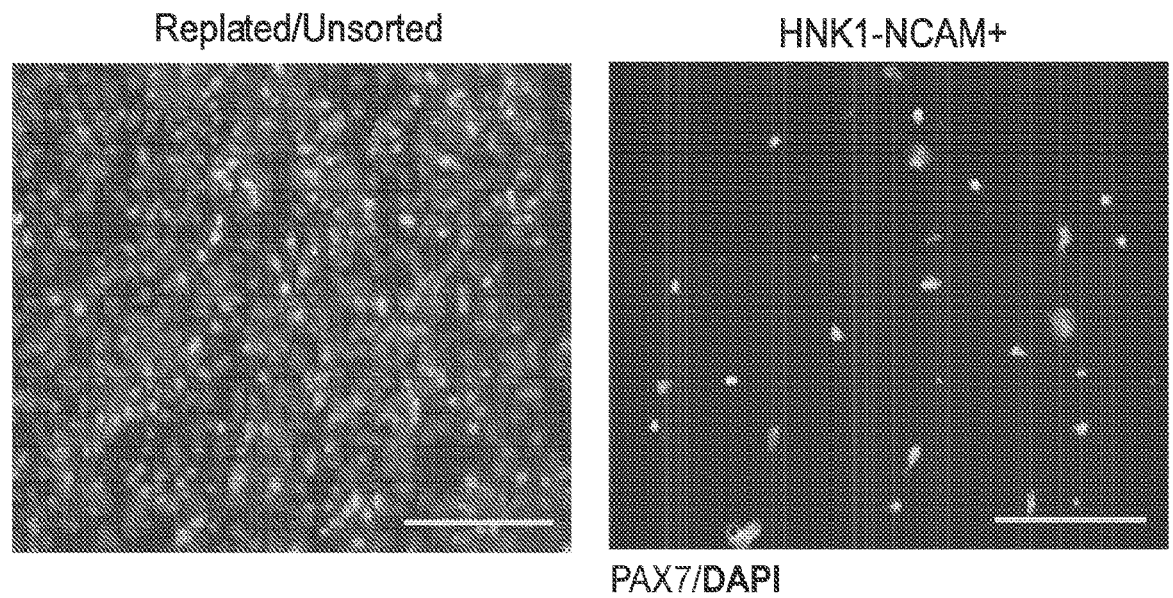
Replated/Unsorted — HNK1-NCAM+
PAX7/DAPI
Immediately post FACS
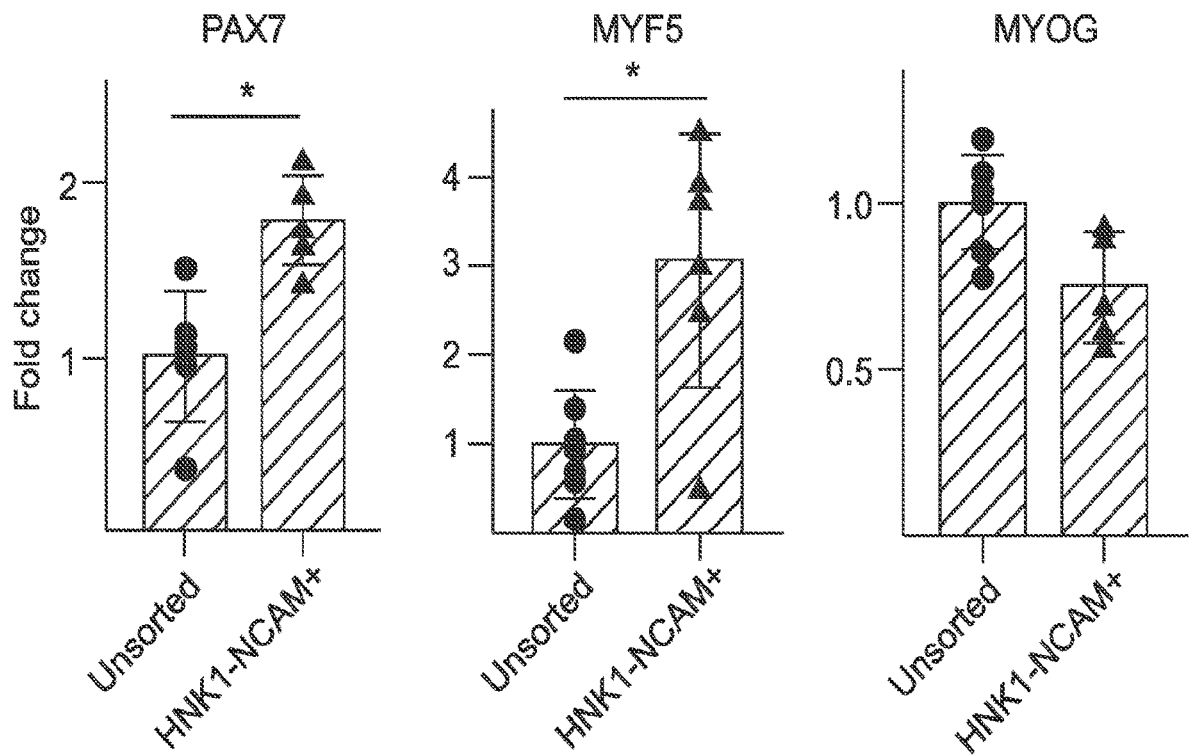

FIG. 5A (Cont.)
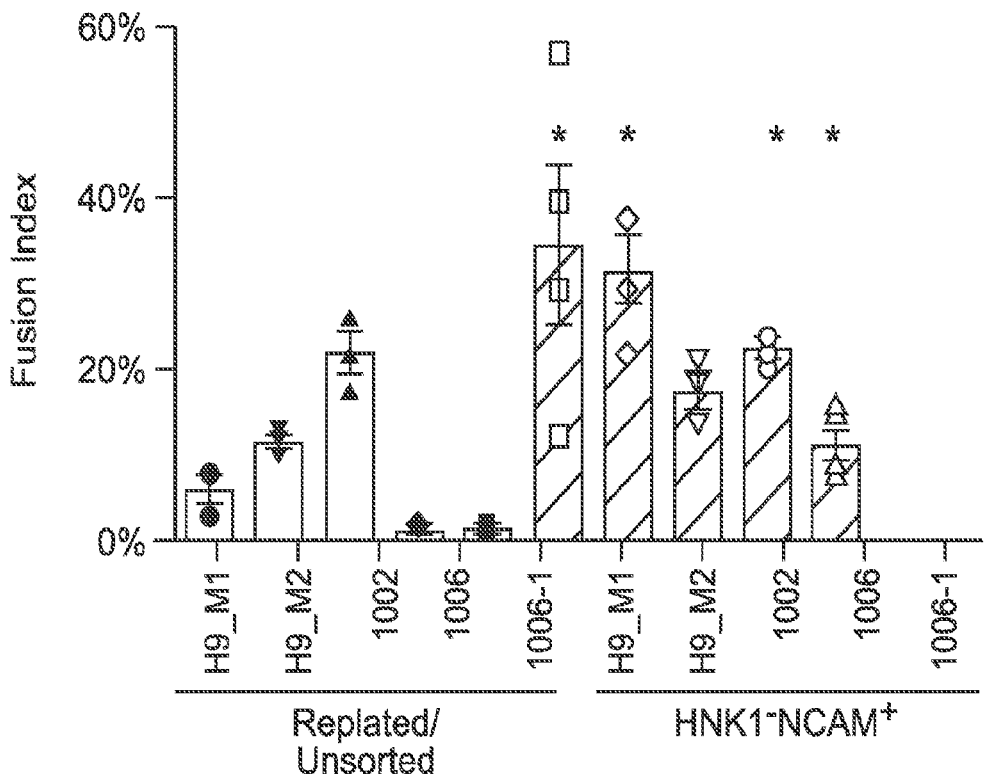
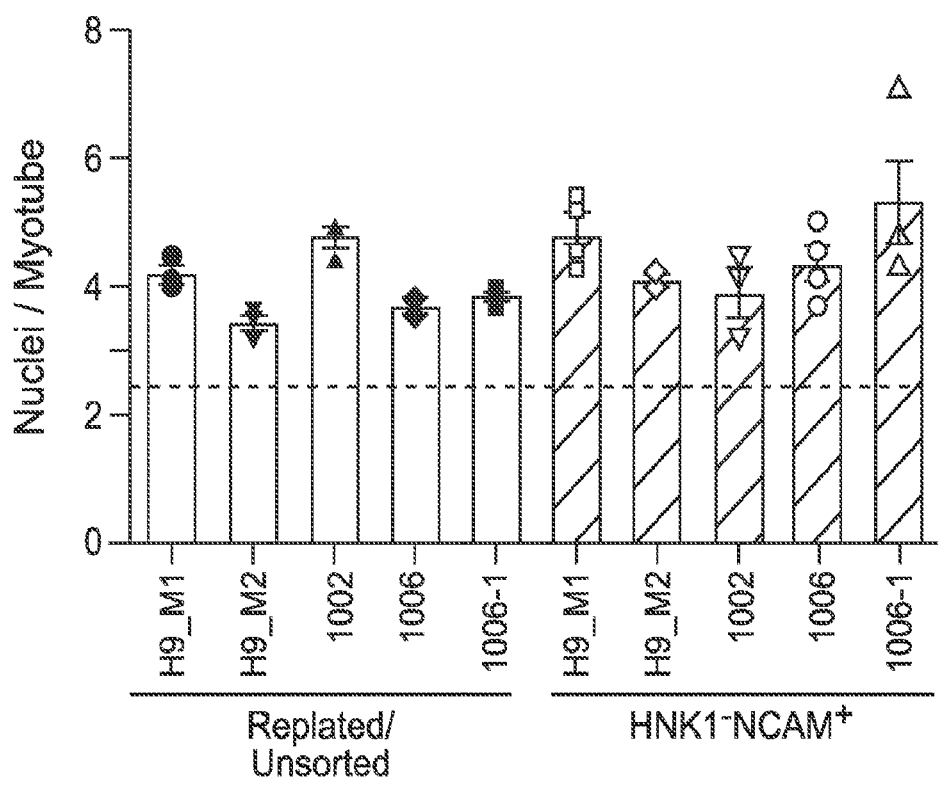

FIG. 5B
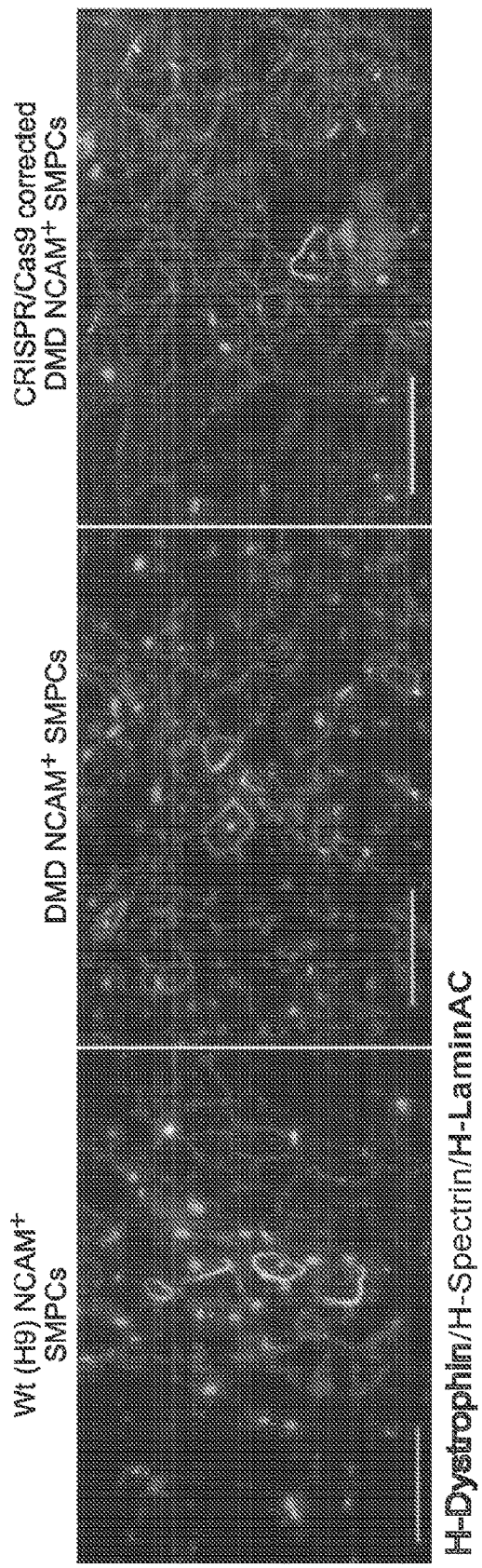
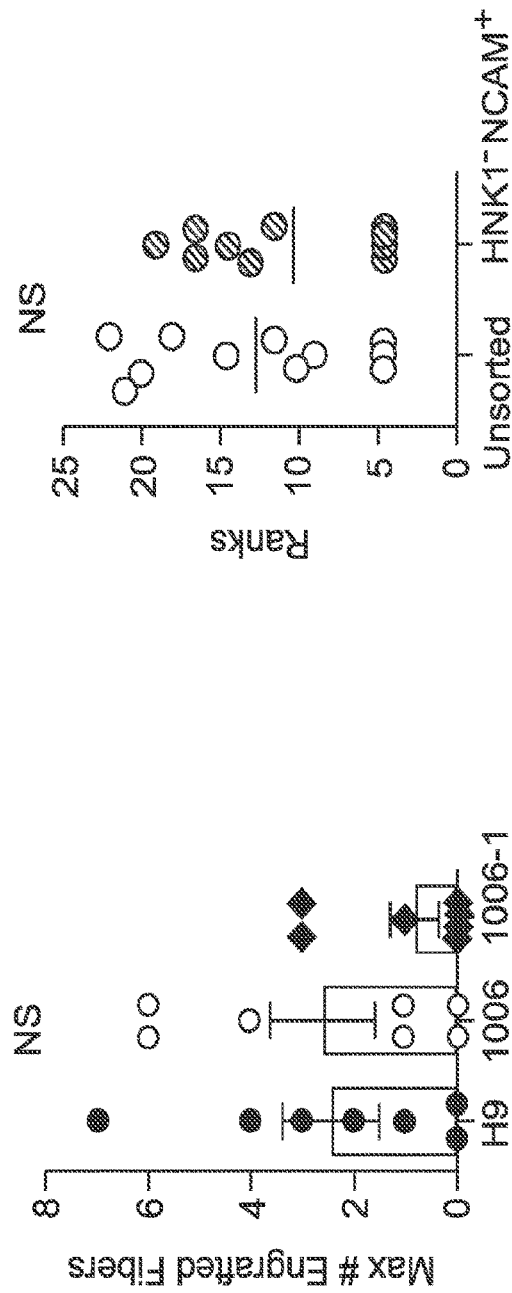

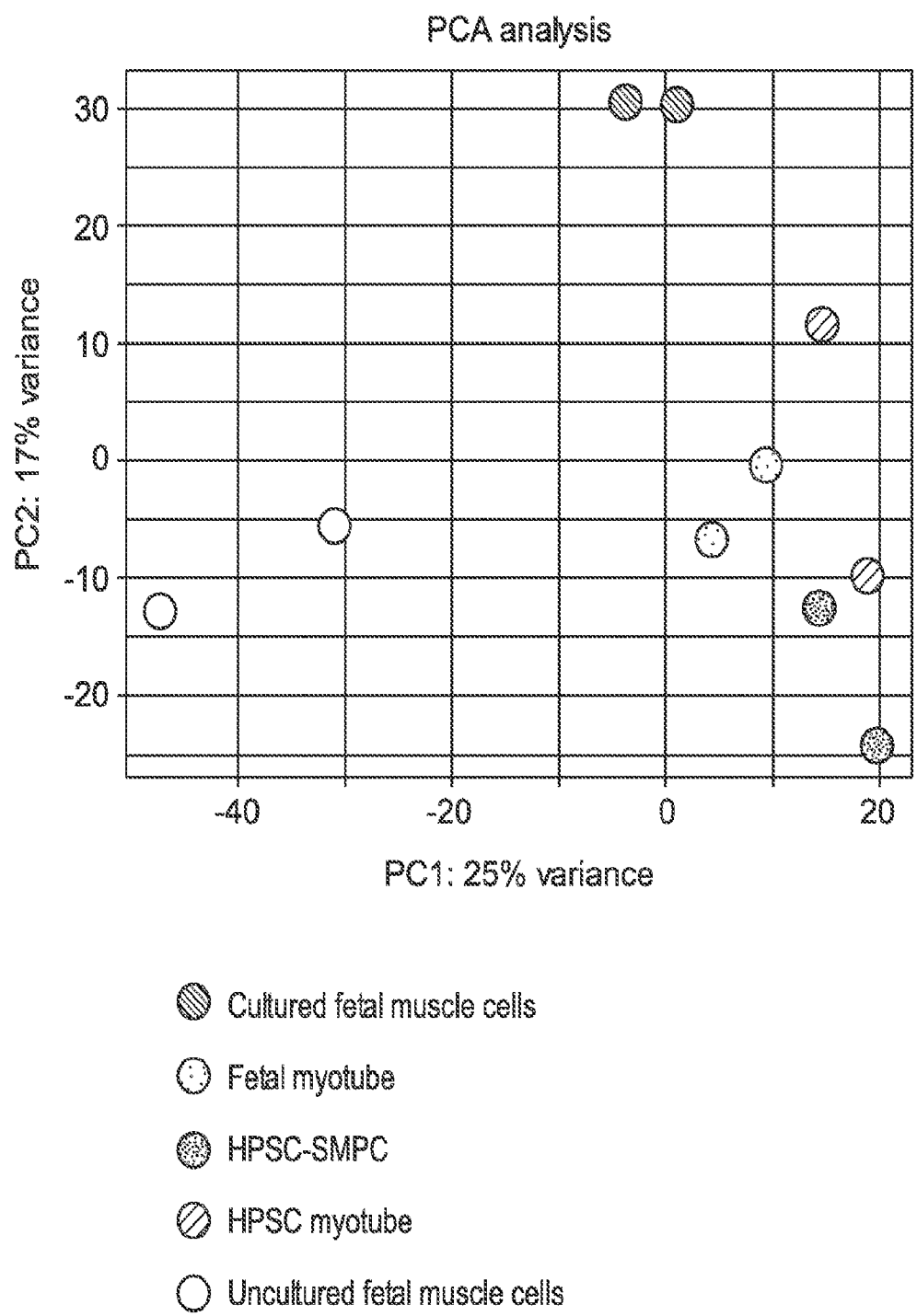

FIG. 7A (Cont.)

| % Lineage negative | | Week 8-9 | | Week 11-14 | | Week 16-18 | |
|---|---|---|---|---|---|---|---|
| | NCAM+ MCAM+ | *,* | 73.7±10.5% | | 31.7±3.6% | | 36.2±8.9% |
| | CD82+ | | 2.5±2.2% | *, | 21.6±9.8% | *,* | 38.9±4.9% |
| P1 | ERBB3+ NGFR- | *, | 4.9±1.9% | | 1.2±0.2% | | 2.4±1.3% |
| P2 | ERBB3+ NGFR+ | | 12.7±5.4% | | 11.2±2.3% | | 12.9±1.4% |
| P3 | ERBB3- NGFR+Hi | | 4.3±1.8% | *, | 12.6±3.3% | *, | 11.2±4.1% |
| P4 | ERBB3- NGFR+Low | | 10.2±2.2% | *, | 28.7±11.5% | *, | 31.0±4.7% |
| P5 | ERBB3- NGFR- | *,* | 50.2±8.8% | | 18.1±6.2% | | 19.5±6.9% |

Positivity of known cell surface markers within ERBB3 and NGFR fetal populations

| % in ERBB3 and NGFR subpopulations | | Week 8-9 | | Week 11-14 | | Week 16-18 | |
|---|---|---|---|---|---|---|---|
| | | NCAM+MCAM+ | CD82+ | NCAM+MCAM+ | CD82+ | NCAM+MCAM+ | CD82+ |
| P1 | ERBB3+ NGFR- | 91.8±3.7% | 0.1±0.1% | 89.1±2.7% | 88.0±3.8% | 87.1±1.2% | 76.7±4.8% |
| P2 | ERBB3+NGFR+ | 98.8±0.3% | 11.8±4.7% | 90.0±7.1% | 84.0±3.5% | 82.9±3.1% | 84.7±4.1% |
| P3 | ERBB3-NGFR+Hi | 63.8±9.3% | 3.0±2.5% | 1.6±0.6% | 0.1±0.1% | 5.1±4.1% | 0.2±0.1% |
| P4 | ERBB3-NGFR+Low | 68.4±11.5% | 0.4±0.3% | 23.8±2.3% | 15.5±3.2% | 15.9±8.2% | 14.2±8.2% |
| P5 | ERBB3-NGFR- | 63.3±17.3% | 0.1±0.1% | 15.9±5.9% | 8.6±4.0% | 12.5±3.7% | 21.5±10% |

FIG. 7B (Cont.)
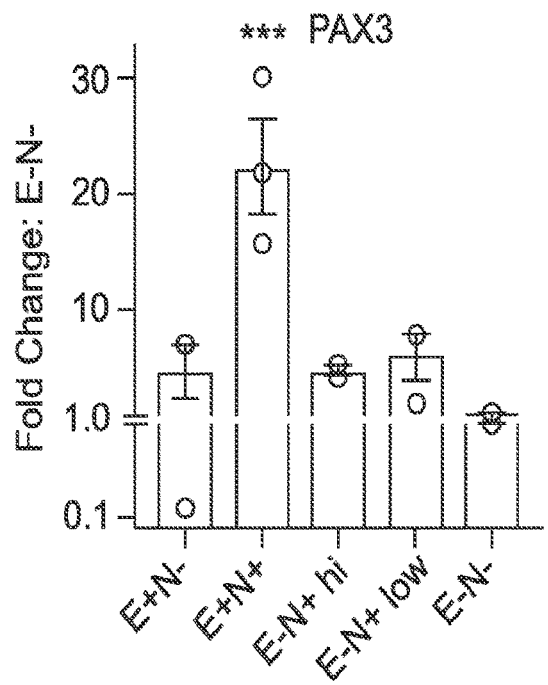
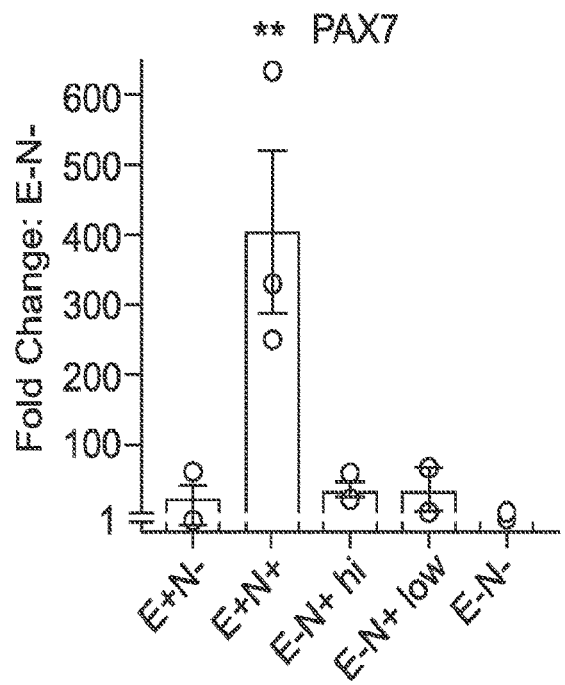
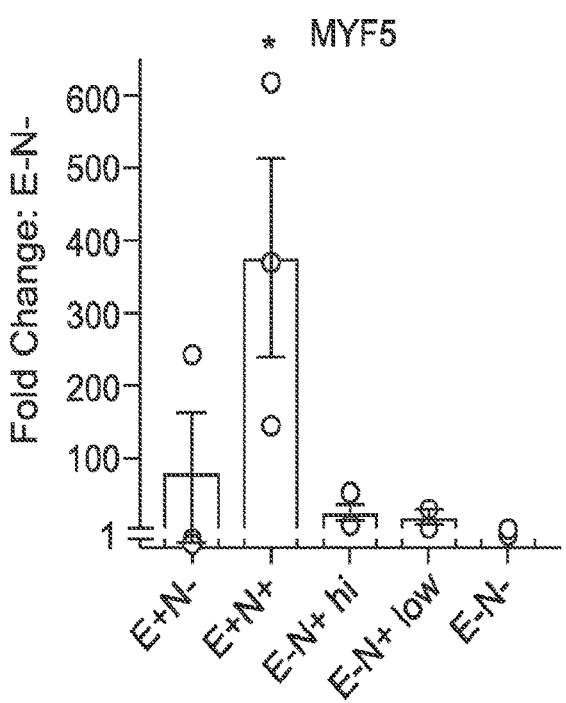
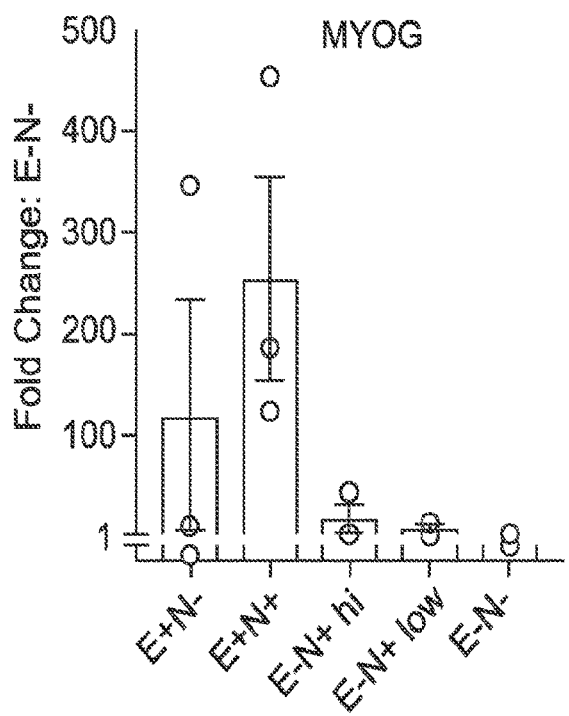

FIG. 7B (Cont.)
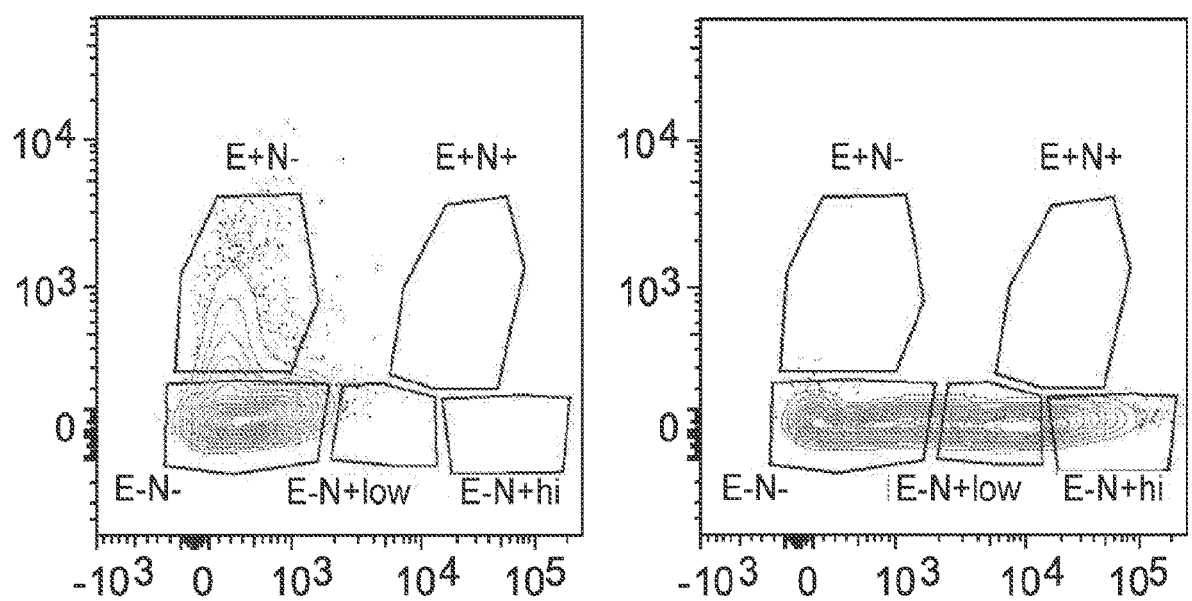
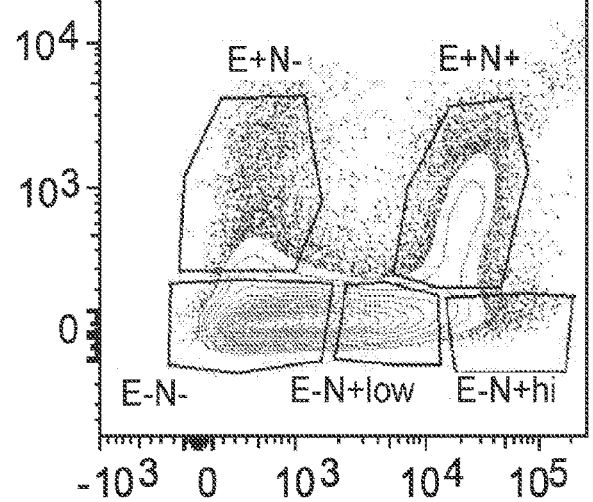

Secondary myogenesis. Week 16-18

Tissue. MYHC/PAX7/DAPI

FIG. 7C (Cont.)
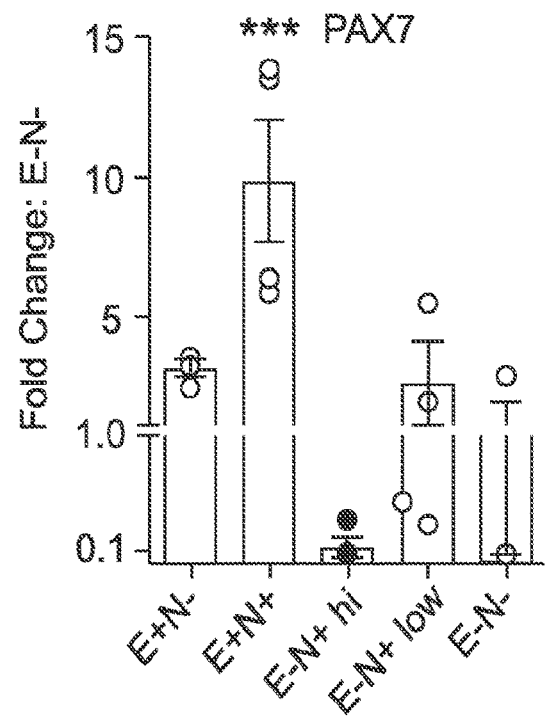
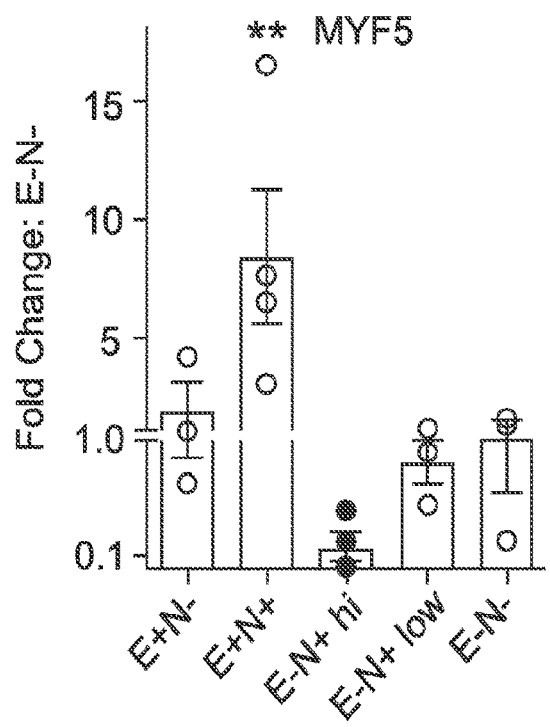
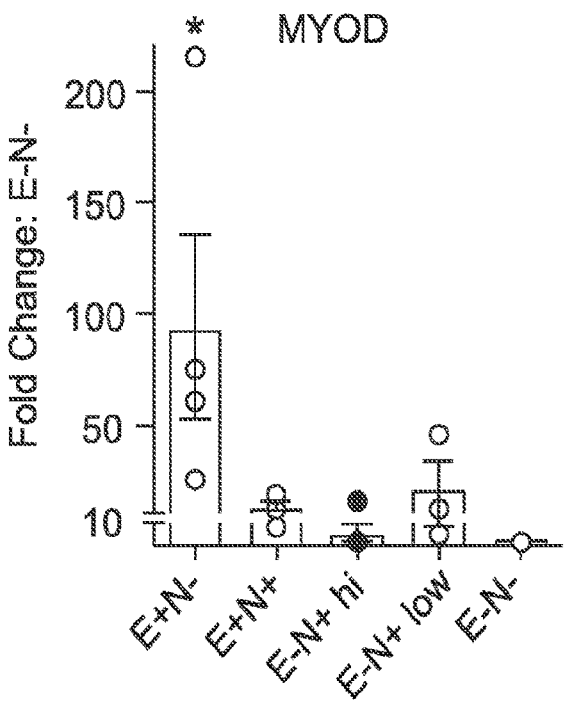
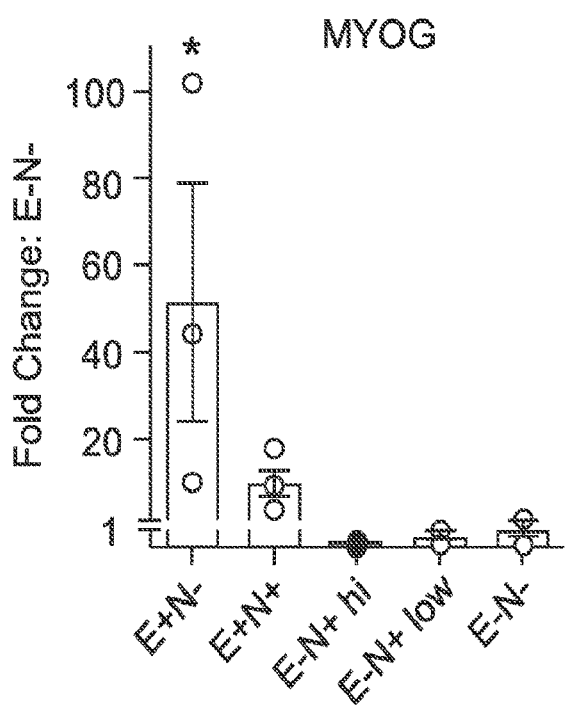

FIG. 7E
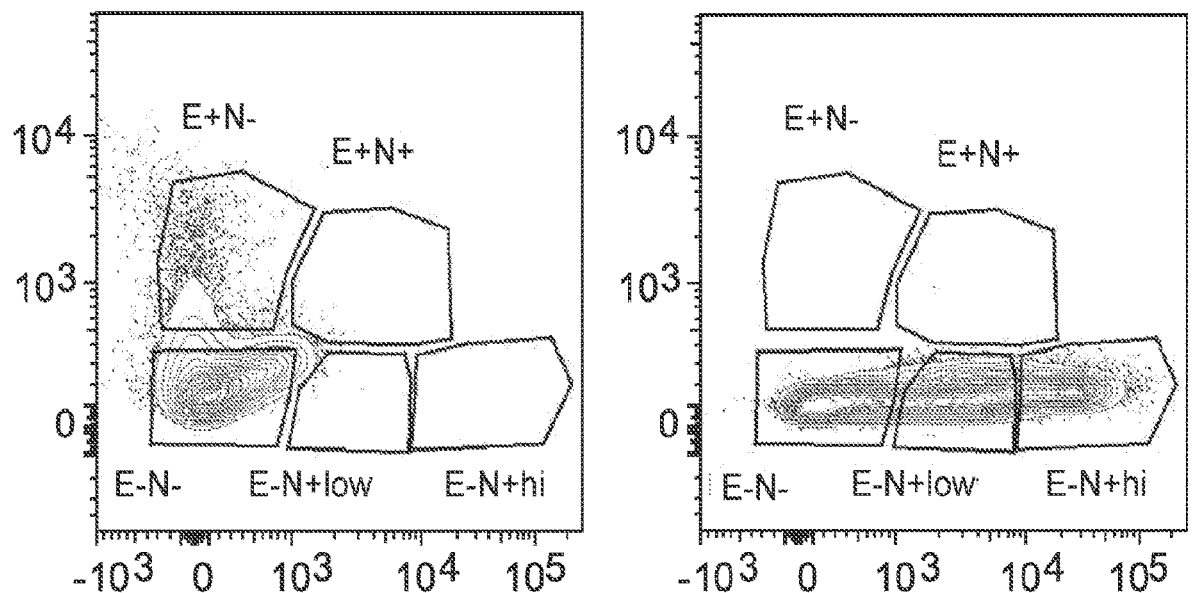
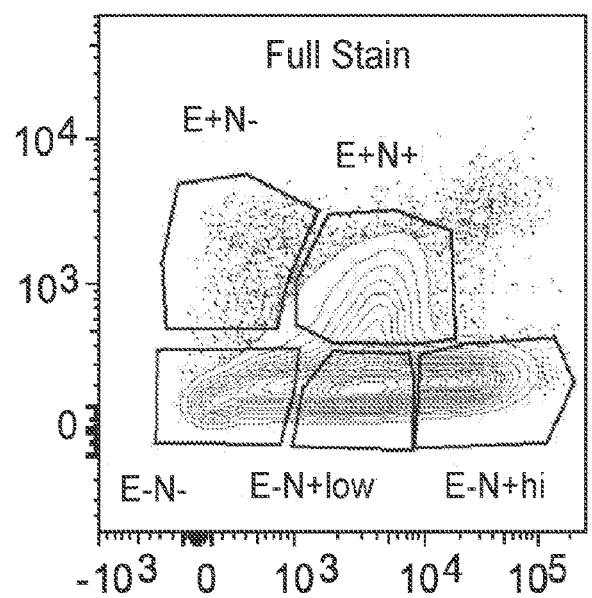

FIG. 7F
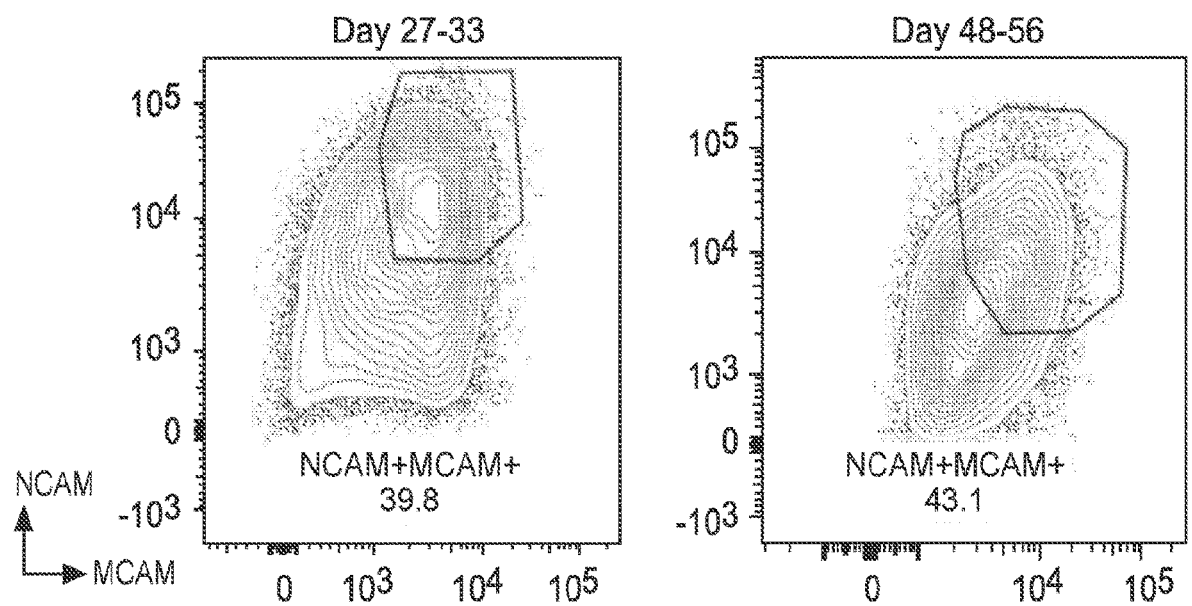
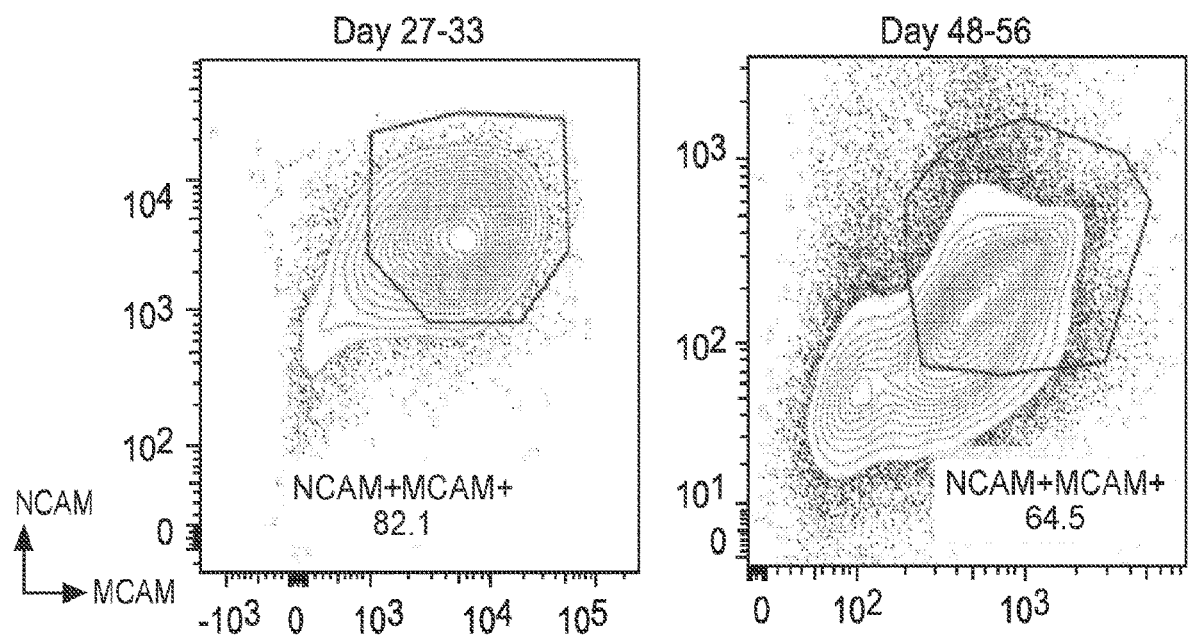

FIG. 7F (Cont.)
Directed differentiation. Method 1
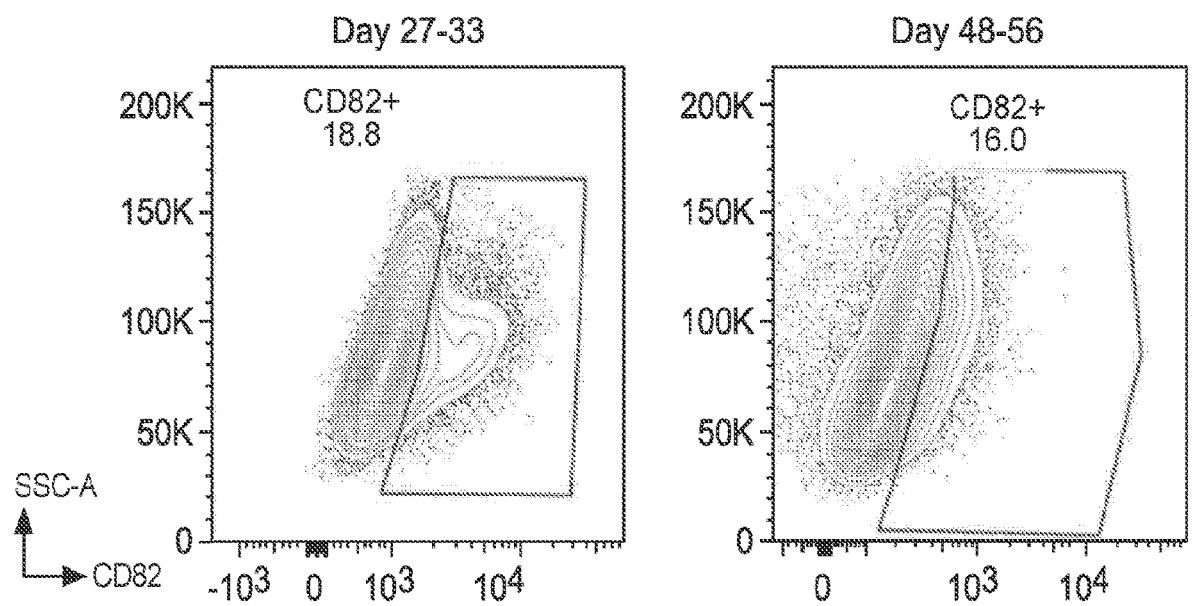
Directed differentiation. Method 2
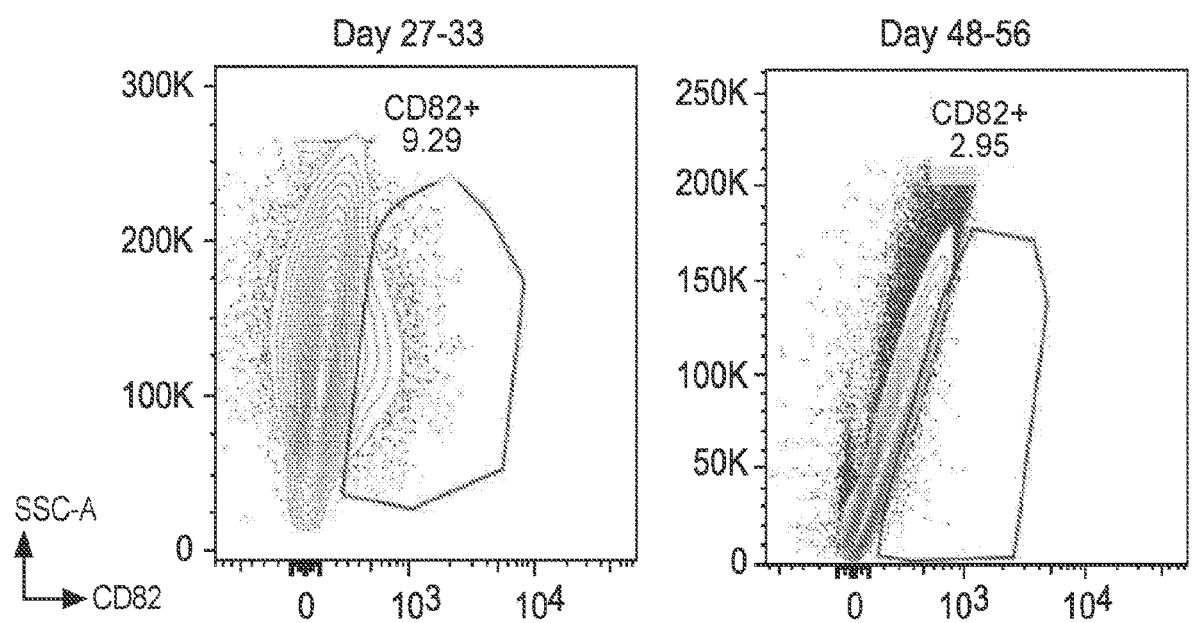

FIG. 7F (Cont.)
Directed differentiation. Method 1
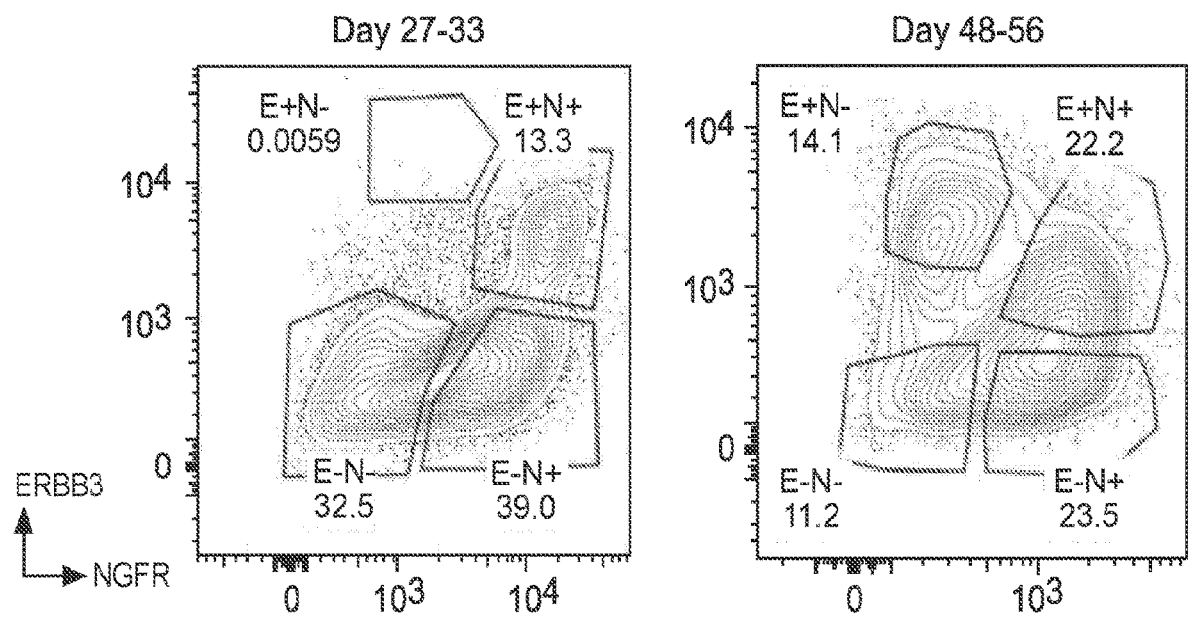
Directed differentiation. Method 2
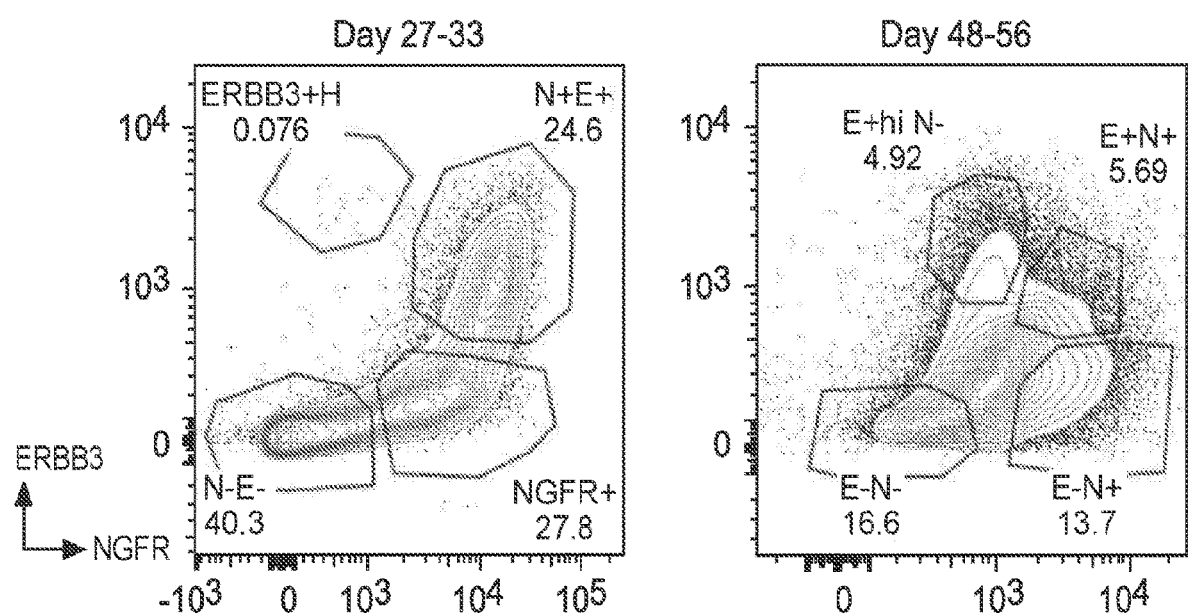

FIG. 7F (Cont.)

| % Lineage HNK1- | Method 1 | | Method 2 | |
|---|---|---|---|---|
| | Day 30 | Day 50 | Day 30 | Day 50 |
| NCAM+MCAM+ | 47.4±12.4% | 37.3±15.1% | 78.0±4.5% | 59.4±12% |
| CD82+ | 19.6±5.9% | 12.1±0.9% | 7.4±4.0% | 12.9±11% |
| ERBB3+Hi NGFR+ | 0.1±0.1% | 9.7±3.1% * | 0.1±0.1% | 6.3±1.8% * |
| ERBB3+ NGFR+ | 5.9±5.4% | 25.1±3.9% * | 33.4±3.7% | 10.7±1.9% |
| ERBB3+ NGFR- | 33.9±3.6% | 22.3±4.7% | 24.6±6.1% | 9.8±2.7% |
| ERBB3- NGFR- | 38.0±14.5% * | 9.0±2.5% | 13.5±4.8% | 26.1±5.7% |

Positivity of known fetal muscle markers within ERBB3 and NGFR hPSC-SMPC populations

| % positivity in ERBB3 and NGFR subpopulations | Method 1 | | | | Method 2 | | | |
|---|---|---|---|---|---|---|---|---|
| | Day 30 | | Day 50 | | Day 30 | | Day 50 | |
| | NCAM+ MCAM+ | CD82+ | NCAM+ MCAM+ | CD82+ | NCAM+ MCAM+ | CD82+ | NCAM+ MCAM+ | CD82+ |
| ERBB3+ single | NA | NA | 95.7% | 7.1% | NA | NA | 44.0% | 10.1% |
| ERBB3+NGFR+ | 84.9% | 33.4% | 59.2% | 18.6% | 56.7% | 22.2% | 77.0% | 55.6% |
| NGFR+ | 34.4% | 5.6% | 31.5% | 2.2% | 28.5% | 2.7% | 88.6% | 20.9% |
| ERBB3-NGFR- | 18.0% | 8.7% | 22.6% | 4.2% | 2.1% | 0.3% | 4.73% | 0.6% |

FIG. 7G (Cont.)
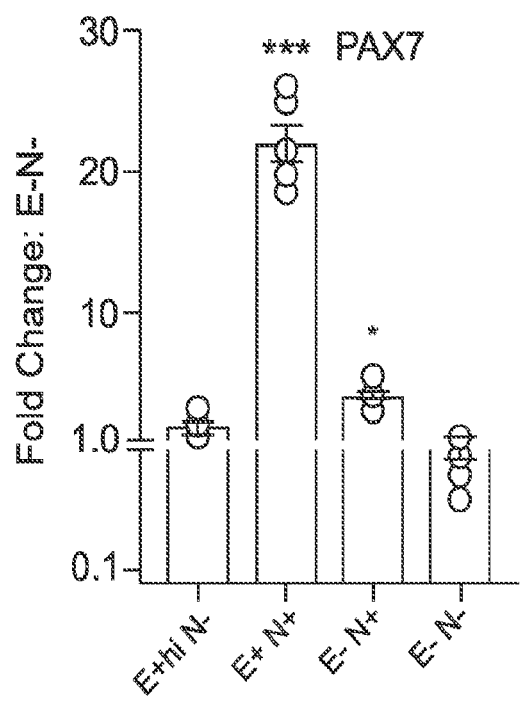
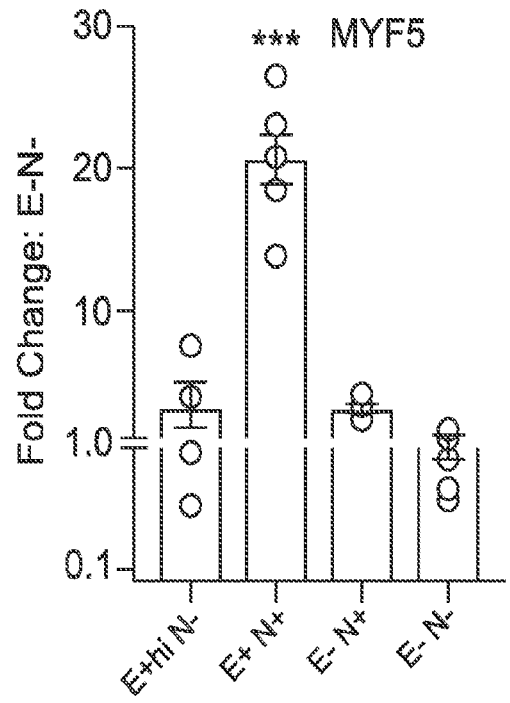
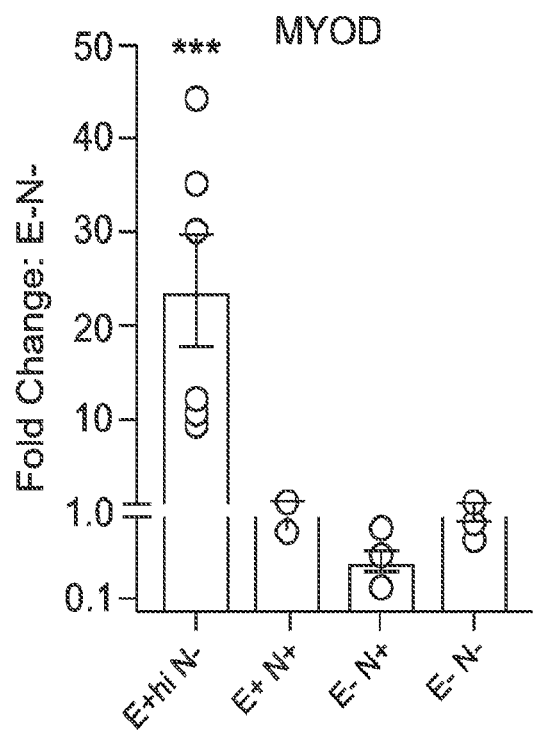
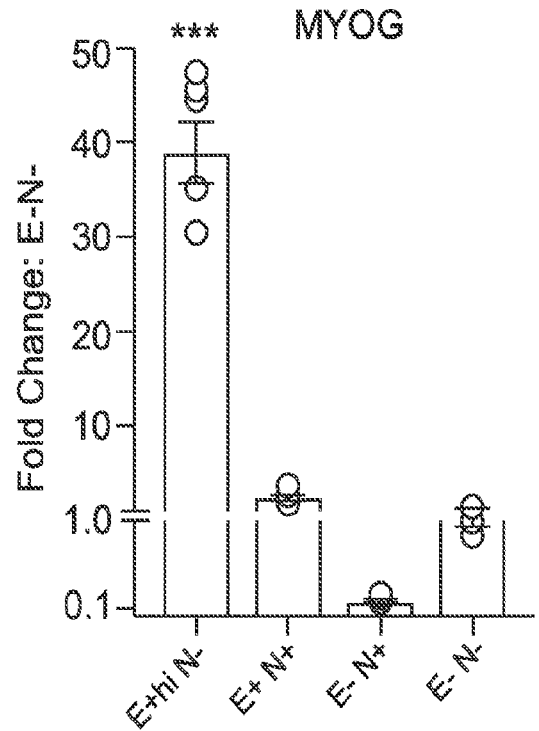

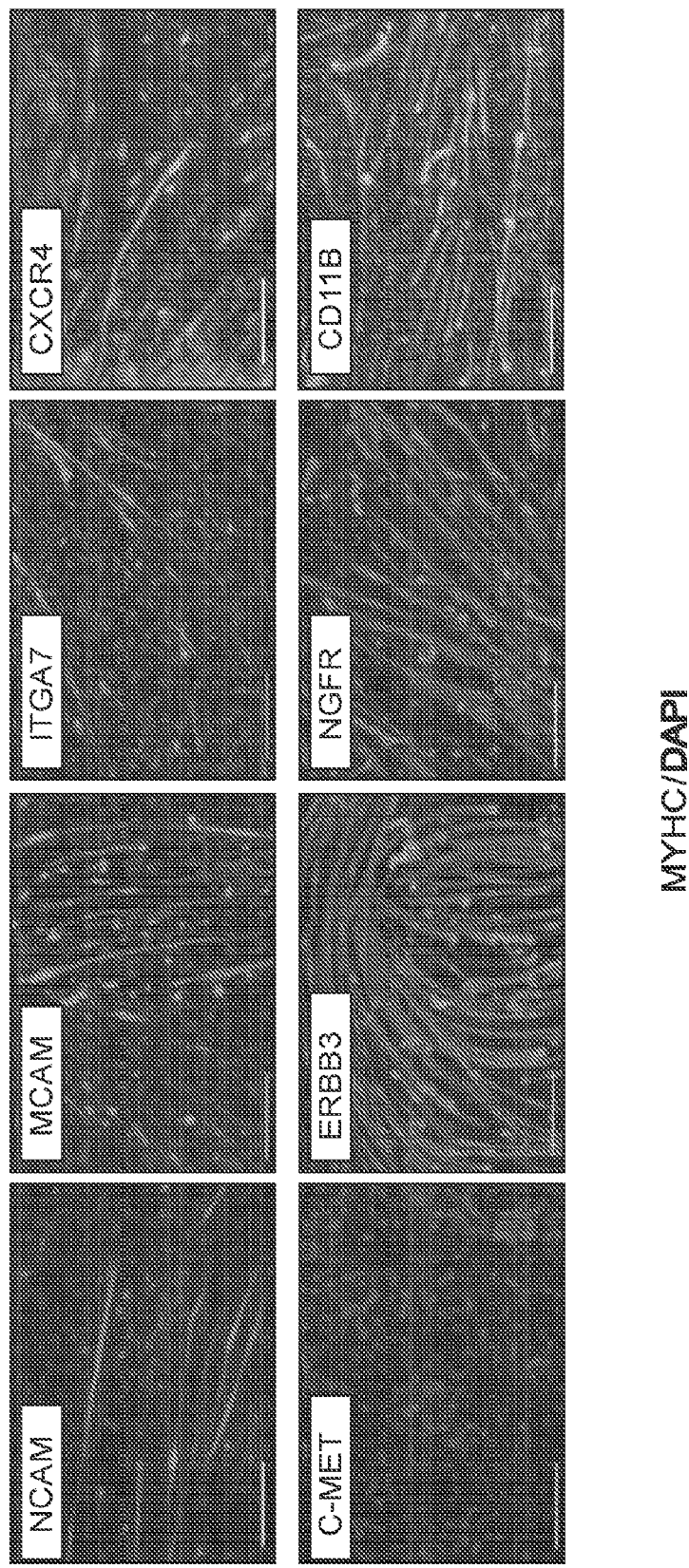

FIG. 8C
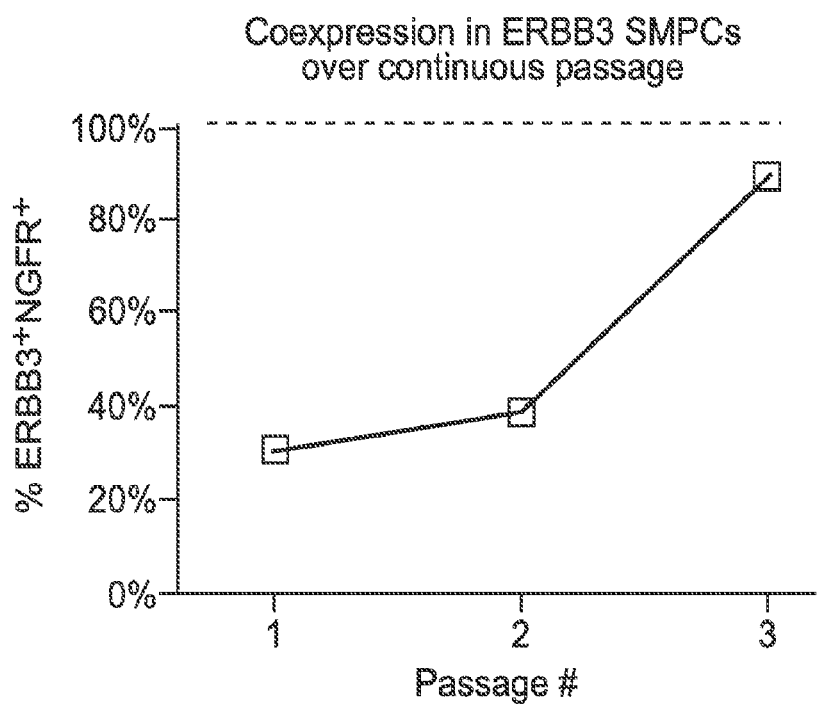
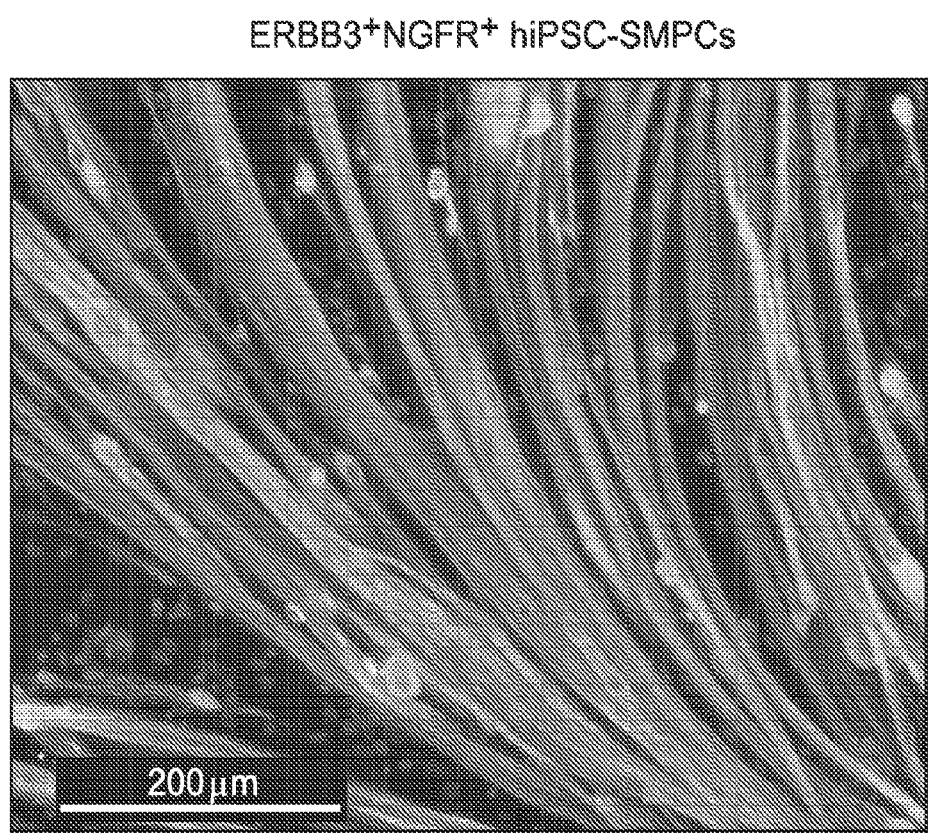
ERBB3+NGFR+ hiPSC-SMPCs

FIG. 9A
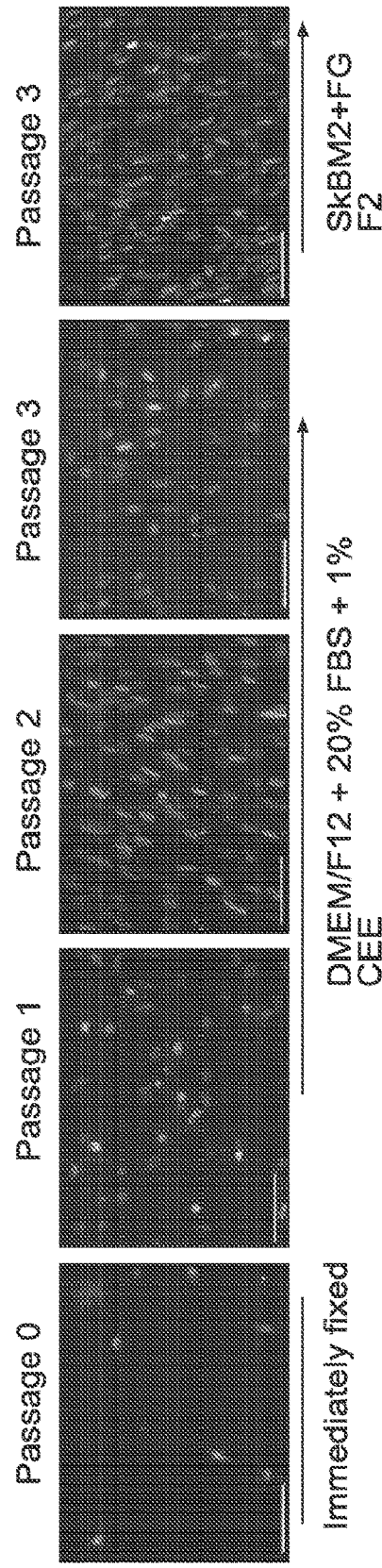
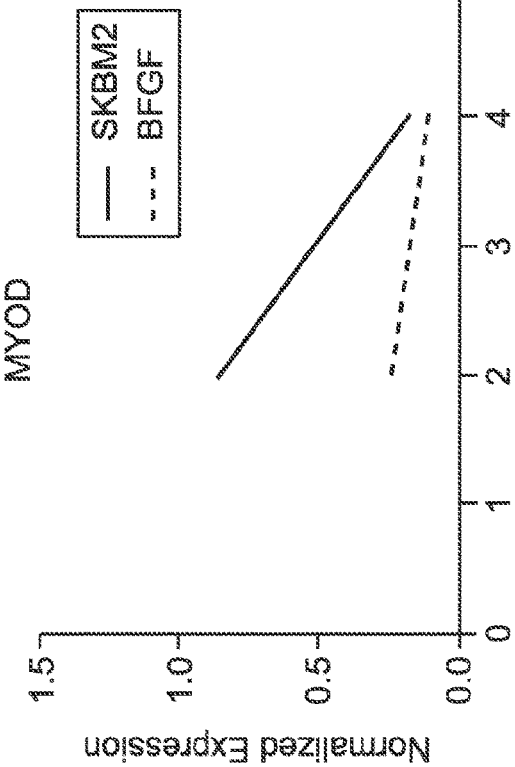
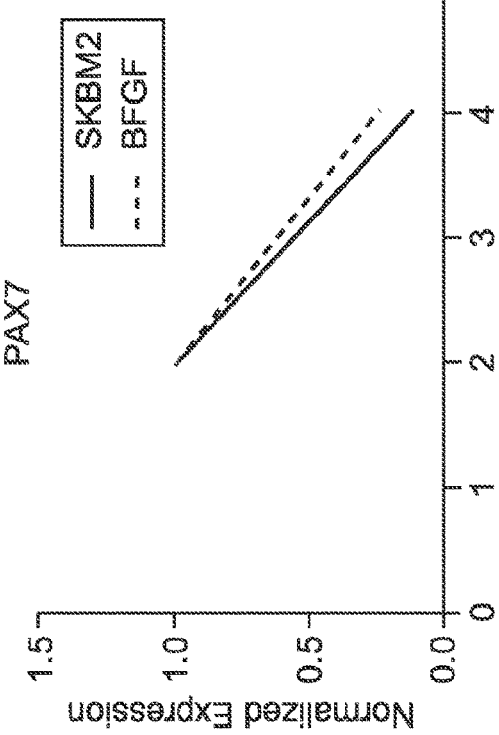

FIG. 9B
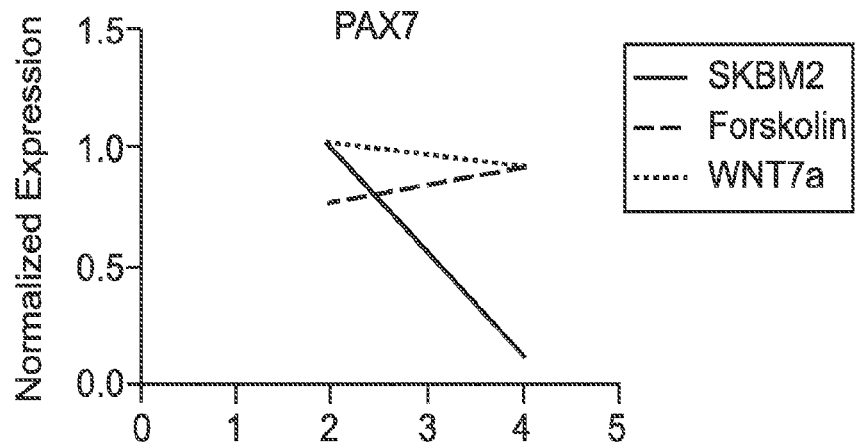
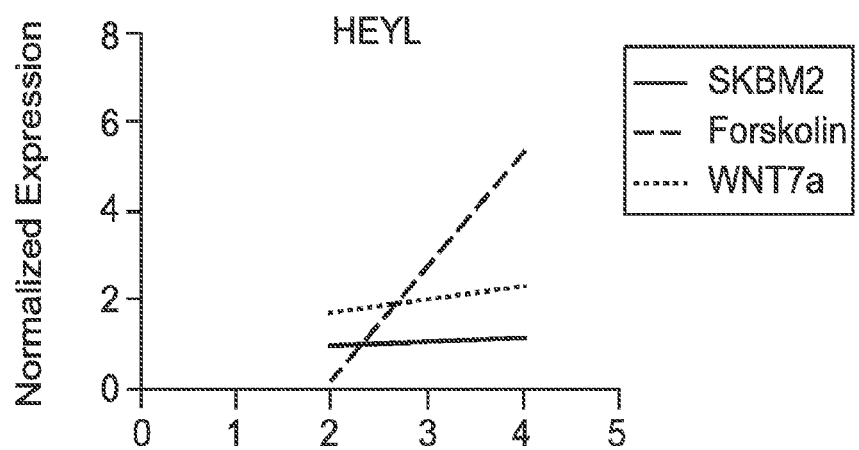
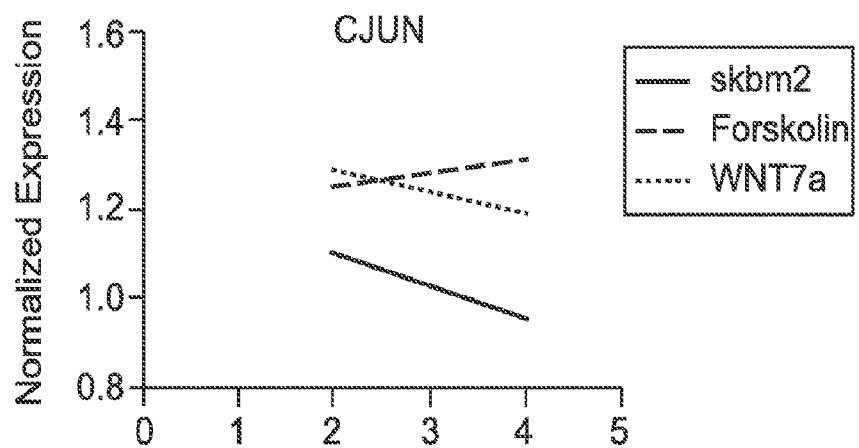

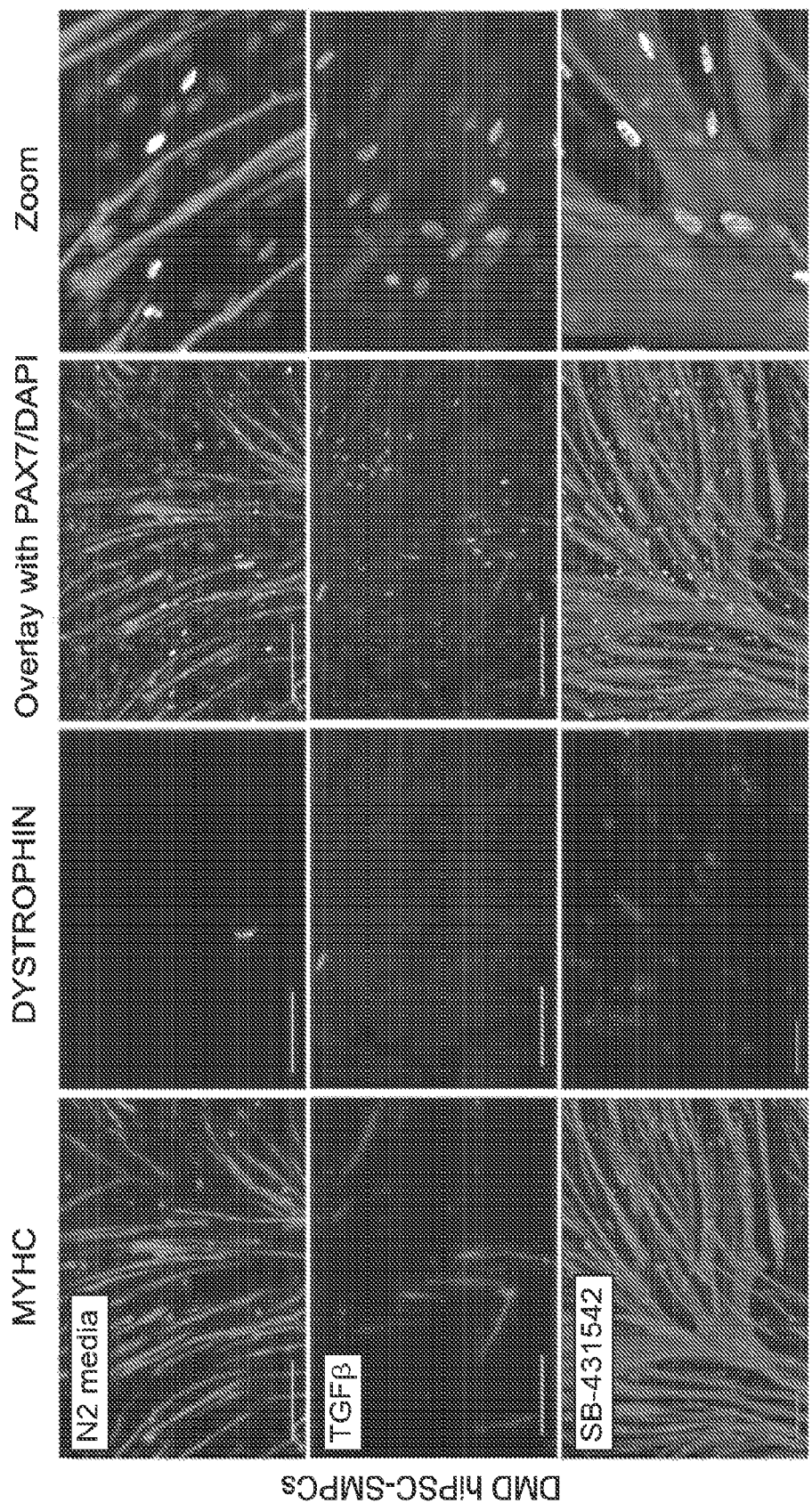

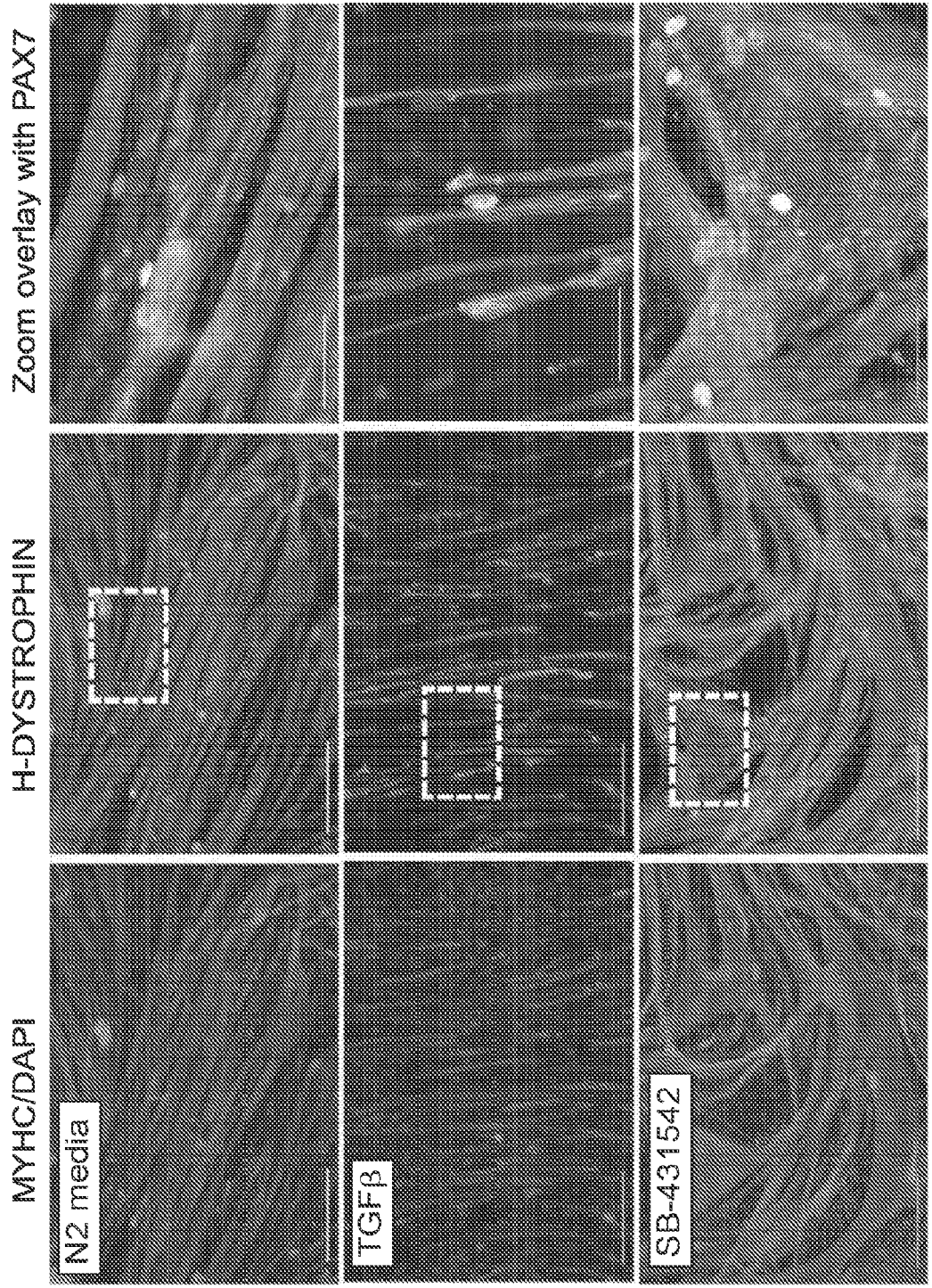

FIG. 10D
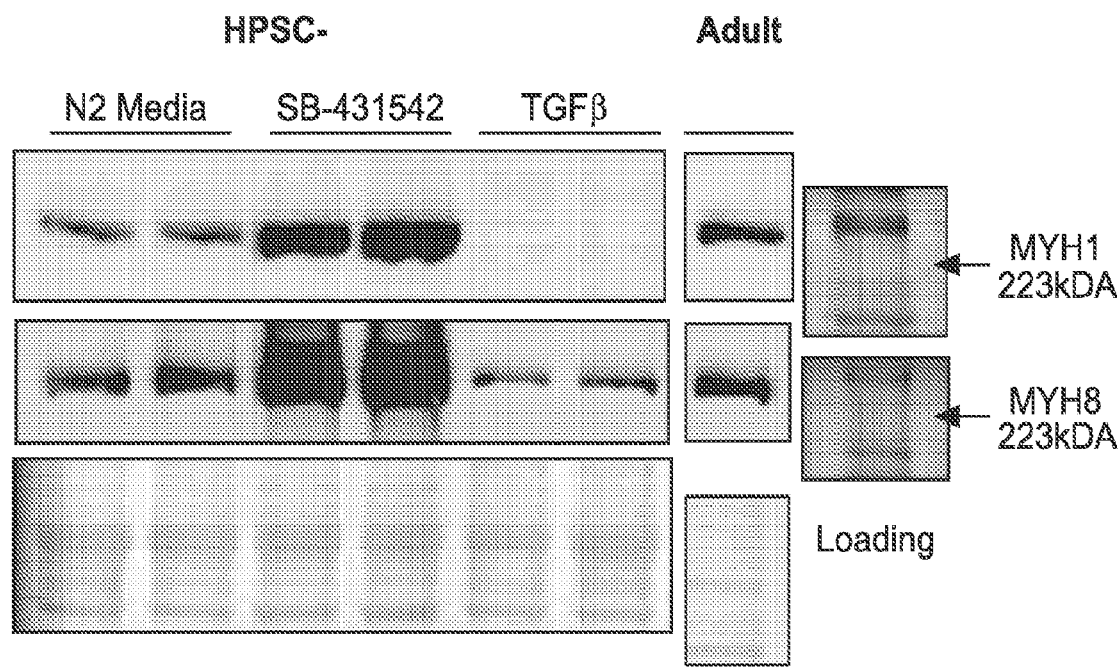
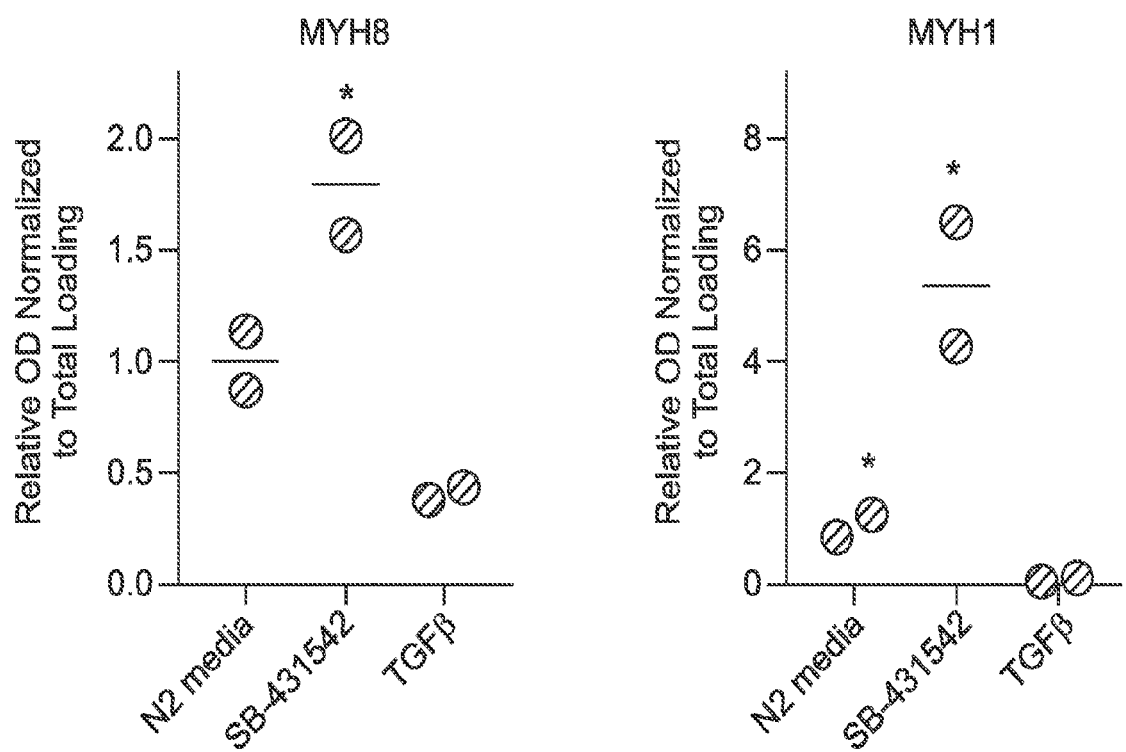

FIG. 10E (Cont.)
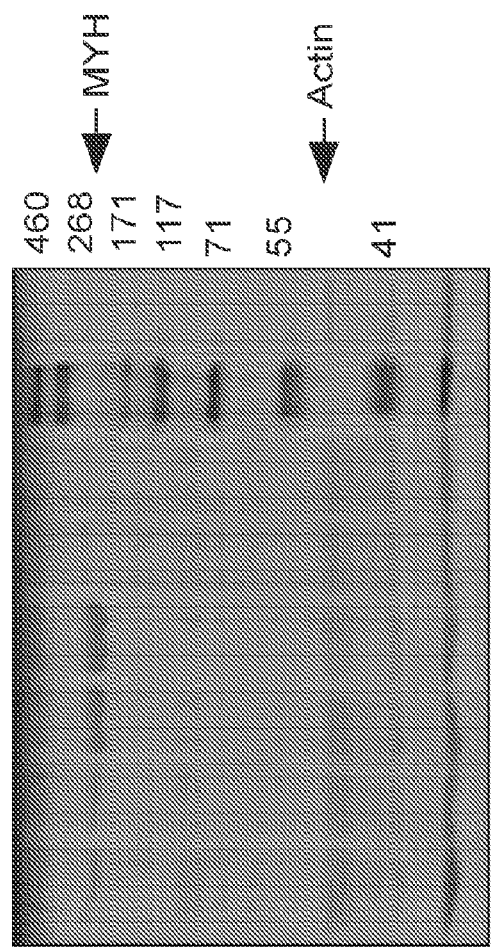
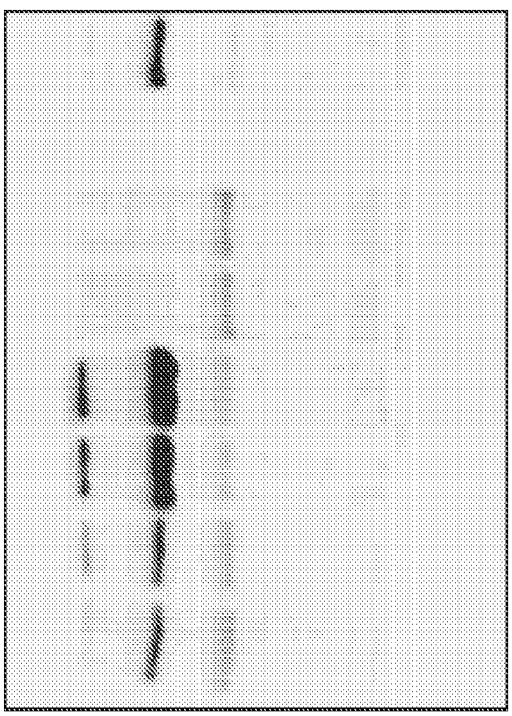

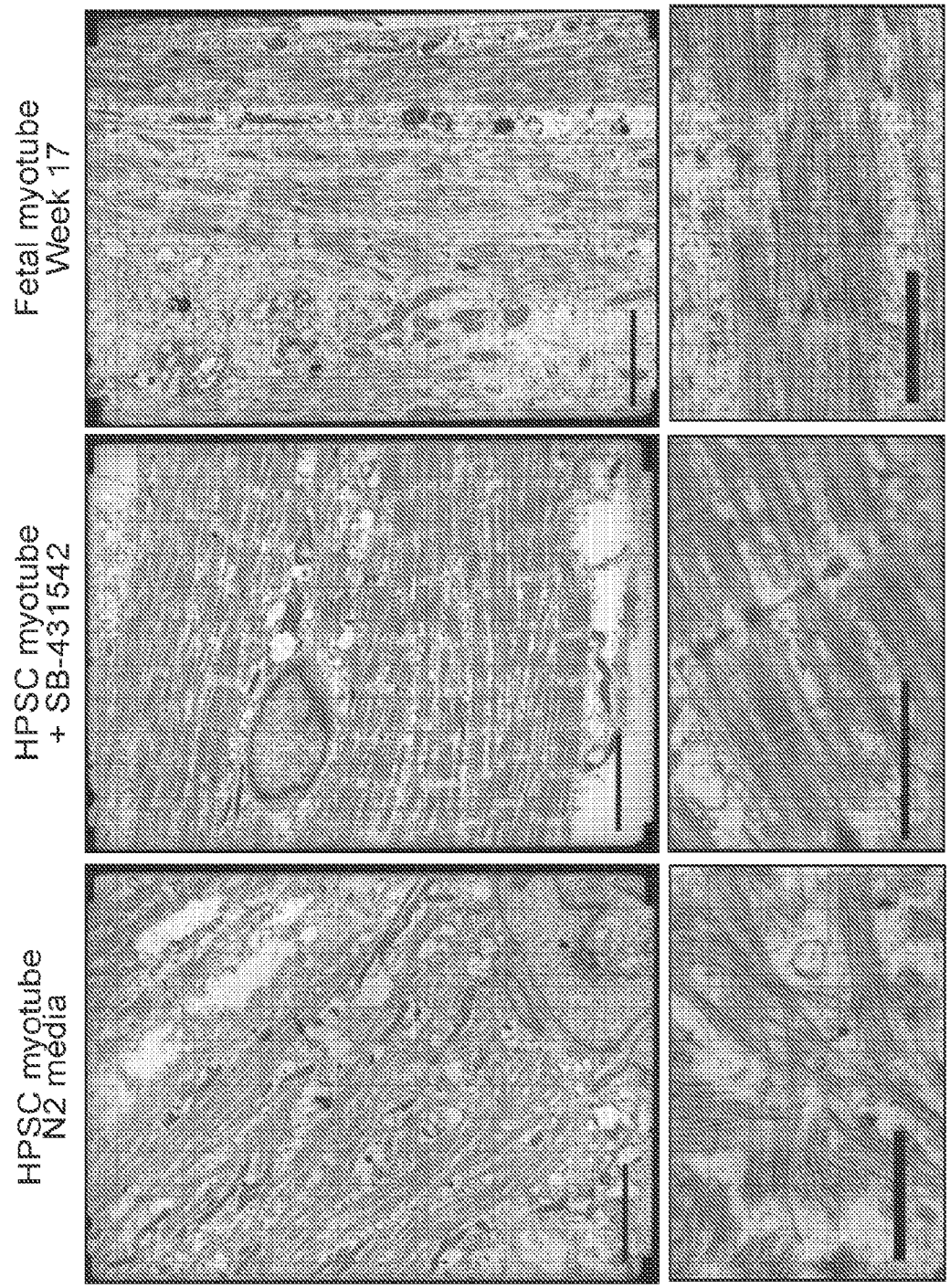

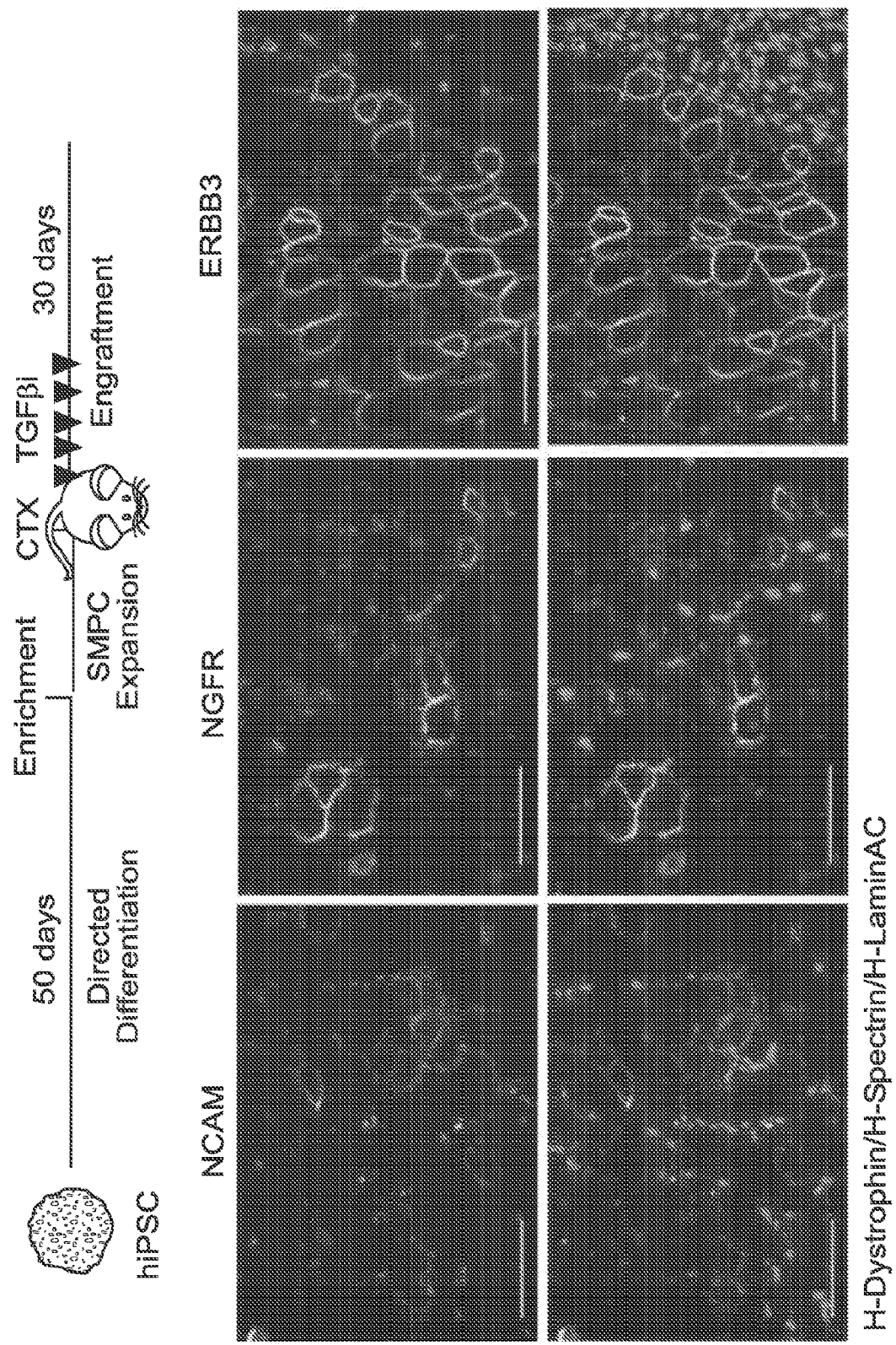

FIG. 12A (Cont.)
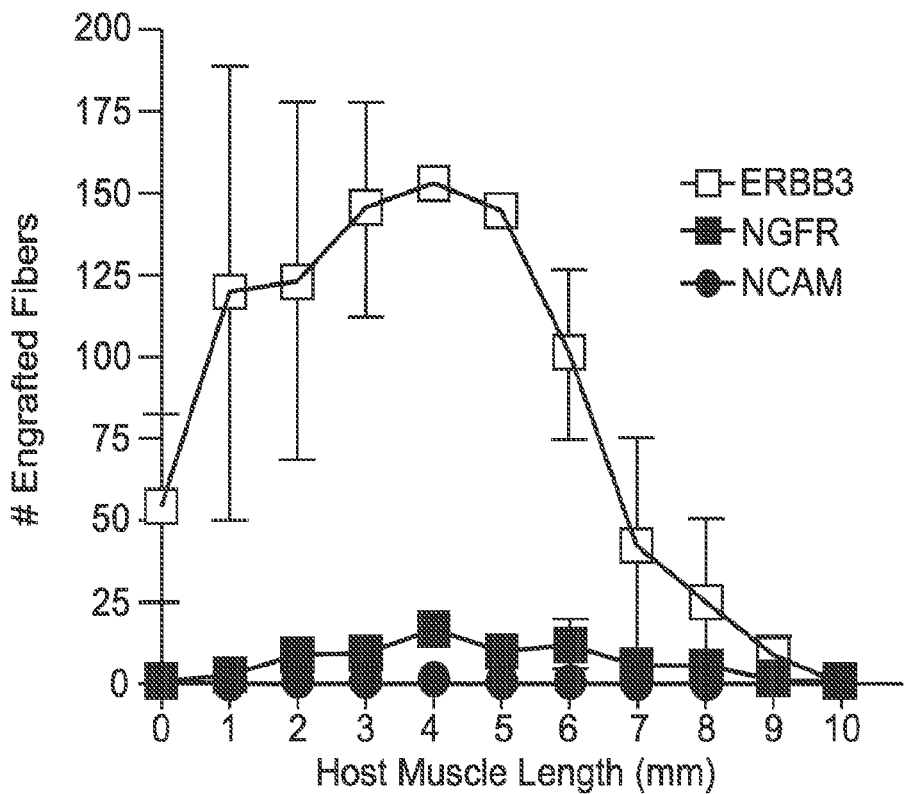
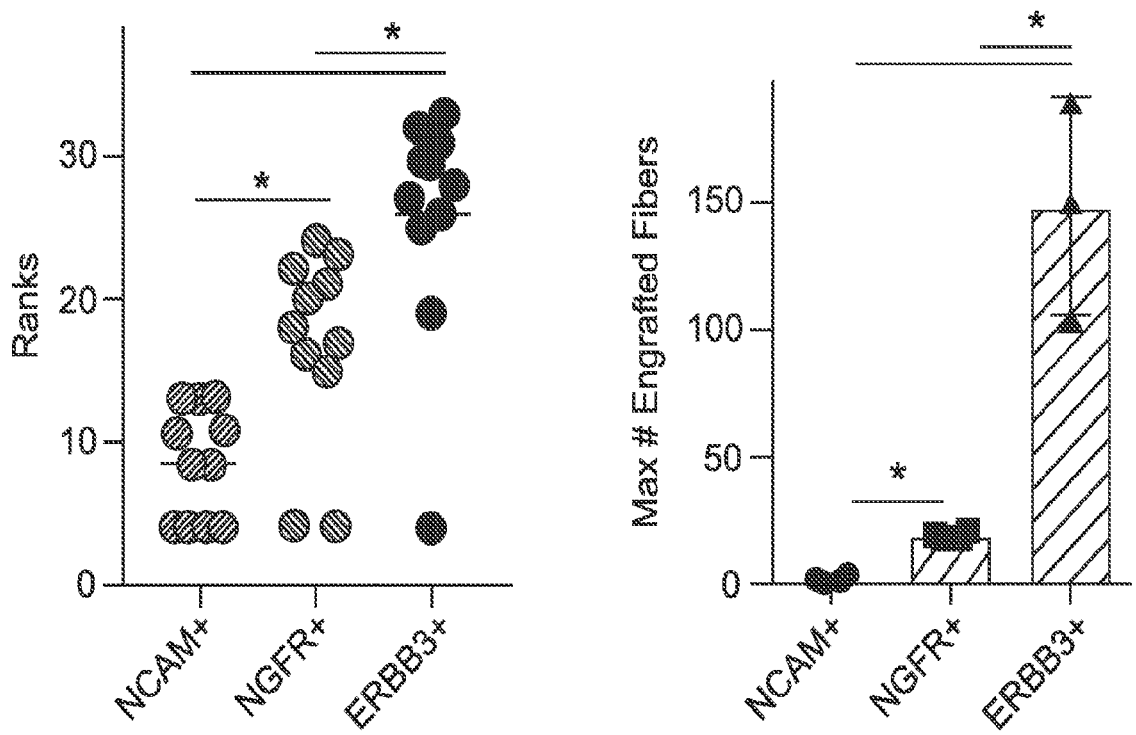

FIG. 12B (Cont.)
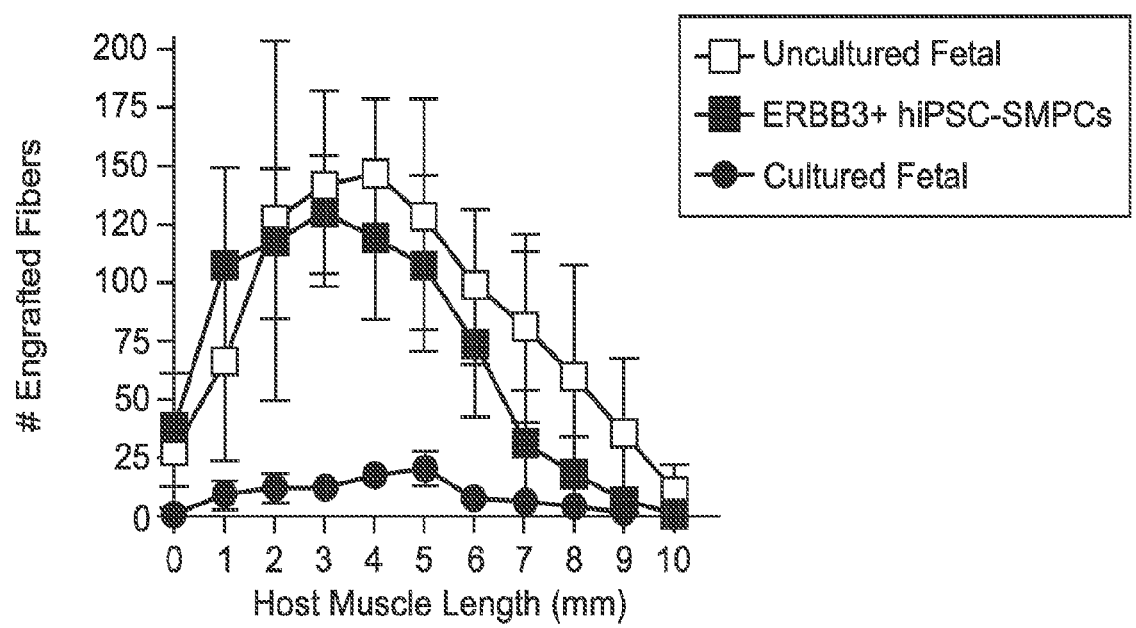
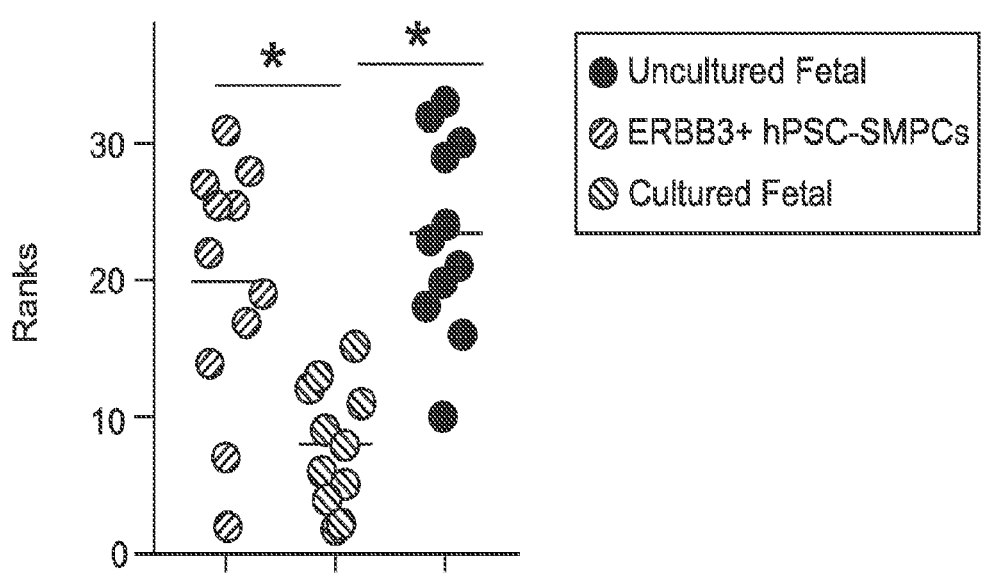

FIG. 13

| Cell Type, Subpopulation | Treatment (+CTX) | HPSC Line or Age | Figure # | \multicolumn{11}{c}{Distal to proximal distance in millimeters} |||||||||||| 
|---|---|---|---|---|---|---|---|---|---|---|---|---|---|---|
| | | | | 0 | 1 | 2 | 3 | 4 | 5 | 6 | 7 | 8 | 9 | 10 | Mean |
| Day 50, hPSC-SMPC | - | H9 | 1 | 0 | 2 | 5 | 10 | 8 | 8 | 3 | 2 | 1 | 0 | 0 | 3.5 |
| Day 50, hPSC-SMPC | - | H9 | 1 | 0 | 3 | 7 | 7 | 2 | 1 | 0 | 0 | 0 | 0 | 0 | 1.8 |
| Day 50, hPSC-SMPC | - | H9 | 1 | 0 | 0 | 0 | 0 | 0 | 0 | 0 | 0 | 0 | 0 | 0 | 0.0 |
| Day 50, hPSC-SMPC | - | H9 | 1 | 0 | 0 | 0 | 0 | 1 | 0 | 0 | 0 | 0 | 0 | 0 | 0.1 |
| Cultured Fetal | - | Week 17 | 1 | 0 | 1 | 5 | 4 | 12 | 35 | 16 | 6 | 3 | 2 | 0 | 7.6 |
| Cultured Fetal | - | Week 17 | 1 | 0 | 7 | 8 | 8 | 6 | 1 | 1 | 3 | 3 | 2 | 0 | 3.5 |
| Cultured Fetal | - | Week 17 | 1 | 0 | 0 | 2 | 6 | 20 | 21 | 5 | 1 | 0 | 0 | 0 | 5.0 |
| Cultured Fetal | - | Week 17 | 1 | 0 | 28 | 30 | 30 | 28 | 21 | 8 | 10 | 8 | 0 | 0 | 14.8 |
| Uncultured Fetal | - | Week 17 | 1 | 0 | 17 | 35 | 77 | 89 | 80 | 62 | 30 | 6 | 0 | 0 | 36.0 |
| Uncultured Fetal | - | Week 17 | 1 | 76 | 150 | 278 | 220 | 148 | 77 | 67 | 50 | 18 | 5 | 0 | 99.0 |
| Uncultured Fetal | - | Week 17 | 1 | 6 | 30 | 66 | 124 | 200 | 227 | 165 | 160 | 154 | 100 | 32 | 114.9 |
| NCAM+ hPSC-SMPC | - | H9 | 2 | 0 | 3 | 5 | 7 | 5 | 3 | 5 | 0 | 0 | 0 | 0 | 2.5 |
| NCAM+ hPSC-SMPC | - | H9 | 2 | 0 | 0 | 0 | 1 | 1 | 0 | 0 | 0 | 0 | 0 | 0 | 0.3 |
| NCAM+ hPSC-SMPC | - | H9 | 2 | 0 | 0 | 0 | 2 | 1 | 1 | 0 | 0 | 0 | 0 | 0 | 0.5 |
| NCAM+ hPSC-SMPC | - | H9 | 2 | 0 | 0 | 0 | 0 | 0 | 0 | 0 | 0 | 0 | 0 | 0 | 0.0 |
| NCAM+ hPSC-SMPC | Irradiation | H9 | 2 | 0 | 1 | 4 | 2 | 0 | 0 | 0 | 0 | 0 | 0 | 0 | 0.6 |
| NCAM+ hPSC-SMPC | Irradiation | 1006 | 2 | 0 | 0 | 0 | 0 | 0 | 0 | 0 | 0 | 0 | 0 | 0 | 0.0 |
| NCAM+ hPSC-SMPC | Irradiation | 1006 | 2 | 0 | 1 | 0 | 0 | 0 | 0 | 0 | 1 | 0 | 0 | 0 | 0.2 |
| NCAM+ hPSC-SMPC | Irradiation | 1006 | 2 | 0 | 0 | 1 | 0 | 0 | 0 | 0 | 0 | 0 | 0 | 0 | 0.2 |
| NCAM+ hPSC-SMPC | Irradiation | 1006 | 2 | 0 | 0 | 0 | 0 | 0 | 0 | 0 | 0 | 0 | 0 | 0 | 0.0 |
| NCAM+ hPSC-SMPC | Irradiation | 1006 | 2 | 0 | 1 | 2 | 3 | 4 | 6 | 2 | 0 | 0 | 0 | 0 | 1.6 |
| NCAM+ hPSC-SMPC | Irradiation | 1006 | 2 | 0 | 0 | 3 | 1 | 0 | 1 | 0 | 0 | 0 | 0 | 0 | 0.5 |
| NCAM+ hPSC-SMPC | - | 1006-1 | 2 | 0 | 0 | 0 | 0 | 0 | 0 | 0 | 0 | 0 | 0 | 0 | 0.0 |
| NCAM+ hPSC-SMPC | - | 1006-1 | 2 | 0 | 1 | 1 | 0 | 0 | 0 | 0 | 0 | 0 | 0 | 0 | 0.2 |
| NCAM+ hPSC-SMPC | - | 1006-1 | 2 | 0 | 0 | 0 | 0 | 0 | 0 | 0 | 0 | 0 | 0 | 0 | 0.0 |

FIG. 13 (Cont.)

| | Sample | Treatment | n | | | | | | | | | | | | | Mean |
|---|---|---|---|---|---|---|---|---|---|---|---|---|---|---|---|---|
| NCAM+ hPSC-SMPC | 1006-1 | Irradiation | 2 | 0 | 0 | 3 | 3 | 0 | 0 | 0 | 0 | 0 | 0 | 0 | 0 | 0.5 |
| NCAM+ hPSC-SMPC | 1006-1 | Irradiation | 2 | 0 | 0 | 0 | 0 | 0 | 0 | 0 | 0 | 0 | 0 | 0 | 0 | 0.0 |
| NCAM+ hPSC-SMPC | 1006-1 | Irradiation | 2 | 0 | 0 | 3 | 0 | 0 | 0 | 0 | 0 | 3 | 0 | 0 | 0 | 0.5 |
| NCAM+ hPSC-SMPC | 1006-1 | Irradiation | 2 | 0 | 0 | 0 | 0 | 0 | 0 | 0 | 0 | 0 | 0 | 0 | 0 | 0.0 |
| NCAM+ hPSC-SMPC | 1006-1 | 10μM TGFβi | 6 | 0 | 2 | 6 | 3 | 1 | 0 | 0 | 0 | 0 | 0 | 0 | 0 | 1.1 |
| NCAM+ hPSC-SMPC | 1006-1 | 10μM TGFβi | 6 | 0 | 0 | 2 | 3 | 2 | 1 | 0 | 0 | 0 | 0 | 0 | 0 | 1.2 |
| NGFR+ hPSC-SMPC | 1006-1 | 10μM TGFβi | 6 | 0 | 4 | 16 | 11 | 9 | 20 | 7 | 4 | 3 | 0 | 0 | 0 | 7.5 |
| NGFR+ hPSC-SMPC | 1006-1 | 10μM TGFβi | 6 | 0 | 2 | 8 | 17 | 8 | 7 | 3 | 8 | 3 | 0 | 0 | 0 | 5.6 |
| NGFR+ hPSC-SMPC | 1006-1 | 10μM TGFβi | 6 | 0 | 1 | 6 | 8 | 16 | 10 | 16 | 10 | 3 | 0 | 0 | 0 | 6.4 |
| NGFR+ hPSC-SMPC | 1006-1 | 10μM TGFβi | 6 | 0 | 1 | 6 | 18 | 10 | 3 | 1 | 3 | 1 | 0 | 0 | 0 | 4.2 |
| ERBB3+ hPSC-SMPC | 1006-1 | 10μM TGFβi | 6 | 82 | 190 | 178 | 151 | 139 | 127 | 75 | 50 | 16 | 0 | 0 | 0 | 107.8 |
| ERBB3+ hPSC-SMPC | 1006-1 | 10μM TGFβi | 6 | 25 | 50 | 68 | 112 | 156 | 151 | 75 | 8 | 0 | 0 | 0 | 0 | 58.6 |
| ERBB3+ hPSC-SMPC | 1006-1 | 10μM TGFβi | 6 | 0 | 7 | 83 | 104 | 41 | 49 | 18 | 4 | 0 | 0 | 0 | 0 | 27.8 |
| ERBB3+ hPSC-SMPC | 1006-1 | 10μM TGFβi | 6 | 6 | 46 | 62 | 96 | 87 | 47 | 41 | 29 | 12 | 8 | 0 | 0 | 39.5 |

| | Sample | n | | | | | | | | | | | | | Mean |
|---|---|---|---|---|---|---|---|---|---|---|---|---|---|---|---|
| Uncultured Fetal | Week 17 | - | 22 | 77 | 100 | 85 | 188 | 78 | 76 | 15 | 12 | 0 | 0 | 0 | 59.4 |
| Cultured Fetal, ERBB3+NGFR+ | Week 17 | - | 0 | 0 | 7 | 36 | 32 | 7 | 1 | 0 | 0 | 0 | 0 | 0 | 7.5 |
| Cultured Fetal, ERBB3+NGFR+ | Week 17 | - | 15 | 65 | 78 | 60 | 13 | 7 | 2 | 0 | 0 | 0 | 0 | 0 | 21.8 |
| CMET+ hPSC-SMPC | 1006-1 | - | 0 | 0 | 0 | 0 | 0 | 0 | 0 | 0 | 0 | 0 | 0 | 0 | 0.0 |
| MCAM+ hPSC-SMPC | 1006-1 | - | 0 | 0 | 0 | 0 | 0 | 0 | 0 | 0 | 0 | 0 | 0 | 0 | 0.0 |
| NGFR+ hPSC-SMPC | 1006-1 | - | 0 | 0 | 0 | 4 | 13 | 8 | 6 | 2 | 0 | 0 | 0 | 0 | 3.0 |
| NGFR+ hPSC-SMPC | 1006-1 | - | 0 | 2 | 2 | 7 | 2 | 0 | 0 | 0 | 0 | 0 | 0 | 0 | 1.2 |
| ERBB3+ hPSC-SMPC | 1006-1 | - | 4 | 25 | 35 | 29 | 21 | 13 | 7 | 2 | 4 | 1 | 0 | 0 | 12.8 |
| ERBB3+ hPSC-SMPC | 1006-1 | - | 0 | 21 | 33 | 70 | 75 | 32 | 34 | 40 | 7 | 0 | 0 | 0 | 28.4 |
| ERBB3+ hPSC-SMPC | 1003-49 | - | 19 | 54 | 37 | 30 | 16 | 2 | 9 | 0 | 0 | 0 | 0 | 0 | 15.2 |

H-LAMIN A/C+ SPECTRIN+DYSTROPHIN+ myofibers per cross section

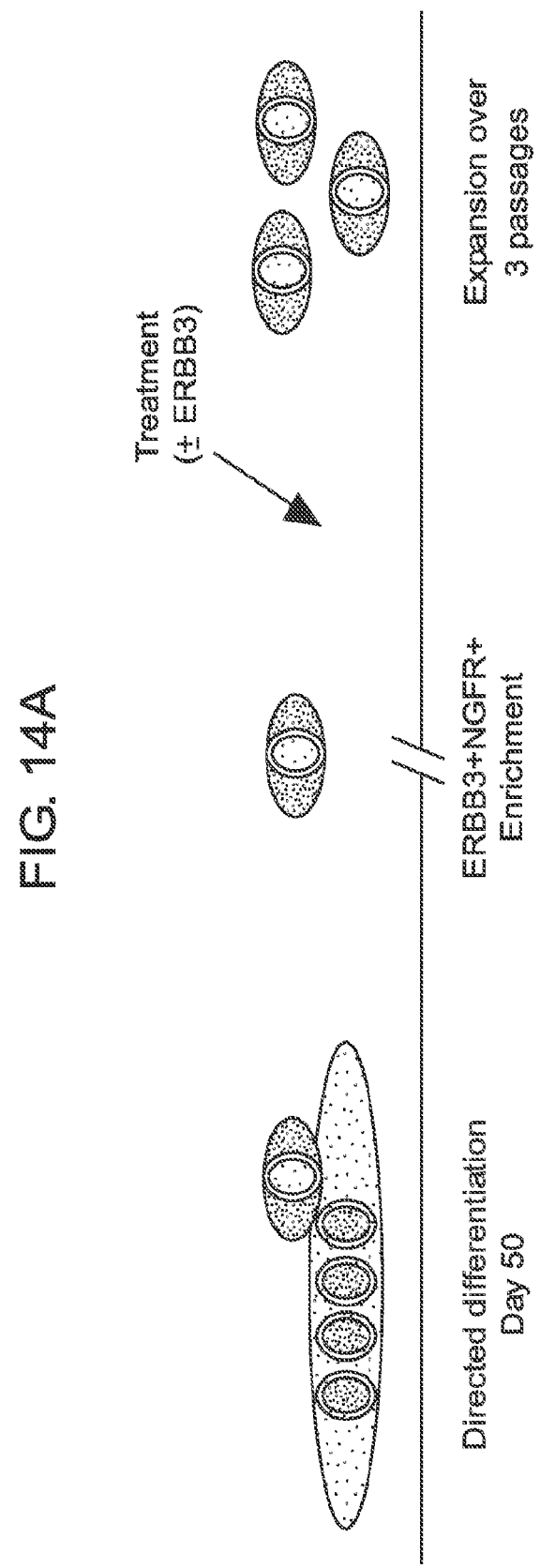

FIG. 15

| IF Antibodies | | | |
|---|---|---|---|
| Antibody | Vendor | Catalog # | Concentration |
| PAX7 | DSHB | PAX7 | 10mg/mL |
| MYOD | Cell Signaling | 13812P | 2mg/mL |
| MYOG | BD Biosciences | 556358 | 2mg/mL |
| MF20 | DSHB | MF20 | 10mg/mL |
| LAMIN AC | Sigma-Aldrich | L9393 | 25mg/mL |
| SPECTRIN | Leica Biosystems | NCL-SPEC1 | 50mg/mL |
| Dystrophin | CIND | MANDYS106 | 1:6 from supernatant |
| Laminin | Sigma-Aldrich | L9393 | 6.25mg/mL |
| NGFR | ThermoFisher Scientific | MA1-18401 | 5mg/mL |
| ERBB3 | Biolegend | 324702 | 5mg/mL |
| MYH1 | DSHB | 6-H1 | 10mg/mL |
| MYH3 | DSHB | BF-G6 | 10mg/mL |
| MYH8 | ThermoFisher | NBP241309 | 10mg/mL |

| FACS Antibodies | | | |
|---|---|---|---|
| Antibody | Vendor | Catalog # | Concentration per 1x10^6 cells in 200ul |
| A2B5 | Miltenyi Biotech | 130-093-581 | 4mL |
| CD11b (ITGAM) | BD Biosciences | 560914 | 2mL |
| CD29 (ITGB1) | eBiosciences | 17-0299-41 | 1.5mL |
| CD31 (PECAM1) | BD Biosciences | 555446 | 1.5mL |
| CD31 (PECAM1) | Miltenyi Biotech | 130-101-158 | 1.5mL |
| CD45 | Biolegend | 12-0459-42 | 1.5mL |
| CD45 | Miltenyi Biotech | 130-098-151 | 1.5mL |
| CD73 | BD Biosciences | 550257 | 4mL |
| CD56 (NCAM) | BD Biosciences | 564057 | 1.5mL |
| CD57 (HNK1) | Sigma | C0678 | 2mL |
| CD57 (HNK1) | BD Biosciences | 555619 | 1.5mL |
| CD140A (PDGFRα) | R&D Systems | FAB1264P | 4mL |
| CD146 (MCAM) | BD Biosciences | 562135 | 1.5mL |
| CD184 (CXCR4) | Biolegend | 306522 | 1.5mL |
| CD235a | Miltenyi Biotech | 130-100-264 | 1.5mL |
| CD271 (NGFR) | BD Biosciences | 562123 | 1.5mL |
| CD309 (VEGFR2) | BD Biosciences | 56095 | 4mL |
| ERBB3 | Biolegend | 324705 | 1.5mL |
| ITGA7 | Novus Biological | NBP1-54412 | 4mL |
| HGFR/c-MET | R&D Systems | FAB3582A | 6mL |

FIG. 17A

| Genes upregulated by NCAM+ cultured fetal muscle cells and NCAM+ hPSC-SMPCs | |
|---|---|
| GO:0022610 Biological adhesion | ITGAL, CLDN5, KITLG, ITGA10, CUZD1, ITGB3, CD97, NRCAM, SRPX, COL7A1, CD93, ITGAV, COMP, COL6A3, PKD2, COL6A2, DLG5, LMLN, SPON2, ADAM9, SPON1, THBS4, EGFR, MYF5, NFASC, NID1, MFGE8, PTPRU, MCAM, COL5A3, RAPH1, LAMA2, TNFAIP6, CDH13, SLC26A6, SNED1, HAS1, ITGA7, ANTXR1, LAMC1, AOC3 |
| GO:0007167 Enzyme linked receptor protein signaling | REPS2, ACVRL1, LTBP2, PDGFA, TIPARP, FOS, MUSK, DGKD, GIGYF1, ADAM9, EGFR, IRS2, PTPRE, SMAD9, NIN, MYO1E, KLF10, TGFBR2, CBL, PTPRU, HGF, CHRDL1, EREG, JUN, CSRNP1, HIPK2, JAK1 |
| GO:0030334 Regulation of cell migration | EGFR, IRS2, ACVRL1, PDGFA, TBX5, ABHD2, PTPRU, ITGB3, TRIB1, LAMA2, CDH13, ACE, HIF1A, CXCR4, ROBO4, ADAM9 |
| GO:0007179 TGFβR signaling pathway | FOS, SMAD9, ACVRL1, LTBP2, PDGFA, KLF10, JUN, TGFBR2, ADAM9 |
| GO:0007517 Muscle organ development | RBP4, MYOD1, CAV1, EVC, TBX5, MYF5, ELN, TIPARP, RCAN1, LAMA2, ZFP91, MUSK, BVES, PAX7, DNER, ITGA7, COL6A3, CHRNA1 |

FIG. 17B

| | Genes upregulated by hPSC-SMPCs and cultured fetal myoblasts |
|---|---|
| GO:0006936<br>Muscle contraction | FXYD1, MYL7, EDN3, MYL4, TNNC2, MYBPC1, TNNC1, EDN2, MYL1, EDN1, GJA1, TTN, TPM1, EDNRA, ACTG2, AGT, MYOM1, HRC, KCNMA1, ACTA1, ACTA2, MYH3, MYLK2, MYH7, ACTN2, CACNG1, TNNI3, MYH8, CACNA1S, TNNI2, TRDN, TNNT3, PSEN2, CACNA1G, CACNA1H, SMPX, RYR2, GAMT, KCNH2, CASQ2, CHRNG |
| GO:0007155<br>Cell adhesion | MPZL3, MPZL2, CADM4, LYPD3, CADM1, NELL1, NELL2, EDIL3, CXCL12, S1PR1, ROBO2, EFNB1, COL22A1, MGP, ACTN2, ACTN3, NCAM2, PGM5, CD36, LSAMP, GPR56, ROR2, LAMC2, MFAP4, UNCX, CDK5R1, EMCN, NEDD9, NINJ1, CX3CL1, SOX9, SEMA5A, KAL1, TTYH1, MSLN, SCARB1, SPP1, PCDH10, ITGA4, CELSR1, PCDH17, CASS4, COL14A1, FREM2, CLDN9, CLDN4, MYBPC2, CLSTN3, MYBPC1, NPNT, CXADR, CNTNAP3, CNTNAP2, PARVG, PCDHB9, EGFL6, NRXN3, SDK2, PCDHB2, LEF1, CPXM2, PCDH8, AMIGO2, CPXM1, CLDN1, CNTN1, CNTN4, DCHS2, CLDN19, PCDHB15, CTNND2, CNTNAP3B, COL2A1, CLDN1, CDH1, CDH2, CLDN11, CDH3, SCARF1, APLP1, CDH6, CDH8, ISLR, VCAM1, CD9, COL9A1, CDH7, IGSF11, COL17A1, FAT3, PCDHB16, AGT, MYBPH, CD4, COL8A2, FLRT3, COL13A1, LRRN2, NLGN3, COL4A6, CCL11, COL19A1, CDH18, DSC3, DSC2, PERP, FEZ1 |
| GO:0030182<br>Neuron differentiation | EDN3, NRTN, EFNA1, GDF7, WNT3A, UCHL1, GJA1, GRIN3A, PAX2, CXCL12, TGFB2, BDNF, HOXC8, S1PR1, NKX6-2, CNTNAP2, ROBO2, UNC5C, KCNMA1, EFNB3, STMN2, NRXN3, EFNB1, EMX2, KIF5C, PTPRR, SLIT2, SLIT3, HOXD9, NCAM2, PRKCQ, CNTN4, SLITRK6, SLITRK5, IGSF9, NGF, DCC, CDK5R1, CCK, RTN4RL1, CLU, CDH1, SCARF1, SEMA5A, LINGO1, ALDH1A2, RAC3, KAL1, B3GNT1, PCSK9, LHX6, POU3F2, DCX, NEFL, SNAP25, BMP4, PARD6B, LMX1B, FSCN2, NTF3, SPTBN4, RTN4R, DPYSL5, RPL24, EPHA4, DLX2, EPHA7, DLX5, NTRK2, ID4, FEZ1 |
| GO:0007268<br>Synaptic transmission | COL4A4, PPFIA3, EDN3, SNCAIP, NTF4, LZTS1, ERBB4, NTF3, GRIK2, EDN1, SNCA, CTNND2, TAC1, MYLK2, NLGN3, CDH2, BDNF, AGT, NTRK2, PSEN2, CNTN4, LGI1, CAMK2A, NGF |
| GO:0007389<br>Pattern specification process | NOG, SHROOM3, WNT3A, FST, EDN1, TP63, GREM1, PAX1, CXCL12, SEMA5A, EDNRA, HOXC6, ALDH1A2, BARX1, HOXC8, FOXF1, SOSTDC1, NKX6-2, NKX3-2, HHIP, ALX4, LFNG, PITX2, MLLT3, MDFI, BMP4, LMX1B, EFNB1, SMAD6, EMX2, DLL3, LEF1, PCDH8, MID1, HOXD9, DLX2, SFRP1, HOXB7, HOXB8, SFRP2, MEOX1, PSEN2, ROR2, UNCX |
| GO:0030326<br>Embryonic limb morphogenesis | NOG, FGF9, CRABP2, GDF5, LEF1, TP63, GREM1, MECOM, MMP13, HOXD9, MSX2, ALDH1A2, MSX1, DKK1, DLX5, PSEN2, RARB, FBN2, ALX4 |

FIG. 17C

| | Genes upregulated by hPSC-myotubes and fetal myotubes |
|---|---|
| GO:0042692 Muscle Cell differentiation | BMP4, MYOD1, TCAP, MYEF2, FGF10, MYOZ1, CSRP2, TPM1, CACNA1S,KRT19, SDC1, MUSK, WNT4, XIRP1, GATA6, FOXF1, CACNA1H, NKX2-5, SNTA1 |
| GO:0007067 Mitosis | KIFC1, KIF11, NEK2, DLGAP5, CCNF, TPX2, KATNB1, BIRC5, AURKA, CDC20, ANLN, AURKB, PTTG1, CEP55, HMGA2, UBE2C, CDC25A, FAM83D, CCNB1, CDCA8, CCNB2, PLK1, CDCA2,MAPRE1, CDCA5 |
| Embryo morphogenesis | BMP4, NOG, TCAP, FGF9, FGF10, SIX2, TP63, CELSR1, GJA5, SLIT2, MSX2, VEGFC, WNT4, EYA1, DKK1, FOXF1, FOXC2, MAB21L2 |

METHODS FOR GENERATING SKELETAL MUSCLE PROGENITOR CELLS

CROSS-REFERENCE

This application claims the benefit of U.S. Provisional Patent Application No. 62/443,499, filed Jan. 6, 2017, which application is incorporated herein by reference in its entirety.

STATEMENT REGARDING FEDERALLY SPONSORED RESEARCH

This invention was made with government support under Grant No. RO1AR064327-01 awarded by the National Institutes of Health. The government has certain rights in the invention.

INTRODUCTION

Human pluripotent stem cells (hPSCs), including human embryonic stem cells (hESCs) and human induced pluripotent stem cells (hiPSCs), have outstanding potential for use in personalized medicine. Directed differentiation of hPSCs to specific lineages for cell therapies is showing promise in the clinical setting and in preclinical animal models for diseases ranging from cardiac myopathy, macular degeneration, diabetes, and Parkinson's disease. However, for many cell lineages, directed differentiation of hPSCs results in progeny that are heterogeneous and functionally immature compared to physiologically relevant cells derived during normal human development. Immature cells derived from hPSCs may inappropriately function, diminishing clinical utility for drug screening and/or cell therapy.

Currently there are no protocols to generate sufficient quantity or quality of skeletal muscle progenitor cells (SMPCs) to enable engraftment of hPSC derived cells for muscle disease. The longstanding protocols used to generate skeletal muscle from hPSCs require viral-mediated overexpression of transcription factors such as MYOD or PAX7, which limits the generation of truly representative myogenic progenitors.

SUMMARY

The present disclosure provides methods of generating skeletal muscle progenitor cells (SMPCs). The present disclosure provides methods of generating immature SMPCs and multinucleated muscle cells, and matured SMPCs and multinucleated muscle cells. The present disclosure provides engraftment methods and treatment methods, involving generating SMPCs and introducing the SMPCs into an individual.

BRIEF DESCRIPTION OF THE DRAWINGS

FIG. 4A-4C depict optimal timing and enrichment strategies for hPSC-SMPCs using human adult SC marker: NCAM.

FIG. 5A-5B depicts sorting SMPCs on NCAM$^+$ for enhanced myogenic activity and engraftment potential.

FIG. 6A-6C depict genetic differences between NCAM$^+$ fetal and NCAM$^+$ hPSC-derived muscle cells.

FIG. 7A-7G depict sorting for cell surface receptors, such as ERBB3 and NGFR, to enrich for more myogenic hPSC-SMPCs compared to NCAM$^+$ cells.

FIG. 8A-8C depict variation in myogenic potential to form myotubes of subpopulations of hPSC-SMPCs; of the eight subpopulations shown, ERBB3$^+$ and NGFR$^+$ subpopulations are the most myogenic.

FIG. 9A-9B depict identification of growth factors and media conditions regulating hPSC-SMPC expansion.

FIG. 10A-10F depicts TGFβ as a regulator of hPSC-SMPC myotube fusion independent of dystrophin expression.

FIG. 12A-12E depicts that ERBB3 enrichment and TGFβi maturation of hPSC-SMPCs improves engraftment potential and dystrophin restoration in mouse models of muscular dystrophy, in vivo.

FIG. 13 presents Table 5.

FIG. 15 presents Table 6, which provides a list of Antibodies, vendors and catalog numbers, and concentrations used for IF and FACS.

FIG. 17A-17C presents Tables 1-3 showing genes upregulated by NCAM$^+$ cultured fetal muscle cells, NCAM$^+$ hPSC-SMPCs, cultured fetal myoblasts, hPSC-SMPCs, hPSC-myotubes, and fetal myotubes. FIG. 17A presents Table 1 showing a gene list of key biological processes upregulated by CD31$^-$CD45$^-$NCAM$^+$ cultured fetal muscle cells and HNK1$^-$NCAM$^+$ hPSC-SMPCs. FIG. 17B presents Table 2 showing a gene list of key biological processes upregulated by CD31$^-$CD45$^-$NCAM$^+$ cultured fetal muscle cells and HNK1$^-$NCAM$^+$ hPSC-SMPCs. FIG. 17C presents Table 3 showing a gene list of key biological processes upregulated by directly-isolated fetal muscle cells and CD31$^-$CD45$^-$NCAM$^+$ cultured fetal muscle cells.

DEFINITIONS

Figure 1A:
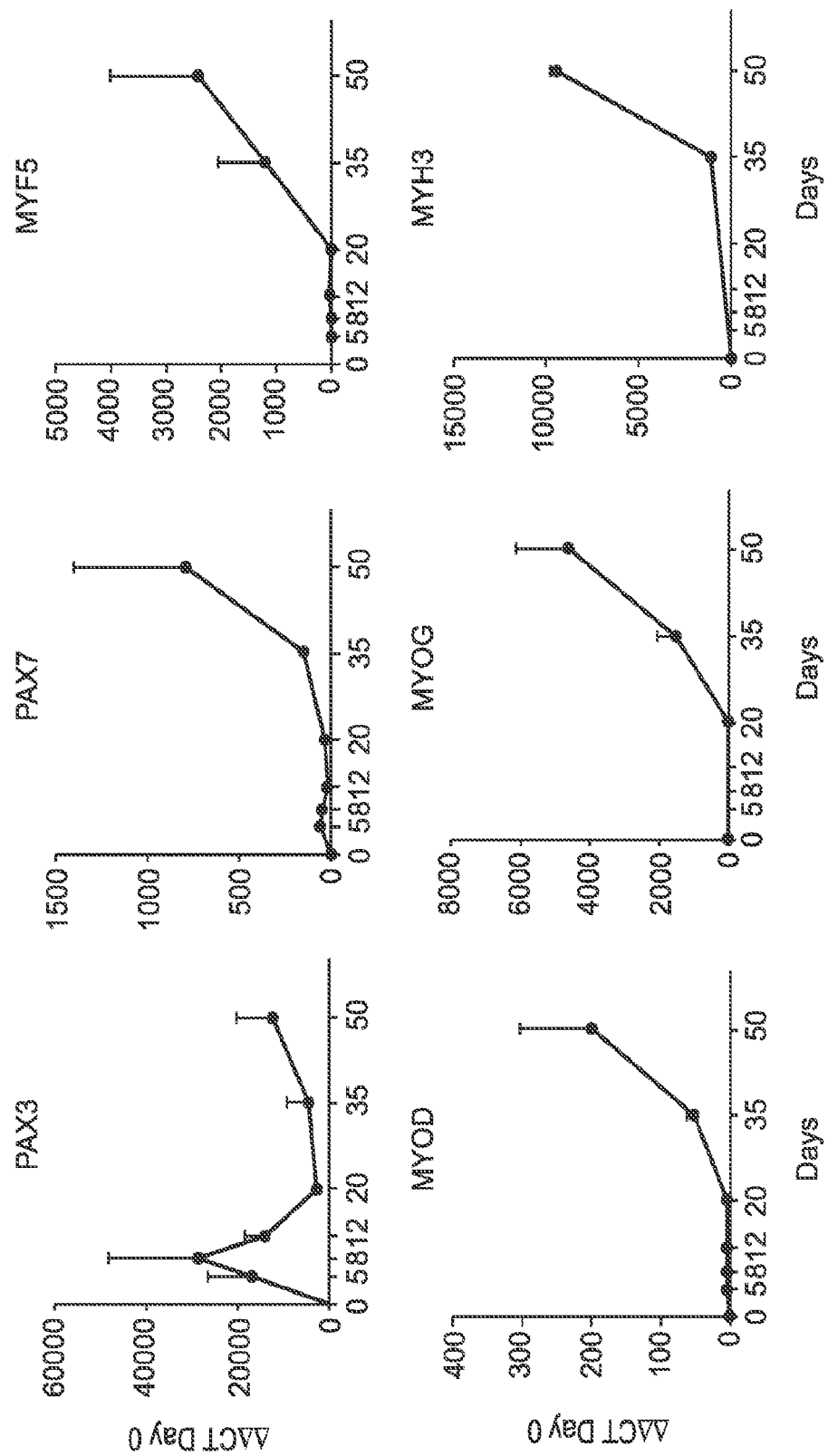
FIG. 1A-1B depict differentiation of human pluripotent stem cells to skeletal muscle progenitor cells.

The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism.

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be the starting cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). See also, the following web site: http:// followed by grants(dot)nih (dot)gov/stem_cells/registry, which lists numerous ESCs such as CHB-1, CHB-2, HUES 5, HUES6, HUES49, HUES 53, NYUES1, NYUES2, NYUES3, UCLA 1, UCLA 2, UCLA 3, WIBR1, WIBR2, WA17, WA18, WA19, etc. Stem cells of interest also include embryonic stem cells from non-human primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1, and may also express TDGF 1, Dnmt3b, FoxD3, GDF3, Cyp26a1, TERT, and zfp42. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

Human fetal skeletal muscle herein is defined as gestational week 6-20 derived from limb or trunk muscle and contains both SMPCs (expressing PAX3, PAX7, MYF5 or MYOD) and multinucleated myotubes (expressing fetal myosin heavy chain 8).

As used herein, the term "enriching" includes any isolation or sorting process that increases the relative abundance of a desired cell type, or cell types, in a population of cells.

As used herein, the term "immature" (as in an "immature" cell) includes SMPCs or muscle cells expressing myosin heavy chain 3 and/or an embryonic gene signature and generates fused cells with less than 3 nuclei per myotube.

As used herein, the term "myotube" includes muscle cells with greater than 2 nuclei and expressing myosin heavy chain and titin.

As used herein, the term "self-renewal" includes SMPCs with the ability to expand as an identical cell type without losing the stem cell marker PAX7 and maintaining the ability to differentiate into myotubes and/or retain engraftment potential.

As used herein, the term "engraftment" includes the ability of donor derived SMPCs to fuse with host myofibers or reside in the muscle stem cell niche.

As used herein, the term "TGF-β signaling pathway" is used to describe the downstream signaling events attributed to TGF-β and TGF-β like ligands. For example, in one signaling pathway a TGF-β ligand binds to and activates a Type II TGF-β receptor. The Type II TGF-β receptor recruits and forms a heterodimer with a Type I TGF-β receptor. The resulting heterodimer permits phosphorylation of the Type I receptor, which in turn phosphorylates and activates a member of the SMAD family of proteins. A signaling cascade is triggered, which is well known to those of skill in the art, and ultimately leads to control of the expression of mediators involved in cell growth, cell differentiation, tumorigenesis, apoptosis, and cellular homeostasis, among others. Other TGF-β signaling pathways are also contemplated for manipulation according to the methods described herein.

The term "inhibitor of the TGF-β signaling pathway" as used herein, refers to inhibition of at least one of the proteins involved in the signal transduction pathway for TGF-β. It is contemplated herein that an inhibitor of the TGF-β signaling pathway can be, for example, a TGF-β receptor inhibitor (e.g., a small molecule, an antibody, an siRNA), a TGF-β sequestrant (e.g., an antibody, a binding protein), an inhibitor of receptor phosphorylation, an inhibitor of a SMAD protein, or a combination of such agents.

The term "TGF-beta receptor" or "TGFβR" is used herein to encompass all three sub-types of the TGF~R family (i.e., TGFβR-1, TGFβR-2, TGFβR-3). The TGFβ receptors are characterized by serine/threonine kinase activity and exist in several different isoforms that can be homo- or heterodimeric.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom treatment or therapy is desired. Individuals include murines (e.g., rats; mice); lagomorphs (e.g., rabbits), ovines, bovines, caprines, canines, felines, non-human primates, and humans.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a skeletal muscle progenitor cell" includes a plurality of such cells and reference to "the TGFβ inhibitor" includes reference to one or more TGFβ inhibitors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of generating skeletal muscle progenitor cells (SMPCs). The present disclosure provides methods of generating immature SMPCs and multinucleated muscle cells, and matured SMPCs and multinucleated muscle cells. The present disclosure provides methods of expanding a SMPC population. The present disclosure provides methods of generating a population of multinucleated muscle cells that express myosin heavy chain. The present disclosure provides methods of performing cell engraftment in an individual in need thereof, the methods involving generating SMPCs according to a method of the present disclosure; and introducing the generated SMPCs into the individual.

Methods for Generating Skeletal Muscle Progenitor Cells

The present disclosure provides methods of generating skeletal muscle progenitor cells (SMPCs). The methods comprise culturing pluripotent stem cells in a chemically defined liquid culture medium for a period of time from 20 days to 70 days (e.g., from 20 days to 25 days, from 25 days to 30 days, from 30 days to 35 days, from 35 days to 40 days, from 40 days to 45 days, from 45 days to 50 days, from 50 days to 55 days, from 55 days to 60 days, from 60 days to 65 days, or from 65 days to 70 days), generating a population of SMPCs that express paired box protein-7 (PAX7). The population so generated comprises at least about 10% PAX7$^+$ SMPCs, at least about 15% PAX7$^+$ SMPCs, at least about 20% PAX7$^+$ SMPCs, at least about 25% PAX7$^+$ SMPCs, at least about 30% PAX7$^+$ SMPCs, at least about 35% PAX7$^+$ SMPCs, at least about 40% PAX7$^+$ SMPCs, or at least about 45% PAX7$^+$ SMPCs. In some cases, the population so generated comprises from about 10% to about 15% PAX7$^+$ SMPCs. In some cases, the population so generated comprises from about 15% to about 20% PAX7$^+$ SMPCs. In some cases, the population so generated comprises from about 20% to about 25% PAX7$^+$ SMPCs. In some cases, the population so generated comprises from about 25% to about 30% PAX7$^+$ SMPCs. In some cases, the population so generated comprises from about 30% to about 35% PAX7$^+$ SMPCs. In some cases, the population so generated comprises from about 35% to about 40% PAX7$^+$ SMPCs. In some cases, the population so generated comprises from about 40% to about 45% PAX7$^+$ SMPCs.

In some cases, the culturing step comprises (in sequence from (i) to (vi): i) culturing the pluripotent stem cells in a chemically defined liquid culture medium comprising a Rho-associated kinase inhibitor from day 1 to day 2; ii) further culturing the cells in a chemically defined liquid culture medium comprising a glycogen synthase kinase-3 (GSK3) inhibitor from day 2 to day 3; iii) further culturing the cells in a chemically defined liquid culture medium from day 2 to day 12, wherein the culture medium comprises neuronal lineage progenitor cells; iv) further culturing the cells in a chemically defined liquid culture medium comprising fibroblast growth factor from day 12 to day 20; v) further culturing the cells in a chemically defined liquid culture medium from day 20 to day 35; and vi) further culturing the cells in a chemically defined liquid culture medium comprising insulin-like growth factor-1 from day 35 to day 50.

In some cases, the culturing step comprises (in sequence from (i) to (vi): i) culturing the pluripotent stem cells in a chemically defined liquid culture medium comprising a Rho-associated kinase inhibitor from day 1 to day 2; ii) further culturing the cells in a chemically defined liquid culture medium comprising a glycogen synthase kinase-3 (GSK3) inhibitor from day 2 to day 3; iii) further culturing the cells in a chemically defined liquid culture medium from day 2 to day 12, wherein the culture medium comprises neuronal lineage progenitor cells; iv) further culturing the cells in a chemically defined liquid culture medium comprising fibroblast growth factor from day 12 to day 20; v) further culturing the cells in a chemically defined liquid culture medium from day 20 to day 35; and vi) further culturing the cells in a chemically defined liquid culture medium comprising insulin-like growth factor-1 and hepatocyte growth factor from day 35 to day 50 (e.g., for a period of time of from 15 days to 22 days).

In some cases, the culturing step comprises (in sequence from (i) to (vi): i) culturing the pluripotent stem cells in a chemically defined liquid culture medium comprising a Rho-associated kinase inhibitor from day 1 to day 2; ii) further culturing the cells in a chemically defined liquid culture medium comprising a glycogen synthase kinase-3 (GSK3) inhibitor from day 2 to day 3, or from day 2 to day 4, or from day 2 to day 8; iii) further culturing the cells in a chemically defined liquid culture medium comprising a BMP and/or TGFβ inhibitor from day 2 to day 6; iv) further culturing the cells in a chemically defined liquid culture medium comprising fibroblast growth factor from day 5 to day 7, or day 12 to day 20; v) further culturing the cells in a chemically defined liquid culture medium from day 20 to day 35; and vi) further culturing the cells in a chemically defined liquid culture medium comprising insulin-like growth factor-1 from day 35 to day 50 (e.g., for a period of time of from 15 days to 22 days).

Pluripotent Stem Cells

Pluripotent stem cells include embryonic stem cells and induced pluripotent stem cells. Pluripotent stem cells can be obtained from various organisms, e.g., a mammal, e.g., a human, a non-human primate, an ungulate (e.g., a horse, a cow, a camel, etc.), a rodent (e.g., a mouse; a rat), a lagomorph (e.g., a rabbit), a cat, a dog, or other mammalian animal. In some cases, the pluripotent stem cell is a human pluripotent stem cell. In some cases, the pluripotent stem cell is a mouse pluripotent stem cell.

Pluripotent stem cells are the starting material for generating SMPCs according to a method of the present disclosure. Suitable pluripotent stem cells include embryonic stem (ES) cells, induced pluripotent stem cells, or embryonic stem cells derived by somatic cell nuclear transfer. In a certain aspect, the pluripotent stem cells may be clonally derived from a single pluripotent stem cell, may comprise a substantial portion of cells clonally derived from a single cell, or may be a pool of multiple populations of cells, wherein each population of cells is clonally derived from a single cell. In some cases, the pluripotent stem cells are a population of cells, for example, derived from a single cell.

In some cases, the pluripotent stem cell used as the starting material for generating SMPCs according to a method of the present disclosure do not include a mutation that is associated with a muscle disease or disorder. In other words, in some cases, the pluripotent stem cell used as the starting material for generating SMPCs according to a method of the present disclosure, would not give rise to a skeletal muscle cell that would, when in a muscle tissue in a mammal, exhibit symptoms of a muscle disease or disorder.

In some cases, the pluripotent stem cell used as the starting material for generating SMPCs according to a method of the present disclosure includes one or more mutations associated with a muscle disease or disorder. In some cases, the pluripotent stem cell is an iPSC generated from a somatic cell obtained from an individual having one or more mutations associated with a muscle disease or disorder.

In some cases, the pluripotent stem cell used as the starting material for generating SMPCs according to a method of the present disclosure is an iPSC generated from a somatic cell obtained from an individual having one or more mutations associated with a muscle disease or disorder, where the one or more mutations have been corrected using an RNA-guided endonuclease, such as a CRISPR/Cas9 system. For example, a CRISPR/Cas9 system can be used to replace a nucleic acid comprising one or more mutations associated with a muscle disease or disorder with a homologous nucleic acid that does not comprise the one or more mutations, where the replacement can be carried out via homology-directed repair In some cases, a CRISPR/Cas9 system is used to replace a nucleic acid comprising one or more mutations associated with Duchenne muscular dystrophy (DMD) with a homologous nucleic acid that does not comprise the one or more mutation associated with Duchenne muscular dystrophy. In some cases, a CRISPR/Cas9 system is used to delete out-of-frame mutations in the gene encoding dystrophin in DMD-hiPSCs to restore the dystrophin reading frame. In some cases, the CRISPR/Cas9 system used to delete mutations in the gene encoding dystrophin in DMD-hiPSCs restores dystrophin protein function in the CRISPR/Cas9-corrected DMD-hiPSC-SMPCs.

In some cases, the CRISPR/Cas9-corrected DMD-hiPSC-SMPCs can be directed to differentiate and restore the dystrophin protein. In some cases, the CRISPR/Cas9-corrected DMD-hiPSC-SMPCs can be directed to differentiate and restore dystrophin similar to those of directly-isolated fetal cells. In some cases, the CRISPR/Cas9-corrected DMD-hiPSC-SMPCs express myogenic transcription factors In some cases, the CRISPR/Cas9-corrected DMD-hiPSC-SMPCs can be directed to differentiate and restore the dystrophin protein. In some cases, the CRISPR/Cas9-corrected DMD-hiPSC-SMPCs can be directed to differentiate and restore dystrophin similar to those of cultured fetal cells.

The term "pluripotent stem cell" refers to a cell capable of giving rise to cells of all three germinal layers, that is, endoderm, mesoderm and ectoderm. Although in theory a pluripotent stem cell can differentiate into any cell of the body, the experimental determination of pluripotency is typically based on differentiation of a pluripotent cell into several cell types of each germinal layer. In cases, a pluripotent stem cell is an embryonic stem (ES) cell derived from the inner cell mass of a blastocyst. In other embodiments, the pluripotent stem cell is an induced pluripotent stem cell derived by reprogramming somatic cells. In some cases, the pluripotent stem cell is an embryonic stem cell derived by somatic cell nuclear transfer. In some cases, the pluripotent stem cell is an induced pluripotent stem cell (iPSC). In some cases, the pluripotent stem cell is obtained from a healthy individual, e.g., an individual who does not have a mutation associated with a muscle disease or disorder; an individual who does not have a muscle disease or disorder; an individual who has normal, healthy skeletal muscle cells.

In some cases, the pluripotent stem cells comprise a mutation associated with a deleterious muscle phenotype. In some cases, the mutation is in a dystrophin gene, a huntingtin gene, an emerin gene, a myotonic protein kinase gene, a merosin gene, a laminin gene, an integrin gene, a fukutin gene, a POMGnT1 gene, a POMT1 gene, a FKRP gene, a LARGE gene, a SGCA gene, a SGCB gene, a SGCG gene, a SGCD gene, a Dysferlin gene, a D4Z4 gene, a Calpain3 gene, a Caveolin3 gene, a TRIM 32 gene, a Telethonin gene, a Titin gene, a Myotilin gene, or a Lamin AC gene.

In some cases, the pluripotent stem cells are obtained from, or are generated from a somatic cell obtained from, an individual having muscle aging, sarcopenia, muscle injury, or a muscle disease or disorder. In some cases, the pluripotent stem cells are obtained from, or are generated from a somatic cell obtained from, an individual having a disease causing muscle wasting, where such diseases include, e.g., neurogenic atrophy, or atrophy from chronic pulmonary, heart, kidney disease, HIV/AIDs, and cancer.

ES Cells

Embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer or in a feeder cell-free defined medium (e.g., TeSR; E8; and the like). The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium. In other methods, mouse ES cells can be grown in serum-free medium in the presence of bone morphogenetic protein and LIF.

Human ES cells can be obtained from blastocysts using any of a variety of methods known in the art. In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor. In other methods, human ES cells can be grown without a feeder cell layer by culturing the cells on a protein matrix such as Matrigel™ or laminin in the presence of "conditioned" medium containing basic fibroblast growth factor. The medium is previously conditioned by coculturing with fibroblasts.

Another source of ES cells is established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 have been established. In addition, subclones H9.1 and H9.2 of the H9 line have been developed. It is anticipated that virtually any ES or stem cell line known in the art and may be used.

The source of ES cells for use in connection with the present disclosure can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction. The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF. As another example, RNAs encoding OCT4, SOX2, NANOG, KLF4 and B18R are introduced into adult fibroblasts. Any of a variety of known methods for generating iPSCs can be used; see, e.g., Yoshioka et al. (2013) *Cell Stem Cell* 13:246; and Poleganov et al. (2015) *Hum. Gene Ther.* 26:751.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used.

In another method, human fetal or newborn fibroblasts are transfected with four genes, Oct4, Sox2, Nanog and Lin28 using lentivirus transduction. At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known. Induction of iPS cells typically requires the expression of or exposure to at least one member from the Sox family and at least one member from the Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, such as Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

IPS cells, like ES cells, have characteristic antigens that can be identified or confirmed by immunohistochemistry or flow cytometry, using antibodies for SSEA-1, SSEA-3 and SSEA-4. Pluripotency of embryonic stem cells can be confirmed by injecting approximately $0.5$-$10 \times 10^6$ cells into the rear leg muscles of 8-12 week old male SCID mice. Teratomas develop that demonstrate at least one cell type of each of the three germ layers.

In some cases, iPS cells are made from reprogramming somatic cells using reprogramming factors comprising an Oct family member and a Sox family member, such as Oct4 and Sox2 in combination with Klf or Nanog as describe above. The somatic cell in certain aspects may be any somatic cell that can be induced to pluripotency, such as a fibroblast, a keratinocyte, a hematopoietic cell, a mesenchymal cell, a liver cell, a stomach cell, or a β islet cell. In a certain aspect, T cells may also be used as source of somatic cells for reprogramming Embryonic Stem Cells Derived by Somatic Cell Nuclear Transfer Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a mammal are introduced into the cytoplasm of spindle-free, mature metaphase II mammal (of the same species) ooctyes by electrofusion. The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo.

Step (i)

As noted above, a method of the present disclosure can comprise a step of culturing a pluripotent stem cell in a chemically defined liquid culture medium comprising a Rho-associated kinase (ROCK) inhibitor for a period of time of from 1 day to 2 days. For example, in some cases, a method of the present disclosure comprises culturing freshly obtained pluripotent stem cells in a chemically defined liquid culture medium comprising a Rho-associated kinase inhibitor for a period of time of from 1 day to 2 days. For example, this culturing step can be carried out from day 1 to day 1 of the culturing time period.

Suitable ROCK inhibitors include, e.g., Y27632, RKI-1447, KD025, HA-100, HA-1077, H1152, AT13148, KD025, HA-1077, GSK429286A, thiazovivin, and K-115. An exemplary ROCK-specific inhibitor is Y-27632, which selectively targets ROCK1 (but also inhibits ROCK2), as well as inhibits TNF-α and IL-1β.

Thiazovivin has the following structure:

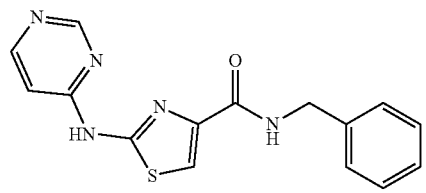 [SMILES: O=C(NCc1ccccc1)c1csc(Nc2ccncn2)n1]

Y27632 has the following structure:

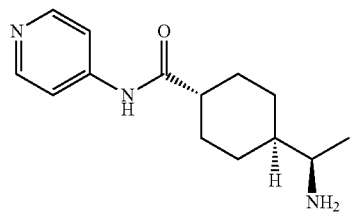

GSK429286A has the following structure:

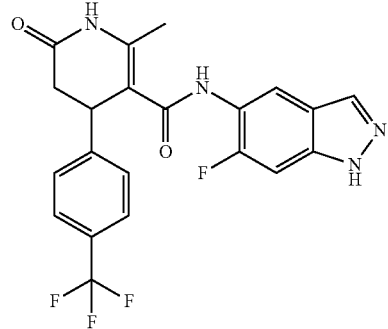 [SMILES: CC1=C(C(=O)Nc2cc3cn[nH]c3cc2F)C(c2ccc(C(F)(F)F)cc2)CC(=O)N1]

HA-1077 (Fasudil) has the following structure:

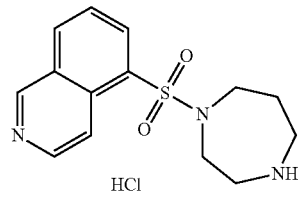 [SMILES: O=S(=O)(c1cccc2cnccc12)N1CCCNCC1 ; Cl]

RKI-1447 has the following structure:

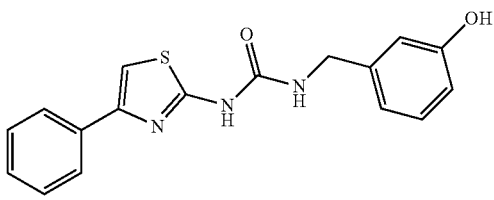 [SMILES: O=C(NCc1cccc(O)c1)Nc1nc(-c2ccccc2)cs1]

KD025 has the following structure:

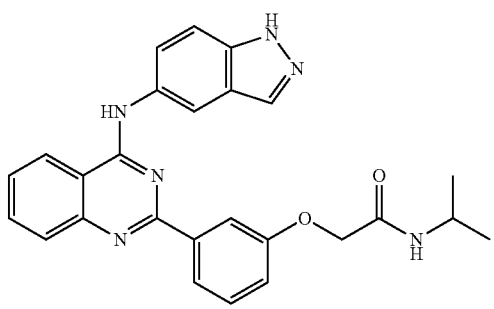 [SMILES: CC(C)NC(=O)COc1cccc(-c2nc(Nc3ccc4[nH]ncc4c3)c3ccccc3n2)c1]

K-115 (ripasudil) has the following structure:

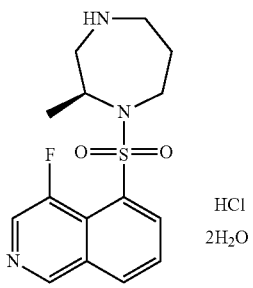 [SMILES: C[C@H]1CNCCCN1S(=O)(=O)c1cccc2cncc(F)c12 ; Cl]

AT13148 has the following structure:

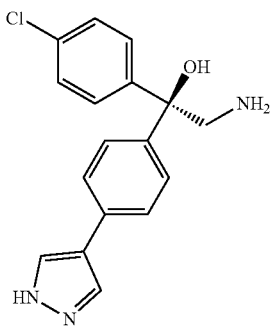 [SMILES: NC[C@@](O)(c1ccc(Cl)cc1)c1ccc(-c2cn[nH]c2)cc1]

Other ROCK inhibitors include, e.g., H-1152, Y-30141, Wf-536, hydroxyl-HA-1077, and SB-772077-B. Other non-limiting examples of suitable ROCK inhibitors include antisense nucleic acid for ROCK, RNA interference inducing nucleic acid (for example, siRNA), competitive peptides, antagonist peptides, inhibitory antibodies, antibody-scFv fragments, dominant negative variants and expression vectors thereof. Further, since other low molecular compounds are known as ROCK inhibitors, such compounds or derivatives thereof can also be used in embodiments (for example, refer to U.S. Patent Publication Nos. 20050209261, 20050192304, 20040014755, 20040002508, 20040002507, 20030125344 and 20030087919, and International Patent Publication Nos. 2003/062227, 2003/059913, 2003/062225, 2002/076976 and 2004/039796, which are hereby incorporated by reference). In certain aspects of the present disclosure, a combination of one or two or more of the ROCK inhibitors can also be used.

A ROCK inhibitor can be present in the chemically defined liquid culture medium at a concentration of about 0.05 μM to about 50 μM, for example, at least or about 0.05 μM, 0.1 μM, 0.2 μM, 0.5 μM, 0.8 μM, 1 μM, 1.5 μM, 2 μM, 2.5 μM, 5 μM, 7.5 μM, 10 μM, 15 μM, 20 μM, 25 μM, 30 μM, 35 μM, 40 μM, 45 μM, or 50 μM, including any range derivable therein, or any concentration effective for promoting cell growth or survival.

At this stage, the cells are grown in feeder cell layer-free conditions. In other words, no added "feeder" cells (such as fibroblasts) are used. No cells other than the pluripotent stem cells are present.

Any chemically defined liquid culture medium, such as Eagle's Basal Medium (BME), BGJb, CMRL 1066, Glasgow MEM, Improved MEM Zinc Option, Iscove's modified Dulbecco's medium (IMDM), Medium 199, Eagle MEM, αMEM, DMEM, Ham, RPMI 1640, and Fischer's media, variations or combinations thereof can be used. Examples of suitable chemically defined liquid culture media are described below.

Suitable chemically defined liquid culture media for Step (i) include, e.g., a TeSR medium (Ludwig et al. (2006) *Nature Biotechnology*, 24, 185-187; Ludwig et al. (2006) *Nat. Methods*, 3(8):637-46). For example, TeSR2 medium or mTeSR1 medium would be suitable. TeSR medium includes basic fibroblast growth factor (bFGF) and transforming growth factorβ (TGFβ). TeSR medium can contain six growth factors, in addition to those present in the basal medium: fibroblast growth factor (FGF), transforming growth factor beta (TGF-β), γ-aminobutyric acid (GABA), pipecolic acid, lithium chloride (LiCl), and insulin.

Step (ii)

As noted above, a method of the present disclosure can comprise, after the step of culturing in a chemically defined liquid culture medium comprising a ROCK inhibitor, a step of culturing a pluripotent stem cell in a chemically defined liquid culture medium comprising further culturing the cells in a chemically defined liquid culture medium comprising a glycogen synthase kinase-3 (GSK3) inhibitor. This culturing step can be carried out for a period of time of from about 0.5 day to 2 days (e.g., from 0.5 day to 1 day, from 1 day to 1.5 days, or from 1 day to 2 days). For example, this culturing step can be carried out from day 2 to day 3 of the culturing time period. The GSK3 inhibitor can be present in the culture medium at a concentration of from about 1 μM to about 10 μM, e.g., from about 1 μM to about 3 μM, from about 3 μM to about 5 μM, or from about 5 μM to about 10 μM. In some cases, the GSK3 inhibitor is CHIR99021. In some cases, CHIR99021 is present in the culture medium at a concentration of from about 1 μM to about 10 μM, e.g., from about 1 μM to about 3 μM, from about 3 μM to about 5 μM, or from about 5 μM to about 10 μM.

Suitable GSK3 inhibitors include, but are not limited to, 6-bromoindirubin-3'-oxime (BIO), CHIR-99021, SB216763, CHIR-98014, TWS119, IM-12, 1-Azakenpaullone, AR-A014418, SB415286, AZD1080, AZD2858, Indirubin, and any derivatives of these compounds.

Additional GSK3 inhibitors include, e.g., kenpaullone, 1-Azakenpaullone, CHIR98014, AR-A014418, CT 99021, SB415286, SB216763, AR-A014418, lithium, SB 415286, and TDZD-8. Further examples of suitable GSK3 inhibitors available from Calbiochem (see, e.g., Dalton et al., WO2008/094597, herein incorporated by reference), include but are not limited to BIO-Acetoxime (2'Z,3'E)-6-Bromoindirubin-3'-acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxybenzyl)-N'-(5-nitro-1,3-thiazol-2-yl)urea (GSK-3beta Inhibitor VIII); 3-(1-(3-Hydroxypropyl)-1H-pyrrolo[2,3-b]pyridin-3-yl]-4-pyrazin-2-yl-pyrr-ole-2,5-dione (GSK-3beta Inhibitor XI); TWS1 19 pyrrolopyrimidine compound (GSK3beta Inhibitor XII); L803 H-KEAPP APPQSpP-NH2 or its Myristoylated form (GSK3beta Inhibitor XIII); 2-Chloro-1-(4,5-dibromo-thiophen-2-yl)-ethanone (GSK3beta Inhibitor VI); AR-A0144-18; SB216763; and SB415286.

In some cases, the GSK3 inhibitor is CHIR99021.
CHIR99021 has the following structure:

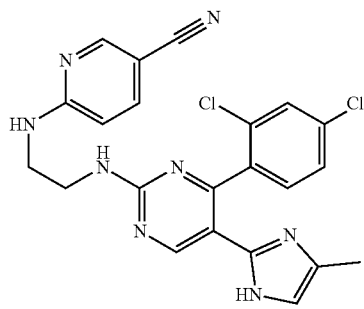 [SMILES: Cc1c[nH]c(-c2cnc(NCCNc3ccc(C#N)cn3)nc2-c2ccc(Cl)cc2Cl)n1]

The cells are cultured in a chemically defined liquid medium. Suitable chemically defined liquid culture media are described below.

In some cases, the cells are cultured in E6 medium. TeSR™-E6 is a defined, serum- and xeno-free medium that is based on the formulation of TeSR™-E8™, but does not contain transforming growth factor β (TGF-β) or basic fibroblast growth factor (bFGF).

Step (iii)

As noted above, a method of the present disclosure can comprise, after the step of culturing in a chemically defined liquid culture medium comprising a GSK3 inhibitor, culturing the cells in a chemically defined liquid culture medium, where the culture medium comprises neuronal lineage progenitor cells. This culturing step can be carried out for a period of time of from about 5 days to 15 days (e.g., from 5 days to 7 days, from 7 days to 9 days, from 9 days to 10 days, from 10 days to 11 days from 11 days to 12 days, or from 13 days to 15 days). For example, this culturing step can be carried out from day 2 or day to day 12 of the culturing time period. This step can be carried out from day 2 to day 12 of the culturing time period.

During Step (iii), mesoderm formation is induced, i.e., the culture conditions result in induction of mesoderm formation. The culture conditions in Step (iii) can induce somatic mesoderm, somite, and dermomyotome.

In some case, step (iii) is carried out in the absence of a bone morphogenetic protein (BMP) inhibitor; i.e., in some cases, the chemically defined liquid culture medium in step (iii) does not include a BMP inhibitor.

The neuronal lineage progenitor cells present in the cell culture comprise human pluripotent stem cell-derived lineages expressing transcription factors PAX6 and SOX2. The neuronal lineage progenitor cells can be derived from the same starting pluripotent stem cells as the SMPCs.

Step (iv)

As noted above, a method of the present disclosure can comprise, after the step of culturing in a chemically defined liquid culture medium comprising neuronal lineage progenitor cells, culturing the cells in a chemically defined liquid culture medium, where the chemically defined liquid culture medium comprises one or more of the following factors: fibroblast growth factor (FGF), e.g., basic FGF; transferrin or a transferrin substitute; L-glutamine or an L-glutamine substitute; monothioglycerol (MTG); and StemPro34. This culturing step can be carried out for a period of time of from about 7 days to 12 days (e.g., from 7 days to 8 days, from 8 days to 9 days from 9 days to 10 days, from 10 days to 11 days, or from 11 days to 12 days). For example, this culturing step can be carried out from day 12 to day 20 of the culturing time period. The factor can be present in the culture medium at a concentration of from about 1 ng/ml to about 100 ng/ml, e.g., from 1 ng/ml to 10 ng/ml, from 10 ng/ml to 15 ng/ml, from 15 ng/ml to 20 ng/ml, from 20 ng/ml to 25 ng/ml, from 25 ng/ml to 50 ng/ml, from 50 ng/ml to 75 ng/ml, or from 75 ng/ml to 100 ng/ml. In some cases, the factor is FGF. In some cases, FGF is present in the culture medium at a concentration of from about 1 ng/ml to about 100 ng/ml, e.g., from 1 ng/ml to 10 ng/ml, from 10 ng/ml to 15 ng/ml, from 15 ng/ml to 20 ng/ml, from 20 ng/ml to 25 ng/ml, from 25 ng/ml to 50 ng/ml, from 50 ng/ml to 75 ng/ml, or from 75 ng/ml to 100 ng/ml.

In some cases, the liquid culture medium is StemPro-34 culture medium containing L-glutamine, MTG, transferrin, and basic FGF. In some cases, the liquid culture medium is StemPro-34 culture medium containing FGF, transferrin or a transferrin substitute, L-glutamine or an L-glutamine substitute, and MTG.

Step (v)

As noted above, a method of the present disclosure can comprise, after the step of culturing in a chemically defined liquid culture medium comprising FGF, culturing the cells in a chemically defined liquid culture medium for a period of time of from about 10 days to about 20 days, e.g., 10 days, 11 days, 12 days, 13 days, 14 days, 15 days, 16 days, 17 days, 18 days, 19 days, or 20 days. In some cases, the period of time is 15 or 16 days. For example, this culturing step can be carried out from day 20 to day 35, from day 21 to day 34, or from day 21 to day 35, of the culturing time period.

Suitable chemically defined liquid culture media are described below. In some cases, the chemically defined liquid culture medium is E6 medium. In some cases, the chemically defined liquid culture medium is Dulbecco's Modified Eagle's Medium (DMEM).

Step (vi)

A further culturing step can comprise further culturing the cells from step (v) in a chemically defined liquid culture medium comprising insulin-like growth factor-1. In this step, the cells are cultured for a period of time of from about 10 days to about 20 days, e.g., 10 days, 11 days, 12 days, 13 days, 14 days, 15 days, 16 days, 17 days, 18 days, 19 days, or 20 days. For example, this culturing step can be carried out from day 35 to day 50, from day 36 to day 49, from day 35 to day 45, or from day 36 to day 50, of the culturing time period.

The chemically defined culture medium for step (vi) includes insulin-like growth factor-1 (IGF1). IGF1 can be present in the culture medium at a concentration of from about 1 ng/ml to about 100 ng/ml, e.g., from 2 ng/ml to 10 ng/ml, from 10 ng/ml to 100 ng/ml, from 1 ng/ml to 10 ng/ml, from 10 ng/ml to 15 ng/ml, from 15 ng/ml to 20 ng/ml, from 20 ng/ml to 25 ng/ml, from 25 ng/ml to 50 ng/ml, from 50 ng/ml to 75 ng/ml, or from 75 ng/ml to 100 ng/ml.

In some cases, the chemically defined culture medium for step (vi) includes IGF1, insulin, transferrin, and selenium. In some cases, the chemically defined culture medium for step (vi) is N2 medium comprising IGF1, insulin, transferrin, and selenium.

Chemically Defined Liquid Culture Media

Any chemically defined liquid culture medium, such as Eagle's Basal Medium (BME), BGJb, CMRL 1066, Glasgow MEM, Improved MEM Zinc Option, Iscove's modified Dulbecco's medium (IMDM), Medium 199, Eagle MEM, αMEM, DMEM, Ham, RPMI 1640, DMEM, DMEM/F12, DMEM, Ham, RPMI 1640, DMEM, DMEM SR medium, E6 medium, N2 medium, E8 medium, and Fischer's media, variations or combinations thereof can be used.

The chemically defined liquid culture medium can include supplements such as B-27 supplement, an insulin, transferrin, and selenium (ITS) supplement, L-Glutamine, NEAA (non-essential amino acids), P/S (penicillin/streptomycin), N2 supplement (5 μg/mL insulin, 100 μg/mL transferrin, 20 nM progesterone, 30 nM selenium, 100 μM putrescine (Bottenstein, and Sato, 1979 PNAS USA 76, 514-517) and β-mercaptoethanol β-ME). It is contemplated that additional factors may or may not be added, including, but not limited to fibronectin, laminin, heparin, heparin sulfate, retinoic acid.

The medium may contain or may not contain any alternatives to serum. The alternatives to serum can include materials which appropriately contain albumin (such as lipid-rich albumin, albumin substitutes such as recombinant albumin, plant starch, dextrans, and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco) In some cases, the chemically defined liquid culture medium does not include albumin. In some cases, the chemically defined liquid culture medium does not include serum.

In some cases, the chemically defined liquid culture medium is a low protein medium. As used herein, "low protein medium" means that a medium contains a low percentage of protein. For example, a "low protein medium" can contain less than about 10%, 9%, 8%, 7%, 6%, 5%, 4%, 3%, 2% or 1% serum, wherein the culturing capacity of the medium is still observed. In certain embodiments, the low protein medium is an albumin free medium.

The medium can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, e.g., from about about 0.1 mM to 0.5, or 0.01, 0.02, 0.03, 0.04, 0.05, 0.1, 0.2, 0.5, 0.8, 1, 1.5, 2, 2.5, 5, 7.5, 10 mM or any intermediate values.

Suitable chemically defined liquid culture media for Step (i) include, e.g., a TeSR medium (Ludwig et al. (2006) *Nature Biotechnology*, 24, 185-187; Ludwig et al. (2006) *Nat. Methods*, 3(8):637-46). For example, TeSR2 medium or mTeSR1 medium would be suitable. TeSR medium includes basic fibroblast growth factor (bFGF) and transforming growth factorβ (TGFβ).

In some cases, a suitable chemically defined liquid culture medium is a serum-free, eukaryotic cell culture medium supplement comprising or obtained by combining one or more ingredients selected from the group consisting of N-acetyl-L cysteine, human serum albumin, Human Ex-Cyte®, ethanolamine HCl human zinc insulin, human iron saturated transferrin, $Se^{4+}$, hydrocortisone, D,L-tocopherol acetate, and 2-mercaptoethanol, wherein the ingredients are present in an amount which, when the supplement is added to a basal cell culture medium, supports the expansion of cells in serum-free culture.

In some cases, a suitable chemically defined liquid culture medium is a serum-free eukaryotic cell culture medium comprising one or more ingredients selected from the group consisting of one or more antioxidants, one or more albumins or albumin substitutes, one or more lipid agents one or more insulins or insulin substitutes, one or more transferrins or transferrin substitutes, one or more trace elements, one or more glucocorticoids, one or more inorganic salts, one or more energy sources, one or more buffering agents, one or more pyruvate salts, one or more pH indicators, one or more amino acids, and one or more vitamins, wherein the medium is capable of supporting the expansion of cells in serum-free culture.

In some cases, a suitable chemically defined liquid culture medium a serum-free, eukaryotic cell culture medium comprising the ingredients N-acetyl-L-cysteine, 2-mercaptoethanol, human serum albumin, D,L-tocopherol acetate, Human Ex-Cyte®, ethanolamine, human zinc insulin, iron-saturated transferrin, $Se^{4+}$, hydrocortisone, $Ca^{2+}$, $K^+$, $Mg^{2+}$, $Na^+$, $CO_3^{2-}$, $PO_4^3$ D-glucose, HEPES buffer, sodium pyruvate, phenol red, glycine, L-alanine, L-asparagine, L-cysteine, L-aspartic acid, L-glutamic acid, L-phenylalanine, L-histidine, L-isoleucine, L-lysine, L-leucine, L-glutamine, L-arginine HCL, L-methionine, L-proline, L-hydroxyproline, L-serine, L-threonine, L-tryptophan, L-tyrosine, and L-valine, biotin, D-calcium pantothenate, choline chloride, folic acid, i-inositol, niacinamide, pyridoxal HCl, riboflavin, thiamine HCl, and vitamin $B_{12}$.

In some cases, the chemically defined liquid culture medium is StemPro34™. See, e.g., U.S. Pat. No. 6,733,746. For example, a suitable chemically defined liquid culture medium can comprise: a) human serum albumin in a concentration range of from about 1000 mg/L to about 15,000 mg/L, e.g., 5000 mg/L; b) Human Ex-Cyte® in a concentration range of from 1 mg/L to 15 mg/L, e.g. 5 mg/L; c) ethanolamine in a concentration range of from about 1 mg/L to about 25 mg/L, e.g., 10 mg/L; d) sodium selenite in a concentration range of from 0.00001 mg/L to 0.01 mg/L, e.g., 0.005 mg/L; e) hydrocortisone in a concentration range of from about 0.003 mg/L to 0.07 mg/L, e.g., 0.04 mg/L; f) D,L-tocopherol in a concentration range of from about 0.005 mg/L to about 0.05 mg/L, e.g., 0.02 mg/L; g) saturated iron in a concentration range of from about 10 mg/L to 500 mg/L, e.g., 100 mg/L; h) human zinc insulin in a concentration range of from about 1 mg/L to about 25 mg/L, e.g., 10 mg/L; i) N-acetyl-L-cysteine in a concentration range of from about 16 mg/L to about 660 mg/L, e.g., 160 mg/L; and β-mercaptoethanol in a concentration range of from about 2 mg/L to about 8 mg/L, e.g., 4 mg/L.

The term "albumin substitute" refers to any compound which may be used in place of human serum albumin (e.g., bovine serum albumin (BSA) or AlbuMAX® I) in the supplement of the present disclosure to give substantially similar results as albumin. Albumin substitutes may be any protein or polypeptide source. Examples of such protein or polypeptide samples include but are not limited to bovine pituitary extract, plant hydrolysate (e.g., rice hydrolysate), fetal calf albumin (fetuin), egg albumin, human serum albumin (HSA), or another animal-derived albumins, chick extract, bovine embryo extract, AlbuMAX® I, and AlbuMAX® II.

The term "transferrin substitute" refers to any compound which may replace transferrin in the supplement of the present disclosure to give substantially similar results as transferrin. Examples of transferrin substitutes include but are not limited to any iron chelate compound. Iron chelate compounds which may be used include but are not limited to iron chelates of ethylenediaminetetraacetic acid (EDTA), ethylene glycol-bis(β-aminoethyl ether)-N,N,N',N'-tetraacetic acid (EGTA), deferoxamine mesylate, dimercaptopropanol, diethylenetriamine-pentaacetic acid (DPTA), and trans-1,2-diaminocyclohexane-N,N,N',N'-tetraacetic adic (CDTA), as well as a ferric citrate chelate and a ferrous sulfate chelate. In some cases, the transferrin is iron saturated transferrin. In some cases, the transferrin is iron saturated human transferrin. In the supplement and the medium of the present invention, the concentration of the transferrin or transferrin substitute which facilitates cell growth, expansion, and differentiation in culture can be determined using only routine experimentation.

The term "insulin substitute" refers to any zinc containing compound which may be used in place of insulin in a liquid culture medium to give substantially similar results as insulin. Examples of insulin substitutes include but are not limited to zinc chloride, zinc nitrate, zinc bromide, and zinc sulfate. A number of insulins are known to those of ordinary skill in the art. See Gilman, A. G. et al, Eds., The Pharmacological Basis of Therapeutics, Pergamon Press, New York, 1990, pp. 1463-1495. In some cases, insulin, rather than an insulin substitute, is used in the supplement and the medium of the present disclosure. In some cases, the insulin is zinc insulin. In some cases, the insulin is human zinc insulin.

The term "expand" refers to the growth and division, and not the differentiation, of cells in culture. The term "expand" generally refers to self-renewal (not differentiation). The term "differentiation" refers to the development of a cell of a particular type into a cell of another type. The development of a pluripotent stem cell into a SMPC is an example of differentiation. The term "specification" refers to generation of one cell type from another during development or from pluripotent stem cells; for example, SMPCs derived from hPSCs or mesoderm is considered "specification."

The term "antioxidant" refers to molecules which inhibit reactions that are promoted by oxygen or peroxides. Antioxidants which may be used in the supplement or the medium of the present disclosure include but are not limited to N-acetyl-L-cysteine or derivatives thereof (see WO 95/00136), 2-mercaptoethanol or derivatives thereof, DX-tocopherol acetate or derivatives thereof, ascorbic acid or derivatives thereof, thiol compounds, such as dithiothreitol and glutathione, or derivatives of thiol compounds, catalase or derivatives thereof, cysteine or derivatives thereof, thiolactate or derivatives thereof, penicillamine or derivatives thereof, mercaptoethanesulfonic acid or derivatives thereof, and mercaptopropionic acid, or derivatives thereof. In some cases, the antioxidants used liquid culture medium suitable for use in a method of the present disclosure are N-acetyl-L-cysteine, 2-mercaptoethanol, and D,L-tocopherol acetate or mixtures or derivatives thereof.

The term "glucocorticoid" refers to steroid compounds which are in the glucocorticoid, as opposed to the mineralocorticoid, class of corticosteroids. The term includes but is not limited to glucocorticoids such as hydrocortisone, cortisol, dexamethasone, and derivatives of these compounds. See Gilman, A. G. et al, Eds., The Pharmacological Basis of Therapeutics, Pergamon Press, New York, 1990, pp. 1440-1462. In some cases, the glucocorticoid is hydrocortisone.

The term "trace element" refers to a moiety which is present in a cell culture medium in only trace amounts. In the present disclosure, this term encompasses $Se^{4+}$, $Ag^+$, $Al^{3+}$, $Ba^{2\backslash}$ $Cd^{2+}$, $Co^2$, $Cr^{3'}$, $Ge^+$, $Se^4$, $Br$, $I$; $Mn^{2+}$, $P$, $Si^{4+}$, $V^{5+}$, $Mo^{6+}$, $Ni^{2+}$, $Rb^+$, $Sn^{2+}$ and $Zr^{4+}$ and salts thereof. Any salt of a given trace element can be used in a liquid culture medium.

The term "lipid agent" refers to an agent which provides a source of lipids or contributes to lipid formation. Suitable lipid agents which can be used in a suitable liquid culture medium include, but are not limited to, Human Ex-Cyte® (Bayer), ethanolamine (or a salt thereof), sitosterol (a plant steroid), rice hydrolysate (a mixture of proteins and lipids), LTI Defined Lipid Mixture, a mixture of arachidonic acid, cholesterol, DL-α-tocopherol-acetate, ethyl alcohol, linoleic acid, linolenic acid, myristic acid, oleic acid, palmitric acid, palmitic acid, Pluronic® F-68, stearic acid, and Tween® 80. In some cases, Human Ex-Cyte® and ethanolamine are used in the supplement and the medium.

The term "energy source" refers to a carbohydrate source. Suitable energy sources which can be included in a suitable liquid culture medium include D-fructose, D-mannose, and D-galactose. In some cases, the energy source used is D-glucose.

The term "buffering agent" refers to an agent that acts to stabilize the hydrogen ion concentration and therefore the pH of a solution by neutralizing, within limits, both acids and bases. Suitable buffering agents which can be used in the supplement and the medium of the present disclosure include N-[2-hydroxyethyl]piperazine-N'-[2-ethanesulfonic acid] (HEPES), β-glycerol-phosphate, and bicarbonate buffer. In some cases, in the supplement and the medium of the present disclosure, HEPES is used.

The term "amino acid" refers to amino acids or their derivatives (e g, amino acid analogs), as well as their D- and L-forms. Examples of such amino acids include glycine, L-alanine, L-asparagine, L-cysteine, L-aspartic acid, L-glutamic acid, L-phenylalanine, L-histidine, L-isoleucine, L-lysine, L-leucine, L-glutamine, L-arginine, L-methionine, L-proline, L-hydroxyproline, L-serine, L-threonine, L-tryptophan, L-tyrosine, and L-valine.

Cell Population Generated by Steps (i) Through (vi)

As noted above, carrying out the culturing steps (i) through (vi) yields a population of cells that comprises at least 10% $PAX7^+$ SMPCs. The population so generated comprises at least about 10% $PAX7^+$ SMPCs, at least about 15% $PAX7^+$ SMPCs, at least about 20% $PAX7^+$ SMPCs, at least about 25% $PAX7^+$ SMPCs, at least about 30% $PAX7^+$ SMPCs, at least about 35% $PAX7^+$ SMPCs, at least about 40% $PAX7^+$ SMPCs, or at least about 45% $PAX7^+$ SMPCs. In some cases, the population so generated comprises from about 10% to about 15% $PAX7^+$ SMPCs. In some cases, the population so generated comprises from about 15% to about 20% PAX7$^+$ SMPCs. In some cases, the population so generated comprises from about 20% to about 25% PAX7$^+$ SMPCs. In some cases, the population so generated comprises from about 25% to about 30% PAX7$^+$ SMPCs. In some cases, the population so generated comprises from about 30% to about 35% PAX7$^+$ SMPCs. In some cases, the population so generated comprises from about 35% to about 40% PAX7$^+$ SMPCs. In some cases, the population so generated comprises from about 40% to about 45% PAX7$^+$ SMPCs.

In some cases, cells of the population of at least 10% PAX7$^+$ SMPCs express one or more transcription factors selected from the group consisting of PAX3, MYF5, MYOD (skeletal muscle), PAX6, TUJ1 (neuronal), NKX2.5, TTN2 (cardiac), CD73 (mesenchymal), EN1, Brachyury, MEOX1, TBX6, LBX1 (early mesoderm), TFAP2, and SOX10 (neural crest).

Enrichment of SMPCs

As noted above, the culturing steps (e.g., steps (i) through (vi)) result in a population of cells comprising at least 10% PAX7$^+$ SMPCs. In some cases, a method of the present disclosure for generating SMPCs comprises: a) culturing a pluripotent stem cell, as described above, generating a population of cells comprising at least 10% PAX7$^+$ SMPCs; and b) enriching the generated population of cells comprising at least 10% PAX7$^+$ SMPCs for nerve growth factor receptor (NGFR)-positive, Erb-B2 receptor tyrosine kinase 3 (ERBB3)-positive, or NGFR$^+$/ERBB3$^+$ double-positive cells to generate a population of single-positive NGFR, single-positive ERBB3, or double-positive NGFR$^+$/ERBB3$^+$-enriched cells, thereby generating an enriched population of cells comprising at least 50% PAX7$^+$ SMPCs.

In some cases, the enriched population of cells comprising at least 50% PAX7$^+$ SMPCs is also at least 50% NGFR positive. In some cases, the enriched population of cells comprising at least 50% PAX7$^+$ SMPCs is also at least 50% ERBB3 positive. In some cases, the enriched population of cells comprising at least 50% PAX7$^+$ SMPCs is also at least 50% NGFR$^+$/ERBB3$^+$ double-positive cells.

In some cases, the enriched cell population comprises from at least 50% PAX7$^+$ SMPCs to about 80% PAX7$^+$ SMPCs, e.g., from about 50% PAX7$^+$ SMPCs to about 55% PAX7$^+$ SMPCs, from about 55% PAX7$^+$ SMPCs to about 60% PAX7$^+$ SMPCs, from about 60% PAX7$^+$ SMPCs to about 70% PAX7$^+$ SMPCs, or from about 70% PAX7$^+$ SMPCs to about 80% PAX7$^+$ SMPCs. In some cases, the enriched cell population comprises at least 75% PAX7$^+$ SMPCs. In some cases, the enriched cell population comprises about 95% PAX7$^+$ SMPCs.

Positive sorting for NGFR$^+$ cells, ERBB3$^+$ cells, or NGFR$^+$/ERBB3$^+$ cells, can be carried out using fluorescent-activated cell sorting (FACS) or magnetic activated cell sorting (MACS). In some case, the selection is carried out using FACS. In some case, the selection is carried out using MACS.

In some embodiments, the immature SMPCs can be sorted based on phenotypic features to enrich for certain populations. In some embodiments, the phenotypic feature is a cell surface marker. Typically, this will involve contacting each cell with an antibody or ligand that binds to a marker of interest expressed by SMPCs, followed by separation of the specifically recognized cells from other cells in the population. A typical method for sorting cells is fluorescence-activated cell sorting (FACS) in which cells expressing the marker are labeled with a specific antibody, typically by way of a fluorescently labeled secondary anti-immuno-globulin. The cells are then separated individually according to the amount of bound label using a suitable sorting device. Such sorting methods permit recovery of a positively selected population of cells that bear the marker of interest, and a negatively selected population of cells that not bear the marker in sufficient density or accessibility to be positively selected.

In some cases, the markers of interest expressed by SMPCs are nerve growth factor receptor (NGFR) and Erb-B2 receptor tyrosine kinase 3 (ERBB3). For example, cells sorted positively for expression of NGFR and ERBB3 can provide a population that is 55% or greater, 60% or greater, 70% or greater, 80% or greater, 90% or greater or greater than 90% (e.g. 95%, 98%. 99% or greater than 99%) NGFR/ERBB3 double positive. In some cases, the proportion of NGFR-positive cells is 55% or greater, 60% or greater, 70% or greater, 80% or greater, 90% or greater or greater than 90% (e.g. 95%, 98%. 99% or greater than 99%). In some cases, the proportion of ERBB3-positive cells is 55% or greater, 60% or greater, 70% or greater, 80% or greater, 90% or greater or greater than 90% (e.g. 95%, 98%. 99% or greater than 99%).

In some cases, ERBB3$^+$NGFR$^+$ expression enriches for PAX7$^+$ and MYF5$^+$ cells.

Negative Selection/Sorting

In some cases, the NGFR$^+$- and/or ERBB3$^+$-enriched cell population comprising at least 50% PAX7$^+$ SMPCs is further selected to remove HKN1$^+$ cells, thereby generating a cell population that comprises from 80% to 100% PAX7$^+$ SMPCs. In some cases, a method of the present disclosure further comprises negatively selecting HKN1$^+$ cells from the the NGFR$^+$- and/or ERBB3$^+$-enriched cell population comprising at least 50% PAX7$^+$ SMPCs, thereby generating a population of HNK1-depleted cells that are NGFR$^+$- and/or ERBB3$^+$-enriched and that comprise from 80% to 100% PAX7$^+$ SMPCs. In some cases, a method of the present disclosure further comprises negatively selecting HKN1$^+$ cells, CD73$^+$ cells, and platelet-derived growth factor receptor (PDGFRa)$^+$ cells from the NGFR$^+$- and/or ERBB3$^+$-enriched cell population comprising at least 50% PAX7$^+$ SMPCs, thereby generating a population of NGFR$^+$- and/or ERBB3$^+$-enriched, HNK1/CD73/PDGFRa-depleted cells. In some cases, ERBB3$^+$-enriched cell populations are further enriched by negatively selecting HKN1$^+$ cells and NGFR$^+$ cells.

Removing (negatively selecting or negatively sorting) HKN1$^+$ cells generates a population of cells comprising from 80% to 100% PAX7$^+$ SMPCs.

In some case, the negative selection is carried out using FACS. In some case, the negative selection is carried out using MACS.

In some cases, the NGFR$^+$- and/or ERBB3$^+$-enriched cell population comprising at least 50% PAX7$^+$ SMPCs is selected (e.g. sorted) to remove for melanoma cell adhesion molecule (MCAM)-positive cells. In some cases, the NGFR$^+$- and/or ERBB3$^+$-enriched cell population comprising at least 50% PAX7$^+$ SMPCs is selected (e.g. sorted) to remove muscle cadherin (M-CAD)-positive cells.

Expansion of SMPCs

Once a population of from about 85% to 100% PAX7$^+$ SMPCs is obtained, as described above, the cell population comprising from about 85% to 100% PAX7$^+$ SMPCs can be expanded to increase the number of cells. For example, in some cases, the steps of: a) culturing (steps (i) through (vi), as described above; b) enriching (e.g., to generate an NGFR$^+$- and/or ERBB3$^+$-enriched cell population comprising at least 50% PAX7$^+$ SMPCs, as described above); and c)

negative sorting (as described above), to generate a cell population comprising from about 85% to 100% PAX7+ SMPCs, generates from about $10^3$ PAX7+ SMPCs to about $10^6$ PAX7+ SMPCs, e.g., from about $10^3$ PAX7+ SMPCs to about $5 \times 10^3$ PAX7+ SMPCs, from about $5 \times 10^3$ PAX7+ SMPCs to about $10^4$ PAX7+ SMPCs, from about $10^4$ PAX7+ SMPCs to about $5 \times 10^4$ PAX7+ SMPCs, from about $5 \times 10^4$ PAX7+ SMPCs to about $10^5$ PAX7+ SMPCs, from about $10^5$ PAX7+ SMPCs to about $5 \times 10^5$ PAX7+ SMPCs, or from about $5 \times 10^5$ PAX7+ SMPCs to about $10^6$ PAX7+ SMPCs. For certain applications, it would be of interest to generate more than $10^6$ PAX7+ SMPCs; to generate such cell numbers, an expansion step can be carried out.

In some cases, a method of the present disclosure comprises expanding an SMPC cell population by culturing the SMPC population in a liquid culture medium comprising one or more of:
a) a cell cycle or cell developmental regulator;
b) an inhibitor of DNA damage and/or cell stress;
c) a factor that promotes self renewal;
d) an ERBB3 pathway activator;
e) an NGFR signaling activator; and
f) a migration factor.

The result is an expanded SMPC population comprising at least 5-fold more SMPCs than the number of SMPCs before expansion, e.g., comprising at least 5-fold, at least 10-fold, at least 15-fold, at least 20-fold, at least 25-fold, at least 50-fold, at least 100-fold, at least 500-fold, at least $10^3$-fold, or more than $10^3$-fold, more SMPCs than the number of SMPCs before expansion.

In some cases, the expanded SMPC population comprises from $10^6$ cells to $5 \times 10^6$ cells, from $5 \times 10^6$ cells to $10^7$ cells, from $10^7$ cells to $5 \times 10^7$ cells, from $5 \times 10^7$ cells to $10^8$ cells, from $10^8$ cells to $5 \times 10^8$ cells, from $5 \times 10^8$ cells to $10^9$ cells, from $10^9$ cells to $5 \times 10^9$ cells, or more than $10^9$ cells.

In some cases, NGFR+ERBB3+ hPSC-SMPCs enrich for PAX7 and MYF5 by at least 5-fold, at least 10-fold, at least 15-fold, at least 20-fold, at least 25-fold, at least 50-fold, at least 100-fold, at least 500-fold, at least $10^3$-fold, or more than $10^3$-fold, compared to NGFR−ERBB3− cells. In some cases, NGFR+ERBB3+ hPSC-SMPCs undergoing differentiation comprise cellular surface marker phenotypes equivalent to fetal myogenic progenitors. In some cases, NGFR+ERBB3+ hPSC-SMPCs, NGFR+ERBB3+ DMD hIPSCs, and CRISPR/Cas9-corrected DMD NGFR+ERBB3+ hiPSCs express myogenic transcription factors.

Suitable cell cycle or cell developmental regulator include, e.g.: a member of the Wnt family, where such members include, e.g., WNT1, WNT7A; a ligand of a frizzled receptor, where such ligands include secreted frizzled-related protein 1 (SFRP1); a fibroblast growth factor family member, where such family members include FGF2; and sonic hedgehog (SHH) or other ligand of the SHH receptor.

Suitable regulators of DNA damage and/or cell stress include forskolin; a histone deacetylase (HDAC) inhibitor; and the like.

Suitable ERBB3 pathway activators include, e.g., epidermal growth factor (EGF), neuregulin-1, neuregulin-2, neuregulin-3, neuregulin-4, and transforming growth factor-alpha (TGF-α).

Suitable ERBB3 pathway inhibitors include neutralizing antibodies targeting the HER3/ERBB3 receptor, and small molecules, such as Sapitinib. ERBB3 pathway inhibitors and small molecules, such as Sapitinib, block ERBB3.

Sapitinib (AZD8931) 2-[4-[4-β-chloro-2-fluoroanilino)-7-methoxyquinazolin-6-yl]oxypiperidin-1-yl]-N-methylacetamide has the following structure:

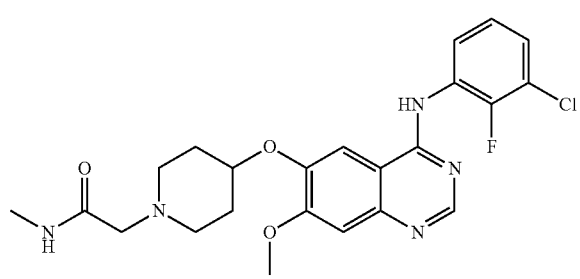 [SMILES: CNC(=O)CN1CCC(Oc2cc3c(Nc4cccc(Cl)c4F)ncnc3cc2OC)CC1]

Suitable NGFR signaling activators include, e.g., a neurotrophin, brain-derived neurotrophic factor, and glial cell line-derived neurotrophic factor.

Suitable migration factors include IL-6, IL-3, Flt-3, hepatocyte growth factor (HGF), and stem cell factor (SCF).

Suitable self-renewal signaling activators include STAT3 pathway activators e.g. IL-6 or LIF.

Generating a Multinucleated Muscle Cell

The present disclosure provides methods of generating a multinucleated muscle cell that expresses a myosin heavy chain polypeptide, the method comprising culturing a population of SMPCs in a liquid culture medium comprising a TGFβ inhibitor. The population of SMPCs can be the expanded population of SMPCs, as described above. In some cases, the multinucleated muscle cell so generated expresses one or more of myosin heavy chain isoform 8, myosin heavy chain 1, and myosin heavy chain 4. In some cases, the multinucleated muscle cell so generated expresses myosin heavy chain isoform 8, myosin heavy chain 1, and myosin heavy chain 4.

The present disclosure provides a method for generating a population of multinucleated muscle cells that express myosin heavy chain, the method comprising engrafting an SMPC population into a rodent, thereby generating a population of multinucleated muscle cells that express myosin heavy chain. The rodent can be a mouse or a rat. In some cases, the multinucleated muscle cell so generated expresses one or more of myosin heavy chain isoform 8, myosin heavy chain 1, and myosin heavy chain 4. In some cases, the multinucleated muscle cell so generated expresses myosin heavy chain isoform 8, myosin heavy chain 1, and myosin heavy chain 4.

The present disclosure provides a method for generating a population of multinucleated muscle cells that express myosin heavy chain, the method comprising engrafting an SMPC population into non-human mammal, thereby generating a population of multinucleated muscle cells that express myosin heavy chain. The non-human mammal can be any of a variety of mammals, e.g., a dog, a rabbit, etc. In some cases, the multinucleated muscle cell so generated expresses one or more of myosin heavy chain isoform 8, myosin heavy chain 1, and myosin heavy chain 4. In some cases, the multinucleated muscle cell so generated expresses myosin heavy chain isoform 8, myosin heavy chain 1, and myosin heavy chain 4.

The present disclosure provides a method for generating a population of multinucleated muscle cells that express myosin heavy chain, the method comprising co-culturing an SMPC population with a motor neuron, thereby generating a population of multinucleated muscle cells that express myosin heavy chain. In some cases, the multinucleated muscle cell so generated expresses one or more of myosin heavy chain isoform 8, myosin heavy chain 1, and myosin heavy chain 4. In some cases, the multinucleated muscle cell so generated expresses myosin heavy chain isoform 8, myosin heavy chain 1, and myosin heavy chain 4.

TGF-Beta Receptor (TGFβR) Inhibitors

As used herein, the term "TGF-β signaling inhibitor" (also referred to as TGF-β signal transduction inhibitor) is a compound that inhibits TGF-β signal transduction by inhibiting any of the factors constituting the TGF-β signal transduction system pathway, such as TGF-β ligand, TGF-β Type I receptors, TGF-β Type II receptors, TGF-β Type III receptors (β-glycan and endoglin), soluble forms of the TGF-β receptors, Smad proteins (1-8), antibodies against receptors and ligands implicated in the signaling pathway, nucleic acid based molecules (e.g., antisense, siRNA, aptamers and ribozymes) targeting the pathway members, or a combination thereof.

An "inhibitor" of TGFβR, as the term is used herein, can function in a competitive or non-competitive manner, and can function, in one embodiment, by interfering with the expression of the TGFβR polypeptide. A TGFβR inhibitor includes any chemical or biological entity that, upon treatment of a cell, results in inhibition of a biological activity caused by activation of the TGFβR in response to binding of its natural ligand. In some cases, the TGF-β signaling pathway inhibitor is either selective for, or specific for, a member of the TGF-β signaling pathway. By "specific" is meant that at the dose necessary for the inhibiting agent to inhibit the TGF-β signaling pathway, the inhibiting agent does not have any other substantial pharmacological action in the cell or host. By "selective" is meant that the dose of the inhibitor necessary for inhibition of the TGF-β signaling pathway is at least 2-fold lower than the dose necessary for activation or inhibition of another pharmacological action as measured by the ED50 or EC50 of the agent for each pharmacological effect; preferably the dose of inhibitor necessary for TGF-β pathway inhibition is at least 5-fold lower, at least 10 fold lower, at least 20-fold lower, at least 30-fold lower, at least 40-fold lower, at least 50-fold lower, at least 60-fold lower, at least 70-fold lower, at least 80-fold lower, at least 90-fold lower, at least 100-fold lower, at least 500-fold lower, at least 1000 fold lower or more, than the dose necessary for another pharmacological action. Thus, to be clear, the agents useful for the methods described herein primarily inhibit the TGF-β signaling pathway with only minor, if any, effects on other pharmacological pathways, and the dose used for inhibition of the TGF-β signaling pathway is sub-clinical or sub-threshold for other pharmacological responses.

Such an inhibitor can act by binding to the intracellular domain of the receptor and blockade of its serine/threonine kinase activity (e.g., ATP binding site). Alternatively, such an inhibitor can act by occupying or sterically hindering the ligand binding site (or a portion thereof) of the TGFβR, thereby rendering the receptor inaccessible to binding by the natural ligand, which prevents activation by that ligand. In addition, the TGFβR inhibitor can also bind to a non-ligand binding site and, for example, produce a conformational shift in the TGFβR, such that a ligand of the TGFβR can no longer access the binding site. An inhibitor can be, for example, a competitive inhibitor, a non-competitive inhibitor, an inverse agonist or a partial agonist of the TGFβR.

Alternatively, such an inhibitor can act by modulating the heterodimerization of TGFβR polypeptides, the interaction of TGFβR with other proteins, or the ubiquitination or endocytic degradation of the receptor. TGFβR inhibitors, include, but are not limited to small molecules, antibodies or antigen-binding antibody fragments, antisense constructs, siRNAs and ribozymes.

In some cases, hPSC-SMPCs comprise a higher expression of the TGF-β genes (e.g. TGFβ1, ACVR1B and MSTN) compared to fetal myotubes. In some cases, TGF-β inhibition improves hPSC-SMPC differentiation and myotube fusion. In some cases, TGF-β inhibition (TGF-βi) increases hPSC-myotube fusion. In some cases, hPSC-myotubes comprise a morphology equivalent to late stage fetal myotubes. In some cases, TGF-β inhibition promotes hPSC myotube maturation to express adult proteins in vitro.

Small Molecule Inhibitors

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Some non-limiting examples of small molecule inhibitors of TGFβRs include 24346-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole, which can be purchased from Calbiochem (San Diego, Calif.). Other small molecule inhibitors include, but are not limited to, SB-431542 (see e.g., Inman et al. 2005; *Molecular Pharmacology* 62:65-74), SB A83-01 (Tojo et al. 2005; *Cancer Science* 96: 791-800), SM16 (see e.g., Fu, K et al., 2008; *Arteriosclerosis,Thrombosis and Vascular Biology* 28(4): 665), and SB-505124 (see e.g., Dacosta Byfield, S., et al., 2004; *Molecular Pharmacology* 65:744-52), among others.

SB-A83-1 (3-(6-Methyl-2-pyridinyl)-N-phenyl-4-(4-quinolinyl)-1H-pyrazole-1-carbothioamide) has the following structure:

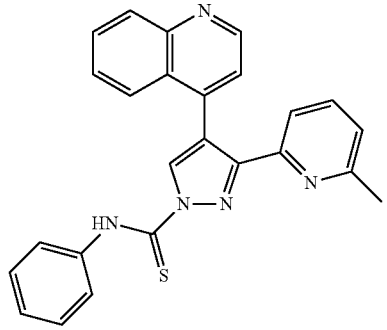 [SMILES: Cc1cccc(-c2nn(C(=S)Nc3ccccc3)cc2-c2ccnc3ccccc23)n1]

SB-431542 (4-[4-(1,3-benzodioxol-5-yl)-5-pyridin-2-yl-1H-imidazol-2-yl]benzamide) has the following structure:

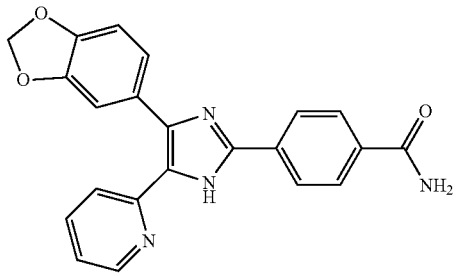 [SMILES: NC(=O)c1ccc(-c2nc(-c3ccc4c(c3)OCO4)c(-c3ccccn3)[nH]2)cc1]

In one embodiment, the specific inhibitor of TGFβR1 Activin receptor-like kinases (ALK) 4, 5 and 7, and SMAD3 phosphorylation SB-431542 is used with the methods described herein. SB-431542 is commercially available from Sigma (product no. 54317; Saint Louis, Mo.). SB-431542 is also referred to by the following chemical names: 4-[4-(1,3-Benzodioxol-5-yl)-5-(2-pyridinyl)-1H-imidazol-2-yl]-benzamide, 4-[4-(3,4-methylenedioxyphenyl)-5-(2-pyridyl)-1H-imidazol-2-yl]-benzamide, or 4-(5-benzol[1,3]dioxol-5-yl-4-pyridin-2-yl-1Himidazol-2-yl)-benzamide hydrate. In one embodiment the specific inhibitor of TGFβRI, ALK4 and ALK7 and SMAD2 phosphorylation A83-01 is used with the methods described herein. A83-01 is commercially available from Sigma (product no. SML 0788; Saint Louis, Mo.). A83-01 is also referred to by the following chemical names: 3-(6-Methyl-2-pyridinyl)-N-phenyl-4-(4-quinolinyl)-1H-pyrazole-1-carbothioamide, 1H-Pyrazole-1-carbothioamide,3-(6-methyl-2-pyridinyl)-N-phenyl-4-(4-quinolinyl)-.

Inhibitors of TGF-β signaling are described in Callahan, J. F. et al., J. Med. Chern. 45, 999-1001 (2002); Sawyer, J. S. et al., J. Med. Chern. 46, 3953-3956 (20031; Gellibert, F. et al., J. Med. Chern. 47, 4494-4506 (2004); Tojo, M. et al., Cancer Sci. 96: 791-800 (2005); Valdimarsdottir, G. et al., APMIS 113, 773-389 (2005); Petersen eta!. Kidney International 73, 705-715 (2008); Yingling, J. M. eta!., Nature Rev. Drug Disc. 3, 1011-1022 (2004); Byfield, S. D. eta!., Mol. Pharmacal., 65, 744-752 (2004); Dumont, N, et al., Cancer Cell 3, 531-536 (2003); WO Publication No. 2002/094833; WO Publication No. 2004/026865; WO Publication No. 2004/067530; WO Publication No. 209/032667; WO Publication No. 2004/013135; WO Publication No. 2003/097639; WO Publication No. 2007/048857; WO Publication No. 2007/018818; WO Publication No. 2006/018967; WO Publication No. 2005/039570; WO Publication No. 2000/031135; WO Publication No. 1999/058128; U.S. Pat. Nos. 6,509,318; 6,090,383; 6,419,928; 9,927,738; 7,223,766; 6,476,031; 6,419,928; 7,030,125; 6,943,191; U.S. Publication No. 2005/0245520; U.S. Publication No. 2004/0147574; U.S. Publication No. 2007/0066632; U.S. Publication No. 2003/0028905; U.S. Publication No. 2005/0032835; U.S. Publication No. 2008/0108656; U.S. Publication No. 2004/015781; U.S. Publication No. 2004/0204431; U.S. Publication No. 2006/0003929; U.S. Publication No. 2007/0155722; U.S. Publication No. 2004/0138188 and U.S. Publication No. 2009/0036382, the contents of each of which are herein incorporated by reference in their entirety.

In some cases, the inhibitor of TGFβ receptor activity is selected from the group consisting of 2-β-(6-Methylpyridin-2-yl)-1H-pyrazol-4-yl)-1,5-naphthyridine; [3-(Pyridin-2-yl)-4-(4-quinoyl)]-1H-pyrazole, 3-(6-Methyl-2-pyridinyl)-N-phenyl-4-(4-quinolinyl)-1H-pyrazole-1-carbothioamide, 4-[4-(1,3-benzodioxol-5-yl)-5-(2-pyridinyl)-1H-imidazol-2-yl]benzamide, 3-(6-Methyl-2-pyridinyl)-N-phenyl-4-(4-quinolinyl)-1H-pyrazole-1-carbothioamide, 4-[4-(1,3-benzodioxol-5-yl)-5-pyridin-2-yl-1H-imidazol-2-yl] benzamide, 4-[3-(2-pyridinyl)-1H-pyrazol-4-yl]-quinoline and 2-β-(6-methylpyridine-2-yl)-1H-pyrazol-4-yl)-1,5-naphthyridine SB A83-01, SB-431542, LY-36494, and SJN-2511 (Repsox).

LY-36494 (4-[3-(2-pyridinyl)-1H-pyrazol-4-yl]-quinoline) has the following structure:

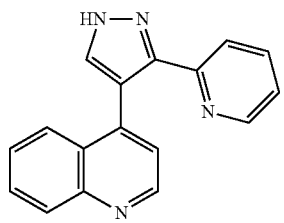 [SMILES: c1ccc(-c2n[nH]cc2-c2ccnc3ccccc23)nc1]

SJN-2511 (2-β-(6-methylpyridine-2-yl)-1H-pyrazol-4-yl)-1,5-naphthyridine) has the following structure:

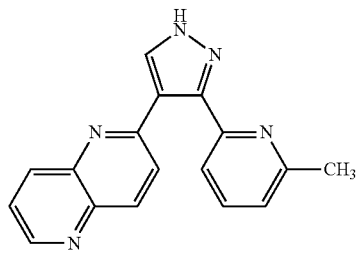 [SMILES: Cc1cccc(-c2n[nH]cc2-c2ccc3ncccc3n2)n1]

In some cases, the inhibitor of TGF-β receptor activity comprises an inhibitor of ALK4, ALK5, or ALK7.

Oligonucleotide based modulators of TGF-β signaling, such as siRNAs and antisense oligonucleotides, are described in U.S. Pat. Nos. 5,731,424; 6,124,449; U.S. Publication Nos. 2008/0015161; 2006/0229266; 2004/0006030; 2005/0227936 and 2005/0287128, each of which are herein incorporated by reference in their entirety. Other antisense nucleic acids and siRNAs can be obtained by methods known to one of ordinary skill in the art.

In some cases, ERBB3+ SMPCs from CRISPR/Cas9-corrected DMD hiPSCs differentiated in the presence of a TGFβR1 inhibitor (e.g. SB-431542) increases myotube formation compared to ERBB3+ SMPCs from CRISPR/Cas9-corrected DMD hiPSCs differentiated with a recombinant TGF-β1 or without a TGFβR1 inhibitor. In some cases, a TGFβR1 inhibitor (e.g. SB-431542) treated hPSC-SMPCs increase expression of MYH1 and MYH8 compared to hPSC-SMPCs in media alone or after treatment with a recombinant TGFβR1. In some cases, fetal week 17 cells or NGFR+ hPSC-myotubes in the presence of a TGFβR1 inhibitor increase sarcomere organization and z-disk patterning compared to fetal week 17 or NGFR+ hPSC-myotubes not treated with a TGFβR1 inhibitor (e.g. SB-431542).

Engraftment Methods

The present disclosure provides a method for performing cell engraftment in a subject in need thereof, the method comprising: a) generating SMPCs according to a method of the present disclosure; and b) introducing the SMPCs into the subject.

In some cases, from $10^6$ SMPCs to $5 \times 10^6$ SMPCs, from $5 \times 10^6$ SMPCs to $10^7$ SMPCs, from $10^7$ SMPCs to $5 \times 10^7$ SMPCs, from $5 \times 10^7$ SMPCs to $10^8$ SMPCs, from $10^8$ SMPCs to $5 \times 10^8$ SMPCs, from $5 \times 10^8$ SMPCs to $10^9$ SMPCs, from $10^9$ SMPCs to $5 \times 10^9$ SMPCs, or more than $10^9$ SMPCs, are introduced into the subject. In some cases, the SMPCs for introduction into the subject are present in a liquid such that the cells are at a density of about $10^6$ SMPCs per 50 µl to about $10^6$ SMPCs per 40 µl, from about $10^6$ SMPCs per 40 µl to about $10^6$ SMPCs per 30 µl, from about $10^6$ SMPCs per 30 µl to about $10^6$ SMPCs per 25 µl, from $10^6$ SMPCs per 25 µl to about $10^6$ SMPCs per 20 µl, from about $10^6$ SMPCs per 20 µl to about $10^6$ SMPCs per 15 µl, from about $10^6$ SMPCs per 15 µl to about $10^6$ SMPCs per 10 µl, or from about $10^6$ SMPCs per 10 µl to about $10^6$ SMPCs per 5 µl.

The introducing step can be carried out via intramuscular administration (e.g., intramuscular injection, via intravenous administration (e.g., intravenous injection), or by any other suitable route (e.g., intraarterial injection). For example, the introducing step can comprise placing into a skeletal muscle of the subject a matrix comprising the SMPCs. As another example, the introducing step can comprise placing into a skeletal muscle of the subject a hydrogel comprising the SMPCs.

In some cases, introducing the TGF-β inhibitor into the subject comprises intramuscular injection into the subject every third day for one week after engraftment. In some cases, introducing the TGF-β inhibitor into the subject comprises intramuscular injection into the subject every third day for two weeks after engraftment. In some cases, introducing the TGF-β inhibitor into the subject comprises intramuscular injection into the subject every third day for three weeks, four weeks, or five weeks after engraftment.

In some cases, the introducing step comprises co-administering a compound or substance, wherein the compound or substance is one or more of a TGF-β inhibitor, a survival factor or a self-renewal factor, a vascular permeabilization factor, an extracellular matrix (ECM) component, and a hydrogel. "Co-administering" includes administering the SMPCs and the compound or substance at substantially the same time (e.g., within 12 hours, within 6 hours, within 4 hours, within 1 hours, within 30 minutes, within 15 minutes, within 10 minutes, or within 5 minutes, or less than 5 minutes) but in separate formulations or compositions. "Co-administering" " includes administering the SMPCs and the compound or substance at substantially the same time (e.g., within 12 hours, within 6 hours, within 4 hours, within 1 hours, within 30 minutes, within 15 minutes, within 10 minutes, or within 5 minutes, or less than 5 minutes), where the SMPCs and the compound or substance are in the same formulation or composition.

Suitable TGFβ inhibitors are described above.

Suitable survival factor or self-renewal factor include, e.g., one or more of fibroblast growth factor (FGF), a TGFβ inhibitor, forskolin, a Wnt family member (e.g., WNT7a), a MAPK inhibitor (e.g., p38 inhibitor), a STAT3 agonist, neuregulin (e.g., NGR1-4), and a Rho-kinase inhibitor (e.g., HA-1077, y-27632, or other ROCK inhibitor, as described above).

Suitable vascular permeabilization factors include vascular endothelial growth factor (VEGF) and stromal derived factor 1 (SDF1).

Suitable ECM components include, e.g., laminin (e g, laminin-211; laminin-521; and the like), collagen, fibrin, etc. Suitable hydrogels include engineered scaffolds such as poly(ethylene glycol) (PEG)-based hydrogels and gelatin-based hydrogels.

Treatment Methods

In some cases, an engraftment method as described above is useful for treating a musculoskeletal disease or disorder. For example, SMPCs can be introduced into or near a treatment site, e.g., into or near a skeletal muscle in need of treatment. Introduction of SMPCs (alone or co-administered with a compound or substance, as described above) into an individual having a musculoskeletal disease or disorder treats the musculoskeletal disease or disorder.

In some cases, the present disclosure provides a method of treating a musculoskeletal disease or disorder, the method comprising: a) generating a population of SMPCs by carrying out a method of the present disclosure for generating SMPCs; and b) introducing into an individual having the musculoskeletal disease or disorder an effective number of the SMPCs. In some cases, the SMPCs will be in suspension in a liquid composition. In some cases, the SMPCs will be in a hydrogel, e.g., embedded within a hydrogel. In some cases, the SMPCs will be in a matrix, e.g., embedded within a matrix. The hydrogel or matrix is biocompatible. In some cases, the hydrogel or matrix is biodegradable in that it biodegrades within the individual. In some cases, the composition, hydrogel, or matrix comprising the SMPCs comprises one or more of a TGF-β inhibitor, a survival factor or a self-renewal factor, and a vascular permeabilization factor. In some cases, the method comprises co-administering the SMPCs with one or more of a TGF-β inhibitor, a survival factor or a self-renewal factor, and a vascular permeabilization factor, where the SMPCs are in a separate composition from the one or more of a TGF-β inhibitor, a survival factor or a self-renewal factor, and a vascular permeabilization factor.

In some cases, an "effective number" of SMPCs is from $10^4$ cells to $10^5$ cells, from $10^5$ cells to $10^6$ cells, from $10^6$ cells to $5 \times 10^6$ cells, from $5 \times 10^6$ cells to $10^7$ cells, from $10^7$ cells to $5 \times 10^7$ cells, from $5 \times 10^7$ cells to $10^8$ cells, from $10^8$ cells to $5 \times 10^8$ cells, from $5 \times 10^8$ cells to $10^9$ cells, from $10^9$ cells to $5 \times 10^9$ cells, or more than $10^9$ cells.

In some cases, an "effective number" of SMPCs is a number of SMPCs that is effective to at least ameliorate a symptom of a musculoskeletal disease or disorder. In some cases, an "effective number" of SMPCs is a number of SMPCs that is effective to improve function of a skeletal muscle in the individual by at least 10%, at least 25%, at least 50%, at least 75%, at least 2-fold, at least 5-fold, or more than 5-fold, compared with the level of function of the skeletal muscle before administration of the SMPCs.

In some cases, an "effective number" of SMPCs is a number of SMPCs that is effective to fuse with host muscle in a manner that restores human muscle protein production.

In some cases, a musculoskeletal disease or disorder is a condition that causes or results in muscle atrophy. Muscle atrophy can result from treatment with a glucocorticoid such as cortisol, dexamethasone, betamethasone, prednisone, methylprednisolone or prednisolone. Muscle atrophy can also be a result of denervation due to nerve trauma or a result of degenerative, metabolic or inflammatory neuropathy. For example, muscle atrophy can be a result of an adult motor neuron disease, Guillain-Barré syndrome, infantile spinal muscular atrophy, amyotrophic lateral sclerosis, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, and metabolic stress or nutritional insufficiency. Muscle atrophy can be a result of myopathy, including for example myotonia; a congenital myopathy, including nemalene myopathy, multi/minicore myopathy and myotubular (centronuclear) myopathy; mitochondrial myopathy; familial periodic paralysis; inflammatory myopathy; metabolic myopathy, such as caused by a glycogen or lipid storage disease; dermatomyositis; polymyositis; inclusion body myositis; myositis ossificans; rhabdomyolysis and myoglobinurias. Myopathy may be caused by a muscular dystrophy syndrome, such as Duchenne muscular dystrophy (DMD), Becker muscular dystrophy (also known as benign pseudohypertrophic muscular dystrophy), myotonic dystrophy, scapulohumeral and fascioscapulohumeral muscular dystrophy, Emery-Dreifuss muscular dystrophy, oculopharyngeal muscular dystrophy, limb girdle muscular dystrophy, Fukuyama congenital muscular dystrophy, or hereditary distal myopathy.

Further examples of musculoskeletal disease or disorder or conditions that result in musculoskeletal disease or disorder include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, cancer, stroke, frailty, memory loss, impaired kidney function, metabolic disorders (including Type-II diabetes, metabolic syndrome, hyperglycemia, obesity, thyroid gland disorder), cachexia (including cachexia associated with a rheumatoid arthritis and cachexia associated with cancer), acute and/or chronic renal disease or failure, liver diseases (examples such as fibrosis, cirrhosis), cancer (including rhabdomyosarcoma, prostate cancer, breast cancer, hepatocellular carcinoma, and gastrointestinal cancer), Parkinson's Disease; anemia, exposure to environmental toxins or drugs, HIV/AIDS, fasting, benign congenital hypotonia, central core disease, burn injury, chronic obstructive pulmonary disease, sepsis, congestive heart failure, aging or an age-related condition, and space travel or time spent in a zero gravity environment.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-60 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A method for generating skeletal muscle progenitor cells (SMPCs), the method comprising:
 a) culturing pluripotent stem cells in a chemically defined liquid culture medium for a period of time from 40 days to 50 days, generating a population of SMPCs that express paired box protein-7 (PAX7), wherein said culturing comprises:
  i) culturing the pluripotent stem cells in a chemically defined liquid culture medium comprising a Rho-associated kinase inhibitor from day 1 to day 2;
  ii) further culturing the cells in a chemically defined liquid culture medium comprising a glycogen synthase kinase-3 (GSK3) inhibitor from day 2 to day 3;
  iii) further culturing the cells in a chemically defined liquid culture medium from day 2 to day 12, wherein the culture medium comprises neuronal lineage progenitor cells;
  iv) further culturing the cells in a chemically defined liquid culture medium comprising fibroblast growth factor from day 12 to day 20;
  v) further culturing the cells in a chemically defined liquid culture medium from day 20 to day 35; and
  vi) further culturing the cells in a chemically defined liquid culture medium comprising insulin-like growth factor-1 from day 35 to day 50,
 thereby generating a population of cells comprising at least 10% PAX7$^+$ SMPCs.

Aspect 2. The method of aspect 1, wherein the culture medium in step (iii) does not include a bone morphogenetic protein (BMP) inhibitor.

Aspect 3. The method of aspect 1, wherein the liquid culture medium in step (iv) comprises one or more of transferrin, a transferrin substitutes, L-glutamine, an L-glutamine substitute, monothioglycerol, StemPro-34 supplement, and fibroblast growth factor.

Aspect 4. The method of aspect 1, wherein the liquid culture medium in step (v) is E6 medium, or Dulbecco's Modified Eagle's Medium (DME).

Aspect 5. The method of aspect 1, wherein the liquid culture medium in step (vi) comprises N2 medium with insulin-like growth factor-1, insulin, transferrin, and selenium.

Aspect 6. The method of aspect 1, wherein the chemically defined liquid culture medium comprises insulin-like growth factor-1 (IGF1) during step (vi) days 35-50.

Aspect 7. The method of aspect 1, wherein the neuronal lineage progenitor cells comprise human pluripotent stem cell-derived lineages expressing transcription factors EN1, HOXA, and NKX2.5.

Aspect 8. The method of aspect 1, wherein the GSK3 inhibitor is CHIR99021.

Aspect 9. The method of aspect 1, wherein the PAX7$^+$ SMPCs express one or more transcription factors selected from the group consisting of PAX3, MYF5, MYOD (skeletal muscle); PAX6, TUJ1 (neural); NKX2.5, TTN2 (cardiac); CD73 (mesenchymal); EN1, Brachyury, MEOX1, TBX6, LBX1 (early mesoderm); or TFAP2, SOX10 (neural crest)

Aspect 10. The method of aspect 1, further comprising enriching the SMPCs for nerve growth factor receptor (NGFR)-positive, Erb-B2 receptor tyrosine kinase 3 (ERBB3)-positive, or NGFR$^+$/ERBB3$^+$ double-positive cells to generate a population of single-positive NGFR, single-positive ERBB3, or double-positive NGFR$^+$/ERBB3$^+$-enriched cells, thereby generating a population of cells comprising at least 50% PAX7$^+$ SMPCs.

Aspect 11. The method of aspect 10, wherein said enriching generates a population of cells comprising at least 75% PAX7$^+$ SMPCs.

Aspect 12. The method of aspect 10, wherein said enriching generates a population of cells comprising at least 95% PAX7$^+$ SMPCs.

Aspect 13. The method of aspect 10, further comprising removing HKN1$^+$ cells.

Aspect 14. The method of aspect 10, further comprising removing HKN1$^+$ cells, CD73$^+$ cells, and platelet-derived growth factor receptor (PDGFRa)$^+$ cells, thereby generating a population of NGFR$^+$- and/or ERBB3$^+$-enriched, HNK1/CD73/PDGFRa-depleted cells.

Aspect 15. The method of aspect 13 or aspect 14, wherein said removing generates a population of cells comprising from 80% to 100% PAX7$^+$ SMPCs.

Aspect 16. The method of aspect 10, comprising enriching the SMPCs for melanoma cell adhesion molecule (MCAM)-positive cells and muscle cadherin (M-CAD)-positive cells.

Aspect 17. The method of any one of aspects 10-16, wherein said enriching is carried out using fluorescent-activated cell sorting or magnetic activated cell sorting.

Aspect 18. The method of any one of aspects 10-17, comprising expanding the SMPC population by culturing the SMPC population in a liquid culture medium comprising one or more of:
 a) a cell cycle or cell developmental regulator;
 b) an inhibitor of DNA damage and/or cell stress;
 c) a signal transducer and activator of transcription-3 (STAT3) pathway activator;
 d) an ERBB3 pathway activator;
 e) an NGFR signaling activator; and
 f) a migration factor,
 thereby generating an expanded SMPC population comprising at least 5-fold more SMPCs than the number of SMPCs before expansion.

Aspect 19. The method of aspect 18, wherein the cell cycle or cell developmental regulator comprises a Wnt family member, a ligand of a frizzled receptor, or a fibroblast growth factor family member.

Aspect 20. The method of aspect 18, wherein the regulator of DNA damage and/or cell stress is forskolin or a histone deacetylase inhibitor.

Aspect 21. The method of aspect 18, wherein the ERBB3 pathway activator is epidermal growth factor (EGF), neuregulin-1, neuregulin-2, neuregulin-3, neuregulin-4, or transforming growth factor-alpha (TGF-α).

Aspect 22. The method of aspect 18, wherein the NGFR signaling activator is a neurotrophin, brain-derived neurotrophic factor, or glial cell line-derived neurotrophic factor.

Aspect 23. The method of aspect 18, wherein the migration factor is IL-6, IL-3, Flt-3, hepatocyte growth factor (HGF), or stem cell factor (SCF).

Aspect 24. The method of any one of aspects 18-23, wherein the number of SMPCs is increased at least 100-fold.

Aspect 25. The method of any one of aspects 18-23, wherein the number of SMPCs is increased at least $10^3$-fold.

Aspect 26. The method of any one of aspects 18-25, comprising generating a multinucleated muscle cell that expresses myosin heavy chain by culturing the expanded SMPC population in a liquid culture medium comprising an inhibitor of TGFβ receptor activity.

Aspect 27. The method of aspect 26, wherein the inhibitor of TGFβ receptor activity is selected from the group consisting of 2-β-(6-Methylpyridin-2-yl)-1H-pyrazol-4-yl)-1,5-naphthyridine; [3-(Pyridin-2-yl)-4-(4-quinoyl)]-1H-pyrazole, 3-(6-Methyl-2-pyridinyl)-N-phenyl-4-(4-quinolinyl)-1H-pyrazole-1-carbothioamide, 4-[4-(1,3-benzodioxol-5-yl)-5-(2-pyridinyl)-1H-imidazol-2-yl]benzamide, SB A83-01, SB-431542, LY-36494, and SJN-2511 (Repsox).

Aspect 28. The method of aspect 26, wherein the inhibitor of TGF-β receptor activity comprises an inhibitor of ALK4, ALK5, or ALK7.

Aspect 29. The method of any one of aspects 1-28, wherein the pluripotent stem cells are human cells.

Aspect 30. The method of any one of aspects 1-28, wherein the pluripotent stem cells are human induced pluripotent stem cells.

Aspect 31. The method of any one of aspects 1-28, wherein the pluripotent stem cells are embryonic stem cells.

Aspect 32. The method of any one of aspects 1-31, wherein the pluripotent stem cells comprise a mutation associated with a deleterious muscle phenotype.

Aspect 33. The method of aspect 32, wherein the mutation is in a dystrophin gene, a huntingtin gene, an emerin gene, a myotonic protein kinase gene, a merosin gene, a laminin gene, an integrin gene, a fukutin gene, a POMGnT1 gene, a POMT1 gene, a FKRP gene, a LARGE gene, a SGCA gene, a SGCB gene, a SGCG gene, a SGCD gene, a Dysferlin gene, a D4Z4 gene, a Calpain3 gene, a Caveolin3 gene, a TRIM 32 gene, a Telethonin gene, a Titin gene, a Myotilin gene, or a Lamin AC gene.

Aspect 34. The method of any one of aspects 1-31, wherein the pluripotent stem cells are obtained from an individual having muscle aging, sarcopenia, muscle injury, or a muscle disease or disorder, or are generated from a somatic cell obtained from an individual having muscle aging, sarcopenia, muscle injury, or a muscle disease or disorder.

Aspect 35. The method of any one of aspects 1-31, wherein the pluripotent stem cells comprise a corrected mutation associated with a deleterious muscle phenotype correct.

Aspect 36. The method of any one of the aspects 1-31, wherein the pluripotent stem cells are obtained from an individual having a secondary disease causing muscle wasting including neurogenic atrophy, or atrophy from chronic pulmonary, heart, kidney disease, HIV/AIDs, or cancer, or are generated from a somatic cell obtained from an individual having a secondary disease causing muscle wasting including neurogenic atrophy, or atrophy from chronic pulmonary, heart, kidney disease, HIV/AIDs, or cancer.

Aspect 37. A method for expanding a skeletal muscle progenitor cell (SMPC) population, the method comprising culturing the SMPC population in a liquid culture medium comprising one or more of:
 a) a cell cycle or cell developmental regulator;
 b) an inhibitor of DNA damage and/or cell stress;
 c) a STAT3 pathway activator;
 d) an ERBB3 pathway activator;
 e) a nerve growth factor receptor (NGFR) signaling activator; and
 f) a migration factor.

Aspect 38. The method of aspect 37, wherein the cell cycle or cell developmental regulator comprises a member of the Wnt family members including WNT7A, ligands of frizzled receptors including secreted frizzled-related protein 1 (SFRP1), or fibroblast growth factor family members including FGF2.

Aspect 39. The method of aspect 37, wherein the ERBB3 pathway activator is epidermal growth factor (EGF), neuregulin-1, neuregulin-2, neuregulin-3, neuregulin-4, or transforming growth factor-alpha (TGF-α).

Aspect 40. The method of aspect 37, wherein the NGFR signaling activator is a neurotrophin, brain-derived neurotrophic factor, or glial cell line-derived neurotrophic factor.

Aspect 41. The method of aspect 37, wherein the migration factor is IL-6, IL-3, Flt-3, hepatocyte growth factor (HGF), or stem cell factor (SCF).

Aspect 42. A method for generating a population of multinucleated muscle cells that express myosin heavy chain, the method comprising culturing a skeletal muscle progenitor cell (SMPC) population in a liquid culture medium comprising a TGFβ inhibitor, thereby generating a population of multinucleated muscle cells that express myosin heavy chain.

Aspect 43. The method of aspect 42, wherein the myosin heavy chain is myosin heavy chain isoform 8, myosin heavy chain 1, or myosin heavy chain 4.

Aspect 44. The method of aspect 42, wherein the TGFβ inhibitor is selected from the group consisting of 2-β-(6-Methylpyridin-2-yl)-1H-pyrazol-4-yl)-1,5-naphthyridine; [3-(Pyridin-2-yl)-4-(4-quinoyl)]-1H-pyrazole, 3-(6-Methyl-2-pyridinyl)-N-phenyl-4-(4-quinolinyl)-1H-pyrazole-1-carbothioamide, 4-[4-(1,3-benzodioxol-5-yl)-5-(2-pyridinyl)-1H-imidazol-2-yl]benzamide, SB A83-01, SB-431542, LY-36494, and SJN-2511 (Repsox).

Aspect 45. A method for generating a population of multinucleated muscle cells that express myosin heavy chain, the method comprising engrafting a skeletal muscle progenitor cell (SMPC) population into a rodent, thereby generating a population of multinucleated muscle cells that express myosin heavy chain.

Aspect 46. A method for generating a population of multinucleated muscle cells that express myosin heavy chain, the method comprising co-culturing a skeletal muscle progenitor cell (SMPC) population with a motor neuron, thereby generating a population of multinucleated muscle cells that express myosin heavy chain.

Aspect 47. A method for performing cell engraftment in a subject in need thereof, the method comprising:
a) generating SMPCs according to the method of any one of aspects 1-41; and
b) introducing the SMPCs into the subject.

Aspect 48. The method of aspect 47, wherein said introducing is via intramuscular administration.

Aspect 49. The method of aspect 47, wherein said introducing is via intravenous administration.

Aspect 50. The method of any one of aspects 47-49, comprising co-administering a TGF-β inhibitor.

Aspect 51. The method of any one of aspects 47-49, comprising co-administering a survival factor or a self-renewal factor.

Aspect 52. The method of aspect 51, wherein the survival factor or self-renewal factor is one or more of fibroblast growth factor (FGF), a TGFβ inhibitor, forskolin, a Wnt family member, a MAPK inhibitor, a STAT3 agonist, neuregulin, and a Rho-kinase inhibitor.

Aspect 53. The method of any one of aspects 47-49, comprising co-administering of a vascular permeabilization factor.

Aspect 54. The method of aspect 53, wherein the vascular permeabilization factor is vascular endothelial growth factor (VEGF), or stromal derived factor 1 (SDF1).

Aspect 55. The method of aspect 47, wherein the SMPCs and reside in the satellite cell niche or near the muscle fibers in vivo following said introduction.

Aspect 56. The method of any one of aspects 47-49, comprising co-administering an extracellular matrix (ECM) component or a hydrogel.

Aspect 57. The method of aspect 56, wherein the ECM component is laminin, laminin-211, laminin-521, nidogen, or collagen.

Aspect 58. The method of aspect 56, wherein the hydrogel is a PEG based hydrogel or a gelatin based hydrogel.

Aspect 59. The method of any one of aspect 47 and 50-58, wherein said introducing comprises introducing into a treatment site.

Aspect 60. The method of any one of aspects 47-59, wherein said introducing treats a muscle disease or disorder.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Generation of Skeletal Muscle Progenitor Cells (SMPCs)

Materials and Methods

Reagents and Cell Culture

Dissociation of Satellite Cells from Adult and Fetal Skeletal Muscle Tissue

Human adult skeletal muscle between 25-67 years of age were obtained from donor autopsy of quadriceps provided by the National Disease Research Interchange (NDRI, N=3), and human fetal skeletal muscle weeks 8-17 were obtained from Novogenix, Inc. and the Gene And Cell Therapy Core at UCLA using Institutional Review Board (IRB) approved de-identified and consented human fetal tissues. Skeletal muscles were dissected from quadriceps and tendons, fat, and connective tissue removed. Whole limbs were taken from human fetal week 8-9 material as the musculature is not clearly defined. Muscle was cleaned in wash buffer (Dulbecco's Modified Eagle Medium (DMEM)/F12 containing $Ca^{2+}$ and $Mg^{2+}$, 0.4% Penicillin/Streptomycin (P/S), 0.2% Primocin) and minced into 2-3 mm pieces in digestion buffer-1 (Wash buffer, 500 u/mL Collagenase II (Roche), 10% FBS). Muscle tissue were incubated in digestion buffer-1 at 37° C., 5% $CO_2$ and titrated every 10 minutes until dissociated cells could pass through p1000 pipettes (approximately 30 minutes). Tissues were washed and dissociated using a sterile mortar and pestle in digestion buffer 2 (DMEM/F12, 10% FBS, P/S, Primocin, Collagenase D (1.5 u/mL) and Dispase (2.4 µ/mL), Roche). Adult tissue was incubated for 1 hour and fetal tissue was incubated at 37° C. overnight, at 37° C. in 5% $CO_2$. At the end of digestion tissues were serially titrated through 10 ml serological pipettes and p1000 pipettes and diluted in 10% fetal bovine serum (FBS) DMEM/F12 to a volume of 50 ml to make filtering through 100 µm meshes to remove debris easier for 5 minutes to remove digestion media, and re-suspended in sterile phosphate-buffered saline (PBS) containing 2% FBS for cell counting. Fetal cells at this stage were cryopreserved in 90% FBS 10% dimethyl sulfoxide (DMSO) for later studies, or immediately used for downstream experiments.

Enrichment of Adult and Fetal Skeletal Muscle Satellite Cells by FACS or Pre-Plating Fetal tissue were highly enriched for muscle stem cells and for in vitro fusion assays muscle stem cells from dissociated week 13-18 fetal muscle cells would efficiently fuse without requiring flow cytometry enrichment. Cells were seeded on matrigel-coated plates and after two days debris were removed and cells were ready for experimentation. However, satellite cells from human adult quadriceps represented only 1-2% of all cells. Thus adult muscle cells were sorted for CD56 (NCAM) and negatively sorted for CD45 (hematopoietic) and CD31 (endothelial) to remove lineage negative cells, as previously described (Xu et al., Stem Cell Reports 5, 419-434 (2015)). For FACS gating, adult cells were first sorted on DAPI to remove dead cells. Forward scatter and side scatter were used to remove debris and doublets. SCs were sorted using BD FACSAriaII cell sorters in the Jonsson Comprehensive Cancer Center at UCLA. SCs were collected in SkBM-2 and plated at 5,000-25,000 cells per 24-well plates. SCs were grown to 70% confluence in SkBM-2.

For RNA sequencing experiments, which required additional purification, fetal week 17 muscle cells were by fluorescence activated cell sorting (FACS) using these adult markers. To prepare cells for FACS during RNA-SEQ experiments, red blood cell lysis buffer was used for 1 minute was used to minimize auto fluorescence, and Human Fc block (2 µL per 1×106 cells) used to minimize non-specific binding of antibodies. In later experiments, CD235a was included with lineage negative antibodies to more gently remove red blood cells. For FACS gating, human and fetal muscle were first sorted on DAPI- and forward scatter to remove dead cells. Forward scatter and side scatter were used to remove debris and doublets. Fluorescent minus one (FMO) controls were used to set lineage negative and $NCAM^+$ gates. Cells were sorted using BD FACSAriaII cell sorters in the Jonsson Comprehensive Cancer Center (JCCC) or Broad Stem Cell Research Center (BSCRC) at UCLA. Cells were collected in SkBM-2 and cultured or immediately engrafted, or RNA immediately isolated for downstream analyses.

HPSC-SMPCs, fetal and adult muscle cells were induced to differentiate in N2 media for seven days. To evaluate muscle progenitor or satellite cell (SC) ability to differentiate and fuse to form myotubes, cultures were immunostained with MYHC, MYOD, and PAX7, or isotype controls. Primary endpoint measurements included 1) the number of myotubes per square millimeter defined as $MYHC^+$ cells containing ≥3 nuclei, 2) the number of myocytes per millimeter squared defined as $MYHC^+$ cells containing ≤2 nuclei, 3) the number of nuclei contained within each myotube or myocyte, and 4) the fusion index defined as nuclei in myotubes as a percentage of the total nuclei population. At least three random 10× images (0.621 $mm^2$) were taken per well and images used to count end point measurements using ImageJ. Image quantification data were then evaluated using One-way ANOVA with Tukey posthoc to calculate significance, $P<0.05$.

Human Pluripotent Stem Cells (hPSC) Lines and Cell Culture Techniques

H9 hESCs were obtained. Fibroblasts taken from patient skin biopsies at the Center for Duchenne Muscular Dystrophy (CDMD) were reprogrammed to derived CDMD 1002 (wild type) and CDMD 1006 (DMD) hiPSC lines as previously described (Young et al., Cell Stem Cell 18, 533-540 (2016)). The CDMD 1006 hiPSCs contained an out of frame mutation in exons 46-47 which prevents dystrophin protein translation and leads to rapid degradation of the DMD RNA transcript. To establish a corrected hiPSC (CDMD 1006-1 or S21), CRISPR/Cas9 gene-editing was used to remove exons 45-55 and restore dystrophin protein expression, as described (Young et al., Cell Stem Cell 18, 533-540 (2016)). Thus three independent cell lines: H9, CDMD 1002, and CDMD 1006; and isogenic line CDMD 1006-1; were used. Between passages 30-60, hPSCs were grown and maintained on hESC-Qualified matrigel-coated plates (Corning, #354277; diluted 1:50 in DMEM/F12) in mTESR medium (Stem Cell Technologies) containing 0.4% P/S (Hyclone). HPSCs were passaged as small colonies every 5-7 days by incubating cells in 1:1000 EDTA in sterile PBS for seven minutes. Ethylenediamine tetraacetic acid (EDTA) was removed and small colonies were gently dissociated in mTESR. Colonies were passaged between 1:6 and 1:10 depending on cell density.

Directed Differentiation Protocols to Generate Skeletal Muscle Progenitor Cells (SMPCs)

Figure 2A:
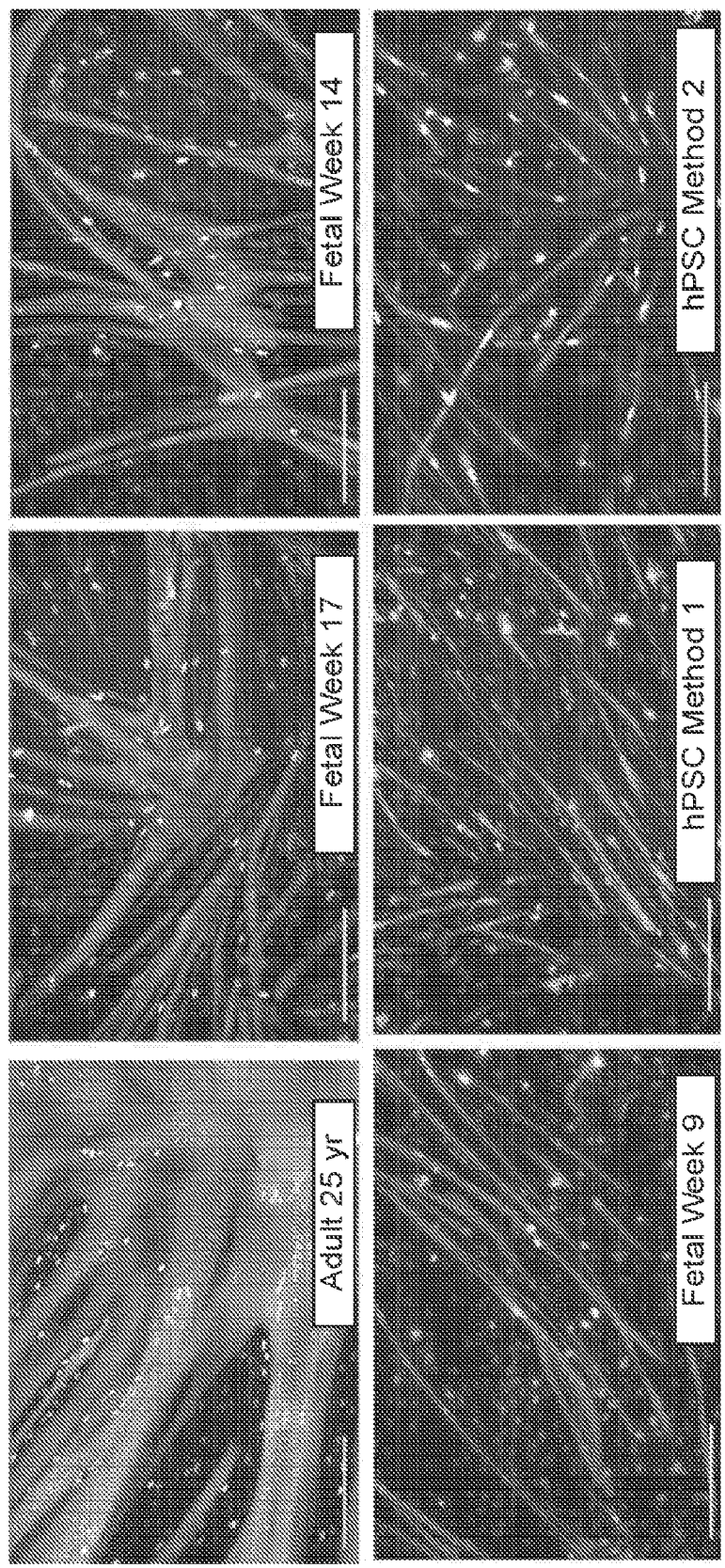
FIG. 2A-2B depicts hPSC-SMPCs are not equivalent to fetal or adult SCs in vitro or in vivo.
Figure 2A:
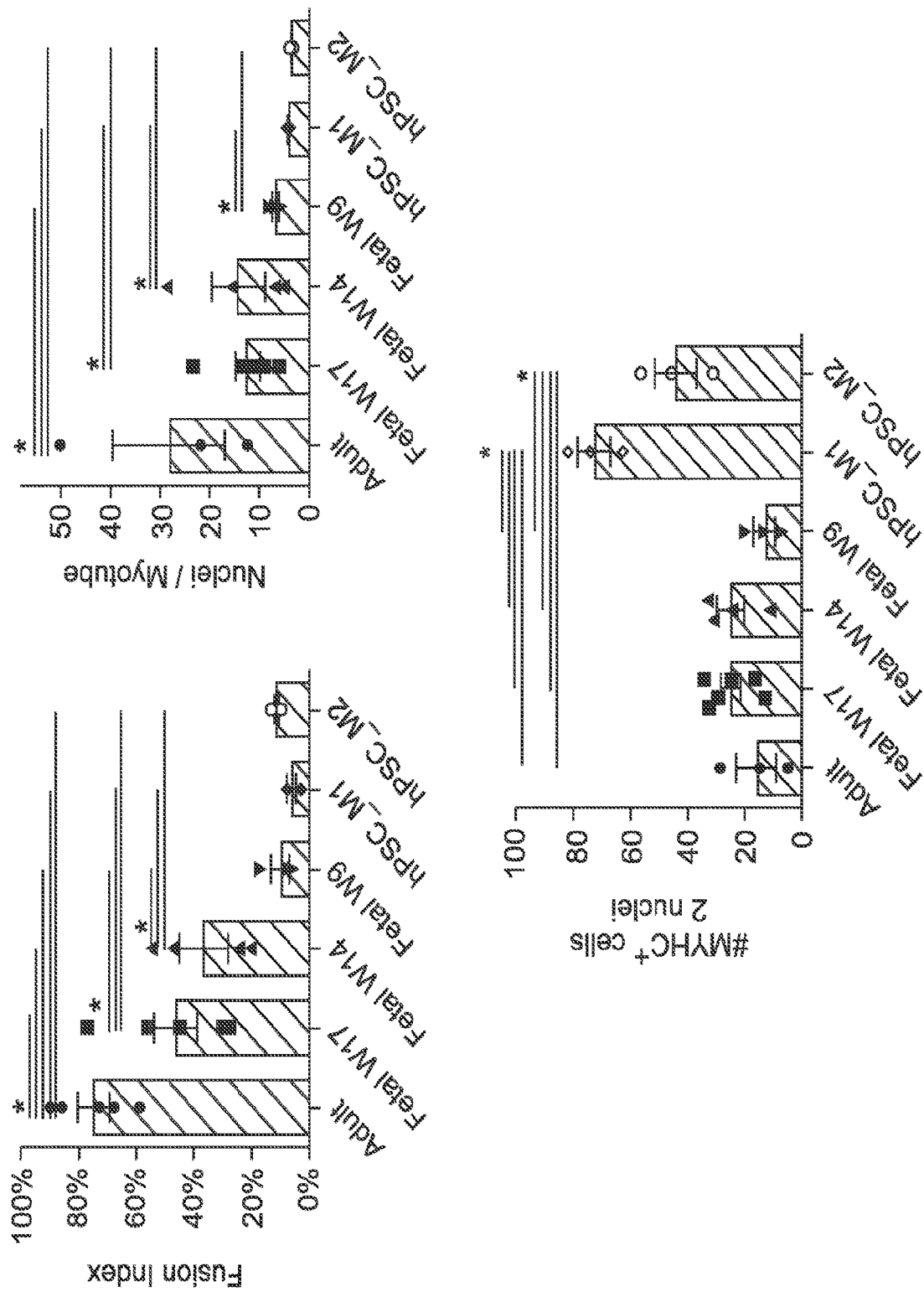
Figure 2B:
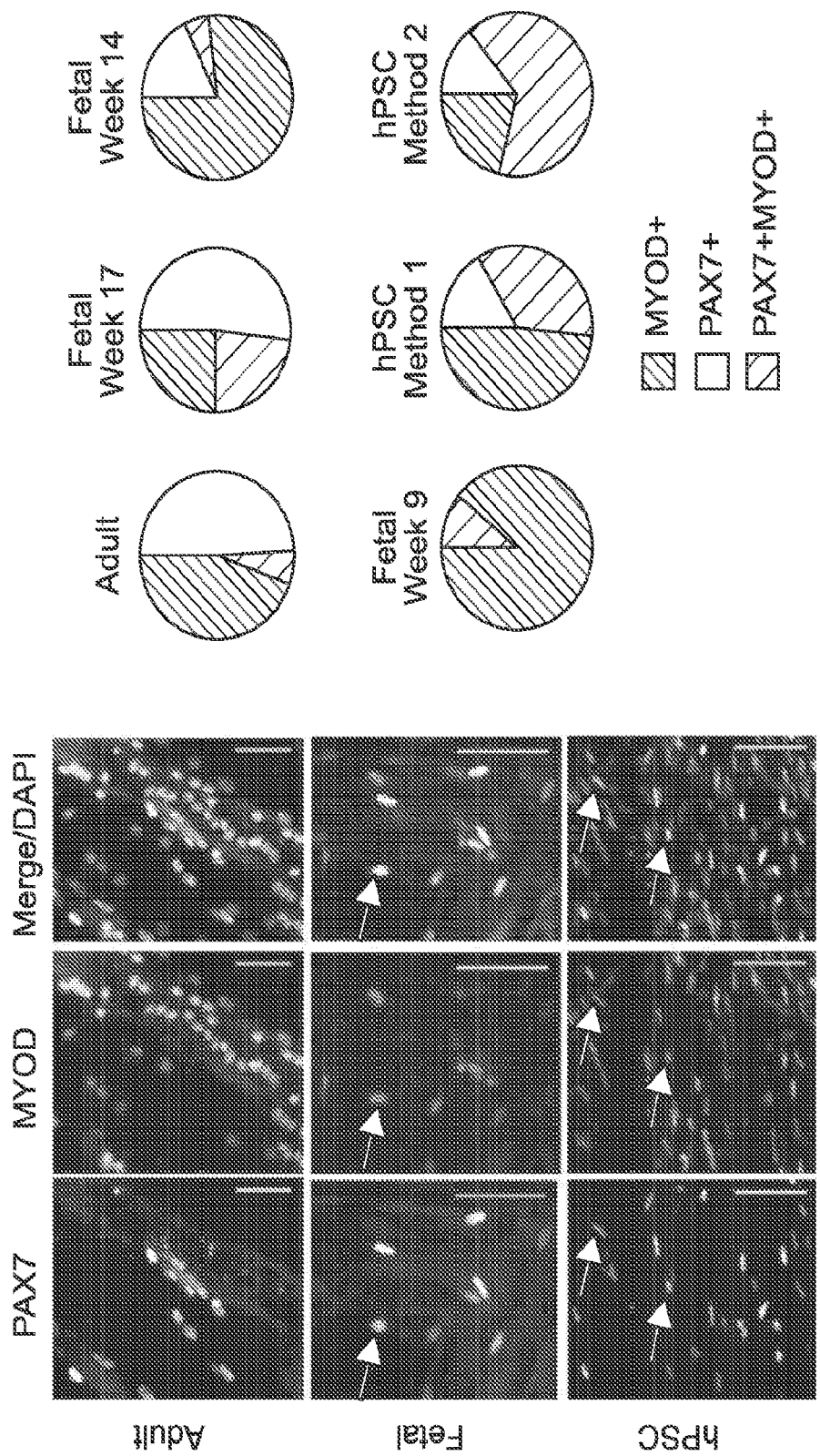

Two separate directed differentiation protocols were used to evaluate directed differentiation of hPSC-SMPCs, as described by (Chal et al., Nat. Biotech. 33, 962-969 (2015); Shelton et al., Stem Cell Reports 3, 516-529 (2014); FIG. 2A-2B). For both directed differentiation protocols, hPSC colonies were cultured in 10 µM ROCK inhibitor for 1 hour prior to being dissociated as single cells in sterile TRYPLE at 37° C. Single cells were collected and centrifuged at 1,000 rpm for 5 minutes. To perform the Shelton et al., protocol single hiPSCs were plated at 375,000 per well (6-well plate), or 75,000 per well (24-well plate) in mTESR containing 10 µM ROCK inhibitor for twenty-four hours to allow for recovery. Single cell hPSCs were then treated with 10 µM CHIR99021 (CHIR; TOCRIS #4423) in E6 medium for two days to induce mesoderm formation. E6 medium was used to differentiate cells from days 2-12. StemPro-34 media containing 20 ng/ml bFGF was added from days 12-20. E6 media was added to cells from days 20-35. At this time point, small $MyHC^+$ myocytes were observed to arise, and N2 media (1% N2 supplement, 1% Insulin-Transferrin-Selenium (ITS, Gibco), and 0.4% P/S) was used to differentiate the SMPCs from days 35-50.

Seeding densities could be slightly modified based on hPSC line. Changes to media coloration during the first ten days were a critical indicator to the overall success of directed differentiation. Too high of a starting seeding density would result in cell death of the pre-somatic lineage cells within the first few days as noted by loss of media discoloration after 24 hours. When this would occur, it is advised to throw away plates and start over as SMPCs would not be generated at the end of 50 days.

To perform the Chal et al., protocol single hiPSCs per were plated at 175,000 per well (6-well plate), or 35,000 per well (24-well plate) in mTESR containing 10 µM ROCK inhibitor for twenty-four hours to allow for recovery. Single cell hPSCs were then treated with 3 µM CHIR (TOCRIS) and 0.5 µM LDN193189 (LDN; STEMGENT #04-0074) in DMEM containing 1% ITS, from days 1-3. FGF-2 (20 ng/ml; R&D Systems) was included to the $CHIR^+LDN$ culture media between days 4-6. CHIR was then removed from media and cells were cultured in 0.5 µM LDN, 10 ng/ml HGF, 2 ng/ml IGF-1, 20 ng/ml FGF-2 was added in DMEM between days 7-8. Cells were then cultured in DMEM, 15% KSR, supplemented with 2 ng/ml IGF1 between days 9-12. From day 13 on, cells were kept in DMEM, 15% KSR supplemented with 10 ng/ml HGF and 2 ng/ml IGF-1. Media was changed every day until day 12, and every second day thereafter.

To monitor success of differentiation, gene expression was measured at days 0, 4, 6, 8, 10, 12, 16, 20, 35, 40, and 50 of directed differentiation for both (Chal et al., Nat. Biotech 33, 962-969 (2015); Shelton et al., Stem Cell Reports 3, 516-529 (2014)) protocols by quantitative polymerase chain reaction (qPCR). For time points between days 0-12 genes OCT4, EN1, T, MIXL1, TBX6, PDGFRa were used to assess somatic lineage development. At later time points PAX7, PAX6, PAX3, TFAP2, MYF5, MYOD, LBX1, MYOG, NKX2.5, TNNT2, NPPA, MYH1, and MYH3 were measured. In the Shelton et al. protocol at time points prior to day 50 few MHC cells had been observed and for passaging (non-FACS) experiments used for in vitro fusion assays cells prior to day 50 were not tested.

Method 1 is used in experiments as shown in FIGS. 1-14. Method 2 was used in experiments as shown in FIGS. 2-3, 5A-5B and FIG. 7F. Other directed differentiation protocols also confirmed the effects of TGF-β inhibition on myotube differentiation (SB-431542; 10 μM) and ERBB3$^+$NGFR$^+$ enrichment of hPSC-SMPCs.

Figure 1B:
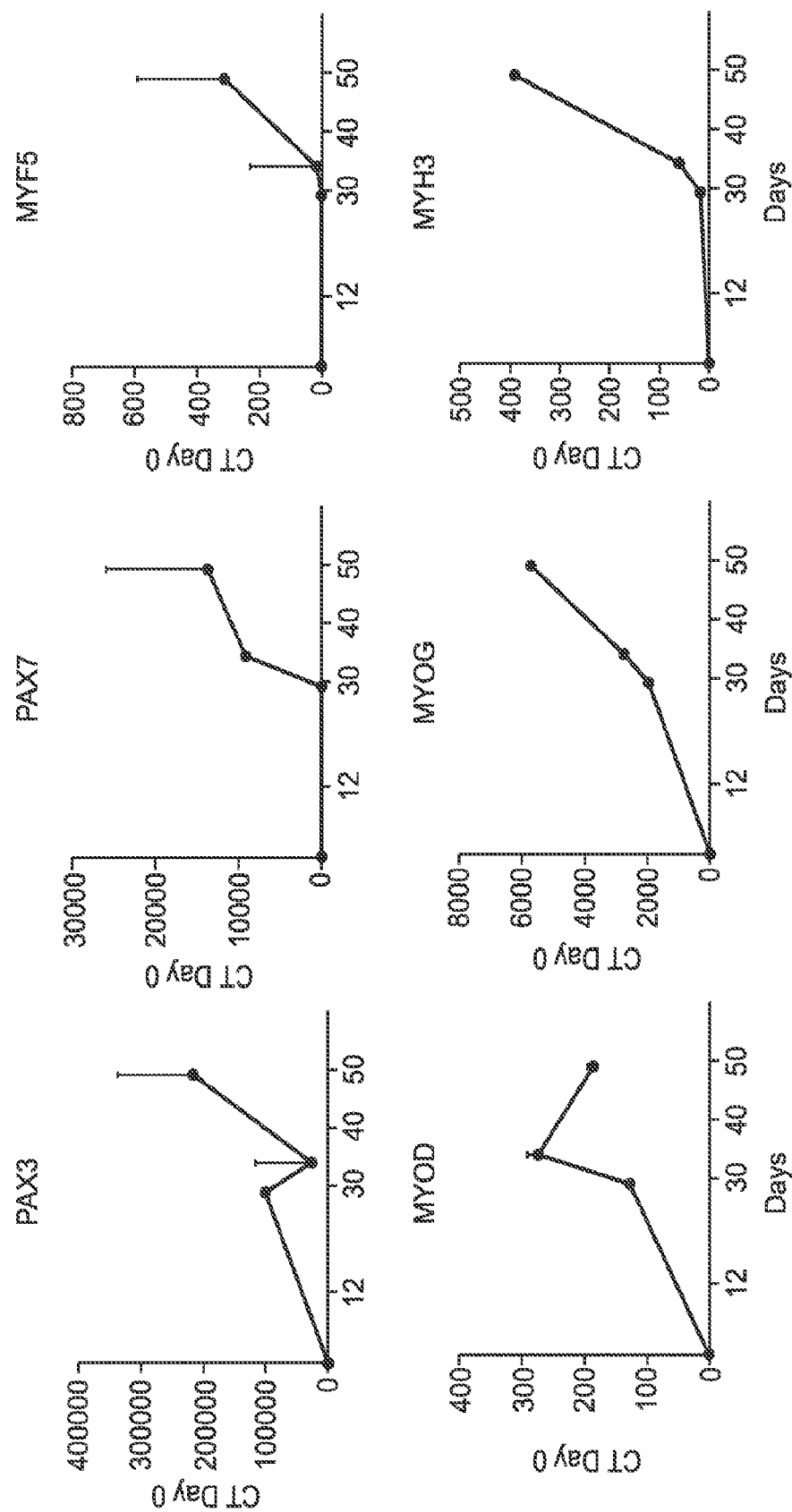

Myogenic gene expression of PAX3, PAX7, MYF5, MYOD, MYOG, and MYH3 were measured at multiple time points by QPCR. (FIG. 1A-1B). Day 50 resulted in the greatest myogenic gene expression for both methods. By day 50 of Method 1, muscle cell contraction was observed in all four independent cell lines tested. Method 2 differentiated faster by day 27 (FIG. 7G); however, to keep comparisons consistent, day 50 was used for analyses.

In Vitro Fusion Assays

HPSC-SMPCs from day 50 cultures were dissociated using TRYPLE and collagenase IV and gently titrated to break apart large three-dimensional structures. HPSC-SMPCs were then filtered through 100-micron meshes to remove left over structures and acquire single cells. HPSC-SMPCs from Methods 1 and 2 were pelleted and seeded at 100,000 cells per well (24-well plate). Separately, these filtered out structures were assayed by quantitative polymerase chain reaction (qPCR) and the cells remaining inside were found to have a neuronal signature. Primary fetal muscle stem cells were directly isolated from tissue, and after 2 days in culture passaged to 100,000 cells per well (24-well plate). Lin-NCAM$^+$ adult satellite cells were plated at 5,000-25,000 cells per well (24-well plate) depending on donor tissue and flow cytometer availability and allowed to grow to 70% confluence, time varied between one-two weeks. Adult satellite cells were not passaged. All cells were cultured in SkBM-2 containing 20 ng/ml bFGF and induced to differentiate in N2 media for seven days. Separate experiments found N2 media was superior to 2% horse serum in its ability to fuse myotubes in all hPSC lines, fetal and adult SCs tested.

To evaluate muscle stem cell ability to differentiate and fuse to form myotubes, cultures were immunostained with MYHC, MYOD, and PAX7, or isotype controls. See IF Staining Section. Primary endpoint measurements included 1) the number of myotubes per square millimeter defined as MYHC cells containing ≥3 nuclei, 2) the number of myocytes per millimeter squared defined as MYHC cells containing ≤2 nuclei, 3) the number of nuclei contained within each myotube or myocyte, 4) the fusion index defined as nuclei in myotubes as a percentage of the total nuclei population, and 5) the differentiation index defined as nuclei in myotubes and myotubes cells as a percentage of the total nuclei population. Three random 10× images (0.621 mm$^2$) were taken per well and images used to count end point measurements using ImageJ. All counted images were exported and saved. At least three separate experiments were repeated, N=3.

Assessment of Population Heterogeneity and Timing of Cell Sorting by FACS to Improve Directed Differentiation and Expansion of hPSC-SMPCs For many directed differentiation protocols, hPSCs form multiple lineages in addition to the primary lineage attempting to be generated i.e. SMPCs. To identify population heterogeneity in hPSC-SMPCs, FACS and immunostaining of candidate lineage markers were performed at days 35-50 of directed differentiation (Method 1) and between days 24-50 (Method 2). In the Shelton et al. protocol, mesenchymal, neuronal, neural crest, cardiac muscle, hematopoietic, and endothelial cell lineages were assessed via expression of CD73 and PDGFRα, TFAP2A, HNK1, VEGFR2, CD45 and CD31, respectively. Both CD73 and PDGFRa were present in cultures at these time points. TFAP2A, VEGFR2, CD45 and CD31 were negligibly expressed in cultures. In later studies it was found that c-MET was primarily expressed by epithelial cells, as evaluated by the expression of epithelial markers E-CAD and TCF2.

For the Chal et al., HNK1 was measured at days 24-50. HNK1 represented a substantial population of cells in these cultures. HNK1 was subsequently removed from all sorting experiments, as it contributed to a major source of non-lineage SMPCs.

To identify the most appropriate time point to acquire HNK1$^-$NCAM$^+$SMPCs, FACS sorted SMPCs from days 35-50 were assessed for myogenic potential from Shelton et al. protocol, and from days 24-50 from Chal et al. protocol. To evaluate PAX7 expression, sorted SMPCs were seeded on 12 mm round bottom coverslips (GG-12-PLL, Neuvitro) coated with Poly-L-Lysine and matrigel. Sorted SMPCs were allowed to settle for 3 hours and then fixed and IF stained for PAX7 or isotype. Alternatively, sorted NCAM SMPCs were seeded at 50,000 per well (24-well plate) and expanded in SkGM-2 (Lonza)$^+$FGF2 until 70% confluence. SMPCs were then differentiated in N2 media and stained with MYHC, MYOD and PAX7. Preliminary studies showed that the Shelton et al. protocol produced the best SMPCs at day 50. While the Chal et al. protocol could produce SMPCs of similar differentiation efficiencies beginning at day 24, to keep experiments consistent Chal et al. SMPCs were isolated and further studied at day 50.

FACS analysis was used to assess mesenchymal, neuronal, neural crest, cardiac muscle, hematopoietic, endothelial cell lineages via expression of CD73 and PDGFRα, N-Cadherin, HNK1, VEGFR2, CD45 and CD31, respectively. Of these markers, HNK1$^+$ neuronal crest cells were most abundant (FIG. 5A), and HNK1$^+$ cells were subsequently removed from all experiments including FIGS. 5-8, 10A-10D, 10F, 11, and 12A-12E.

To identify the most appropriate time point to enrich hPSC-SMPCs, a pilot study containing three independent wells FACS sorted HNK1$^+$NCAM$^+$SMPCs from days 35, 40 and 50 (Method 1), and from days 24, 30, and 50 (Method 2). For method 1, sorted cells at day 50 produced the greatest number of MYHC$^+$ cells, and for method 2, days 30 and 50 produced the greatest number of MYHC$^+$ cells.

To evaluate PAX7 expression, sorted hPSC-SMPCs were seeded on 12 mm round bottom coverslips (GG-12-PLL, Neuvitro) coated with Poly-L-Lysine and matrigel. Sorted hPSC-SMPCs were allowed to settle for 3 hours and then fixed and immune-stained for PAX7 or mouse IgG1 isotype.

Figure 5A:
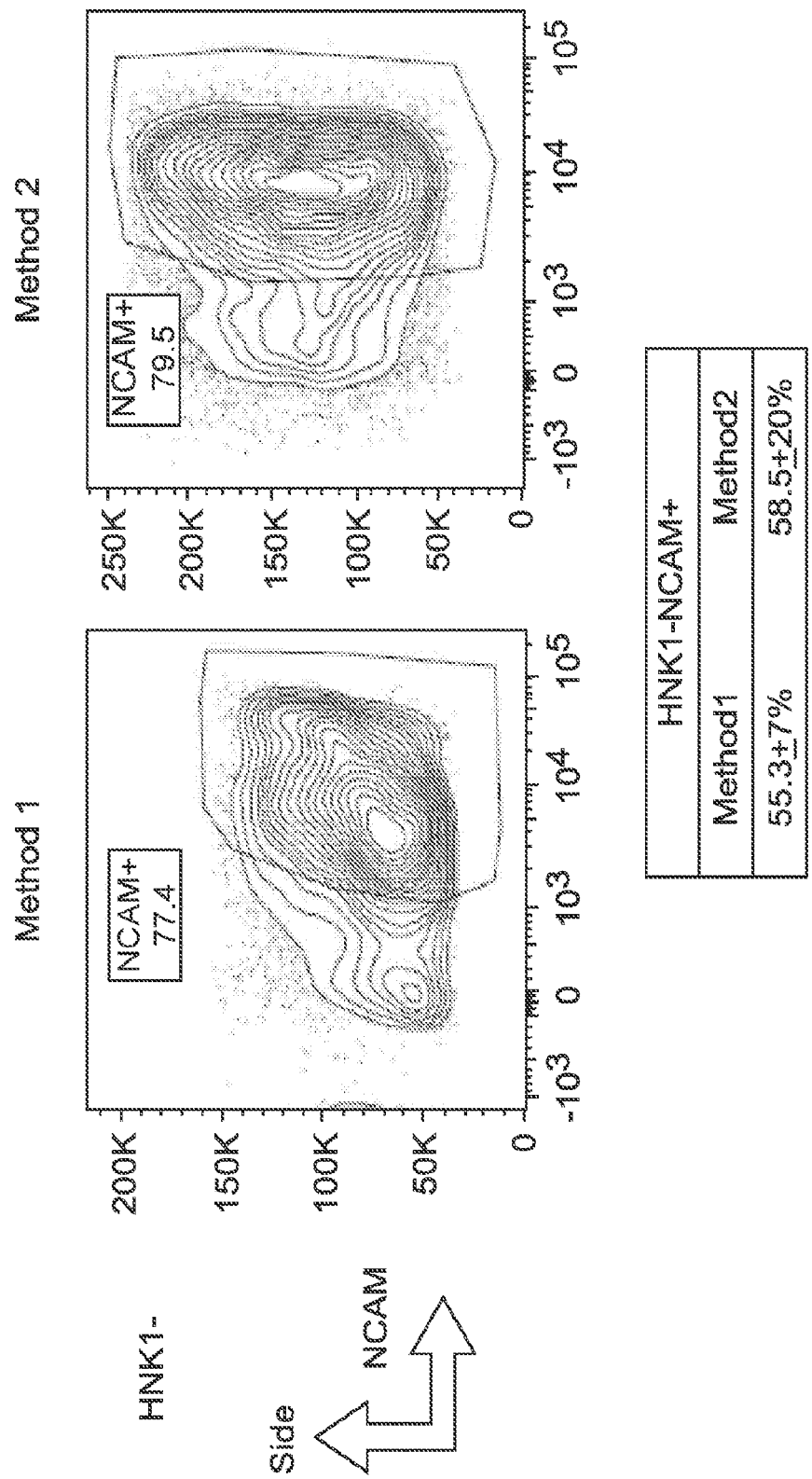
Figure 5A:
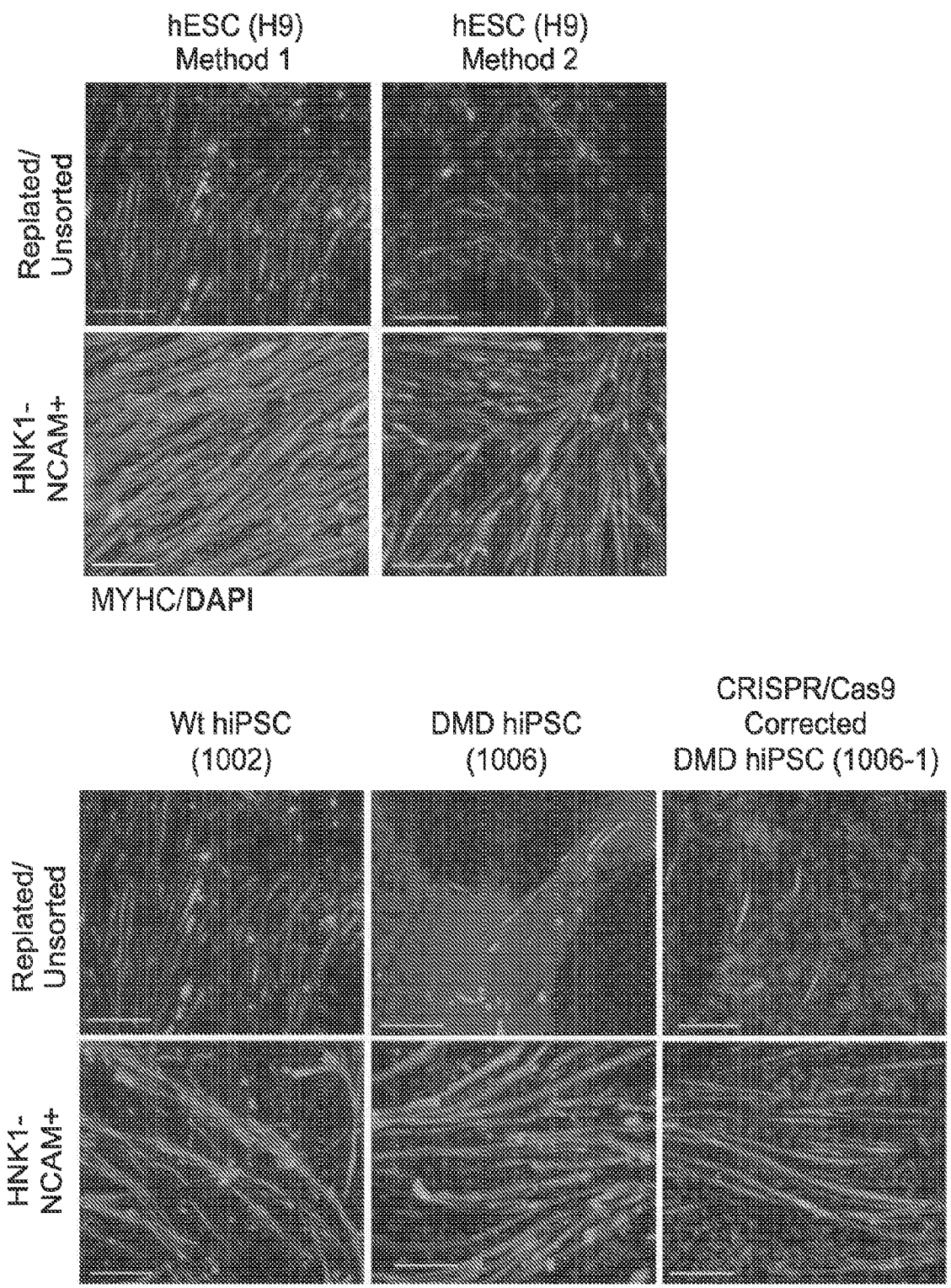
Figure 5A:
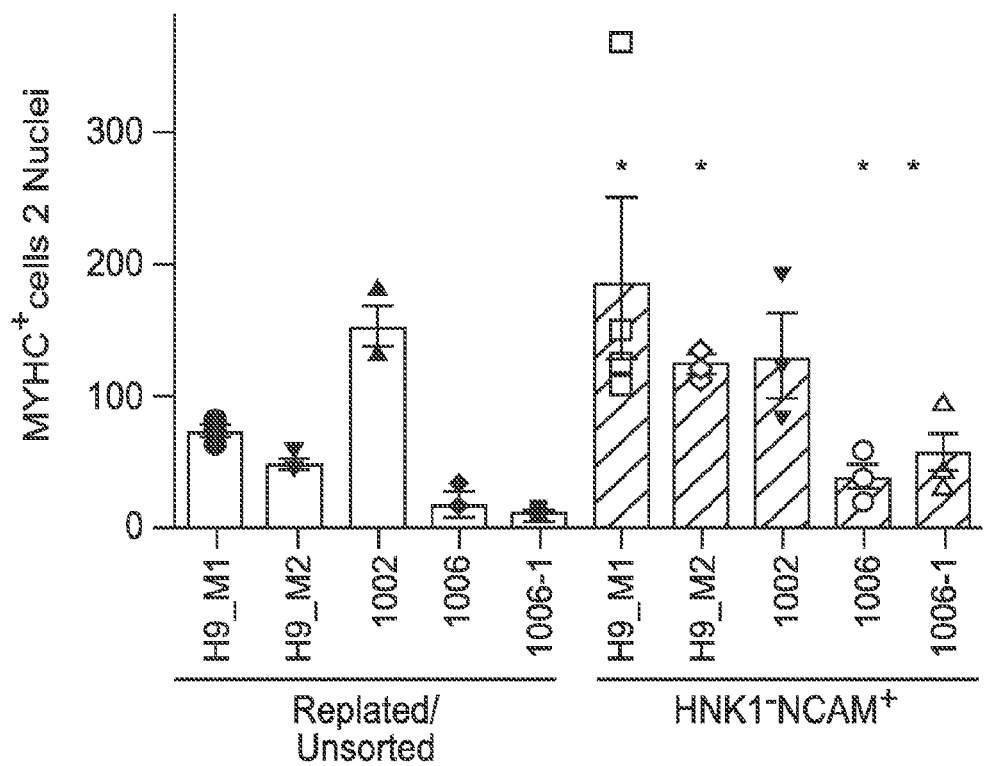

Alternatively, cells were collected in SkBM-2 and immediately lysed for QPCR and PAX7 gene expression was measured (FIG. 5A).

Assessment of Growth Factors to Improve Directed Differentiation and Expansion of hPSC-SMPCs To improve on the directed differentiation of hPSC-SMPCs candidate growth factors fibroblast growth factor 2 (FGF2) (10 ng/ml), epidermal growth factor (EGF) (10 µg/ml), HGF (200 ng/ml), insulin-like growth factor (IGF) (100 ng/ml), and combinations were tested for their ability derive and differentiate SMPCs from hPSCs (Rommel et al., Nat. Cell Biol 3, 1009-1013 (2001)). Furthermore, while Chal et al. include growth factors HGF, IGF, and FGF2 to direct differentiation hPSC-SMPCs, they do not report on the individual and/or combined contributions of these growth factors. Thus, the role of these growth factors in directed differentiation was investigated.

To test the ability of growth factors to capture $PAX3^+$ cells and specify their differentiation to $PAX7^+$ cells, growth factors were added daily between days 20-35 of the Shelton et al. protocol during E6 media phase. Muscle markers: PAX7, MYF5, MYOD, MYOG, MYHC3, DMD, and TFAP2A, were evaluated to E6 media (no treatment) at day 35 via qPCR, and expressed as fold-change versus day 20 of directed differentiation. All growth factors tested decreased the expression of myogenic markers compared to E6 media alone. HGF completed eliminated myogenic marker expression and EGF increased the expression of neuronal marker TFAP2A.

Between days 35-50, addition of IGF, HGF, and combined growth factors in N2 media were tested for their ability to differentiate SMPCs to myotubes. Muscle markers: PAX7, MYF5, MYOD, MYOG, and MYH3 were evaluated to N2 media (no treatment) at day 50 via qPCR, and expressed as fold-change versus day 35 of directed differentiation. Addition of IGF (but not HGF) increased all myogenic markers compared to medium alone. IGF alone was also more potent than $IGF^+HGF$.

After day 50 during passaging and expansion experiments, removal of FGF2 from the basal media of passaged SMPCs activated MYOD, and thus FGF2 was important for helping maintain PAX7 expression during progenitor expansion for at least 3 passages (FIG. 4B). It was found that 20% FBS, 1% CEE, FGF2 in DMEM/F12 activated SMPCs to express MYOD more readily and these cells would lose myogenic potential after 3 passages.

At day 50, myogenic genes PAX7, MYF5, MYOD, MYOG, and MYH3 were measured by QPCR and expressed as fold-change versus day 35 of directed differentiation. Addition of IGF-1, but not HGF, increased myogenic markers. Subsequently, IGF-1 was added to N2 media in all experiments (FIGS. 5-8, 10A-10D, 10F, 11, and 12A-12E). SkBM-2 media (containing EGF, Insulin, Dexamathesone, 10% FBS) was found to better support $PAX7^+$ cells after passaging. The addition of FGF2 in SkBM-2 further helped to decrease MYOD and MYOG expression (data not shown). Subsequently, FGF2 was added to SkBM-2 media in experiments (FIGS. 5-8, 10A-10D, 10F, 11, and 12A-12E).

Sample Collection for RNA Sequencing and Analyses

Week 17 fetal skeletal muscle cells (passage 2) were labeled with $CD45^-CD31^-NCAM^+$ and hPSC-SMPCs (H9) after 50 days of directed differentiation labeled with $HNK^-NCAM^+$, and FACS sorted. Cells were collected in SkBM-2 and RNA was isolated using RNeasy Microkits (Qiagen). Alternatively, FACS-sorted fetal and hPSCSMPCs were cultured in N2 for 7 days to form myotubes and then collected for sequencing. Week 17 fetal muscle cells were also taken directly from upper leg muscles and RNA immediately isolated, N=2 for all samples. RNA was taken to UCLA's Jonsson Comprehensive Cancer Center (JCCC) for sequencing on the Illumina HiSeq 3000 using KAPA amplification. Samples were sequenced with 13-15 million reads.

Samples were aligned in TopHat (v2.0.8b) (Trapnell et al., Bioinformatics 25, 1105-1111 (2009)) to the human genome (hg19, UCSC) and Ensembl *Homo sapiens* GTF file (GRCh37). The average alignment rate per sample was 88.82% and average reads aligned per sample was 15,365,455. Cufflinks (v2.1.1) (Trapnell et al., Nat. Biotech28, 511-515 (2010)) was used to assess gene expression per sample and Cuffdiff from Cufflinks was used to evaluate differentiation expression. Genes with an FDR q-value threshold of 0.05 were considered significant. These genes were submitted to the Database for Annotation, Visualization and Integrated Discovery (DAVID) (Huang et al., Nucleic Acids Research 37, 1-13 (2009); Lempicki, Nature Protocols 4, 44-57 (2009)) to find biological meaning among the samples. Select gene ontology terms with Bonferroni value $<P$ 0.05 are shown (Tables 1-3 of FIG. 17A-17C). Heatmap was created in R, version 3.2.3, using packages "gplots" and "pheatmap." Data was loaded into Gene Expression Omnibus (http://www(dot)ncbi(dot)nlm(dot)nih(dot)gov/geo/) with accession number to be included with final submission. Select gene ontology terms with are shown (FIG. 6A-6B) and all gene ontology $P<0.05$ are included in Tables 1-3 of FIG. 17A-17C. Heatmaps were created in R, version 3.2.3, using packages "gplots" and "pheatmap." Data was loaded into Gene Expression Omnibus (http://www(dot)ncbi(dot)nlm(dot)nih(dot)gov/geo/) with accession number (NCBI #GSE87365). Gene Set Enrichment Analysis (GSEA) was used to determine whether an a priori defined set of genes was statistically significant between groups. Gene set permutation was used.

For gene lists of key biological processes upregulated by $CD31^-CD45^-NCAM^+$ cultured fetal muscle cells and $HNK1^-NCAM^+$ hPSC-SMPCs, differentially expressed genes identified by RNA Seq (Q<0.05). Genes were uploaded into The Database for Annotation, Visualization and Integrated Discovery (DAVID) and all biological processes $<p$ 0.05 are shown.

For gene lists of key biological processes upregulated by directly-isolated fetal muscle cells and hPSC-SMPCs. Differentially expressed genes identified by RNA Seq (q<0.05). Genes were uploaded into The Database for Annotation, Visualization and Integrated Discovery (DAVID) and all biological processes $<p$ 0.05 are shown.

For gene lists of key biological processes upregulated by directly-isolated fetal muscle cells and $CD31^-CD45^-NCAM^+$ cultured fetal muscle cells. Differentially expressed genes identified by RNA Seq (q<0.05). Genes were uploaded into The Database for Annotation, Visualization and Integrated Discovery (DAVID) and all biological processes $<p$ 0.05 are shown.

Utilization of WGCNA from Fetal Musculoskeletal Tissues to Identify Candidate Cell Surface Markers The raw sequencing data for the muscle specific gene set used to generate the Weighted Gene Co-Expression Network Analysis (WGCNA) across musculoskeletal tissues is available in Geo using accession number (GSE106292). To identify muscle-specific cell surface receptors, a WGCNA dataset of fetal week 17 musculoskeletal tissue was utilized including: chondrocytes ($Lin^-CD146^-BMPR1B^+$), Osteoblasts ($Lin^-ALP^+$), myoblasts ($Lin-CD56^+CD146$) and ligament and tendon ($Lin^-$) isolated and purified by flow cytometry. WGCNA analysis produced a list of over 400 genes associated with muscle-specific receptors or membrane proteins. To identify candidate enrichment markers, genes were cross-referenced to known myogenic markers in Pubmed NCBI. From these data, NCAM (CD56), MCAM (CD146), ITGA7, ERBB3, NGFR (CD271), CXCR4, and ITGAM (CD11B) were selected for further analysis. Although not enriched in the fetal muscle module, c-MET and CD82 were included in analyses.

Subpopulation FACS Analyses of Human Fetal Week 9-18 Muscle Cells and hPSC-SMPCs From RNA-SEQ data a list of candidate receptors that were highly upregulated in Lin-NCAM$^+$ human fetal were chosen from a list of over 400 genes. Data sets were further cross-referenced with a tissue-specific gene list of human week 17 fetal specimens. Weighted gene coexpression network analysis (WGCNA) with essentially no reads in other tissues was further used to select candidates for hPSC-SMPC subpopulation analyses and enrichment.

In other experiments, ITGB1, CXCR4, and M-Cadherin were tested on day 50 unsorted hPSC-SMPCs. ITGB1 was strongly expressed by all hPSC-SMPCs, thus was a poor enrichment marker. Both CXCR4 and M-Cadherin showed a small shift in positive cells. CXCR4 showed a greater positive and distinctive shift and was selected for further evaluation.

In additional experiments immediately dissociated human fetal muscle from week 13 and week 18 limb were stained for NCAM, MCAM, c-MET, ITGA7, ERBB3, and NGFR. Live/dead cell viability dye (APC-Cy7) and Lineage negative CD235a, CD45, and CD31 were used to exclude non-muscle cells. Samples were analyzed on the Becton Dickinson Fortessa in UCLA's Broad Stem Cell Research Center (BSCRC) flow cytometry core. FlowJo-OSX version 10 was used for analyses of surface receptor expression.

At day 50, cell lines of directed differentiation cultures were FACS sorted for the following surface markers: 1006 (NCAM, MCAM, NGFR, CD11b), 1006-1 (all), 1002 (NCAM, ERBB3, NGFR, NGFR$^+$ERBB3$^+$), and H9 (NCAM, ITGA7, NGFR). Uncultured fetal cells were additionally FACS sorted for ERBB3, NGFR, NGFR$^+$ERBB3$^+$, and negative populations and 15,000 cells used per cytospin chamber for analyses of PAX7 and MYTOD. For hPSC-SMPC subpopulation experiments, typically 100,000-500,000 SMPCs were isolated for culture, however as few as 10,000 cells could be successfully isolated. Cells were collected in SkBM2$^+$FGF2, plating in matrigel-coated plates and allowed to recover from flow for several days. Cells could then be expanded, cryopreserved, or assessed for myogenic activity in vtiro and in vivo. QPCR for FIG. 4C took place on subpopulations after three passages, between 7-14 days after sorting to allow for sufficient expansion. Levels of PAX7 or MYOD may be higher immediately after sorting from directed differentiation cultures as was using NCAM sorted cells.

Enrichment of ERBB3+NGFR+hPSC-SMPCs and Human Fetal Muscle

Human fetal muscle at weeks 9-18 were dissociated as described, or hPSC-SMPCs were taken from directed differentiation. Cells were filtered through 100 μm meshes, washed in PBS, and re-suspended in FACS buffer (2% FBS in PBS) at a concentration of 5×10$^6$ cells/ml. Human Fc block was used to prevent non-specific binding, but additional brilliant violet (BV) dye blocking was not used. In samples containing BV antibodies, far-red live/dead cell viability dye (Thermo-Fisher L10120) was used, instead of DAPI to prevent fluorescent spillover. In all FACS experiments, fetal and hPSC-SMPCs were stained for ERBB3, NGFR, MCAM, CD82 and NCAM, and lineage negative markers CD235a, CD45, and CD31 used to exclude non-muscle cells. Samples were labeled with antibodies for 45 minutes at 4 C, filtered through 40 μm tubes, and analyzed by the Becton Dickinson Fortessa, or sorted using an ARIA-II flow cytometers in UCLA's Broad Stem Cell Research Center flow cytometry core. Fluorescence minus one (FMO) controls were used as gating controls in all experiments. Samples were analyzed in FlowJo-OSX version 10.

Figure 7A:
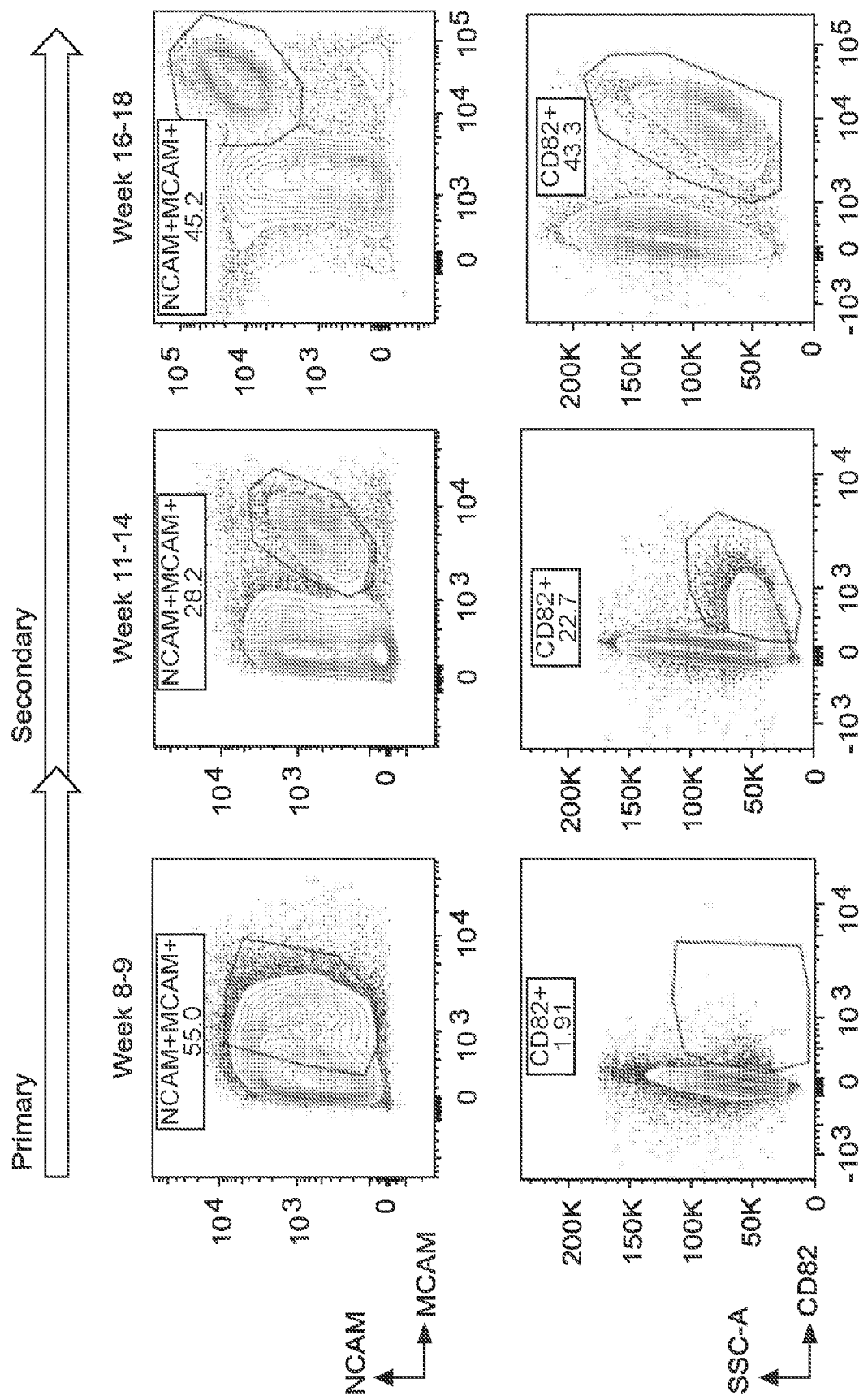
Figure 7A:
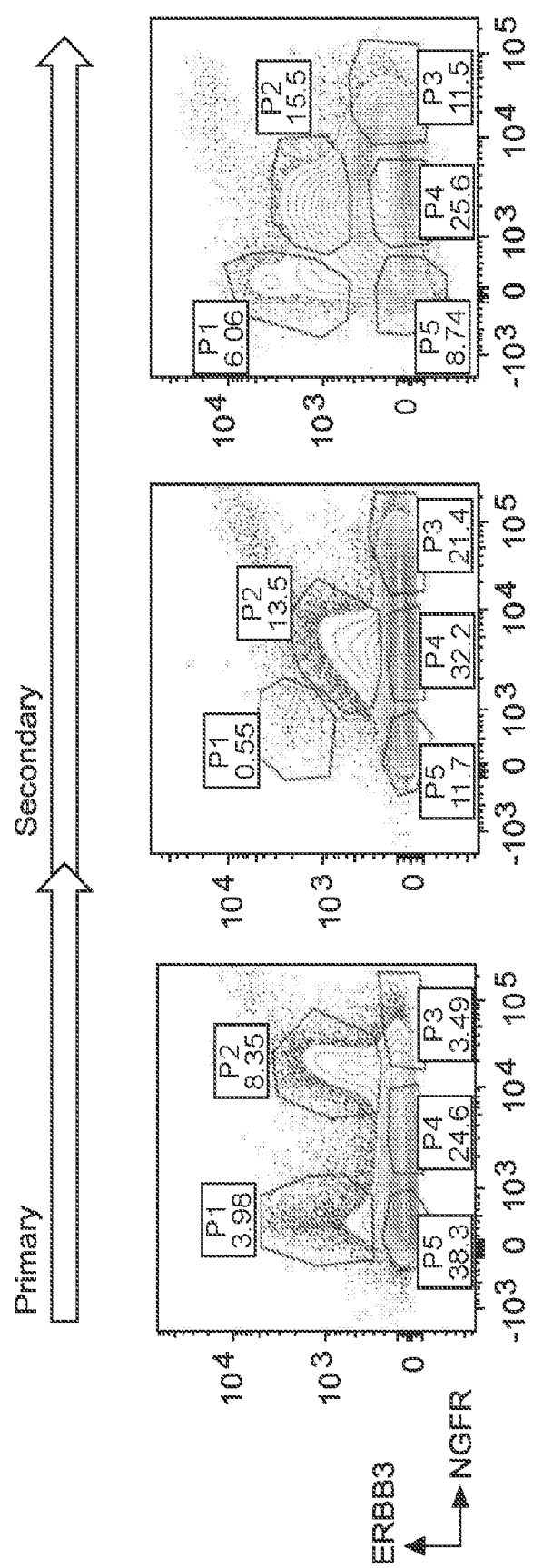
Figure 12B:
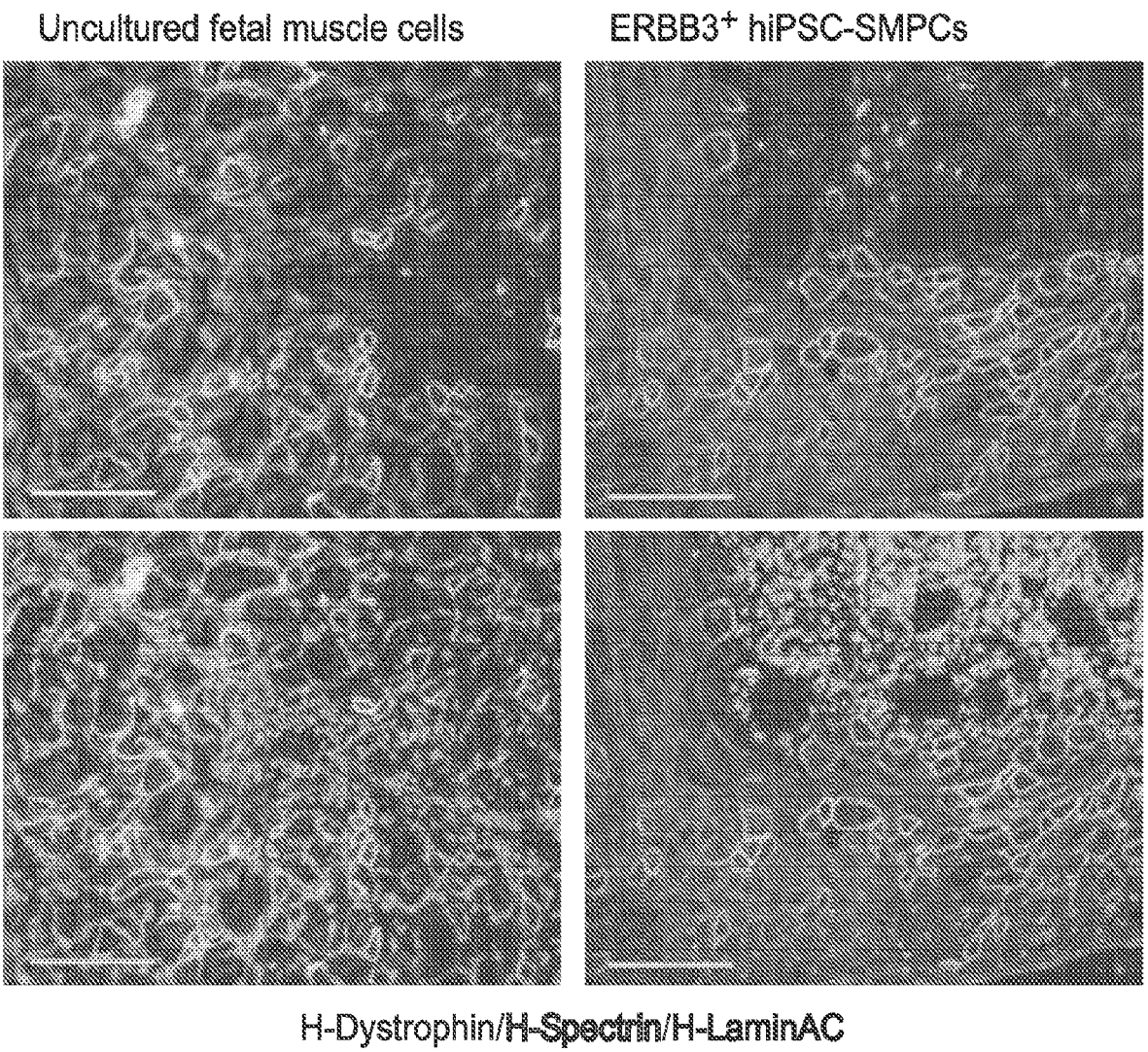

For hPSC-SMPC experiments, 200,000 ERBB3$^+$NGFR$^+$ cells were typically isolated per 6-well of directed differentiation culture, but as few as 10,000 cells could be successfully cultured. Cells were collected in SkBM-2$^+$bFGF, seeded on matrigel-coated culture plates, and allowed to recover from FACS for 3-5 days. Cells were then passaged for in vitro experiments, engrafted for in vivo experiments, or cryopreserved using 10% DMSO in 90% FBS. Four directed differentiation protocols were tested for ability to enrich HINK1$^-$ERBB3$^+$NGFR$^+$ SMPCs. While variability in myogenic potential exists, in all protocols, ERBB3$^+$NGFR$^+$ cells were the most myogenic (FIG. 7G). When using a single marker, ERBB3 was best able to enrich for muscle progenitors with in vitro and in vivo myogenic potential (FIG. 12A-12B).

Myogenic activity in vitro was assessed up to 10 passages or in vivo less than 4 passages. Longer culturing periods decreased myogenic activity in vitro and in vivo. Upon culturing, double positive ERBB3$^+$NGFR$^+$ populations were found to increase NGFR positivity (ERBB3$^+$NGFR$^{+Hi}$) by FACS analysis. When sorted on ERBB3$^+$NGFR$^{+Hi}$, both cultured/passaged week 17 fetal cells and passaged hPSC-SMPCs were enriched for myogenic markers, but expressed significantly higher levels of MYOG compared to uncultured fetal muscles or non-passaged hPSC-SMPCs. Thus, ERBB3$^+$NGFR$^{+Hi}$ expressing cultured cells activate after continuous passaging suggesting these muscle progenitors cannot be expanded or supported as myogenic cells for long periods.

TGFβ Regulates Skeletal Muscle Differentiation and Maturation Across Three Independent hPSC Lines.

To test effects of TGFβ on SMPC differentiation, small molecule inhibitors of TGFβ signaling, SB-431542; and A83-01 were evaluated. SB-431542 was more potent than A83-01 (1-20 μM, data not shown), and SB-431542 (10 μM) is shown in FIG. 10B-10D, 10F, 12A-12E, and 11A-11B. Recombinant TGFβ1 (10 ng/ml, Peprotech) was also evaluated. NCAM$^+$ or ERBB3$^+$ hPSC-SMPCs were differentiated for 5-7 days in N2 media+/−TGFβi, (FIGS. 11A-11B, 10B-10D, and 10F). To evaluate maturation status, wild type hiPSC-SMPCs (1002), fetal week 14 and 17 muscle progenitors, and adult SCs were cultured in parallel. Three subpopulations of hPSC-SMPCs, negatively sorted for HNK1$^-$, were tested: NCAM$^+$, ERBB3$^+$, and double positive ERBB3$^+$NGFR$^+$. All muscle cells were treated with TGFβi (SB-431542, 10 μM) or TGFβ (10 ng/ml) in N2 media containing IGF-1 for 7 days (FIG. 12C-12E). Cells were immunostained or evaluated by QPCR.

Engraftment Procedures

Mdx/C57BL10 mice were crossed to Nod scid gamma (NSG) mice. Each pup was breed and genotyped for homozygosity (mdx-NSG) using Transnetyx. Mdx-NSG mice were housed in the Humanized Mouse Core at UCLA, an immunocompromised core facility. All animal work was conducted under protocols approved by the UCLA ARC in the OARO. Mdx-NSG mice ages 6-8 weeks were subjected to a muscle injury by intramuscular injection of 50 µl of 10 µM cardiotoxin (Naja Mossambica-Mossambica, Sigma), 24 hours prior to cell injections.

To prepare cells for transplantation, hPSC-SMPCs were dissociated using TRYPLE and titrated to break apart three-dimensional (3D) structures. SMPCs were filtered through 100 um meshes, centrifuged at 600 g, and resuspended in Hank's Balanced Salt Solution (HBSS) at $1 \times 10^6$ cells/per 5 µls. FACS-sorted hPSC-SMPCs were expanded in SkBM-2+bFGF for less than three passages, or less than seven days to prevent precocious MYOD activation. Cultured fetal muscle were dissociated from tissue and cultured in SkBM-2+bFGF for three passages before engraftment. Directly-isolated fetal muscle cells were dissociated as described, and immediately transplanted. Pelleted cells were kept at 4° C. and transported to the Mouse Core. Mice were anesthetized using 2% isofluorane, and 5-10 µl of cells in solution were injected into the tibialis anterior (TA) muscle using Hamilton micro-syringes.

For irradiation experiments, a custom chamber was built using 3 cm thick cerrobend shielding block which allowed mouse hind limbs to be selectively irradiated. Mice were subjected to 18-gray gamma irradiation over a 12.2-minute period using a cesium-137 irradiator. Mice were anesthetized with ketamine during the procedure and treated with 500 cc saline daily to control for weight loss. Cardiotoxin was performed 24 hours post irradiation, and cells injected 48 hours post irradiation. An increase in HNK1$^-$NCAM$^+$ hPSC-SMPC engraftment following irradiation (N=9 mice; Table 5 of FIG. 13) was not observed.

For engraftment experiments using TGFβi, 10 µM SB-431542 was added to cell suspension in HBSS and co-delivered during cell injections. 30 □L of 10 µM SB-431542 was injected intramuscularly every third day for two weeks post-engraftment. As a control, HBSS was injected at corresponding time points. All mice survived engraftment procedures and TGFβ treatment.

After 30 days, mdx-NSG mice were euthanized and TA muscles dissected and immediately embedded in OCT compound and flash-frozen in isopentane cooled by liquid Nitrogen. Embedded muscles were stored at −80° C. until sectioned in 9-10 µm slices using a Leica microcryotome (LSXII). To determine the position of each cross section for cell engraftment quantification, 1200 µm of TA muscle were removed and 20 sections collected on positively-charged microscope slides in 50 µm intervals, and 300 µm of tissue were collected for RNA or western blots. Serial quadrants were collected until the entire TA was sectioned. Microscope slides were kept in aluminum foil covered boxes at −20° C.

Testing the Effects of TGFβ Skeletal Muscle Differentiation and Maturation in hPSC Lines Two small molecules inhibitors of TGFβ signaling, SB-431542, a specific inhibitor of TGFβR1 Activin receptor-like kinases (ALK) 4, 5 and 7, and SMAD3 phosphorylation (Inman et al., Molecular Pharmacology 62, 65-74 (2002)); and A83-01, a selective inhibitor of TGFβRI, ALK4 and ALK7 and SMAD2 phosphorylation (Tojo et al., Cancer Science 96, 791-800 (2005)) were evaluated. Initially, 10 µM of each small molecule were independently tested. Subsequently, concentrations between 1-20 µM of SB-431542 were tested on wild-type hiPSCs. Recombinant TGFβ1 (10 ng/ml) was included to evaluate the opposing role of exogenous TGFβ in regulating myogenic activity. Three independent lines: hESC (H9), DMD hiPSCs (1006), CRISPR/Cas9 DMD hiPSCs (1006-1), and wild type hiPSC (1002) were used to measure differentiation. 1006 and 1006-1 lines are shown in FIGS. 5A-5B. H9 lines are not shown, but demonstrated similar effects. NCAM hPSC-SMPCs were differentiated for 7-10 days in N2 with or without TGFβi. Cells were immunostained or evaluated by QPCR using standard methods.

To further compare the maturation status of hPSC-SMPCs, wild type hiPSC-SMPCs (1002), fetal week 14 and 17, and adult satellite cells were cultured in parallel. Three subpopulations of hiPSC-SMPCs, negatively sorted for HNK1, were used: NCAM$^+$, ERBB3$^+$, and double positive ERBB3$^+$NGFR$^+$. Muscle tissue muscles were cultured and differentiated in N2 for 7 days. All groups were treated with or without TGFβi (SB-431542, 10 µM), in N2 media+IGF1 for 7 days. At this time cells were fixed for immunostaining or RNA collected for QPCR.

Transmission Electron Microscopy

HPSC subpopulations and fetal muscle cells were differentiated±TGFβi for 7 days on EM-grade plastic coverslips coated in matrigel 1:50. Cells were fixed in 4% PFA and 1% glutaraldehyde overnight. Cells were taken to the Electron Microscopy Core Facility for processing. A Reichert Ultracut ultramicrotome was used to thinly section tissue. Cells were imaged using a JEOL 100CX transmission electron microscope.

RT-PCR Validation and Primers

Primers were designed using the NCBI primer blast tool. Primer validation was performed using SMPCs/satellite cells (SCs) or myotubes known to express the following genes. CDNA concentrations were diluted serially by 5-fold from 1× to 1/625× beginning at 5 ng/µL. PCR efficiencies were calculated and primers with 0.9-1.1 efficiency were used for experiments.

TABLE 4

| Primer/Gene | Forward Sequence 5'-3' | Reverse Sequence 5'-3' |
|---|---|---|
| GAPDH | CGC CCC CGG TTT CTA TAA ATT G (SEQ ID NO: 1) | AAG AAG ATG CGG CTG ACT GT (SEQ ID NO: 2) |
| PAX3 | AGC TCG GCG GTG TTT TTA TCA (SEQ ID NO: 3) | CTG CAC AGG ATC TTG GAG ACG (SEQ ID NO: 4) |
| PAX7 | CTG GCC AAA AAT GTG AGC CT (SEQ ID NO: 5) | TAG GGT TGG GCT GGG AAT TG (SEQ ID NO: 6) |
| MYOD | TTA ACC ACA AAT CAG GCC GG (SEQ ID NO: 7) | CAA AGT GCT GGC AGT CTG AAT G (SEQ ID NO: 8) |
| MYOG | AGA TGT GTC TGT GGC CTT CC (SEQ ID NO: 9) | AGC TGG CTT CCT AGC ATC AG (SEQ ID NO: 10) |

TABLE 4-continued

| Primer/Gene | Forward Sequence 5'-3' | Reverse Sequence 5'-3' |
|---|---|---|
| MYF5 | TGC CCT TGT TAA TTA CCG GAG CGA (SEQ ID NO: 11) | TAT GCA GGA GCC GTC GTA GAA GT (SEQ ID NO: 12) |
| HEYL | GGA AGA AAC GCA GAG GGA TCA (SEQ ID NO: 13) | CAA GCG TCG CAA TTC AGA AAG (SEQ ID NO: 14) |
| HES1 | CCT GTC ATC CCC GTC TAC AC (SEQ ID NO: 15) | CAC ATG GAG TCC GCC GTA A (SEQ ID NO: 16) |
| DMD | ACC TAT TGG AGG CGA CTT TCC (SEQ ID NO: 17) | TCC TTC CAA AGG CTG CTC TG (SEQ ID NO: 18) |
| MYH1 | CCT TCT GGA GCA GGA CAG AA (SEQ ID NO: 19) | CAA AGC AAA GTT TAT TGC ATG TG (SEQ ID NO: 20) |
| Myh3 | ATT GCT TCG TGG TGG ACT CAA (SEQ ID NO: 21) | GGC CAT GTC TTC GAT CCT GTC (SEQ ID NO: 22) |
| MYH4 | GTA GTT GTC TGC TTT GAG CCT G (SEQ ID NO: 23) | TTG TAG GGG TTG ACG GTG AC (SEQ ID NO: 24) |
| MYH8 | AAT GCA AGT GCT ATT CCA GAG G (SEQ ID NO: 25) | ACA GAC AGC TTG TGT TCT TGT T (SEQ ID NO: 26) |
| TFAP2 | CTG AAT TTC TCA ACC GAC AAC A (SEQ ID NO: 27) | CAT ATC TGT TTT GTA GCC AGG AG (SEQ ID NO: 28) |
| NKX2.5 | GTT GTC CGC CTC TGT CTT CT (SEQ ID NO: 29) | TCT ATC CAC GTG CCT ACA GC (SEQ ID NO: 30) |
| E-CAD | CGAGAGCTACACGTTCACGG (SEQ ID NO: 31) | GGGTGTCGAGGGAAAAATAGG (SEQ ID NO: 32) |
| COL3A1 | GGAGCTGGCTACTTCTCGC (SEQ ID NO: 33) | GGGTGTCGAGGGAAAAATAGG (SEQ ID NO: 34) |
| αSMA | AAAAGACAGCTACGTGGGTGA (SEQ ID NO: 35) | GCCATGTTCTATCGGGTACTTC (SEQ ID NO: 36) |
| TCF21 | TCCTGGCTAACGACAAATACGA (SEQ ID NO: 37) | TTTCCCGGCCACCATAAAGG (SEQ ID NO: 38) |
| MAPK14 | TAA GGC GCC CTC AAG ATC AA (SEQ ID NO: 39) | GAG CTT CTT CAC TGC CAC AC (SEQ ID NO: 40) |
| ENO3 | GGCTGGTTACCCAGACAAGG (SEQ ID NO: 40) | TCGTACTTCCCATTGCGATAGAA (SEQ ID NO: 41) |
| CKM | CTGACAAGCACAAGACTGACC (SEQ ID NO: 42) | CTGCTGAGCACGTAGTTAGGG (SEQ ID NO: 43) |

IF Staining Protocol and Antibodies Used

Embryonic, fetal, or adult SMPCs or myotubes were washed in PBS and fixed in 4% PFA for 15 minutes. Cells were washed and permeabilized with 0.3% Triton-X for 5 minutes. Cells were then blocked in 10% goat serum containing 0.2% tween-20 in PBS for at least 1 hour. Primary antibodies were added to 2% goat serum in PBS and incubated on cells overnight at 4 C. Primaries were washed three times for five minutes and secondary antibodies in PBS were added for 60-75 minutes. Secondary antibodies were washed and cells were counterstained with 1:1000 DAPI. Cells were imaged using a Zeiss inverted fluorescent microscope. IF and FACS antibodies used can be found in FIG. 15.

Example 1: HPSC-SMPCs Derived by Differentiation Have Reduced Fusion Efficiency Compared to Fetal Muscle and Adult Muscle Satellite Cells FIGS. 1-2. To evaluate myogenic potential of hPSC-SMPCs relative to fetal and adult satellite cells (SCs), multiple directed differentiation protocols were evaluated, and two selected for further analysis. Both methods consistently generated muscle cells expressing myogenic transcription factors (TFs) PAX7, MYF5, MYOD, and MYOG and spontaneously contracting myotubes (FIG. 1A-1B). HPSC-SMPCs were dissociated/replated and compared to equivalent numbers of muscle cells isolated from human fetal weeks 9, 14, and 17, and adult skeletal muscle tissues (FIG. 2A). Cells isolated from adult muscle formed myotubes most efficiently, and contained the most nuclei (24.5 nuclei/myotube, p<0.05). The fusion indices and nuclei per myotube from fetal weeks 14-17 were significantly greater than fetal week 9 and hPSC-SMPCs (p<0.05), while week 9 fetal muscle cells were not statistically different from hPSC-myotubes (p=0.3).

In myogenic development, cells undergoing proliferation and differentiation co-exist26. To better understand the timing and heterogeneity of myogenic TF expression during myotube differentiation, PAX7 and MYOD were evaluated (FIG. 2B). Indeed, all fetal muscle cultures contained PAX7+MYOD+ SMPCs. Myotubes derived from adult SCs expressed PAX7+ or MYOD+ single nuclei, but few PAX7+ MYOD+ nuclei were present in adult cultures. HPSC-SMPCs from either directed differentiation method contained the largest fraction of PAX7+MYOD+ nuclei, and many MYOD+ nuclei were not contained within MYHC+ myotubes. Together, these data suggest that hPSC-SMPCs inefficiently differentiate to form myotubes and/or represent a distinct developmental stage.

Figure 3:
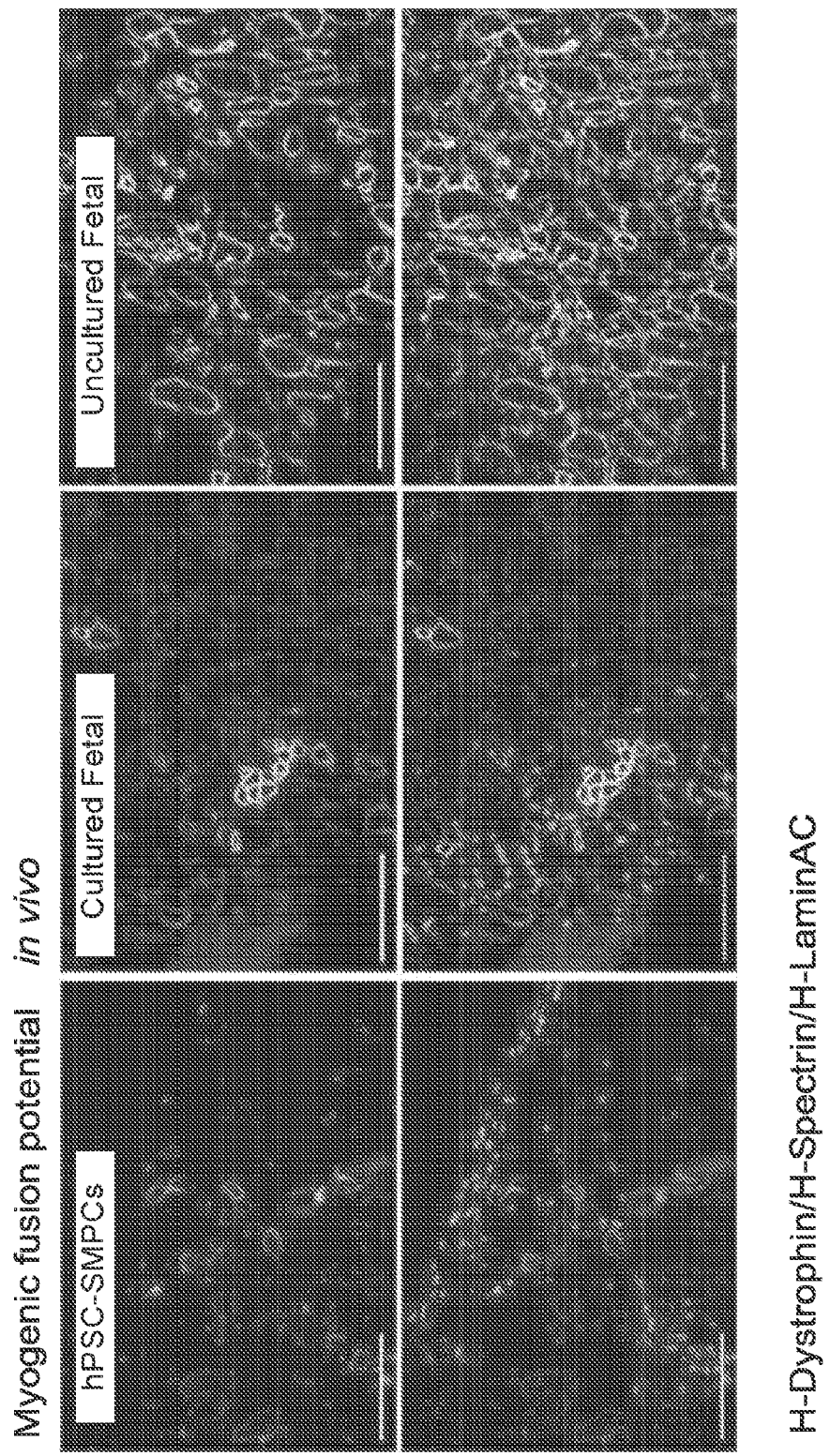
FIG. 3 depicts the engraftment potential of uncultured fetal muscle cells, cultured fetal muscle cells and hPSC-SMPCs, demonstrating hPSC-SMPCs are not equivalent to fetal SCs in vivo and that directly isolated cells engraft more efficiently.

Example 2: HPSC-SMPCs Have Limited Engraftment Potential In Vivo Compared to Immediately Isolated Human Fetal Satellite Cells FIG. 3. Directed differentiation of hPSCs has yet to generate SMPCs with robust engraftment potential in vivo. It has been shown that cultured human fetal muscle cells also engraft inefficiently. Notably, directly-isolated adult SCs engraft more efficiently than cultured SCs, but engraftment of directly-isolated human fetal muscle cells has never been tested. Cultured and uncultured human fetal muscle cells (all directly-isolated mononuclear cells) were utilized to benchmark hPSC-SMPC engraftment potential, and assess whether the developmental state or culturing of fetal cells correlated with changes in engraftment. In parallel to cultured and uncultured fetal muscle cells, hPSC-SMPCs were transplanted into the tibialis anterior (TA) of cardiotoxin-pretreated mdx-NSG mice, which are immunocompromised and lack dystrophin expression (FIG. 3). At 30 days, several hundred hPSC-SMPCs, marked by human (h)-LaminA/C, were detected in the muscle. However, most had not fused with the host muscle (as marked by h-LaminA/C+Spectrin+ and h-Dystrophin+) nor did they reside in the SC position. Instead, most h-LaminA/C+ hPSC-SMPCs were found in the perimysium and epimysium of the host TA muscle (FIG. 3). In contrast, both cultured and uncultured fetal cells resulted in increased number of h-dystrophin+ cells compared to hPSC-SMPCs (p<0.05, Table 5 of FIG. 13). While restoration of h-dystrophin+ myofibers by cultured fetal muscle was less than 1% of host TA, uncultured fetal cell engraftment was significantly more efficient, restoring 10-15% h-dystrophin+ myofibers in host muscle, a level of dystrophin expression that has been reported to result in functional improvement in mouse.

To evaluate the in vivo myogenic potential of hPSC-SMPCs compared to cultured and directly-isolated fetal muscle cells, engrafted myofibers were counted at eleven points (0-10 millimeters) throughout the TA of mdx-NSG mice, and ranked all counts using Kruskal-Wallis analysis of variance tests (FIG. 3). Directly-isolated fetal muscle cells had significantly higher engraftment efficiency than cultured fetal cells or hPSC-SMPCs (p<0.0001).

Example 3: Improvements to Directed Differentiation of hPSC-SMPCs Using Defined Media, Growth Factors and FACS Sorting To determine whether earlier or longer term hPSC-SMPCs had a better engraftment potential, at 35, 40 and 50 days of directed differentiation unsorted hPSC-SMPCs were engrafted in NSG mice. Data show that day 50 SMPCs were the most myogenic (FIG. 4A).

Neural cell adhesion molecule (NCAM or CD56) has been described as a human SC marker. To determine if sorting on NCAM improves hPSC myogenicity, SMPCs were enriched for HNK1−NCAM+ by FACS at 35, 40 and 50 days of directed differentiation, and NCAM enrichment at day 50 produced more myogenic cells in vitro than earlier time points (FIG. 4B).

Figure 4C:
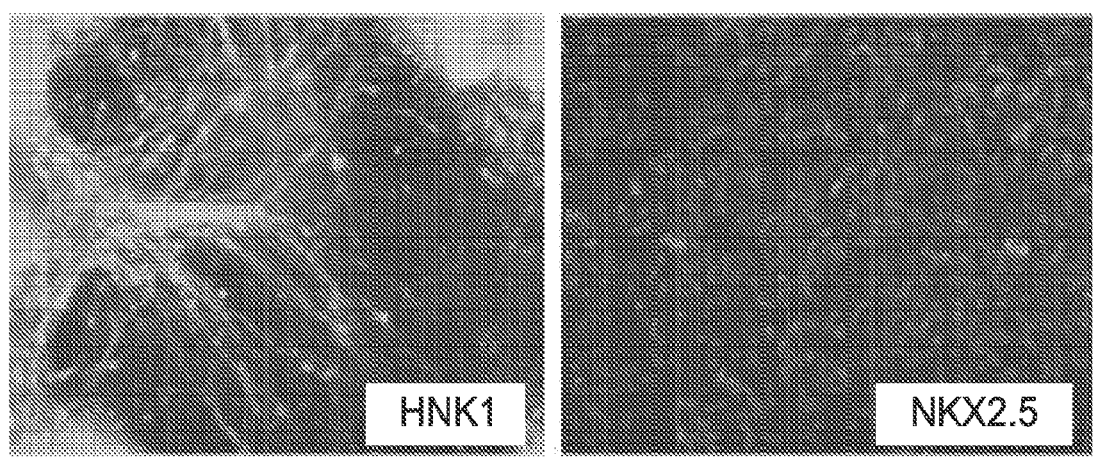

Directed differentiation of hPSCs results in a heterogeneous mixture of multiple cell types. Using FACS, it was determined that HNK1+ neural crest cells comprised up to 30% of cells, and removal of HNK1+ cells enriched for SMPCs (FIG. 4C). Mesenchymal cells (CD73 and PDGFRα) comprised 5-10% of cells, but these lineages were not removed as they could potentially form SMPCs. All other lineage markers tested, including VEGFR2+ cardiac muscle, A2B5+ neurons, CD45+ and CD31+ cells were negligible at <2% of the cells in culture.

Immediately after sorting day 50 hPSC-SMPCs, 78% of HNK1−NCAM+ SMPCs were PAX7+ compared to 17% of passaged unsorted SMPCs at the same time point.

Example 4: Enriching for HNK1-NCAM+ SMPCs Increases Myogenic Cell Numbers but does not Increase Myogenicity In Vivo To enrich for cells with increased myogenicity, a previously described sorting strategy that removes HNK1+ cells (a neuroectodermal marker) and selects for neural cell adhesion molecule (NCAM). NCAM is also expressed by human fetal muscle and adult SCs. HNK1−NCAM+ cells were isolated and evaluated their myogenic potential using two directed differentiation methods. HNK1−NCAM+ enrichment increased PAX7 and MYF5 expression by approximately 1.7-fold compared to unsorted hPSC-SMPCs (p<0.05, FIG. 5A). In both protocols, HNK1−NCAM+ SMPCs could be grown in SkBM2+FGF2, and when induced to differentiate, the number of MYHC+ cells increased compared to dissociated/replated SMPCs (p<0.05, FIG. 5A).

HPSC line variability is known to greatly affect the propensity of in vitro differentiation and suggest DMD hiPSCs inefficiently differentiate to skeletal muscle in vitro. After NCAM sorting, hiPSC-SMPCs from wild type, DMD and a CRISPR/Cas9-corrected DMD line could be differentiated to produce equivalent numbers of myotubes (FIG. 5A). All hiPSC lines differentiated less well than the H9 hESC line. Thus, the absence or presence of dystrophin did not affect myogenic differentiation in vitro.

Sorting of HNK1−NCAM+ was evaluated to see if sorting of HNK1−NCAM+ could improve the in vivo engraftment potential of hPSC-SMPCs. However, unlike in vitro, NCAM+ sorting did not improve engraftment compared to unsorted SMPCs (FIG. 5B). Irradiation was unable to improve hPSC-SMPC engraftment potential (Table 5 of FIG. 13). In summary, enriching hPSC-SMPCs for HNK1−NCAM+ does not increase engraftment potential despite modestly increasing myogenic potential in vitro.

Figure 6A:
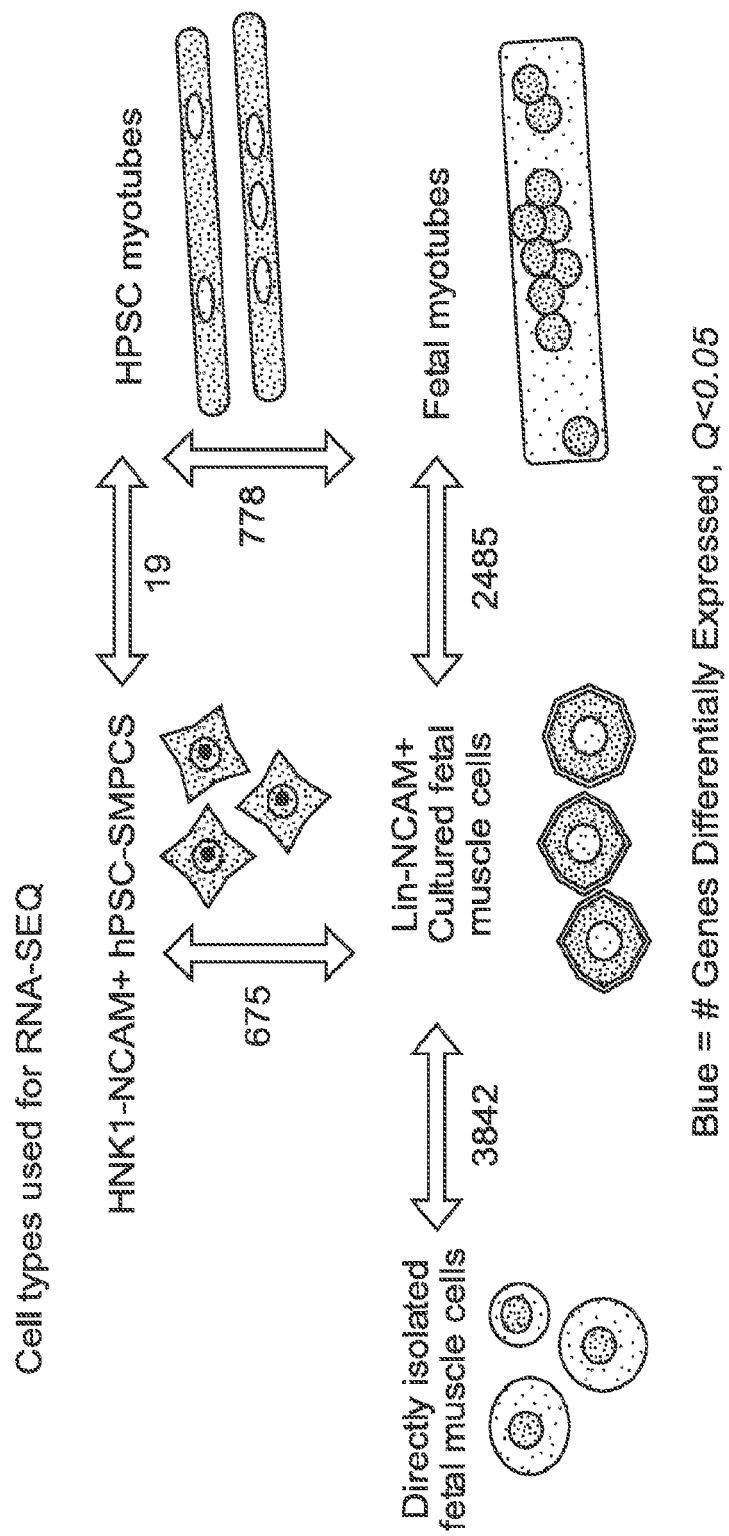

Example 5: RNA-SEQ Identifies Differences Between Fetal and hPSC-Derived Muscle Cells FIG. 6A-6C. To better understand functional differences between fetal myogenic cells, hPSC-SMPCs, and their differentiated progeny, RNA-SEQ was performed on unsorted, directly-isolated fetal muscle cells (all mononuclear), NCAM+ cultured fetal muscle cells and hPSC-SMPCs, and myotubes generated from both fetal muscle and hPSCs (FIG. 6A). Genes related to myogenic progenitor identity, including PAX7 and MYF5, were enriched in cultured fetal muscle cells compared to hPSC-SMPCs. In contrast, hPSC-SMPCs demonstrated substantial enrichment of TFs and structural proteins related to myogenic differentiation, such as MYOG. Principle component analysis confirmed hPSC-SMPCs clustered more closely with myotubes (FIG. 3B). Moreover, Gene Ontology (GO) analysis identified multiple categories associated with development that were enriched in NCAM$^+$ hPSC-SMPCs, suggesting that this population contains embryonic cell types. NCAM$^+$ cultured fetal cells were also enriched for gene categories related to cell migration (FIG. 17A). Comparison of directly-isolated fetal muscle cells to hPSC-SMPCs generated similar results, and GO analysis revealed potential factors, including HGF and LIF, associated with supporting fetal muscle (Tables 1-3 of FIG. 17A-17C). While evaluation of all mononuclear cells from directly-isolated fetal muscle compared to cultured cells provided a comprehensive analysis of cells contained within the highest in vivo myogenic potential, identification of potential surface markers was not feasible because of contaminating cell types (endothelium, hematopoietic) present in the unsorted fetal muscle cell samples.

Example 6: Muscle Tissue-Specific Surface Markers Enable Enrichment of Myogenic Cells from hPSC-SMPCs To identify putative surface markers enriched on myogenic cells versus other skeletogenic lineages, the results of a Weighted Gene Co-Expression Network Analysis (WGCNA) performed across five fetal musculoskeletal tissues: muscle, bone, cartilage, ligament and tendon were utilized. In WGCNA, as modules of genes are defined based on their expression levels in each cell type, candidate cell surface markers associated with myogenesis and/or enriched in the muscle module were chosen for further evaluation as possible markers of hPSC-SMPCs. Candidate receptors were screened for ability to increase myogenic potential using the 1006-1 CRISPR/Cas9-corrected DMD-hiPSC line. Of the populations tested, cells positive for NGFR (CD271) and ERBB3 were the most myogenic and able to form myotubes more efficiently than NCAM$^+$ cells in vitro ($p<0.05$, FIG. 8A-8B). Therefore, these two candidate surface markers were chosen to improve isolation of hPSC-SMPCs.

Example 7: Sorting for Cell Surface Receptors Identified on Human Fetal Muscle Cells During Development Enables Enrichment of More Myogenic hPSC-SMPCs FIG. 7A-7G. Cell surface markers that were expressed by fetal muscle cells and that would enable isolation of hPSC-SMPCs with improved myogenic potential were identified. RNA-SEQ data was cross-referenced to an unpublished GWAS dataset that compared human fetal NCAM$^+$ muscle cells to bone, cartilage, and heart, in order to identify receptors unique to fetal muscle tissue. Candidate receptors were further selected for known roles in skeletal muscle development from NCBI. Cell surface markers MCAM (CD146), ITGA7, CXCR4, c-MET, NGFR (CD271), ERBB3 (EGFR3) and ITGAM (CD11b) were identified.

To evaluate the profiles of muscle specific markers during human developmental myogenesis, human fetal muscle at weeks 9-18 and NCAM$^+$ hPSC-SMPCs were labeled with respective receptor antibodies and co-expression analyzed by FACS. C-MET was present in population of fetal week 9 muscle, which decreased by week 13-14, and then reappeared in the majority of week 17 muscle cells. Similar c-met$^+$ population shifts in mouse have been noted and may be because human week 9 fetal muscle marks the end of primary myogenesis, and by week 17 a secondary wave of c-MET$^+$ progenitors has been re-established. Fetal week 17 cells were the first to co-express ITGA7 with c-MET. However, in hPSC-SMPCs, ITGA7 and c-MET were not co-expressed.

RNA-SEQ identified two markers specific to week 17 fetal muscle capable of enriching hPSC-SMPCs. hPSC-SMPCs most closely resemble week 8-9 (late primary) muscle progenitors in their functional capacity. It was hypothesized that ERBB3$^+$ and NGFR$^+$ cells would be present throughout human developmental myogenesis. As early as fetal week 8, a myogenic population of ERBB3$^+$NGFR$^+$ cells were identified that persisted throughout the time points examined (FIGS. 7C and 7D). At weeks 8-9, the ERBB3$^+$NGFR$^+$ population enriched for several myogenic TFs ($p<0.05$, N=3). This is important because other known fetal markers, NCAM$^+$MCAM$^+$ and CD82, were either non-specific to muscle or not expressed at these time points, respectively. NCAM$^+$MCAM$^+$ and CD82 began to co-express with ERBB3$^+$NGFR$^+$ cells at fetal week 11.5 (FIGS. 7A-7C, and 7E).

By fetal week 17, two distinct ERBB3 subpopulations were identified containing myogenic activity (FIG. 7C). ERBB3$^+$NGFR$^+$ cells enriched for PAX7 and MYF5 by 8-10-fold compared to ERBB3 NGFR cells, ($p<0.01$, N=5), while ERBB3$^+$NGFR cells enriched for MYOD and MYOG by 40-fold ($p<0.05$); NGFR$^{+Lo}$ERBB3 cells weakly expressed myogenic TFs, but did contain a population with some myogenic potential. Primary and secondary fetal muscle progenitors could also be distinguished by their positivity for ERBB3 and NGFR, as expression of NGFR was much higher during weeks 8-9 (FIG. 7A). Thus, the combination of these markers distinguished fetal muscle progenitors at different stages of development and differentiation. Upon sorting and differentiation to form myotubes, the ERBB3$^+$NGFR$^+$ fraction reached close to 100% fusion efficiency within 4 days, whereas NGFR$^{+Lo}$ERBB3$^-$ generated few myotubes (FIG. 7C). ERBB3$^+$NGFR$^-$ cells did not proliferate or form myotubes. Fetal ERBB3$^+$NGFR$^+$ cells are specifically enriched for PAX7 expressing myogenic progenitors during fetal myogenesis.

Figure 8B:
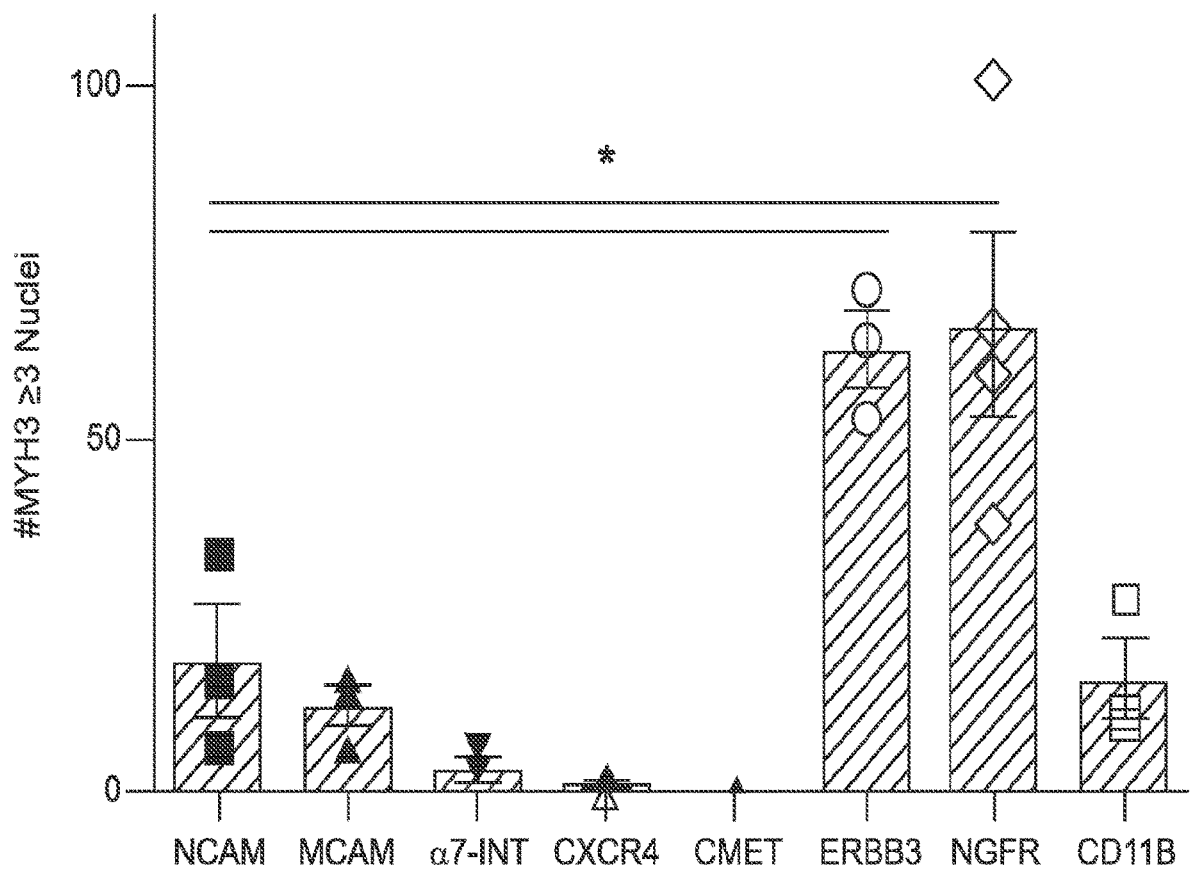

FIGS. 8A-8B To better characterize the biological role of surface receptors in therapeutically relevant hiPSC-SMPCs, subpopulations were enriched from day 50 directed differentiation cultures of CRISPR/Cas9-corrected DMD hiPSC-SMPCs by flow cytometry. Subpopulations were expanded in culture, and differentiated in N2 media in vitro or engrafted in vivo. Similar to the co-expression observed in FACS analyses, MCAM$^+$ subpopulations produced a nearly identical fusion index and number of MYHC$^+$ cells compared to NCAM$^+$ in vitro (FIG. 8A) and also did not efficiently engraft (Table 5). CXCR4, ITGA7, and c-MET subpopulations resulted in little to no myogenic activity in vitro or in vivo. Whether these surface receptors are preferentially expressed by other cell lineages in directed differentiation cultures (such as epithelial cells), or the culture conditions optimized for NCAM$^+$ SMPCs could not support these subpopulations, was not sufficiently tested. In contrast, NGFR and ERBB3 subpopulations were found to be highly myogenic and were able to fuse over 3-fold more efficiently than NCAM in vitro (FIGS. 8A-8B).

Culturing single-positive ERBB3$^+$ SMPCs over three passages leads to the activation and co-expression of double-positive ERBB3$^+$NGFR$^+$ SMPCs. These data show that activation of hPSC-SMPCs towards a myoblast-like cell occurs during expansion and demonstrates that ERBB3 and NGFR can be used as markers to identify different stages of activation. At 3 passages, the double-positive ERBB3+ NGFR+ cells are able to differentiate to form myotubes.

Example 8: ERBB3 and NGFR Enrich for PAX7 and Myogenic Capacity in hPSC-SMPCs

Based on ERBB3 and NGFR expression on fetal myogenic progenitors, the ability of these markers to enrich hPSC-SMPCs was evaluated. In all directed differentiation protocols tested, an ERBB3+NGFR+ SMPC population was detected as early as day 27 (FIG. 7F). By 50 days of directed differentiation, both protocols produced two distinct ERBB3 subpopulations, distinguished by NGFR expression, which resembled secondary myogenesis (FIG. 7G). Sorting these subpopulations revealed that ERBB3+NGFR+ hPSC-SMPCs enriched for PAX7 and MYF5 by 20-fold compared to ERBB3−NGFR− cells ($p<0.001$, $N=4$), while ERBB3+NGFR− cells were enriched for MYOD and MYOG ($p<0.001$). ERBB3+NGFR+ SMPCs could be induced to form homogeneous myotubes.

To test the versatility of these markers, four hPSC lines, including DMD hiPSCs and isogenic CRISPR/Cas9-corrected DMD hiPSCs, were evaluated. Across all lines, myogenic potential was highly enriched in the ERBB3+NGFR+ subpopulation, as defined by expression of myogenic TFs and differentiation potential in vitro (FIG. 7G). However, double positivity based on NGFR levels varied across cell lines. Upon passaging, NGFR levels increase and are associated with decreased myogenic potential in fetal and hPSC-SMPCs. Thus, the combination of surface markers informs on the SMPC differentiation state, in which the ERBB3+ fraction was consistently the most myogenic.

Example 9: Factors Identified by Human Fetal RNA-SEQ Enable Self-Renewal of hPSC-SMPCs Ex Vivo without Loss of Myogenic Potential (PAX7)

HiPSC-SMPC subpopulations enrich for PAX7 but activate and increase expression of MYOD after passaging. The addition of FGF2 to expansion media reduces activation (MYOD) but does not rescue PAX7 expression. (FIG. 9A). Addition of WNT7A or Forskolin to SKBM2 rescues PAX7 expression compared to SKBM2 alone through four passages. WNT7A or Forskolin similarly stabilize or increase stemness factors: NOTCH signaling marker HEYL and CJUN (FIG. 9B).

Example 10: TGFβ Inhibition Induces hPSC-SMPC Differentiation and Myotube Fusion FIG. 10. Despite enabling myogenic enrichment, differentiation of ERBB3+NGFR+ populations isolated from hPSCs yielded myotubes that were often thinner and contained fewer nuclei than later stage fetal or adult counterparts. To understand the basis for these differences, the RNA-SEQ data was analyzed to compare hPSC-myotubes and fetal myotubes to their progenitors.

To test the effects of TGFβ on hPSC-SMPC differentiation, two small molecules inhibitors of TGFβ signaling, SB-431542, a specific inhibitor of TGFβR1 Activin receptor-like kinases (ALK) 4, 5 and 7, and SMAD3 phosphorylation; and A83-01, a selective inhibitor of TGFβRI, ALK4 and ALK7 and SMAD2 phosphorylation were evaluated. Initially, 10 µM of each small molecule were independently tested. SB-431542 is shown in FIG. 10A-10F. Subsequently, concentrations between 1-20 µM of SB-431542 were tested on wild-type hiPSCs. Recombinant TGFβ1 (10 ng/ml) was included to evaluate the opposing role of exogenous TGFβ in regulating myogenic activity. Three independent lines: hESC (H9), DMD hiPSCs (1006), CRISPR/Cas9 DMD hiPSCs (1006-1), and wild type hiPSC (1002) were used to measure differentiation. H9 lines demonstrated similar effects. These data revealed that activators of TGF-β signaling decreased during the course of fetal myotube differentiation (FIG. 10B). In contrast, hPSC-SMPCs had higher expression of TGF-β signaling genes (e.g. TGFβ1, ACVR1B and MSTN) and hPSC myotubes failed to down-regulate TGF-β signaling (MSTN, INHBA and TGFβ2) relative to fetal myotubes.

To test the function of TGF-β signaling in hPSC-derived myotube differentiation, TGF-β was assessed during hPSC-SMPC to myotube formation. Compared to N2 media alone, addition of TGF-β1 completely inhibited myotube formation ($p<0.05$). In contrast, TGF-β inhibition (TGF-βi) using SB-431542 or A83-01 significantly increased hPSC-myotube fusion and produced morphology similar to late stage fetal myotubes (FIGS. 10A-10D, 10F). Single PAX7+ cells remained in hPSC-myotube cultures in the presence of either TGF-β1 or TGF-βi (FIG. 10C), suggesting TGF-βi does not deplete PAX7+ SMPCs. Cells were immunostained or evaluated by QPCR using standard methods.

TGF-β regulation of hPSC myotube differentiation is independent of dystrophin expression. In two independent DMD and isogenic CRISPR/Cas9-corrected DMD hiPSC lines (1006 and 1003), the fusion indices of hPSC-SMPCs increased by 2-5 fold with TGF-βi compared to no treatment (FIG. 10A; $p<0.05$). Inhibition of improper TGF-β levels during hPSC-SMPC differentiation can improve myogenesis in vitro.

Example 11: NGFR+ERBB3+ SMPCs Combined with TGFβ Enrich and Mature hPSC-Myotubes In Vitro FIG. 11A-11B. To test whether ectopic TGF-β signaling inhibited hPSC-SMPCs from forming more mature myotubes, embryonic (MYH3), fetal (MYH8), and adult (MYH1) myosins were measured at both the RNA and protein levels. Results showed that without TGF-βi, hPSC-myotubes predominately expressed embryonic and fetal myosins. Although ERBB3+NGFR+ enrichment increased expression of embryonic and fetal myosins relative to NCAM sorting ($p<0.01$), enrichment did not increase adult myosin expression (FIG. 11A-11B).

Figure 10A:
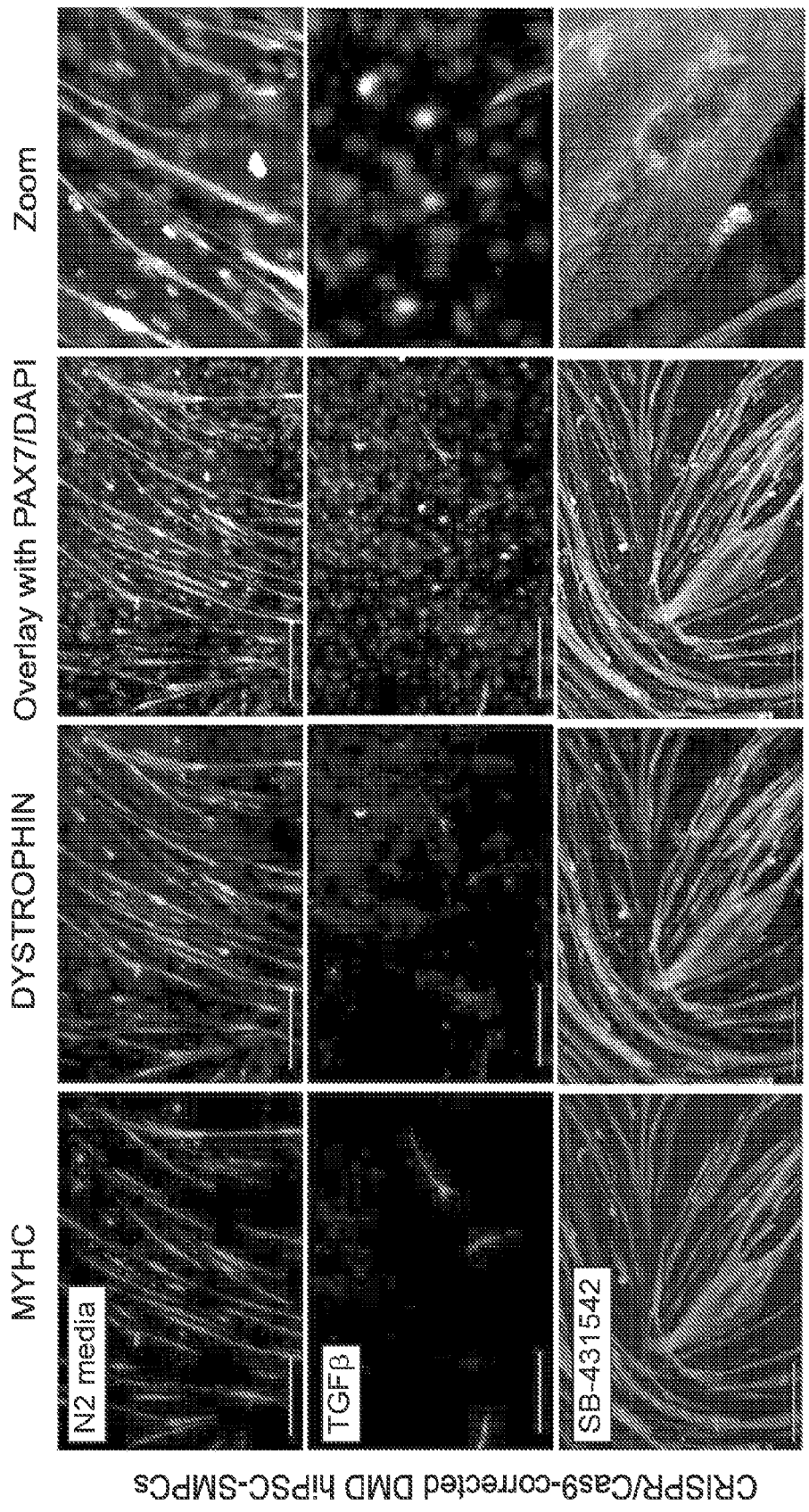
Figure 10A:
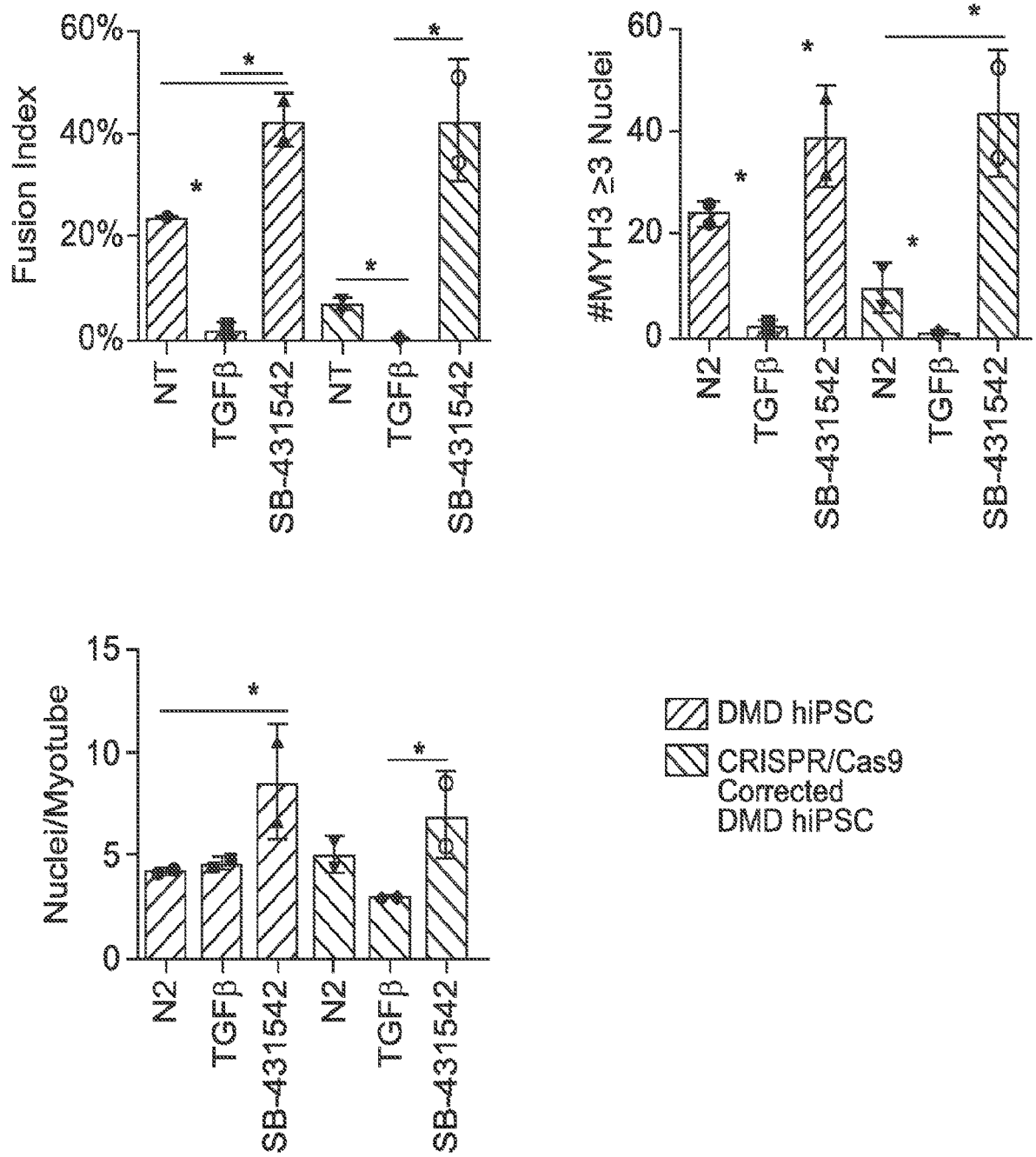
Figure 10E:
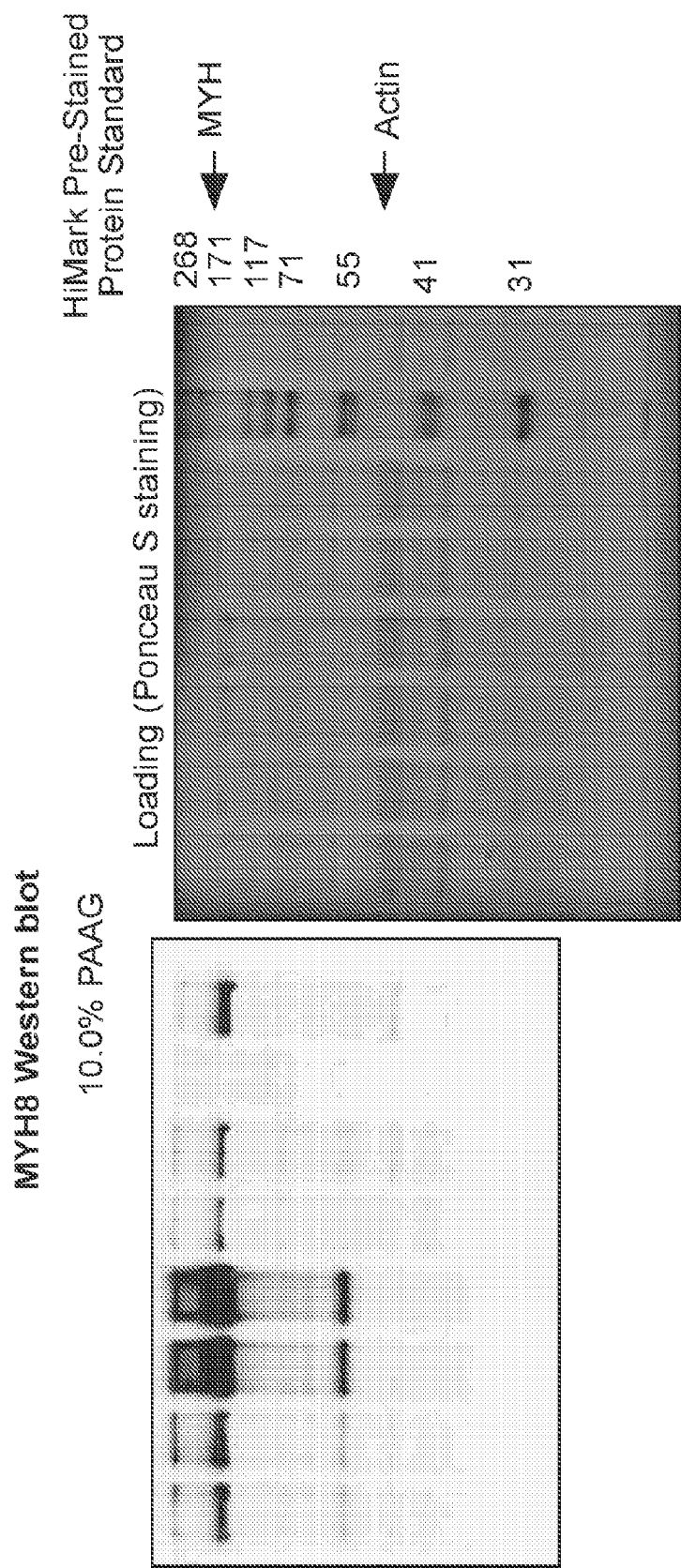
Figure 11A:
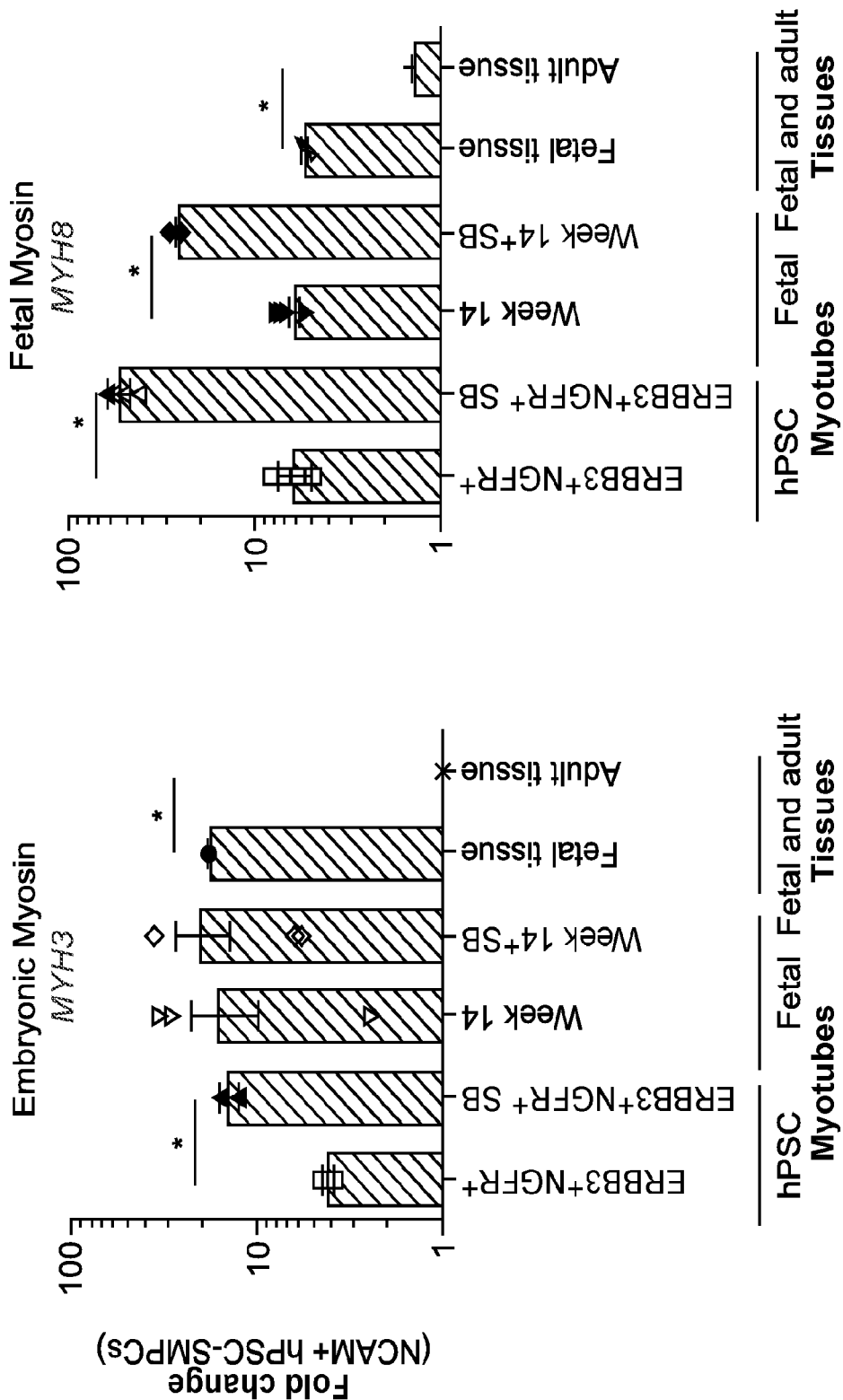
FIG. 11A-11B depict the effect of TGFβi on myosin expression in myotubes, on sarcomere organization and on z-disk patterning and engraftment (FIG. 11A); and TGFβi regulation of myosin genes MYH3, MYH8 and MYH1 in muscle tissue (FIG. 11B).
Figure 11A:
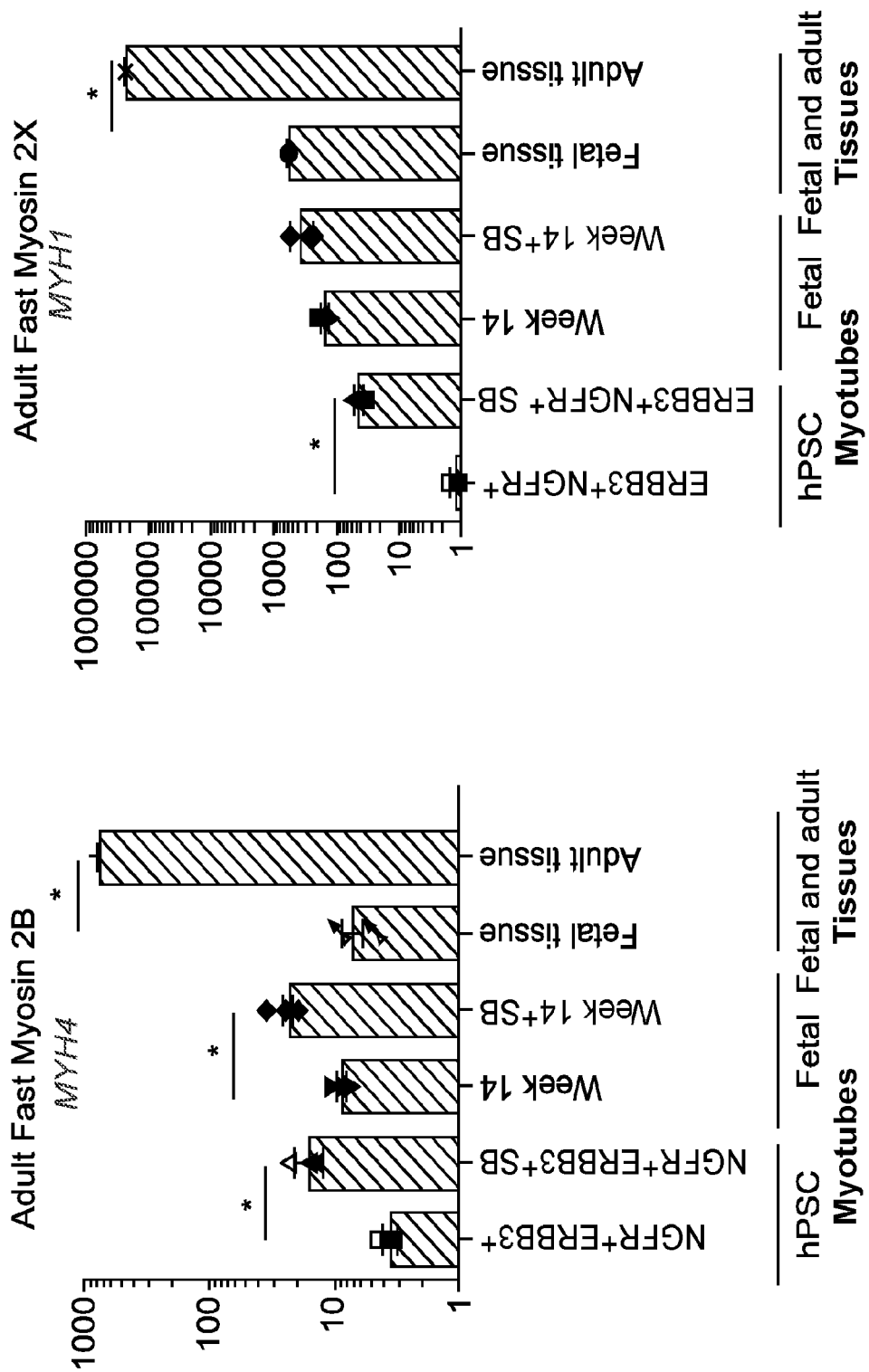
Figure 11B:
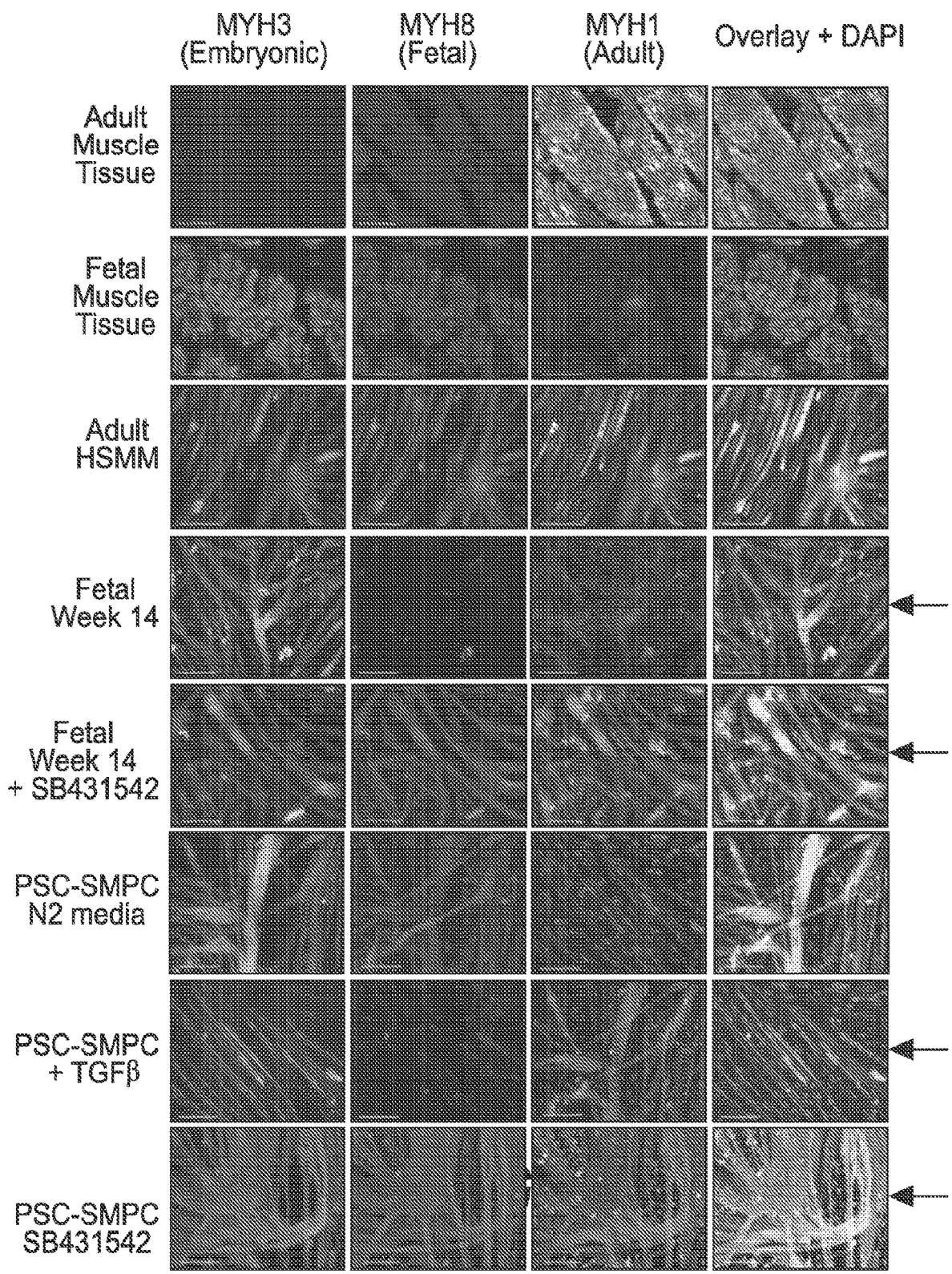
Figure 12C:
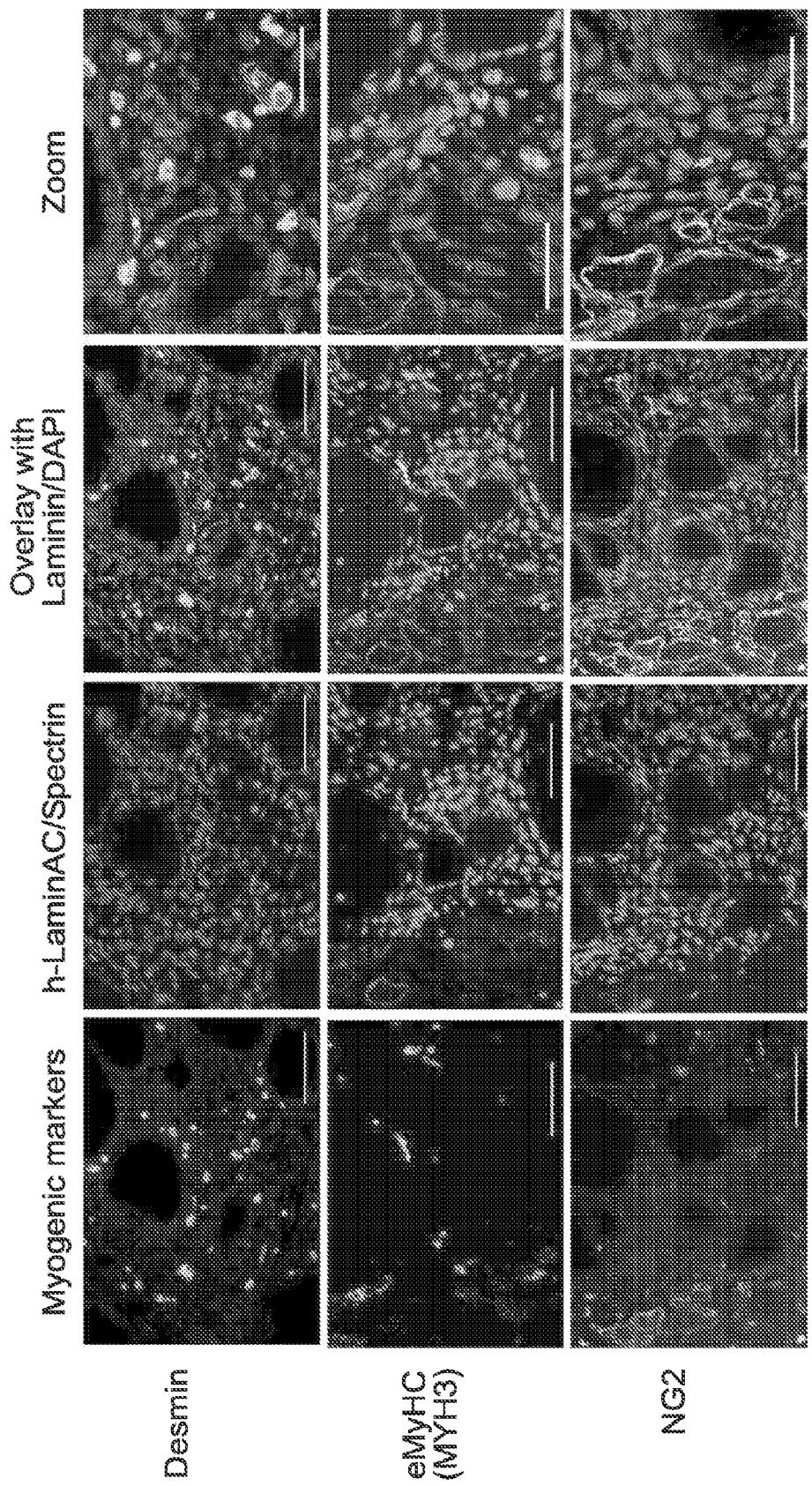
Figure 12D:
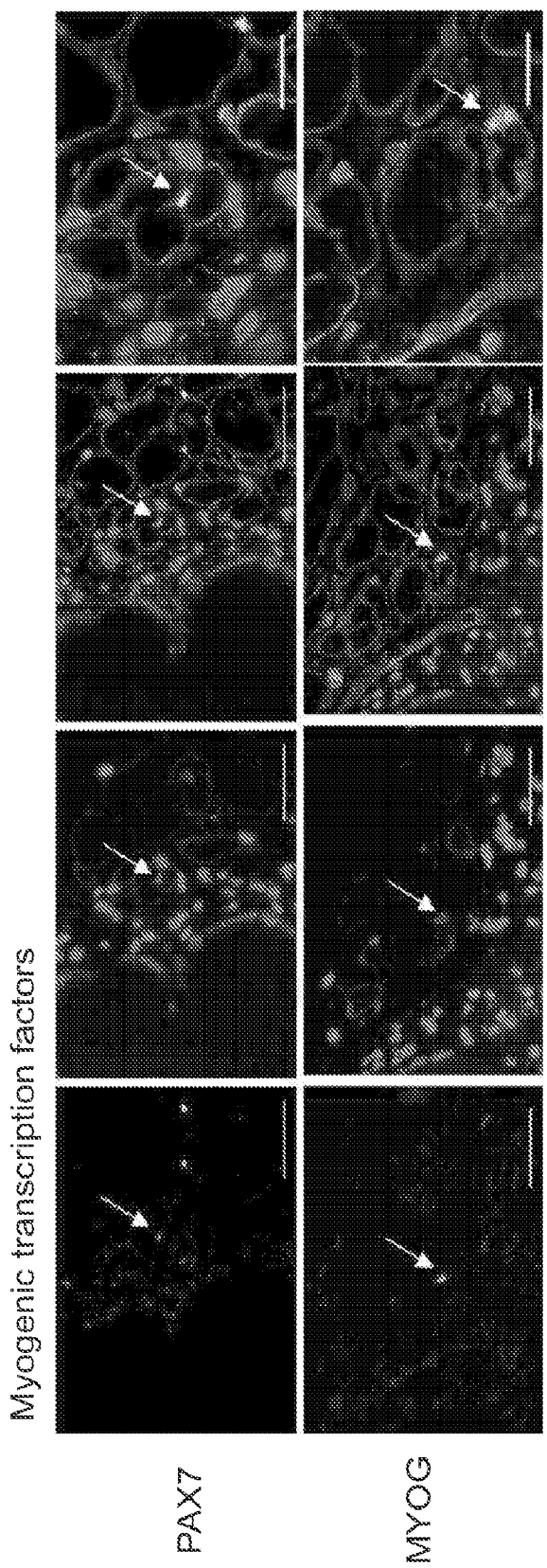
Figure 12E:
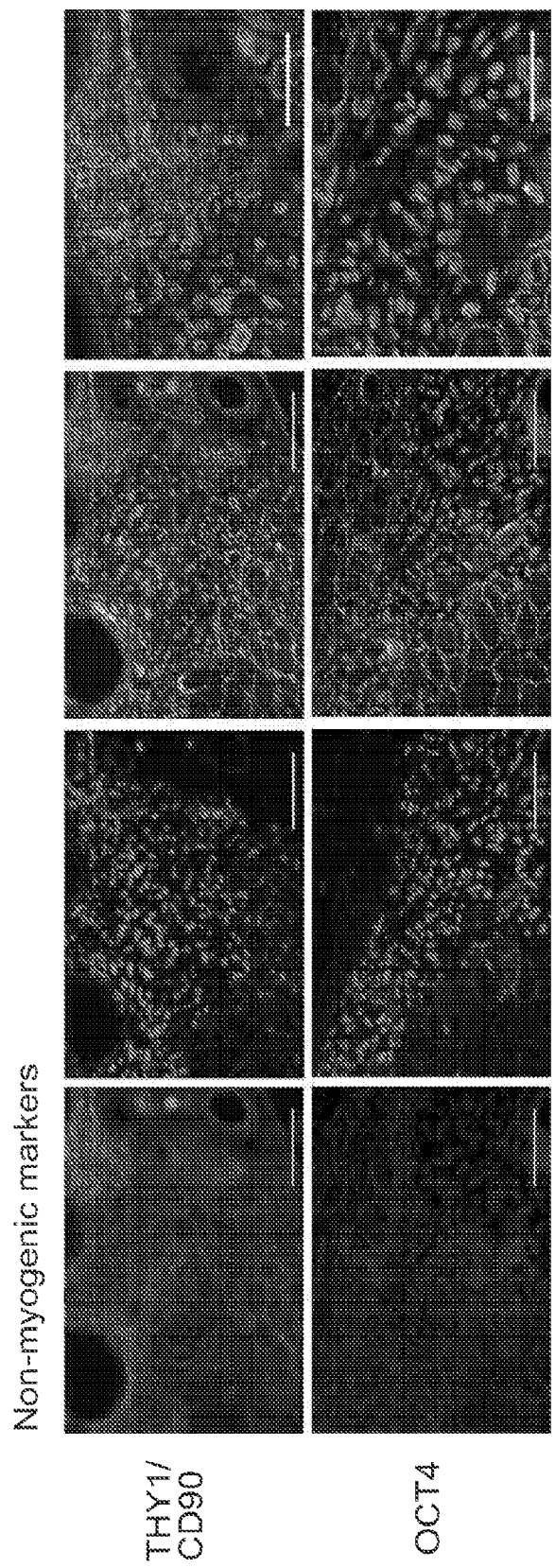

Upon TGF-βi, expression of all myosins increased in hPSC-myotubes, and expression of MYH8 and MYH1 in ERBB3+NGFR+ hPSC myotubes equaled or surpassed that of fetal myotubes, respectively (FIG. 11A-11B). Western blot analysis confirmed that TGF-βi also increased MYH8 and MYH1 protein levels in hPSC myotubes relative to adult myotubes ($p<0.05$, FIGS. 10D-10E). TGF-βi was more effective at inducing myosin expression in hPSC-SMPCs than in fetal or adult myogenic progenitors, which is in agreement with mouse embryonic and fetal myogenic progenitors.

As another measure of maturation, ultrastructural changes were evaluated in hPSC-myotube morphology relative to fetal myotubes by transmission electron microscopy. In the absence of TGF-βi, NGFR+ hPSC-myotubes displayed disorganized sarcomere patterning (FIG. 10F), while TGF-βi promoted formation of better-organized sarcomeres and z-disk patterning. In contrast, untreated fetal myotubes evidenced limited organization. TGF-βi facilitates hPSC-myotube maturity, and additively increases myogenicity of enriched hPSC-SMPC subpopulations.

TGFβi additively increased MYH3 and MYH8 expression in all hPSC subpopulations across three independent lines. When TGFβi was combined with NGFR$^+$ERBB3$^+$ enrichment, MYH8 expression surpassed that of fetal and adult SC-derived myotubes Immunostaining showed that fetal week 14 myotubes only express MYH8 after treatment with TGFβi (FIG. 11B).

Adult muscle tissue predominantly expressed MYH1, and fetal week 17 myotubes also expressed MYH1. Importantly, untreated hPSC-myotubes do not express adult myosin genes. However, when treated with TGFβi all hPSC-myotubes increased MYH1 expression to levels equaling fetal myotubes. A key regulator of the transition from primary to secondary myogenesis is Nuclear Factor-1X (NFIX). NFIX also interacts with members of TGFβ family including myostatin. NFIX expression was found to be increased in hPSC-myotubes after TGFβi (P<0.05; FIG. 11A). However, there was no difference in NFIX expression among SMPC subpopulations.

To further evaluate maturation, ultrastructural changes in hPSCmyotube morphology relative to fetal week 14 and 17 myotubes were measured by transmission electron microscopy (TEM). TEM demonstrated more organized sarcomeres and apparent z-disk patterning in NGFR$^+$ myotubes after TGFβi. However, in the absence of TGFβi, NGFR$^+$ myotubes displayed a disorganized sarcomere patterning, and sarcomeres of NCAM$^+$ myotubes were lesser defined corresponding to the elongated and thin morphology as observed in FIG. 5B. Interestingly, while fetal myotubes contained sarcomeres, z-disk patterning was irregular. Fetal myotubes were observed to have greater cytoplasm not occupied by striations than hPSC-myotubes.

Example 12: In Vivo Engraftment of ERBB3$^+$ hiPSC-SMPCs Restores Dystrophin to Levels Approaching Uncultured Fetal Muscle To test whether ERBB3 or NGFR enrichment could improve engraftment in mdx-NSG mice, single marker enrichment strategies using CRISPR/Cas9-corrected DMD hiPSC lines were tested as for therapeutic relevance. Compared to NCAM$^+$ sorting, both NGFR$^+$ and ERBB3$^+$ SMPCs significantly increased the number of engrafted myofibers as shown by h-LaminA/C$^+$Spectrin$^+$Dystrophin$^+$ positivity (Table 5, p<0.05). ERBB3$^+$SMPCs are strongly enriched for cells capable of generating muscle in vivo.

As shown in FIG. 10A-10F, myotubes generated from enriched SMPCs are immature due to precocious TGF-β signaling, and TGF-βi additively increased SMPC myogenicity. Co-delivery of TGF-βi during injection and for two weeks following transplantation increased numbers of h-LaminA/C$^+$Spectrin$^+$Dystrophin$^+$ myofibers in all SMPCs subpopulations tested (Table S1). Mice injected with ERBB3$^+$ hiPSC-SMPCs and treated with TGF-βi, improved the maximum number of h-dystrophin$^+$ fibers to 137±22 per cross section (FIG. 7A). Across all points measured, this represented a 50-fold greater engraftment than NCAM$^+$ cells also treated with TGF-βi (p<0.001). A percentage of h-LaminA/C$^+$ cells remained positive for myogenic or non-myogenic markers after engraftment in mdx-NSG mice at 30 days (FIG. 12C-12E).

To evaluate how our hPSC-SMPC enrichment and maturation strategy compared with in vivo myogenic potential of cultured or directly-isolated fetal muscle cells, the number of engrafted myofibers were quantified at intervals throughout the TA of mdx-NSG mice, using Kruskal-Wallis ranks tests (FIG. 12B). ERBB3$^+$ hPSC-SMPCs enabled engraftment surpassing cultured fetal muscle (p<0.003) and approached levels equivalent to directly-isolated fetal cells (p=0.43). Together, these results demonstrate a major advance in the ability to obtain engraftable SMPCs from hPSCs.

As shown by engraftment efficiency quantifications, TGFβi mediated maturation in vivo combined with NGFR$^+$ enrichment, enabled hiPSC-SMPC engraftment to levels that surpassed cultured fetal muscle cells (Table 5) and approached levels equivalent to directly isolated fetal cells. Table 5 is presented in FIG. 13.

FIG. 1A-1B. Directed differentiation of human pluripotent stem cells to skeletal muscle progenitor cells. Timeline of hPSC to SMPC differentiation using FIG. 1A Method 1, and FIG. 1B, Method 2 Immunostaining of myogenic markers counterstained with DAPI, and QPCR of myogenic markers show progress of hPSC-SMPC differentiation over 50 days using each method (N=5 method 1 and N=3 method 2 independent directed differentiations; QPCR show mean±SEM). Scale bar equals 200 µm.

FIG. 2A-2B. hPSC-SMPCs have reduced in vitro and in vivo myogenic potential relative to fetal or adult SCs. FIG. 2A. Human muscle obtained from fetal week 9-17, adult 25 yrs or hPSCs differ in ability to form MYHC$^+$ myotubes in vitro (red). PAX7 (white), MYOD (green) and DAPI (blue) are also shown. Scale bar equals 200 µm. Fusion index (% of nuclei within MYHC$^+$ cells ≥3 nuclei/total nuclei) and nuclei per myotube are greatest in adult and fetal, while hPSCs primarily had ≤2 MYHC nuclei/mm$^2$; (mean±SEM; N=3 adult or N=5 fetal tissues, N=3 hPSC independent directed differentiations; One-way ANOVA posthoc Tukey; *p<0.05). FIG. 2B. Co-localization of PAX7 (white) and MYOD (green) differ across developmental stages (shown by arrows). Pie charts show the proportion of PAX7 and MYOD expression in each cell type (N=3 adult and N=5 fetal tissues, N=3 hPSC independent directed differentiations). Scale bar equals 50 µm.

FIG. 3. Timing and engraftment potential of hPSC-SMPCs taken directly from directed differentiation cultures at days 35 and 50 (Method 1, N=3 mice per group). Images show limited human cells (h-Lamin AC, red) or fusion (h-Spectrin, red) in NSG mice (laminin, green) thirty days post-engraftment.

FIG. 5A-5B. HNK1-NCAM$^+$ increases myogenic cell numbers but does not increase myogenicity in vivo. FIG. 5A. HNK1-NCAM$^+$ FACS sorted hPSC-SMPCs have increased PAX7 (red) and MYF5 expression compared to replated/unsorted day 50 SMPCs by immunofluorescence (IF) and QPCR (Method 1; N=6 unsorted or N=5 NCAM hPSC-SMPCs from independent directed differentiations; mean±SEM; two-tailed t-test; *p<0.05). Scale bar equals 100 µm. FACS plots show mean±SD of HNK1$^-$ and HNK1$^-$NCAM$^+$ as percentage of live non-doublet cells. HNK1$^-$NCAM$^+$ cells show increased myotube differentiation when hPSC-SMCPs are derived from two methods. HPSC myotubes differentiate independent of dystrophin expression. IF shows MYHC (red) and DAPI. Scale bar equals 200 µm. Graph shows quantification of myotube fusion from all hPSC lines, (N=3 independent hPSC-myotube experiments, mean±SEM, two-tailed t-test of NCAM vs. unsorted for each hPSC line; *p<0.05). FIG. 5B. HNK1$^-$NCAM$^+$ wild type, DMD and CRISPR corrected hPSC-SMPCs all engraft inefficiently in vivo. IF and quantification of H-LaminA/C$^+$ H-Spectrin$^+$ (red) and H-dystrophin (green) are shown. Graphs quantify the maximum number of engrafted myofibers in a single cross section (left; mean±SEM, two-tailed t-test; NS p>0.05), and the mean±SEM of engrafted myofibers (N=7 mice per group) from multiple cross sections along the length of the muscle (right; Mann-Whitney U-test; NS p>0.05).

Figure 6C:
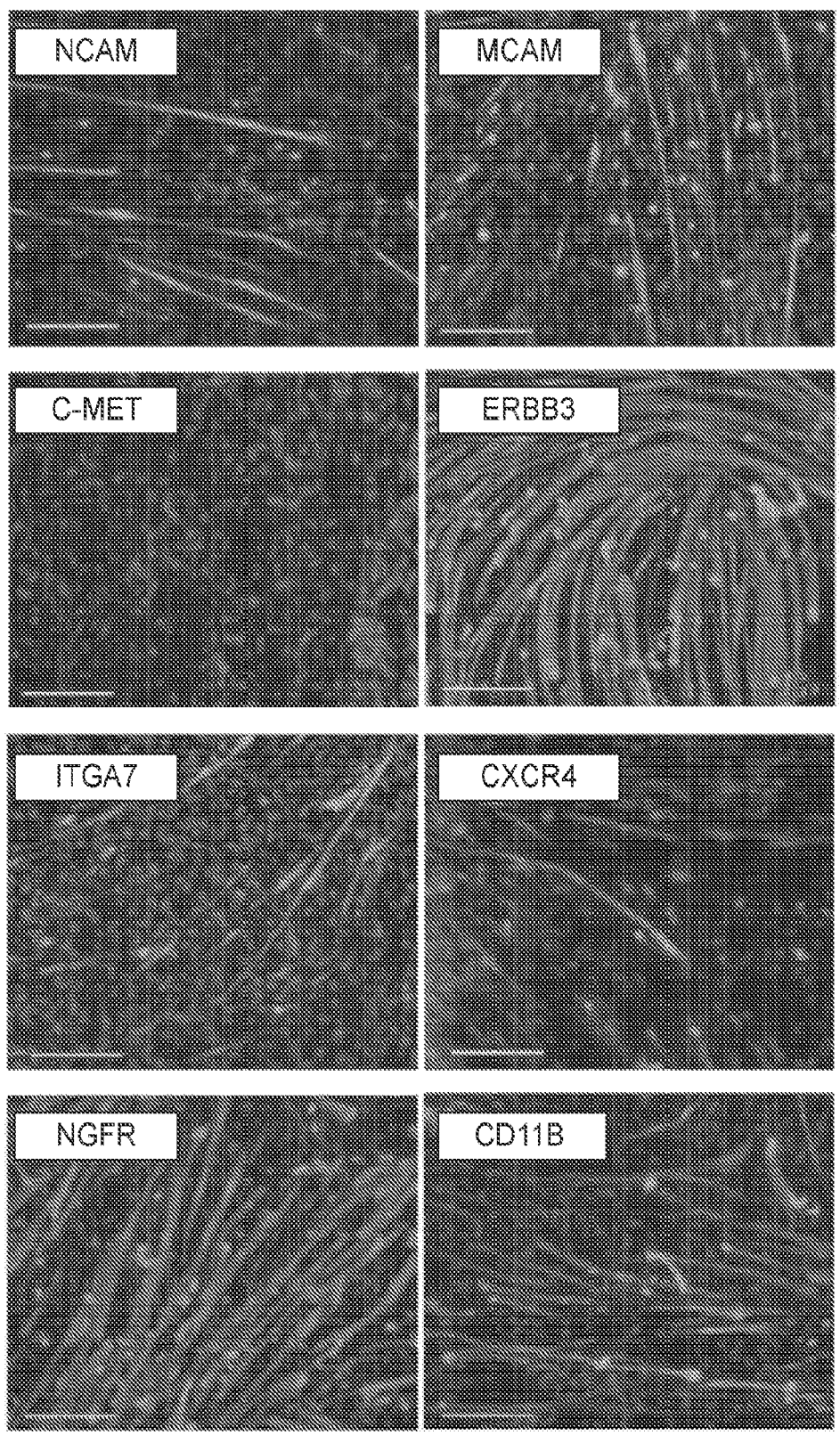
Figure 6C:
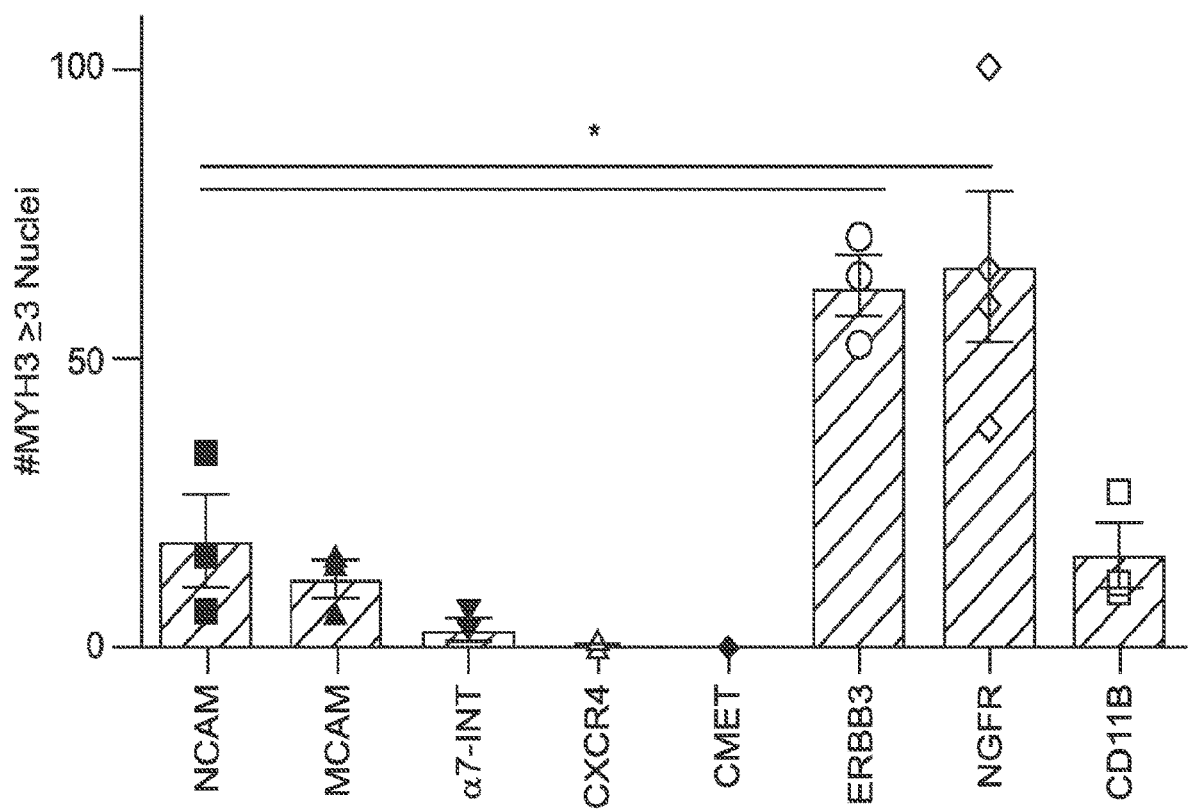

FIG. 6A-6C. RNA-SEQ identifies unique gene signatures in fetal and hPSC-derived muscle. FIG. 6A. Differential gene expression using CuffDiff of all profiled cell types are shown (N=2, q<0.05, blue). FIG. 6B. Principal Component Analysis (PCA) analysis of the 5 cell types. Gene lists and key biological processes upregulated in hPSC-SMPCs, cultured fetal, or directly-isolated fetal muscle cells are shown in Tables S2-S4 (N=2; q<0.05). FIG. 6C. Illustration of profiled fetal musculoskeletal tissue and WGCNA identification of candidate cell surface receptors enriched in fetal muscle cells versus other musculoskeletal tissues are shown. Screen for fetal muscle receptors identifies ERBB3 and NGFR that enrich for hPSC-SMPCs. CRISPR/Cas9-corrected DMD hiPSC-SMPCs (1006-1) were sorted on eight candidate subpopulations and were fused in vitro and stained for MYHC (red) and DAPI (blue). Graph shows quantification of myotube differentiation (N=3 independent hPSC-myotube experiments; mean±SEM; One-way ANOVA posthoc Dunnett; *p<0.05).

Figure 7B:
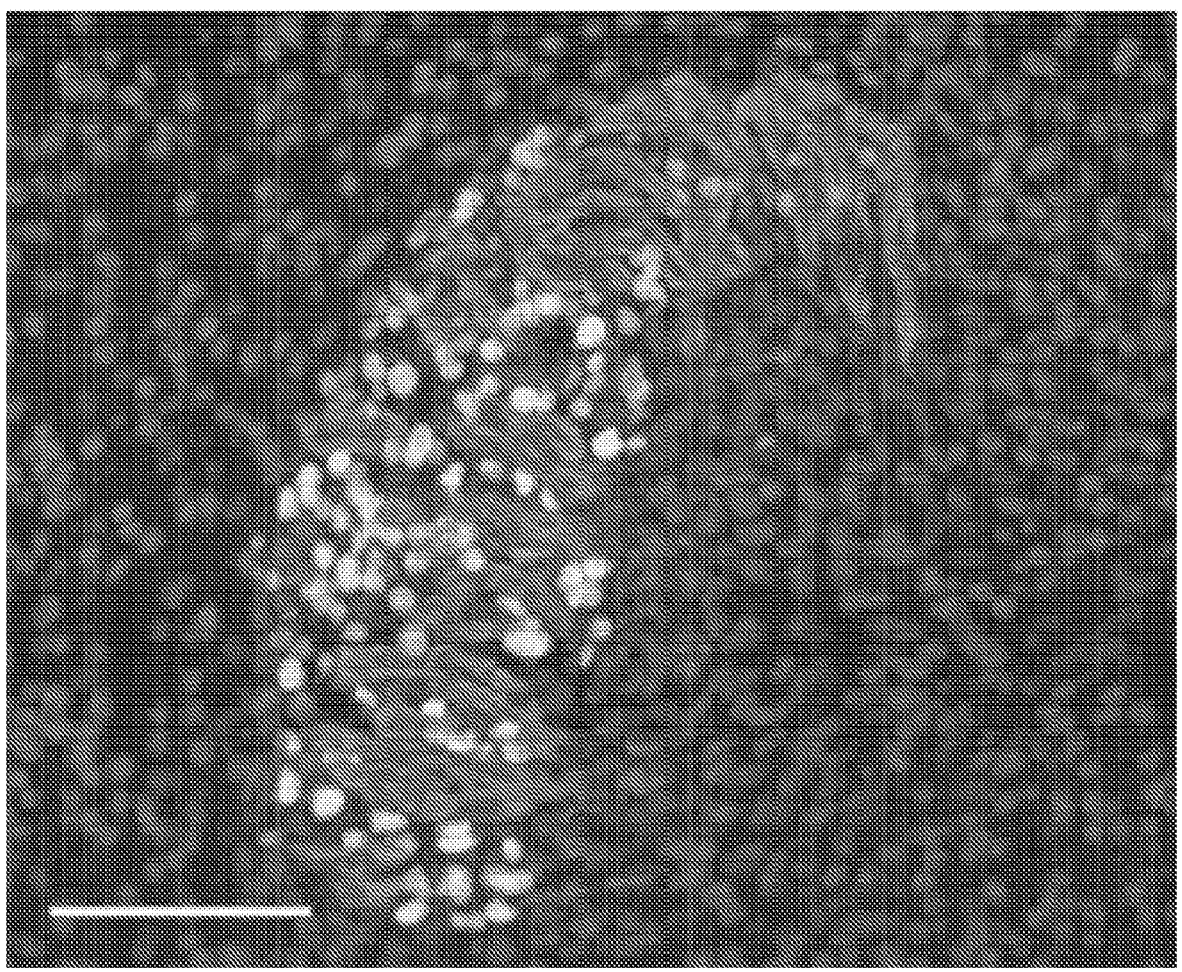
Figure 7B:
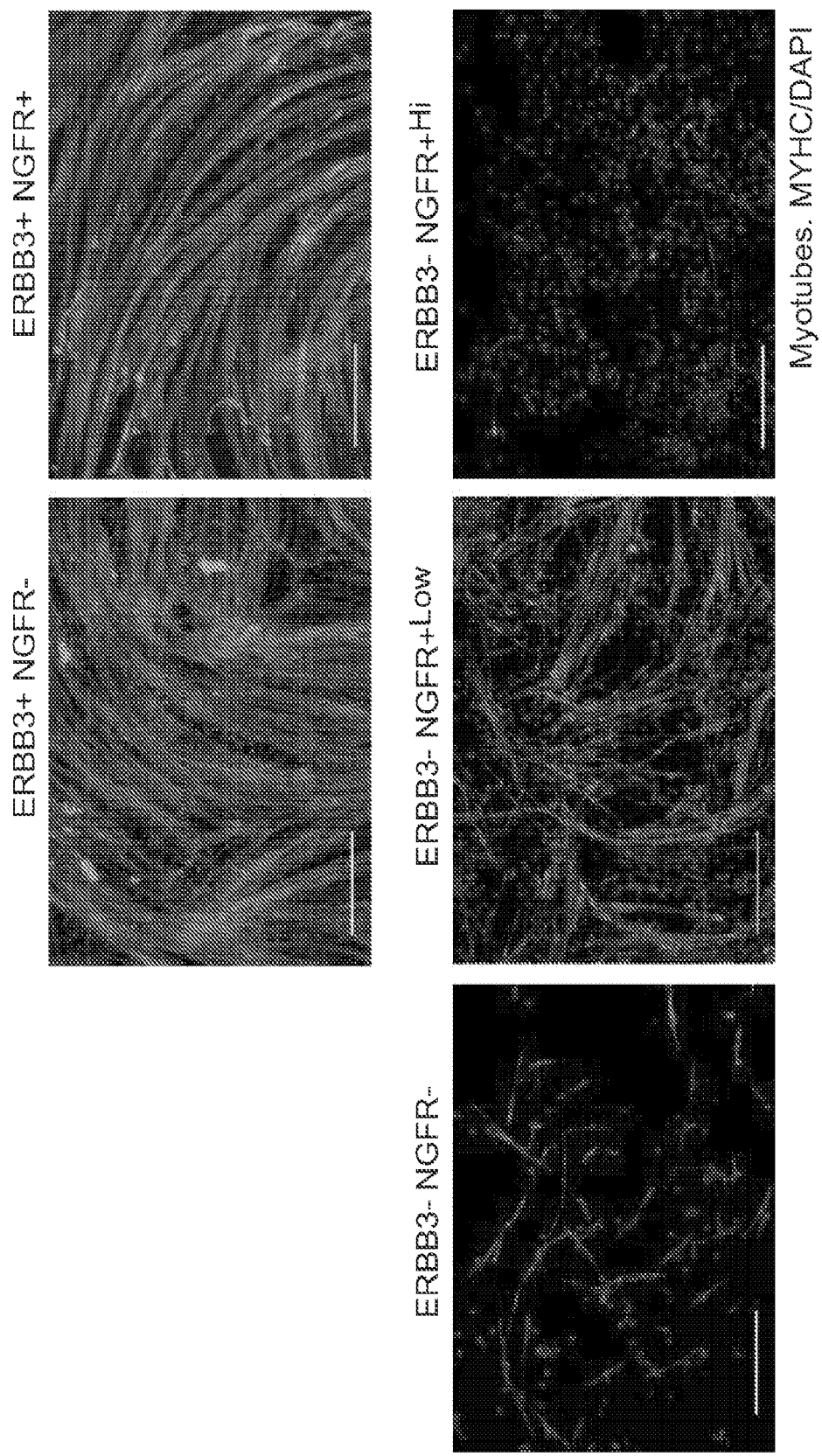
Figure 7C:
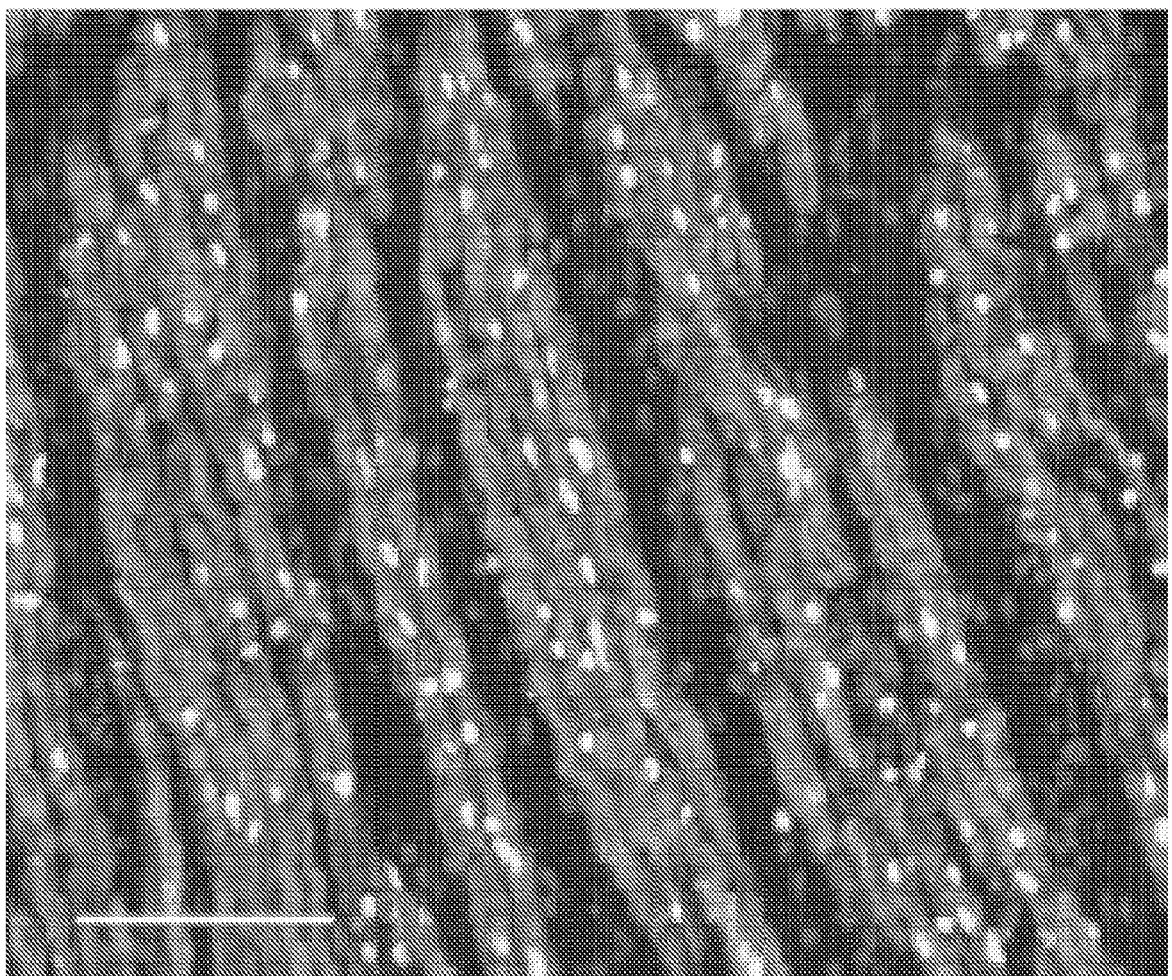
Figure 7D:
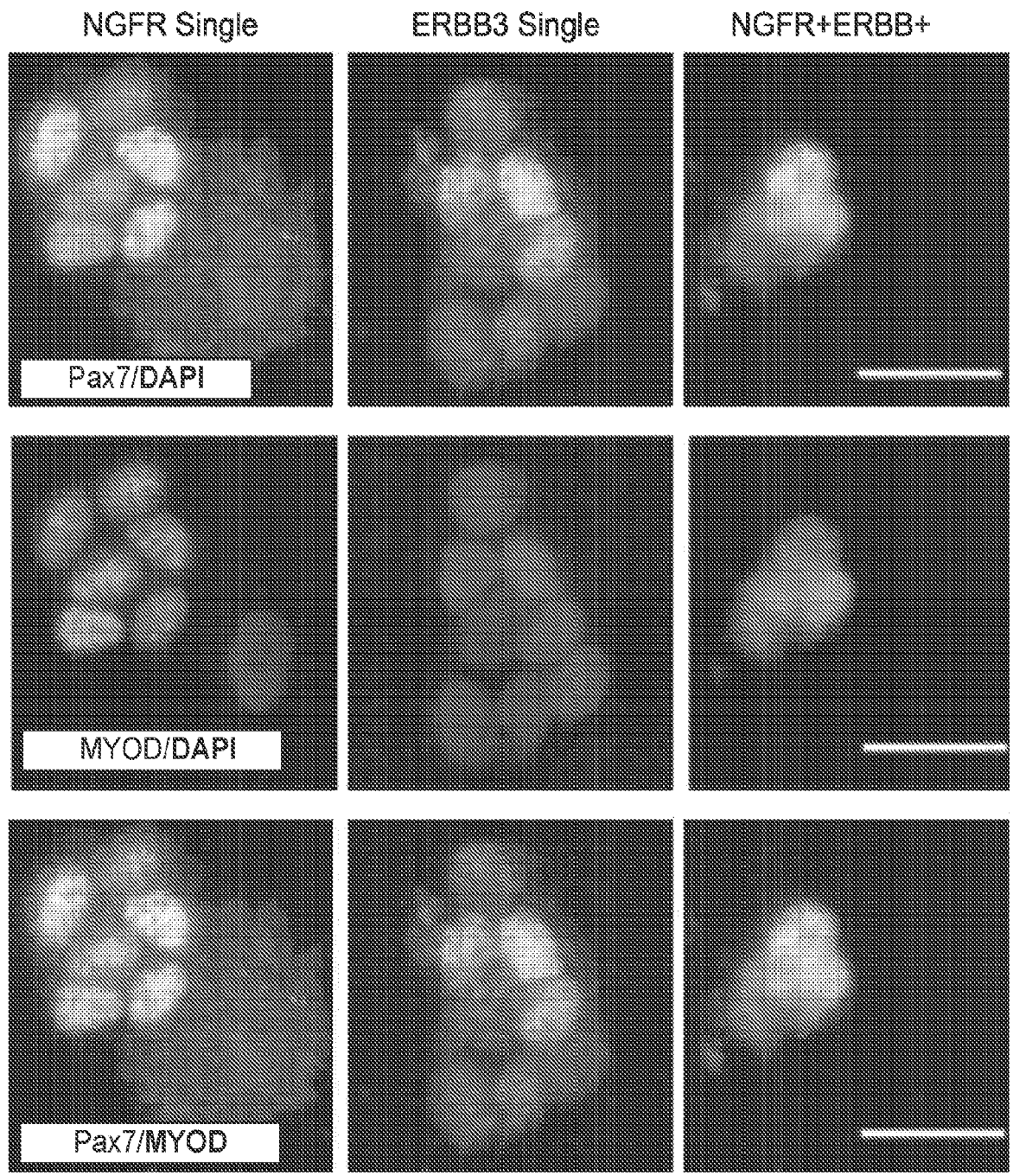
Figure 7E:
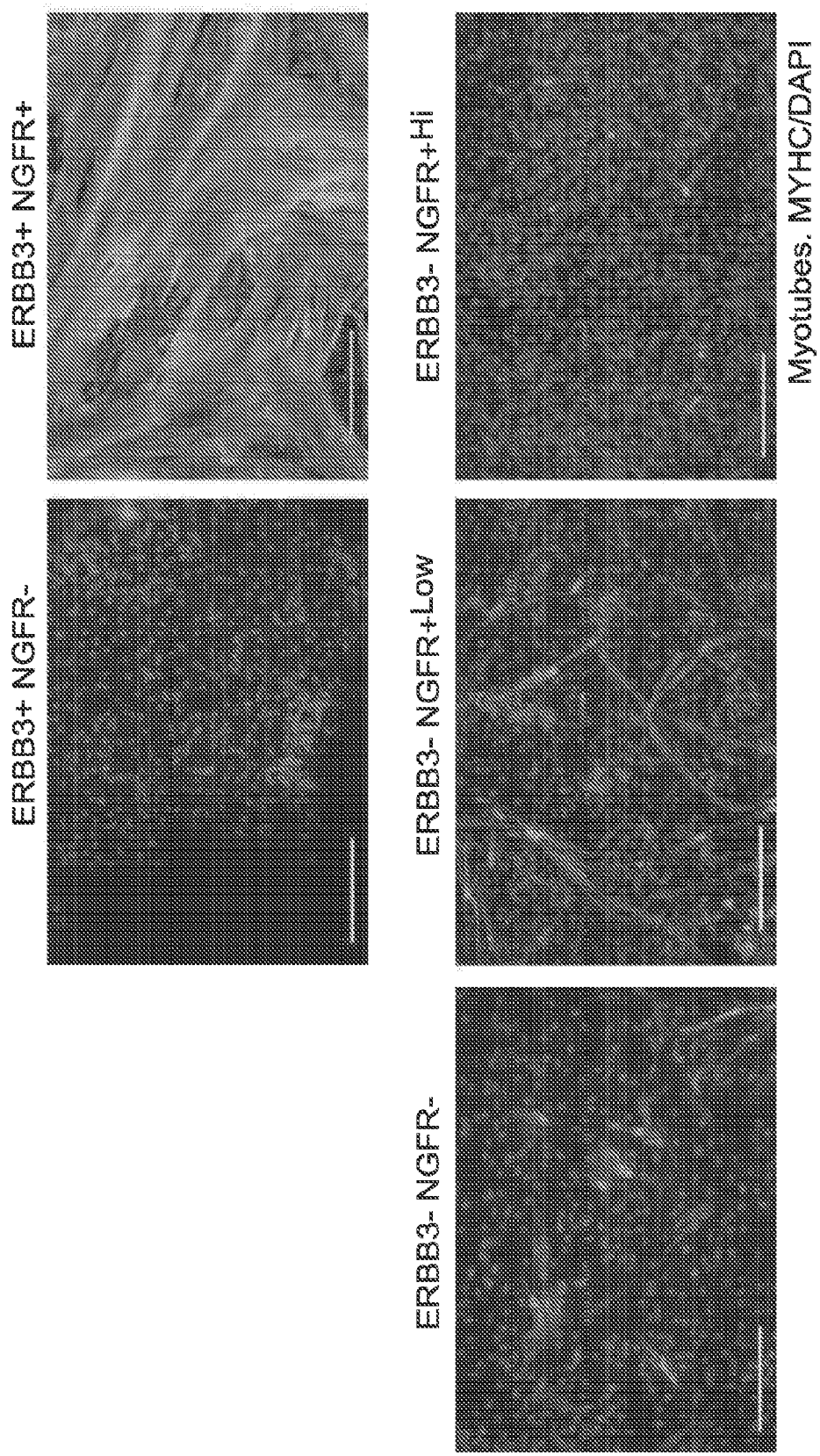
Figure 7G:
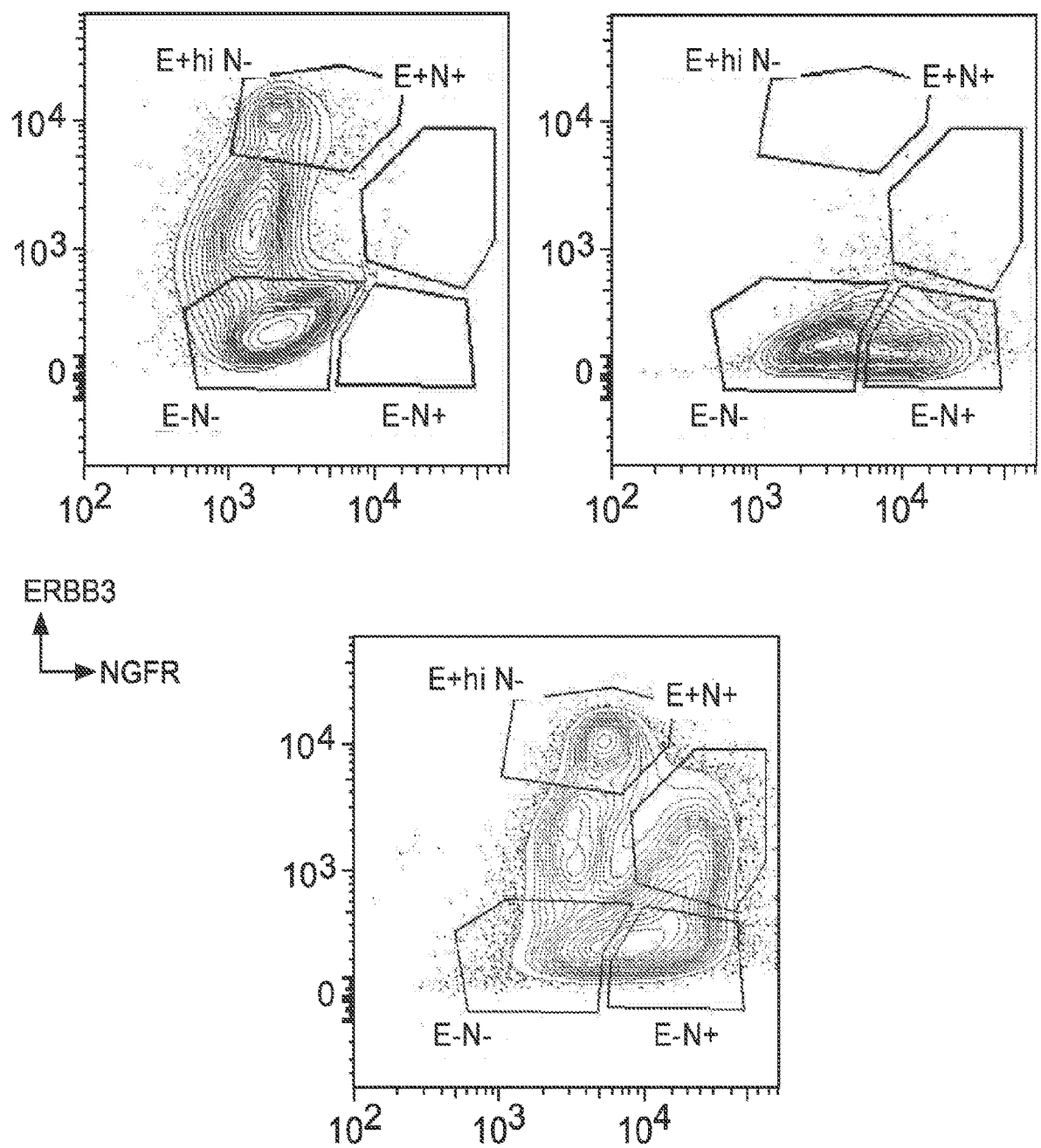
Figure 7G:
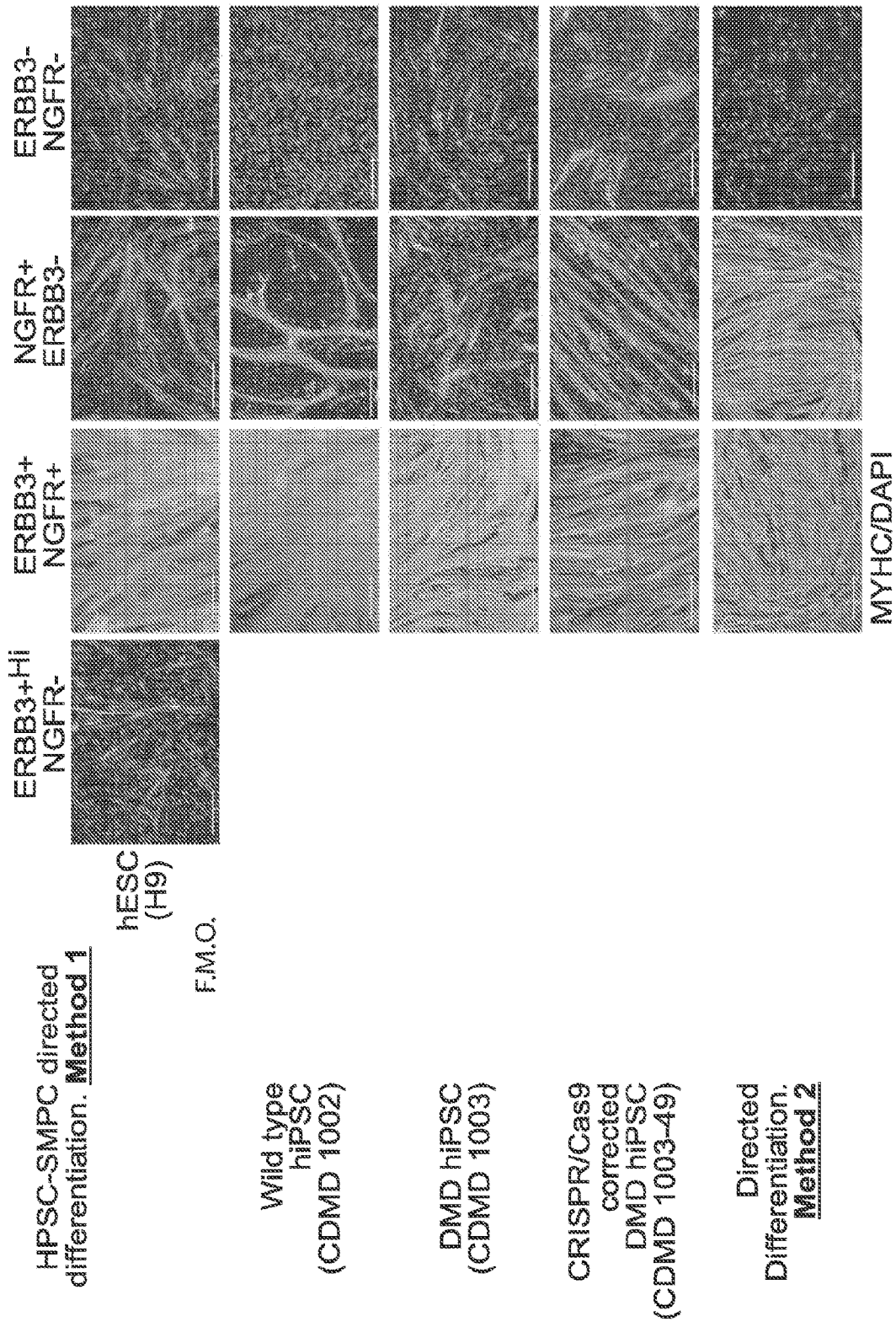
Figure 7G:
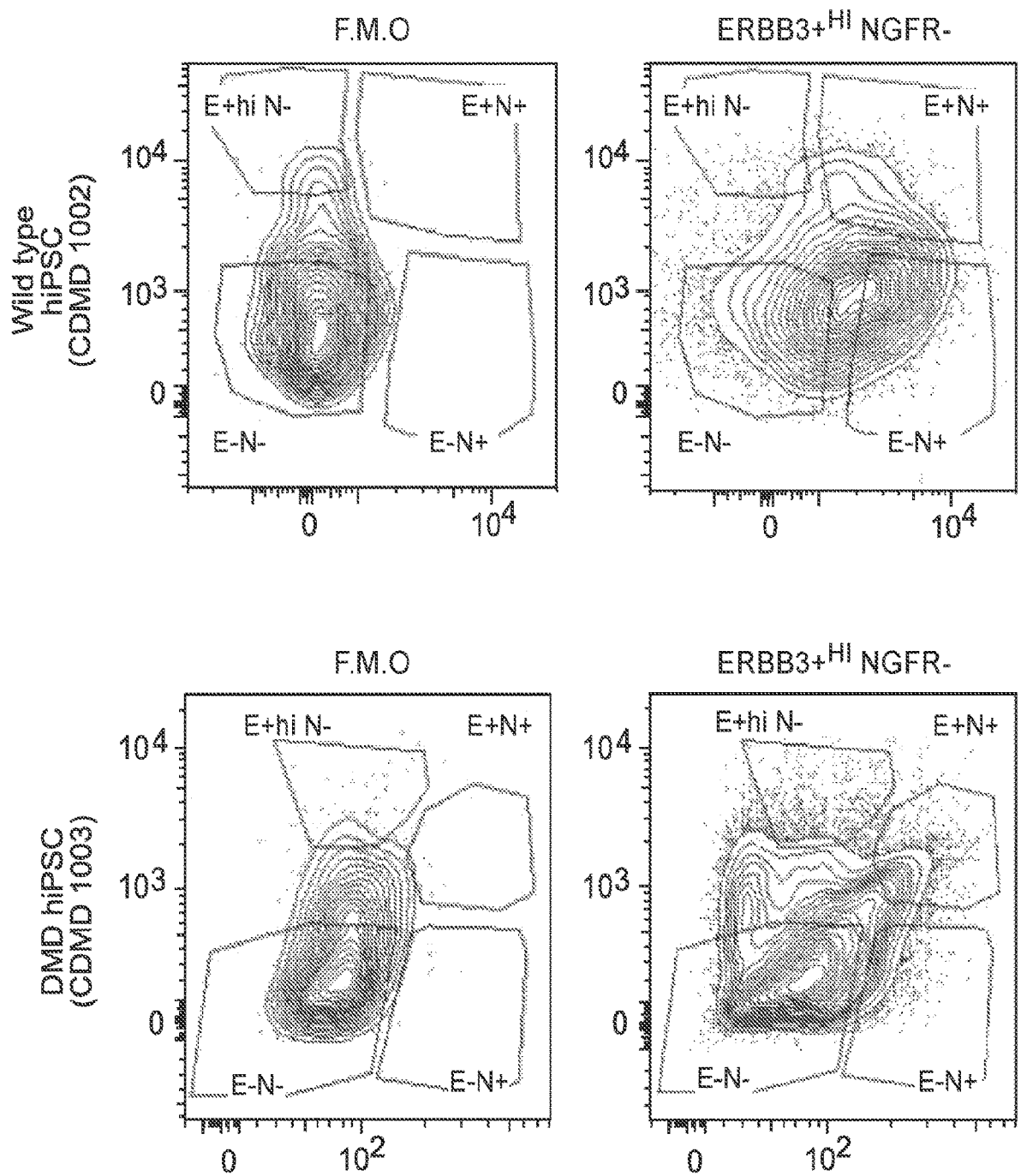
Figure 7G:
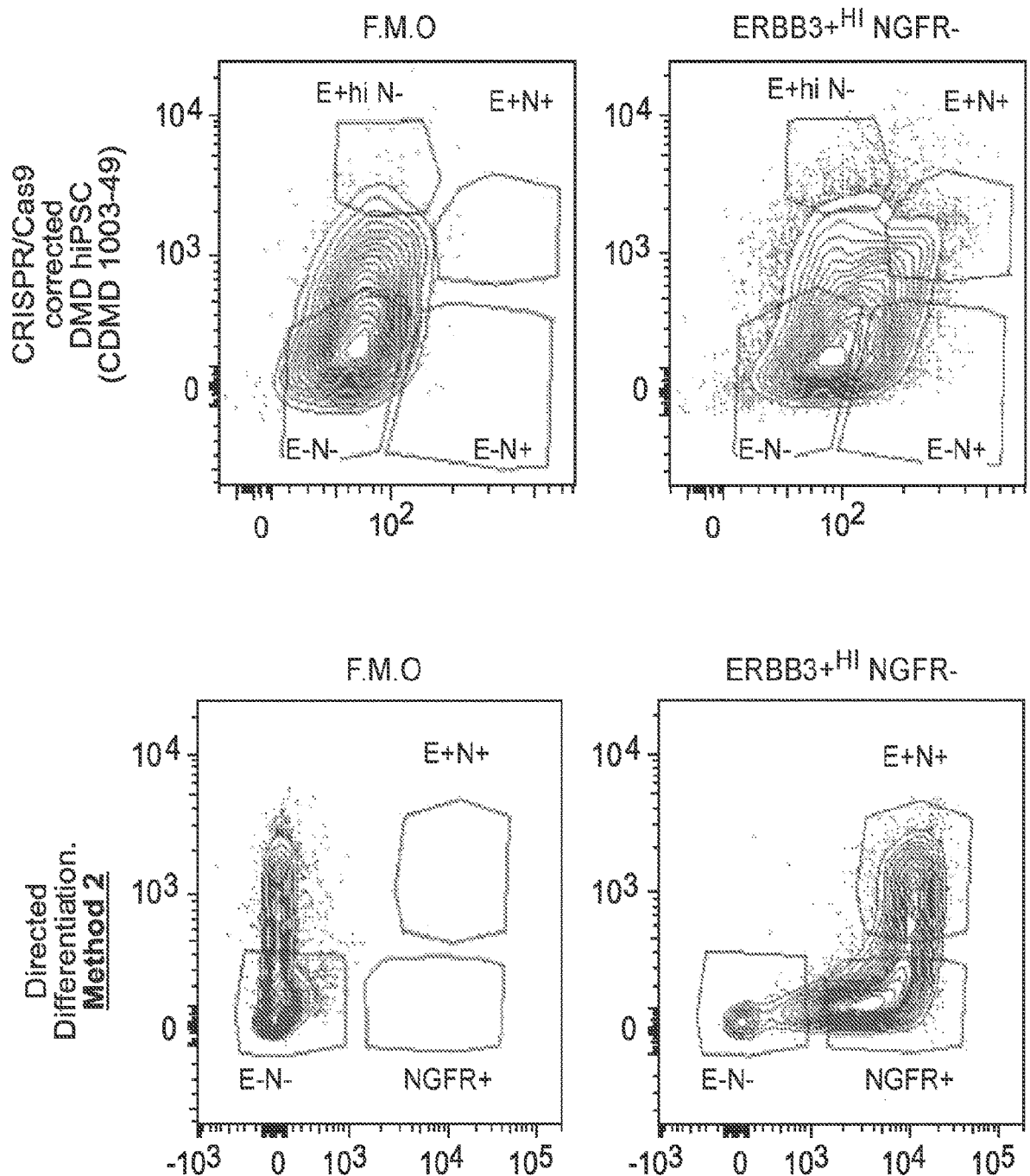

FIG. 7A-7G. FIG. 7A shows characterization of ERBB3 and NGFR expression at multiple stages of human developmental myogenesis. FACS analyses of key cell surface markers during primary (weeks 6-9; late primary week 9 is shown; N=4), early secondary (weeks 11-14; N=4), and secondary fetal myogenesis (weeks 16-18; N=6). FACS plots show subpopulations based on NCAM$^+$MCAM$^+$, CD82$^+$, and ERBB3$^+$NGFR$^+$ expression from directly-isolated human fetal muscle tissues. All subpopulations were gated on forward and side scatter to remove debris, height and width to remove doublets, live cells, and lineage negative (CD235a$^-$CD31$^-$CD45$^-$) cells. ERBB3 and NGFR positivity identify at least 5 fetal subpopulations. Table represents mean±SD percentage of positive cells for all fetal subpopulations, (*p<0.05; two-tailed t-test; comma indicates comparison between a population at different stages of fetal myogenesis). Characterization of NCAM$^+$MCAM$^+$ and CD82$^+$ positivity within ERBB3 and NGFR subpopulations show mean±SD percentage of known fetal surface markers during the transition to secondary fetal myogenesis (weeks 6-9, N=4; weeks 11-14; N=4; weeks 16-18, N=6). FIG. 7B-7C. Increased myogenic ability resides in the ERBB3$^+$NGFR$^+$ fraction of human fetal muscle during primary and secondary myogenesis. Five subpopulations of human myogenic cells were identified based ERBB3 and NGFR expression during Primary myogenesis (weeks 8-10) (FIG. 7B) and secondary myogenesis (fetal weeks 16-18) (FIG. 7C). IF of fetal week 9 skeletal muscle tissue demonstrated establishment of the limb myofibers, and week 17 tissue demonstrated maturation to multinucleated myofibers. IF shows MYHC (red), PAX7 (green), and DAPI (blue). Scale bar equals 100 μm. FACS plots of isotype controls and full stain (live, non-doublet CD45$^-$CD31$^-$CD235a$^-$ cells) show ERBB3$^+$NGFR$^+$ populations lose NGFR$^{+Hi}$ positivity during the transition from primary and secondary myogenesis. Statistical analyses of all fetal populations identified by FACS are shown in FIG. 7C. FIG. 7E. Graphs show fold change of myogenic gene expression of immediately sorted subpopulations compared to ERBB3$^-$NGFR$^-$ cells (N=3 week 8-10 tissues and N=5 week 16-18 tissues; mean±SEM; One-way ANOVA posthoc Dunnett; increase: *p<0.05, p<0.01, *p<0.001). Sorted populations were expanded in SkBM-2 for 24 hours and induced to differentiate to myotubes in N2 media for 5 days, highlight differences in in vitro myogenic potential between progenitors and subpopulations at different stages of human myogenesis. Myotubes were stained with MYHC (red) and DAPI (blue) (N=3 independent hPSC-myotube experiments). Scale bar equals 200 μm. FIG. 7F. Characterization of ERBB3 and NGFR across hPSC-SMPC directed differentiation. FACS analyses of key cell surface markers during directed differentiation of hPSC-SMPCs from two protocols; method 1, and method 2. FACS plots show subpopulations based on NCAM$^+$MCAM$^+$, CD82$^+$, and ERBB3$^+$NGFR$^+$ expression from days 27-33 and 48-56 using H9 hESC line. All subpopulations were first gated on forward and side scatter to remove debris, height and width to remove doublets, live cells, and lineage negative (HNK1$^-$) cells. ERBB3$^+$NGFR$^+$ FACS plots identify 4 hPSC-SMPC subpopulations. Table represents mean±SD percent positive cells for all hPSC subpopulations (*p<0.05; two-tailed t-tests; population comparison between days 27-33 and 48-56 within each protocol; N=2 method 1 days 27-33; N=3 method 2 days 27-33, N=5 methods 1-2 days 48-56). Where N=2, statistics±SD were not performed. Characterization of NCAM$^+$MCAM$^+$ and CD82$^+$ positivity within ERBB3 and NGFR hPSC-SMPC populations show mean±SD percentage across time points of directed differentiation protocols. FIG. 7G. Increased myogenic ability resides in the ERBB3$^+$NGFR$^+$ fraction of SMPCs from multiple hPSC lines and directed differentiation protocols. Up to four myogenic populations were identified based on ERBB3 and NGFR expression after hPSC-SMPC directed differentiation. FACS gating of fluorescent minus one (F.M.O.) controls and full staining demonstrate variability and need to optimize ERBB3$^+$NGFR$^+$ sorting strategies across multiple hPSC lines and directed differentiation protocols. Shown are live non-doublet HNK1-cells from hESC, wild type, DMD and CRIPSR/Cas9 corrected hiPSC lines after 50 days of directed differentiation from method 1, or 27 days of directed differentiation from method 2 (method 1: N=5 H9, N=3 CDMD 1002, N=2 CDMD 1003, N=3 CDMD 1003-49, method 2: N=2 H9; where N=number of independent directed differentiations). Surface marker FACS analyses of hPSC-SMPCs from methods 1 and 2 are shown in FIG. 7F. Graphs show fold change of myogenic gene expression of immediately sorted subpopulations compared to ERBB3$^-$NGFR$^-$ cells (N=3; mean±SEM; One-way ANOVA posthoc Dunnett; increase: *p<0.05, ***p<0.001). Sorted subpopulations were expanded in SkBM-2 for 72 hours and induced to differentiate in N2 media for 5 days. IF evaluating the myogenic potential of each sorted and differentiated population is shown using MYH3 (red) and DAPI (blue) (N=3 independent hPSC-myotubes experiments). Scale bar equals 200 μms. ERBB3$^+$NGFR$^+$ mark the majority of myogenic cells. FACS plots demonstrate in some protocols all ERBB3$^+$ cells are positive for NGFR$^+$.

Figure 10B:
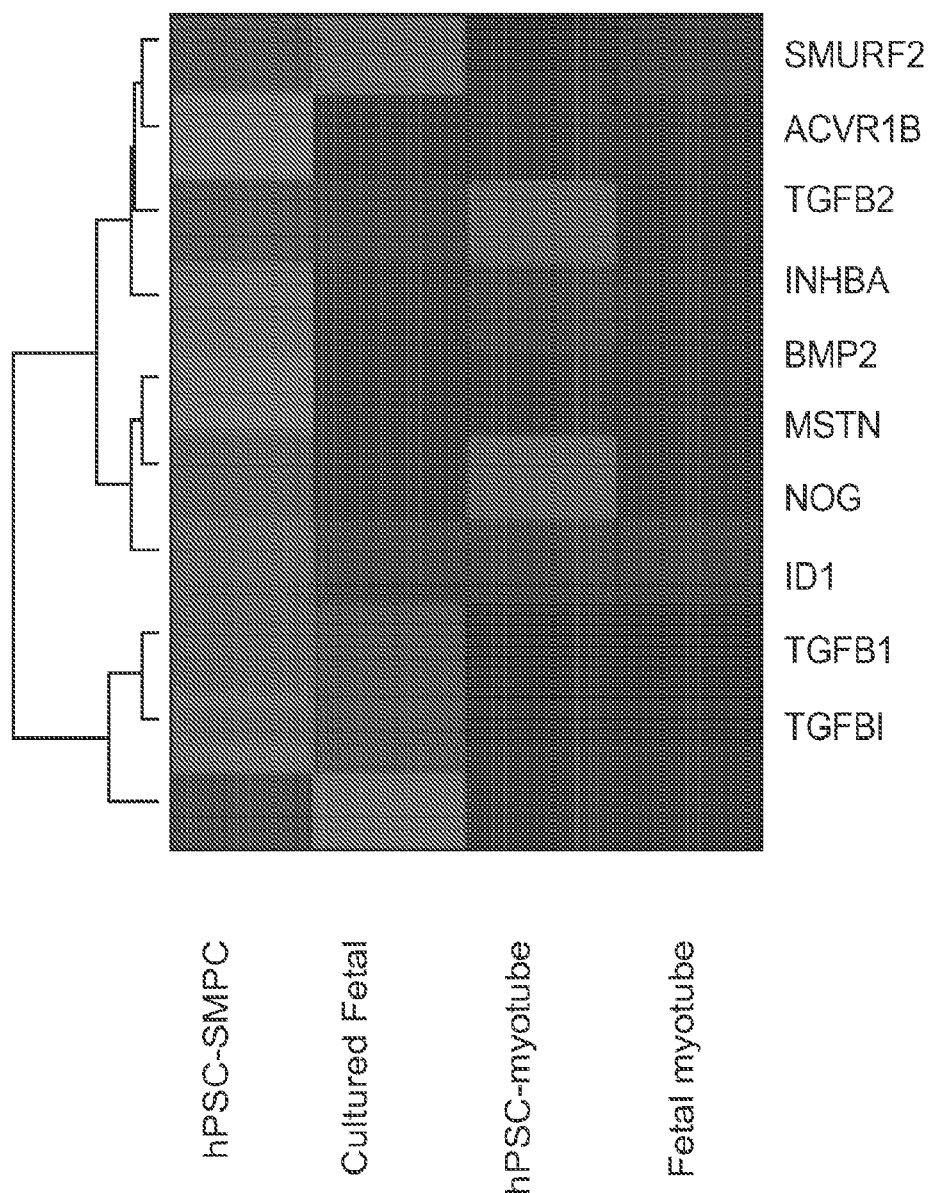

FIG. 10A-10F. Inhibition of TGFβ signaling induces hPSC skeletal muscle maturation. FIG. 10A. TGFβ inhibition induces myotube fusion in hPSC-SMPCs and acts independently from dystrophin expression. Original data used to quantify myotube fusion±TGF-βi. HNK1$^-$NCAM$^+$ SMPCs from DMD hiPSCs, or CRISPR/Cas9-corrected DMD hiPSCs were differentiated in N2 media alone, in the presence of recombinant TGF-β1, or TGF-β inhibitor SB-431542. HPSC-myotubes were stained with MYHC (red), H-Dystrophin (green), and PAX7 (white). Scale bar equals 200 μm. Zoom images shows no change in PAX7 expression with treatment. Bottom. Quantification of myotube differentiation shows increased fusion and nuclei per myotube with TGF-βi (N=3 experiments, mean±SEM; two-tailed t-tests, *p<0.05). FIG. 10B. Heat map of TGF-β signaling genes reveals high TGF-β in hPSC myotubes as determined by RNA-SEQ FPKM values. FIG. 10C. ERBB3$^+$ SMPCs from 1006-1 CRISPR/Cas9-corrected DMD hiPSCs were differentiated in N2 media alone, with recombinant TGF-β1, or in the presence of TGFβ inhibitor SB-431542 (N=6). HPSC-myotubes were stained with MYHC (red), H-Dystrophin (green), PAX7 (white), and DAPI (blue). Scale bar equals 200 μms. Zoom images show no change in PAX7 expression with either treatment but an increase in myotube formation was seen with TGFβ inhibition. FIG. 10D. Western blot analysis showing TGFβ inhibitor SB-431542 treated hPSC-SMPCs have increased expression of MYH1 and MYH8 compared to N2 media alone or after treatment with recombinant TGFβ1 (N=2 independent myotube experiments; student t-test; *p<0.05). Ponceau S stained gel is shown for loading control. Ladder and unprocessed blots are included in FIG. 10E. FIG. 10F. Transmission electron microscopy of fetal week 17 or NGFR$^+$ hPSC-myotubes±TGFβi demonstrate increased sarcomere organization and z-disk patterning after SB-431542 treatment (N=2 independent myotube experiments). Scale bar equals 3 μms (top). FIG. 10E. Unprocessed scan of western blot gels and loading controls. MYH1 and MYH8 were run on 7.5% and 10.0% polyacrylamide gels (PAAG), respectively. Gels were then counterstained with Ponceau S to measure total protein. Arrows mark band size of myosin (223 kDA) and actin (42 kDA).

FIG. 11A-11B. Evaluation of myosin expression by muscle tissue and myotubes derived from adult, fetal, and hPSCs. IF staining and QPCR of MYH3 (embryonic), MYH8 (fetal), MYH4 (adult) and MYH1 (adult) show relative maturation status of muscle tissues and myotubes. Adult tissue primarily expresses MYH1 while human fetal week 17 tissue express MYH3 and MYH8. Adult myotubes (HSMM) differentiated in vitro primarily express MYH8 and lowly express MYH1. Fetal week 17 myotubes express MYH8, while fetal week 14 express only MYH3. HPSC-SMPCs sorted for NGFR$^+$ERBB3 have mixed expression of MYH3 and MYH8 and when treated with TGFβ primarily express MYH3. Treatment with TGFβ inhibitor, SB431542, increases MYH8 and MYH1 expression in fetal myotubes and in ERBB3$^+$NGFR$^+$ hPSC-SMPCs (N=3, mean±SD; two-tailed t-tests compared within each group±TGF-βi, *p<0.05). Arrows show predominant expression of MYH3 (green) and MYH8 (red). Scale bar equals 200 μm.

FIG. 12A-12E. In vivo engraftment of CRISPR/Cas9-corrected DMD hiPSC-SMPCs restores dystrophin to levels approaching uncultured fetal muscle. FIG. 12A. CRISPR/Cas9-corrected DMD hiPSC-SMPCs were enriched for surface markers and upon engraftment were co-delivered with the TGFβi (SB-431542). IF of h-Lamin A/C (red) denotes human cells, and j-Spectrin (red) and h-dystrophin (green) denote areas fused with mdx-NSG muscle fibers thirty days post engraftment. Graphs show the average±SEM number of engrafted human$^+$ myofibers from multiple cross sections along the length of the muscle (N=3 NCAM, N=4 NGFR, N=4 ERBB3 engrafted mice per group; Kruskal-Wallis ranks tests; *p<0.05, **p<0.01), and maximum number of engrafted myofibers in a single cross section (One-way ANOVA posthoc Tukey; *p<0.05). FIG. 12B. CRISPR/Cas9-corrected ERBB3$^+$ SMPCs plus TGFβi engraft equivalent to uncultured (directly-isolated) fetal muscle cells. Graphs show the mean±SEM number of engrafted myofibers from multiple cross sections along the length of the muscle (N=3 fetal SMPCs, N=4 ERBB3$^+$ SMPCs engrafted mice per group; Kruskal-Wallis ranks tests; *p<0.05). FIG. 12C-12E. Expression of myogenic and non-myogenic markers by engrafted hPSC-SMPCs. Myogenicity of SMPCs was evaluated 30 days post engraftment in mdx-NSG mice (N=2 for all markers). FIG. 12C. Myogenic structural markers Desmin, MYH3, and NG2 (green) are co-expressed by some h-LaminAC or h-LaminAC/Spectrin (red). Scale bar equals 100 μm and zoom scale bar equals 50 μm. FIG. 12D. Myogenic transcription factors show stemness (PAX7, green) and differentiation (MYOG, green) in h-LaminAC+ cells. Arrows mark identity. Scale bar equals 20 μm and zoom scale bar equals 20 μm. FIG. 12E. Non-myogenic markers show potential hPSC-SMPC to mesenchymal cell switch (CD90, green) in dystrophic muscle tissue. OCT4 (pluripotency marker, green) is not expressed. Scale bar equals 100 μm and zoom scale bar equals 50 μm.

FIG. 13. Engraftment quantification of all human fetal and hPSC skeletal muscle in all mdx-NSG mice. Total number of human (h) LaminAC$^+$Spectrin$^+$ and h-Dystrophin$^+$ engrafted fibers per cross section were counted from multiple cross sections throughout tibialis anterior muscle of mdx-NSG mice, 30 days after engraftment. All quantifications from 11 regions, 0-10 millimeters, are shown for engrafted fetal and hPSC skeletal muscle. All mdx-NSG mice were pretreated with 10 μM cardiotoxin and additional treatments are listed. The figure number corresponds to data in the manuscript, or -indicates data not shown. To generate manuscript figures, the region with the greatest number of h-LaminAC$^+$Spectrin$^+$Dystrophin$^+$ engrafted fibers was used to calculate maximum engraftment. To calculate differences in engraftment efficiency between cell types, engraftment counts from all mice within a given cell type were averaged, and then ranked in comparison to engraftments from other cell types using Mann Whitney U-tests when comparing two groups, or Kruskal-Wallis tests when comparing three or more groups, (p<0.05 is significant).

Figure 14A:
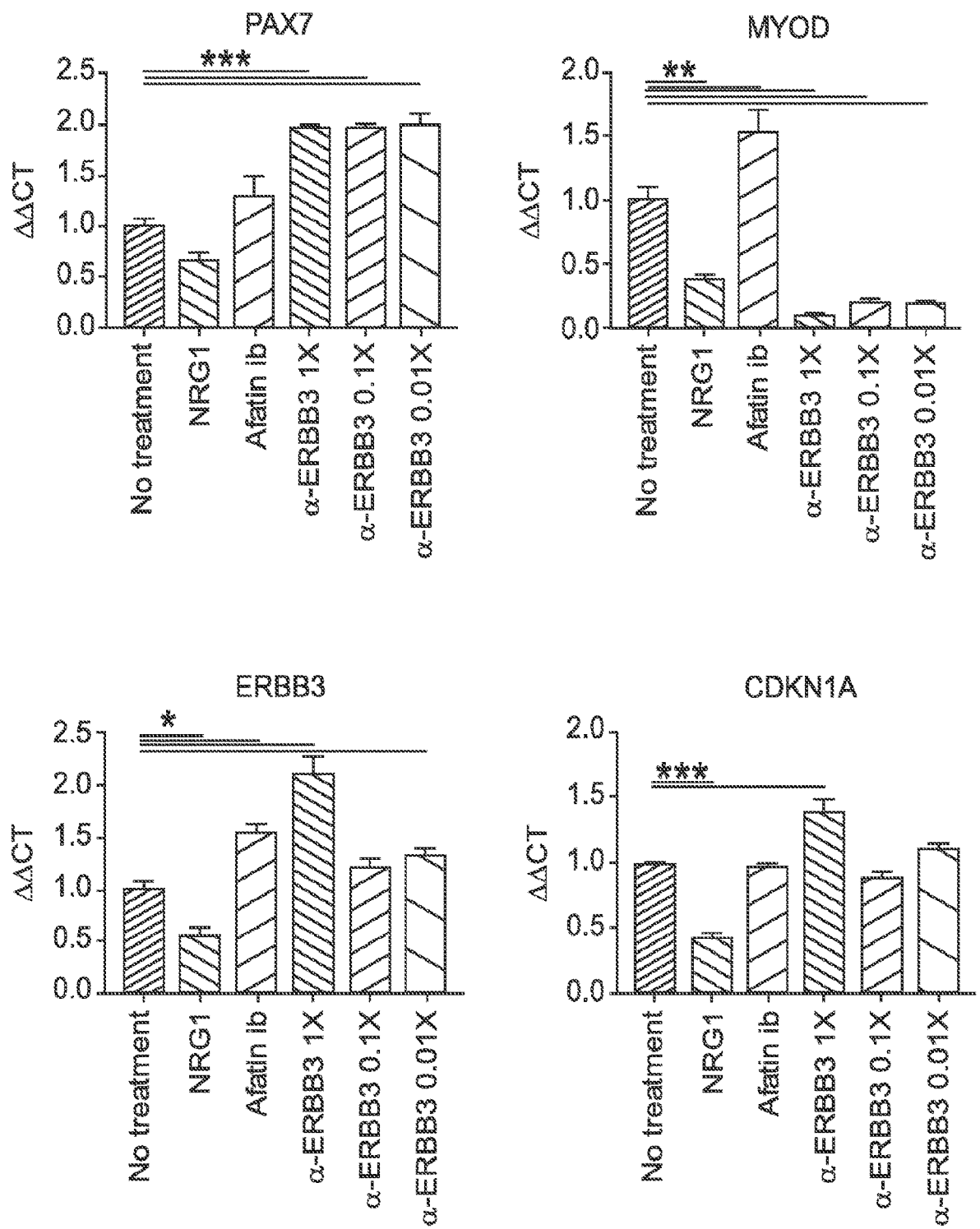
FIG. 14A-14B depict that targeting the ERBB3 pathway during SMPC expansion retains PAX7 expression.
Figure 14B:
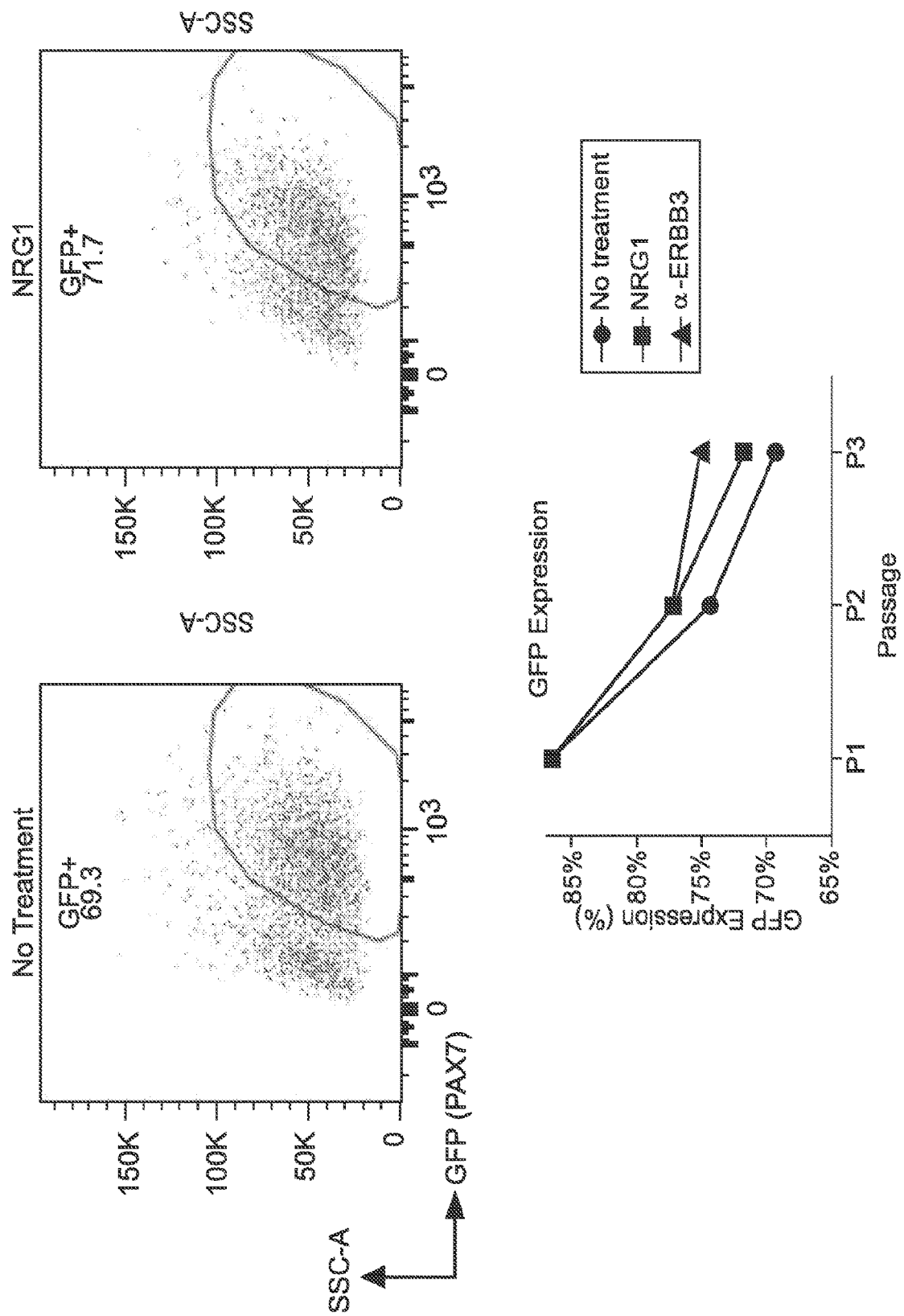
Figure 16:
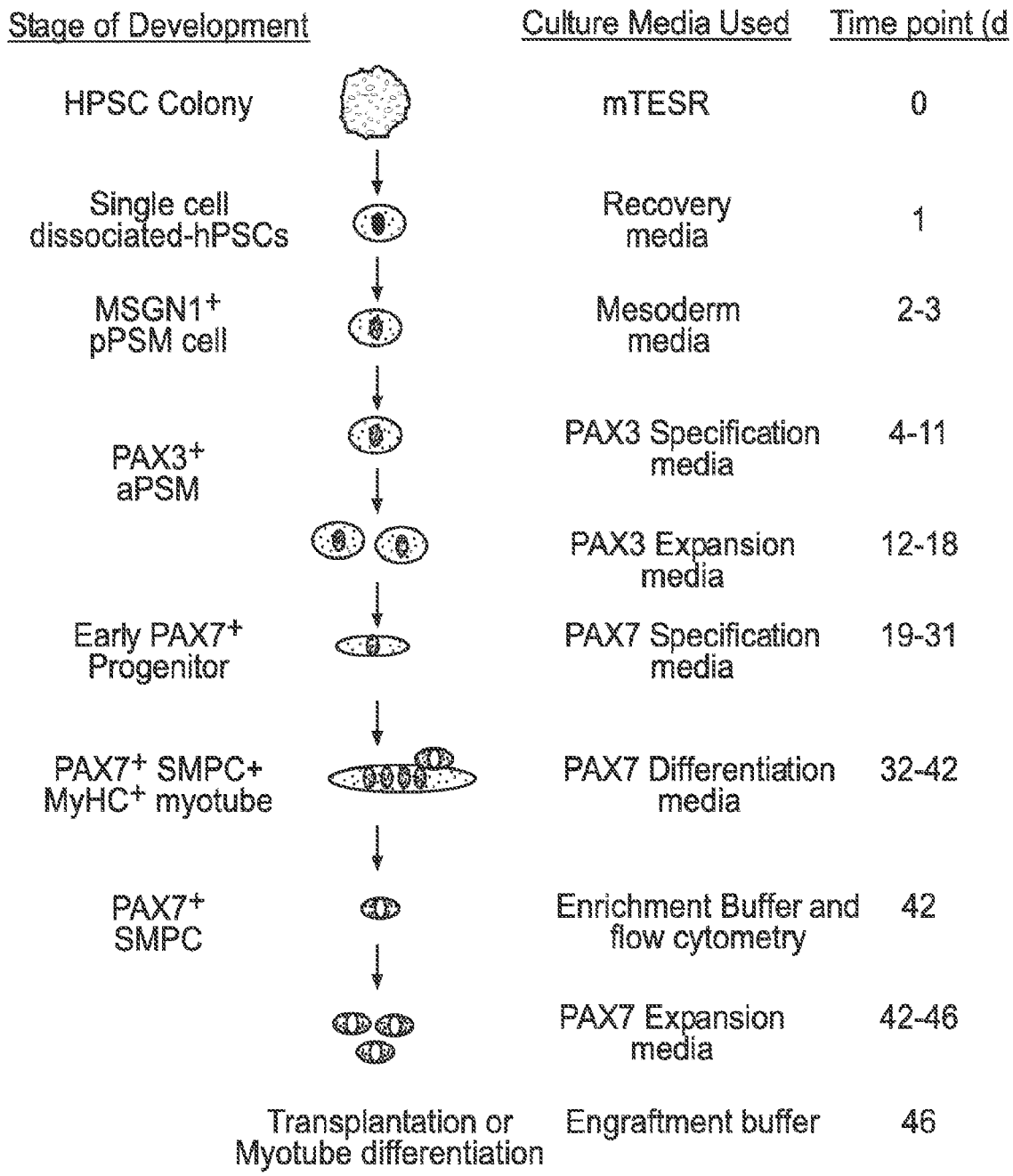
FIG. 16 presents a flow diagram of directed differentiation of human pluripotent stem cells to skeletal muscle progenitor cells.

FIG. 14A-14B. Targeting the ERBB3 pathway during SMPC expansion retains PAX7 expression. FIG. 14A. Diagram illustrates treatment strategy after SMPC enrichment from directed differentiation cultures. Treatment with regulators of ERBB3 regulate SMPC gene expression. All doses of a neutralizing ERBB3 antibody resulted in increased PAX7 and decreased MYOD expression. FIG. 14B. Flow cytometry analyses of PAX7 (GFP) during expansion over multiple passages shows neutralization of ERBB3 reduces the loss of PAX7 over time. FACS plots are of passage 3 (P3) cells.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for generating skeletal muscle progenitor cells (SMPCs), the method comprising:
  a) culturing pluripotent stem cells in a chemically defined liquid culture medium for a period of time to generate a population of SMPCs that express paired box protein-7 (PAX7), wherein said culturing comprises:
    i) culturing the pluripotent stem cells in a chemically defined liquid culture medium comprising a Rho-associated kinase inhibitor from day 1 to day 2 only;
    ii) (1) culturing the cells from step i) in a chemically defined liquid culture medium comprising a glycogen synthase kinase-3 (GSK3) inhibitor from day 2 to day 3 only;
    ii) (2) culturing the cells from step ii) (1) in a chemically defined liquid culture medium from day 3 to day 12 only;
    iii) culturing the cells from step ii) (2) in a chemically defined liquid culture medium comprising fibroblast growth factor from day 12 to day 20 only;
    iv) culturing the cells from step iii) in a chemically defined liquid culture medium from day 20 to day 35 only; and
    v) culturing the cells from step iv) in a chemically defined liquid culture medium comprising insulin-like growth factor-1 from day 35 to day 50 only,
  thereby generating a population of cells comprising at least 50% PAX7* SMPCs, which also express nerve growth factor receptor (NGFR), Erb-B2 receptor tyrosine kinase 3 (ERBB3) or both; and
  b) enriching for SMPCs that are nerve growth factor receptor (NGFR)-positive and Erb-B2 receptor tyrosine kinase 3 (ERBB3)-positive.

2. The method of claim 1, wherein the chemically defined liquid culture medium in step (iii) does not include a bone morphogenetic protein (BMP) inhibitor.

3. The method of claim 1, wherein the chemically defined liquid culture medium in step (iii) further comprises one or more of transferrin, a transferrin substitute, L-glutamine, an L-glutamine substitute, and monothioglycerol.

4. The method of claim 1, wherein the chemically defined liquid culture medium in step (iv) is Dulbecco's Eagle's Medium (DMEM) or is a defined, serum-free and xeno-free medium that does not contain transforming growth factor β (TGF-β) or basic fibroblast growth factor (bFGF).

5. The method of claim 1, wherein the chemically defined liquid culture medium in step (v) comprises N2 medium with insulin-like growth factor-1, insulin, transferrin, and selenium.

6. The method of claim 1, wherein the GSK3 inhibitor is CHIR99021.

7. The method of claim 1, wherein the PAX7$^+$ SMPCs express one or more transcription factors selected from the group consisting of PAX3, MYF5, MYOD (skeletal muscle); PAX6, TUJ1 (neural); NKX2.5, TTN2 (cardiac);

CD73 (mesenchymal); EN1, Brachyury, MEOX1, TBX6, LBX1 (early mesoderm); or TFAP2, SOX10 (neural crest).

8. The method of claim 1, further comprising removing HNK1$^+$ cells.

9. The method of claim 1, further comprising enriching the population of SMPCs for melanoma cell adhesion molecule (MCAM)-positive cells and muscle cadherin (M-CAD)-positive cells.

10. The method of claim 1, further comprising expanding the population of SMPCs by culturing the population of SMPCs in a liquid culture medium comprising one or more of:
   a) a cell cycle or cell developmental regulator;
   b) an inhibitor of DNA damage and/or cell stress;
   c) a signal transducer and activator of transcription-3 (STAT3) pathway activator;
   d) an ERBB3 pathway activator;
   e) an NGFR signaling activator; and
   f) a migration factor,
   thereby generating an expanded SMPC population comprising at least 5-fold more SMPCs than the number of SMPCs before expansion.

11. The method of claim 10, further comprising generating a multinucleated muscle cell that expresses myosin heavy chain by culturing the expanded SMPC population in a liquid culture medium comprising an inhibitor of TGFβ receptor activity.

12. The method of claim 1, wherein the pluripotent stem cells comprise a mutation associated with a deleterious muscle phenotype.

13. The method of claim 12, wherein the mutation is in a dystrophin gene, a huntingtin gene, an emerin gene, a myotonic protein kinase gene, a merosin gene, a laminin gene, an integrin gene, a fukutin gene, a POMGnT1 gene, a POMT1 gene, a FKRP gene, a LARGE gene, a SGCA gene, a SGCB gene, a SGCG gene, a SGCD gene, a Dysferlin gene, a D4Z4 gene, a Calpain3 gene, a Caveolin3 gene, a TRIM 32 gene, a Telethonin gene, a Titin gene, a Myotilin gene, or a Lamin AC gene.

14. The method according to claim 1, and further comprising expanding the population of cells comprising at least 50% PAX7$^+$ SMPCs by culturing the population of SMPCs in a liquid culture medium comprising one or more of:
   a) a cell cycle or cell developmental regulator;
   b) an inhibitor of DNA damage and/or cell stress;
   c) a STAT3 pathway activator;
   d) an ERBB3 pathway activator;
   e) a nerve growth factor receptor (NGFR) signaling activator; and
   f) a migration factor.

15. The method according to claim 1, which further comprises culturing the population of cells comprising at least 50% PAX7$^+$ SMPCs (a) in a liquid culture medium comprising a TGFβ inhibitor, or (b) with a motor neuron.

16. The method according to claim 1, and further comprising introducing the population of cells comprising at least 50% PAX7$^+$ SMPCs into a subject.

17. The method of claim 16, wherein the subject has a muscle disease or disorder.

* * * * *

SEQUENCE LISTING

<160> NUMBER OF SEQ ID NOS: 43

<210> SEQ ID NO 1
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 1
cgcccccggt ttctataaat tg    22

<210> SEQ ID NO 2
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 2
aagaagatgc ggctgactgt    20

<210> SEQ ID NO 3
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 3
agctcggcgg tgtttttatc a    21

<210> SEQ ID NO 4
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 4
ctgcacagga tcttggagac g    21

<210> SEQ ID NO 5
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 5
ctggccaaaa atgtgagcct    20

<210> SEQ ID NO 6
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 6
tagggttggg ctgggaattg    20

<210> SEQ ID NO 7
<211> LENGTH: 20
<212> TYPE: DNA
<213> ORGANISM: Artificial Sequence

```
<220> FEATURE:
<223> OTHER INFORMATION: synthetic nucleic acid

<400> SEQUENCE: 7
ttaaccacaa atcaggccgg                                          20

<210> SEQ ID NO 8
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 8
caaagtgctg gcagtctgaa tg                                       22

<210> SEQ ID NO 9
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 9
agatgtgtct gtggccttcc                                          20

<210> SEQ ID NO 10
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 10
agctggcttc ctagcatcag                                          20

<210> SEQ ID NO 11
<211> LENGTH: 24
<212> TYPE: DNA
<213> ORGANISM: Artificial Sequence
<220> FEATURE:
<223> OTHER INFORMATION: synthetic nucleic acid

<400> SEQUENCE: 11
tgcccttgtt aattaccgga gcga                                     24

<210> SEQ ID NO 12
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 12
tatgcaggag ccgtcgtaga agt                                      23

<210> SEQ ID NO 13
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 13
ggaagaaacg cagagggatc a                                        21
```

<210> SEQ ID NO 14
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 14
caagcgtcgc aattcagaaa g                                          21

<210> SEQ ID NO 15
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 15
cctgtcatcc ccgtctacac                                            20

<210> SEQ ID NO 16
<211> LENGTH: 19
<212> TYPE: DNA
<213> ORGANISM: Artificial Sequence
<220> FEATURE:
<223> OTHER INFORMATION: synthetic nucleic acid

<400> SEQUENCE: 16
cacatggagt ccgccgtaa                                             19

<210> SEQ ID NO 17
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 17
acctattgga ggcgactttc c                                          21

<210> SEQ ID NO 18
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 18
tccttccaaa ggctgctctg                                            20

<210> SEQ ID NO 19
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 19
ccttctggag caggacagaa                                            20

<210> SEQ ID NO 20
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 20
caaagcaaag tttattgcat gtg                                           23

<210> SEQ ID NO 21
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 21
attgcttcgt ggtggactca a                                             21

<210> SEQ ID NO 22
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 22
ggccatgtct tcgatcctgt c                                             21

<210> SEQ ID NO 23
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 23
gtagttgtct gctttgagcc tg                                            22

<210> SEQ ID NO 24
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 24
ttgtaggggt tgacggtgac                                               20

<210> SEQ ID NO 25
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 25
aatgcaagtg ctattccaga gg                                            22

<210> SEQ ID NO 26
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 26
acagacagct tgtgttcttg tt                                            22

<210> SEQ ID NO 27

```
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 27
ctgaatttct caaccgacaa ca                                            22

<210> SEQ ID NO 28
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 28
catatctgtt ttgtagccag gag                                           23

<210> SEQ ID NO 29
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 29
gttgtccgcc tctgtcttct                                               20

<210> SEQ ID NO 30
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 30
tctatccacg tgcctacagc                                               20

<210> SEQ ID NO 31
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 31
cgagagctac acgttcacgg                                               20

<210> SEQ ID NO 32
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 32
gggtgtcgag ggaaaaatag g                                             21

<210> SEQ ID NO 33
<211> LENGTH: 19
<212> TYPE: DNA
<213> ORGANISM: Artificial Sequence
<220> FEATURE:
<223> OTHER INFORMATION: synthetic nucleic acid

<400> SEQUENCE: 33
```
ggagctggct acttctcgc                                             19

<210> SEQ ID NO 34
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 34
gggtgtcgag ggaaaaatag g                                          21

<210> SEQ ID NO 35
<211> LENGTH: 21
<212> TYPE: DNA
<213> ORGANISM: Artificial Sequence
<220> FEATURE:
<223> OTHER INFORMATION: synthetic nucleic acid

<400> SEQUENCE: 35
aaaagacagc tacgtgggtg a                                          21

<210> SEQ ID NO 36
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 36
gccatgttct atcgggtact tc                                         22

<210> SEQ ID NO 37
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 37
tcctggctaa cgacaaatac ga                                         22

<210> SEQ ID NO 38
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 38
tttcccggcc accataaagg                                            20

<210> SEQ ID NO 39
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 39
taaggcgccc tcaagatcaa                                            20

<210> SEQ ID NO 40
<211> LENGTH: 20
<212> TYPE: DNA

-continued

```
<213> ORGANISM: Artificial Sequence
<220> FEATURE:
<223> OTHER INFORMATION: synthetic nucleic acid

<400> SEQUENCE: 40
gagcttcttc actgccacac                                                   20

<210> SEQ ID NO 41
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 41
tcgtacttcc cattgcgata gaa                                               23

<210> SEQ ID NO 42
<211> LENGTH: 21
<212> TYPE: DNA
<213> ORGANISM: Artificial Sequence
<220> FEATURE:
<223> OTHER INFORMATION: Synthetic nucleic acid

<400> SEQUENCE: 42
ctgacaagca caagactgac c                                                 21

<210> SEQ ID NO 43
<211> LENGTH: 21
<212> TYPE: DNA
<213> ORGANISM: Artificial Sequence
<220> FEATURE:
<223> OTHER INFORMATION: Synthetic nucleic acid

<400> SEQUENCE: 43
ctgctgagca cgtagttagg g                                                 21
```